(12) United States Patent
Court et al.

(10) Patent No.: US 9,371,532 B2
(45) Date of Patent: Jun. 21, 2016

(54) PLASMIDS AND PHAGES FOR HOMOLOGOUS RECOMBINATION AND METHODS OF USE

(71) Applicant: The United States of America as represented by the Secretary of the Department of Health and Human Services, Washington, DC (US)

(72) Inventors: Donald L. Court, Frederick, MD (US); Simanti Datta, Kolkata (IN); Nina Costantino, Frederick, MD (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 3 days.

(21) Appl. No.: 14/481,795

(22) Filed: Sep. 9, 2014

(65) Prior Publication Data
US 2014/0377809 A1    Dec. 25, 2014

Related U.S. Application Data

(60) Division of application No. 13/928,237, filed on Jun. 26, 2013, now Pat. No. 8,859,277, which is a continuation of application No. 12/688,764, filed on Jan. 15, 2010, now Pat. No. 8,541,229, which is a division of application No. 11/134,795, filed on May 20, 2005, now Pat. No. 7,674,621.

(60) Provisional application No. 60/655,729, filed on Feb. 22, 2005, provisional application No. 60/653,259, filed on Feb. 14, 2005, provisional application No. 60/573,504, filed on May 21, 2004.

(51) Int. Cl.
| | | |
|---|---|---|
| C12N 15/74 | (2006.01) | |
| C12N 15/73 | (2006.01) | |
| C12N 15/70 | (2006.01) | |
| C12N 7/00 | (2006.01) | |

(52) U.S. Cl.
CPC  *C12N 15/74* (2013.01); *C12N 7/00* (2013.01); *C12N 15/70* (2013.01); *C12N 15/73* (2013.01); *C12N 2795/10321* (2013.01); *C12N 2795/10343* (2013.01)

(58) Field of Classification Search
None
See application file for complete search history.

(56) References Cited

U.S. PATENT DOCUMENTS

| | | |
|---|---|---|
| 5,258,289 A | 11/1993 | Davis et al. |
| 5,789,166 A | 8/1998 | Bauer et al. |
| 5,888,732 A | 3/1999 | Hartley et al. |
| 6,281,000 B1 | 8/2001 | Chartier et al. |
| 6,355,412 B1 | 3/2002 | Stewart et al. |
| 6,365,408 B1 | 4/2002 | Stemmer |
| 6,472,177 B1 | 10/2002 | Szybalski et al. |
| 6,509,156 B1 | 1/2003 | Stewart et al. |
| 6,699,692 B2 | 3/2004 | Filho et al. |
| 7,674,621 B2 | 3/2010 | Court et al. |
| 2002/0013956 A1 | 1/2002 | Borts et al. |
| 2002/0151059 A1 | 10/2002 | Te Riele et al. |
| 2003/0224521 A1 | 12/2003 | Court et al. |
| 2004/0092016 A1 | 5/2004 | Court et al. |
| 2005/0079618 A1 | 4/2005 | Court et al. |

FOREIGN PATENT DOCUMENTS

| | | |
|---|---|---|
| WO | WO 95/22625 | 8/1995 |
| WO | WO 99/29837 | 6/1999 |
| WO | WO 01/04288 | 1/2001 |
| WO | WO 02/14495 | 2/2002 |
| WO | WO 02/40678 | 5/2002 |
| WO | WO 02/062988 | 8/2002 |

OTHER PUBLICATIONS

Birge, "Bacterial and Bacteriophage Genetics," 3$^{rd}$ Ed., Springer-Verlag New York, Inc., p. 215, 1995.
Birge, "Bacterial and Bacteriophage Genetics," 3$^{rd}$ Ed., Springer-Verlag New York, Inc., p. 226, 1994.
Blatny et al., "Improved Broad-Host-Range RK2 Vectors Useful for High and Low Regulated Gene Expression Levels in Gram-Negative Bacteria," *Plasmid* 38:35-51, 1997.
Bubeck et al., "Rapid cloning by homologous recombination in vivo," *Nucl. Acid. Res.* 21: 3601-3602, 1993.
Capecchi, M., "Altering the Genome by Homologous Recombination," *Science* 244: 1288-1292, Jun. 1989.
Churchward et al., "The nucleotide sequence of replication and maintenance functions encoded by plasmid pSC101," *Nucl. Acid. Res.* 11(16):5645-5659, 1983.
Copeland et al., "Recombineering: a powerful new tool for mouse functional genomics," *Nat. Rev. Genet.* 2: 769-779, 2001.
Costantino et al., "Enhanced levels of k Red-mediated recombinants in mismatch repair mutants," *Proc, Natl. Acad. Sci. USA* 100(26):15748-15753, Dec. 23, 2003.
Court et al., "Genetic Engineering Using Homologous Recombination," *Annu. Rev. Genet*.36: 361-388, 2002.
Court et al., "Mini-lambda: a tractable system for chromosome and BAC engineering," *Gene* 315:63-69, 2003.
Cox, "Recombinational DNA Repair of Damaged Replication Forks in *Escherichia coli*," *Annu. Rev. Genet*. 35: 53-82, 2001.
Datsenko et al., "One-step inactivation of chromosomal genes in *Escherichia coli* K12 using PCR products," *Proc Natl Acad Sci* 97:6640-6645, 2000.
Degryse et al., "In vivo intermolecular recombination in *Escherichia coli*: application to plasmid constructions," *Gene* 170: 45-50, 1996.

(Continued)

*Primary Examiner* — Jennifer Dunston
(74) *Attorney, Agent, or Firm* — Klarquist Sparkman, LLP

(57) ABSTRACT

Lambda phages that can be used to introduce recombineering functions into host cells are disclosed. Also disclosed are plasmids that can be used to confer recombineering functions to a variety of strains of *E. coli* and to other bacteria, including *Salmonella, Pseudomonas, Cyanobacteria, Spirochaetes*. These plasmids and phages can be isolated in vitro and can be used to transform bacterial cells, such as gram negative bacteria.

40 Claims, 65 Drawing Sheets

(56) References Cited

OTHER PUBLICATIONS

Derbise et al., A rapid and simple method for inactivating chromosomal genes in Yersinia, *FEMS Immunology and Medical Microbiology* 38:113-116, 2003.
Ellis et al., "High efficiency mutagenesis, repair, and engineering of chromosomal DNA using single-stranded oligonucleotides," *Proc, Natl. Acad. Sci. USA* 98: 6742-6746, 2001.
Gabant et al., "Direct selection cloning vectors adapted to the genetic analysis of gram-negative bacteria and their plasmids," *Gene* 207:87-92, 1998.
Hall et al., "Homologous pairing and strand exchange promoted by the *Escherichia coli* RecT protein," *Proc. Natl. Acad. Sci.* 91: 3205-3209, 1994.
Harfe et al., "Mismatch repair proteins and mitotic genome stability," *Mut. Res.* 451: 151-167, 2000.
Higgins et al., "A Model for Replication Repair in Mammalian Cells," *J. Mol. Biol.* 101: 417-425, 1976.
Honigman et al., "Plasmid vectors for positive selection of DNA inserts controlled by lambda PL promoter, repressor and antitermination function," *Gene* 13(3): 289-298 (1981).
Iyer et al., "Classification and evolutionary history of the single-strand annealing proteins, RecT, Redβ, ERF and RAD52," *BMC Genomics* 3(8), 11 pages, Mar. 21, 2002.
Jasin et al., "Deletion of an essential gene in *Escherichia coli* by site-specific recombination with linear DNA fragments," *J. Bacteriol.* 159: 783-6, 1984.
Karakousis et al., "The Beta Protein of Phage λ Binds Preferentially to an Intermediate in DNA Renaturation," *J. Mol. Biol.* 276: 721-731, 1998.
Keim et al., "The RecE recombination pathway mediates recombination between partially homologous DNA sequences: structural analysis of recombination products," *J. Struct. Biol.* 104: 97-106, 1990.
Kleckner et al., "Properties of the translocatable tetracycline resistance element Tn10 in *Escherichia coli* and bacteriophage lamba," *Genetics* 90:427-461, Nov. 1978.
Kovach et al., "Four new derivatives of the broad-host-range cloning vector pBBR1MCS, carrying different antibiotic-resistance cassettes," *Gene* 166:175-176, 1995.
Kusano et al., "Involvement of RecE exonuclease and RecT annealing protein in DNA double-strand break repair by homologous recombination," *Gene* 138: 17-25, 1994.
Kuzminov et al., "Recombinational Repair of DNA Damage in *Escherichia coli* and Bacteriophage λ," *Microbiology and Molecular Biology Reviews* 63(4):751-813 Dec. 1999.
Leder et al., "ek2 derivatives of bacteriophage lambda useful in the cloning of DNA from higher organisms: The lamdagtWES system," *Science* 196(4296):175-177, Apr. 1977.
Lee et al., "A highly efficient *Escherichia coli*-based chromosome engineering system adapted for recombinogenic targeting and subcloning of BAC DNA," *Genomics* 73: 56-65, 2001.
Li et al., "The Beta Protein of Phage λ Promotes Strand Exchange," *J. Mol. Biol.* 276: 733-744, 1998.
Liu et al., "A Highly Efficient Recombineering-Based Method for Generating Conditional Knockout Mutations," *Genome Research* 13:476-484, 2003.
Lloyd and Low, "Homologous Recombination," www.mbio.ncsu.edu/ESU/MB758lectures04/ES119.pdf, printed Mar. 20, 2004.
Lowman et al., "Temperature-mediated regulation and downstream inducible selection for controlling gene expression from the bacteriophage lambda pL promoter," *Gene* 96:133-136, 1990.
Maas et al., "Multicopy single-stranded DNA of *Escherichia coli* enhances mutation and recombination frequencies by titrating MutS protein," *Molec. Microbiol.* 19: (3) 505-509, 1996.
Matz et al., "The rex gene of bacteriophage lambda is really two genes," *Genetics* 102:319-327, Nov. 1982.
Milman, "Expression Plasmid Containing the Lambda Pl Promoter and c1857 Repressor," *Meth. Enzymol.* 153:482-491, 1987.
Moerschell et al., "Transformation of yeast with synthetic oligonucleotides," *Proc. Natl. Acad. Sci. U.S.A.* 85: 524-528, 1988.

Muniyappa et al., "The homologous recombination system of phage λ," *J. Bio. Chem.* 261: 7472-7478, Jun. 1986.
Murphy et al., "Lambda Red-mediated recombinogenic engineering of enterohemorrhagic and enteropathogenic *E. coli,*" *BMC Mol Biol* 4:11, 2003.
Murphy et al., "PCR-mediated gene replacement in *Escherichia coli,*" *Gene* 246: 321-330, 2000.
Murphy, K.C., "Use of bacteriophage λ recombination functions to promote gene replacement in *Escherichia coli,*" *J. Bacteriol.* 180: 2063-2071, 1998.
Muyrers et al., "Point mutation of bacterial artificial chromosomes by ET recombination," *EMBO Rep.* 1: 239-243, 2000.
Muyrers et al., "Rapid modification of bacterial artificial chromosomes by ET-recombination," *Nucleic Acids Res.* 27: 1555-1557, 1999.
Muyrers et al., "RecE/RecT and Redα/Redβ initiate double-stranded break repair by specifically interacting with their respective partners," *Genes Dev.* 14: 1971-1982, 2000.
Muyrers et al., "Techniques: Recombinogenic engineering-new options for cloning and manipulating DNA," *Trends Biochem. Sci.* 26: 325-331, 2001.
Nistala et al., "A reliable and efficient method for deleting operational sequences in PACs and BACs," *Nucleic. Acid. Res.* 30: 10 e 41, 2002.
Nussbaum et al., "Restriction-stimulated homologous recombination of plasmids by the RecE pathway of *Escherichia coli,*" *Genetics* 130: 37-49, 1992.
Oliner et al., "In vivo cloning of PCR products in *E. coli,*" *Nucleic Acids Res*/ 21(22): 5192-5197, 1993.
Oppenheim et al., "In vivo recombineering of bacteriophage λ by PCT fragments and single-strand oligonucleotides," *Virology* 319(2):185-189, Feb. 20, 2004.
Passy et al., "Rings and filaments of β protein from bacteriophage λ suggests a superfamily of recombination proteins," *Proc. Natl. Acad. Sci. U.S.A.* 96: 4279-4284, 1999.
Postow et al., "Topological challenges to DNA replication: Conformations at the fork," *Proc. Natl. Acad. Sci. USA* 98 (15): 8219-8226, 2001.
Poteete, "What makes the bacteriophage λ Red system useful for genetic engineering: molecular mechanism and biological function," *FEMS Microbiol. Lett.* 201: 9-14, 2001.
Ray and Skalka, "Lysogenization of *Escherichia coli* by Bacteriophage Lambda: Complementary Activity of the Host's DNA Polymerase I and Ligase and Bacteriophage Replication Proteins O and P," *J. Virology* 18(2):511-517, May 1976.
Reuven et al., "The herpes simplex virus type 1 alkaline nuclease and single-stranded DNA binding protein mediate strand exchange in vitro," *J. Virology* 77(13):7425-7433, 2003.
Santucci-Darmanin et al., "The DNA mismatch-repair MLH3 protein interacts with MSH4 in meiotic cells, supporting a role for this MutL homolog in mammalian meiotic recombination," *Hum. Mol. Genet.* 11: 1697-1706, 2002.
Sawitzke et al., "The phage lambda orf gene encodes a trans-acting factor that suppresses *Escherichia coli* recO, recR, and recF mutations for recombination of lambda but not of *E. coli,*" *J. Bacteriol.* 176(21):6730-6737, Nov. 1994.
Seitz et al., "A hybrid bacterial replication origin," *EMBO Reports* 21(11):1003-1003, 2001.
Smith et al., "Bacterial fitness and plasmid loss: the importance of culture conditions and plasmid size," *Can. J Microbiol.* 44(4):351-355, Apr. 1998.
Smith, "Mechanism and control of homologous recombination in *Escherichia coli,*" *Ann Rev. Genet.* 21: 179-201, 1987.
Swaminathan et al., "Rapid Engineering of Bacterial Artificial Chromosomes Using Oligonucleotides," *Genesis* 29: 14-21, 2001.
Symington et al., "Intramolecular recombination of linear DNA catalyzed by the *Escherichia coli* RecE recombination system," *J. Mol. Biol.* 186: 515-525, 1985.
Thomason et al., "Recombineering in Prokaryotes." In: *Phages: Their Role in Bacterial Pathogenesis and Biotechnology*, Waldor et al., eds. Adhya ASM Press, Herndon, VA, p. 383-399, 2005.
Tsuzuki et al., "Embryonic stem cell gene targeting using bacteriophage λ vectors generated by phage-plasmid recombination," *Nucleic Acids Research* 26(4):988-993 (1998).

(56) References Cited

OTHER PUBLICATIONS

Vanneste et al., "Role of antibiotic production by Erwinia hericola Eh252 in biological control of Erwinia amylovora," *Journal of Bacteriology* 174(9):2785-2796, 1992.

Vellani et al., "Bacteriophage SPP1 Chu is an alkaline exonuclease in the SynExo family of viral two-component recombinases," *J. Bacteriology* 185(8):2465-2474, 2003.

www-db.embl-hei8delberg.de/jss/servlet/de.embl.bk.wwwTools. GroupLeftEMBL.ext.html, printed Mar. 20, 2004.

Yang et al., "Homologous recombination based modification in *Escherichia coli* and germline transmission in transgenic mice of bacterial artificial chromosome," *Nat. Biotechnol.* 15: 859-865, 1997.

Yokochi et al., "Evidence for Conservative (Two-Progeny) DNA Double-Strand Break Repair," *Genetics* 139:5-17, Jan. 1995.

Yu et al., "An efficient recombination system for chromosome engineering in *Escherichia coil,*" *Proc. Natl. Acad. Sci. USA* 97: 5978-5983, 2000.

Zahrt et al., "Barriers to recombination between closely related bacteria: MutS and RecBCD inhibit recombination between Salmonella typhimurium and Salmonella typhi," *Proc. Natl. Acad. Sci. USA* 94:9786-9791, 1997.

Zhang et al., "A new logic for DNA engineering using recombination in *Escherichia coli,*" *Nat. Genet.* 20: 123-128, 1998.

Zhang et al., "DNA cloning by homologous recombination in *Escherichia coli,*" *Nat. Biotechnol.* 18: 1314-1317, 2000.

Zhang et al., "Phage annealing proteins promote oligonucleotide-directed mutagenesis in *Escherichia coli* and mouse ES cells," *BMC Molecular Biology* 4(1), 14 pages, 2003.

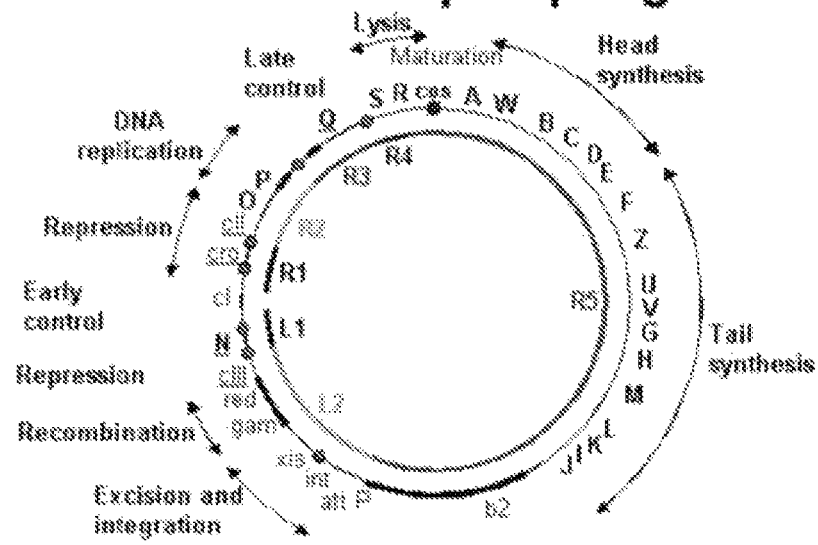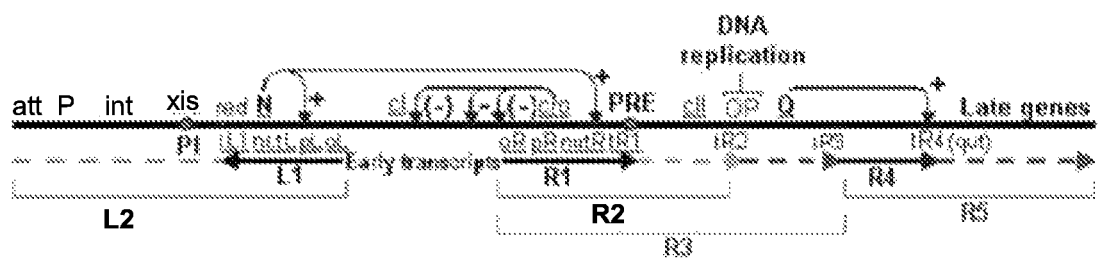
FIG. 2

```
           PvuII    Tn5 site             tL3
    1  CAGCTGTCTCTTATACACATCTCCGCTGTGCTTTCAGTGGATTTCGGATAACAGAAAGGCCGGGAAATACCCAGCCTC
       GTCGACAGAGAATATGTGTAGAGGCGACACGAAAGTCACCTAAAGCCTATTGTCTTTCCGGCCCTTTATGGGTCGGAG 79  GCTTTGTAACGGAGTAGACGAAAGTGATTGCGCCTACCCGGATATTATCGTGAGGATGCGTCATCGCCATTGCTCCCC
       CGAAACATTGCCTCATCTGCTTTCACTAACGCGGATGGGCCTATAATAGCACTCCTACGCAGTAGCGGTAACGAGGGG

226◄ R  W  Q  E  G

157  AAATACAAAACCAATTTCAGCCAGTGCCTCGTCCATTTTTTCGATGAACTCCGGCACGATCTCGTCAAAACTCGCCAT
       TTTATGTTTTGGTTAAAGTCGGTCACGGAGCAGGTAAAAAAGCTACTTGAGGCCGTGCTAGAGCAGTTTTGAGCGGTA

221◄ F  V  F  G  I  E  A  L  A  E  D  M  K  E  I  F  E  P  V  I  E  D  F  S  A  M
                                                          StuI
  235  GTACTTTTCATCCCGCTCAATCACGACATAATGCAGGCCTTCACGCTTCATACGCGGGTCATAGTTGGCAAAGTACCA
       CATGAAAAGTAGGGCGAGTTAGTGCTGTATTACGTCCGGAAGTGCGAAGTATGCGCCCAGTATCAACCGTTTCATGGT

195◄ Y  K  E  D  R  E  I  V  V  Y  H  L  G  E  R  K  M  R  P  D  Y  N  A  F  Y  W

313  GGCATTTTTTCGCGTCACCCACATGCTGTACTGCACCTGGGCCATGTAAGCTGACTTTATGGCCTCGAAACCACCGAG
       CCGTAAAAAAGCGCAGTGGGTGTACGACATGACGTGGACCCGGTACATTCGACTGAAATACCGGAGCTTTGGTGGCTC

169◄ A  N  K  R  T  V  W  M  S  Y  Q  V  Q  A  M  Y  A  S  K  I  A  E  F  G  G  L
                     SmaI
  391  CCGGAACTTCATGAAATCCCGGGAGGTAAACGGGCATTTCAGTTCAAGGCCGTTGCCGTCACTGCATAAACCATCGGG
       GGCCTTGAAGTACTTTAGGGCCCTCCATTTGCCCGTAAAGTCAAGTTCCGGCAACGGCAGTGACGTATTTGGTAGCCC

143◄ R  F  K  M  F  D  R  S  T  F  P  C  K  L  E  L  G  N  D  S  C  L  G  D  P

469  AGAGCAGGCGGTACGCATACTTTCGTCGCGATAGATGATCGGGGATTCAGTAACATTCACGCCGGAAGTGAAcTCAAA
       TCTCGTCCGCCATGCGTATGAAAGCAGCGCTATCTACTAGCCCCTAAGTCATTGTAAGTGCGGCCTTCACTTgAGTTT

117◄ S  C  A  T  R  M  S  E  D  R  Y  I  I  P  S  E  T  V  N  V  G  S  T  F  E  F

547  CAGGGTTCTGGCGTCGTTCTCGTACTGTTTTCCCCAGGCCAGTGCTTTAGCGTTAACTTCCGGAGCCACACCGGTGCA
       GTCCCAAGACCGCAGCAAGAGCATGACAAAAGGGGTCCGGTCACGAAATCGCAATTGAAGGCCTCGGTGTGGCCACGT

91◄ L  T  R  A  D  N  E  Y  Q  K  G  W  A  L  A  K  A  N  V  E  P  A  V  G  T  C

625  AACCTCAGCAAGCAGGGTGTGGAAGTAGGACATTTTCATGTCAGGCCACTTCTTTCCGGAGCGGGGTTTTGCTATCAC
       TTGGAGTCGTTCGTCCCACACCTTCATCCTGTAAAAGTACAGTCCGGTGAAGAAAGGCCTCGCCCCAAAACGATAGTG

65◄ V  E  A  L  L  T  H  F  Y  S  M  K  M  D  P  W  K  K  G  S  R  P  K  A  I  V

703  GTTGTGAACTTCTGAAGCGGTGATGACGCCGAGCCGTAATTTGTGCCACGCATCATCCCCCTGTTCGACAGCTCTCAC
       CAACACTTGAAGACTTCGCCACTACTGCGGCTCGGCATTAAACACGGTGCGTAGTAGGGGGACAAGCTGTCGAGAGTG

```
                    PstI                          Exo
781  ATCGATCCCGGTACGCTGCAGGATAATGTCCGGTGTCATGCTGCCACCTTCTGCTCTGCGGCTTTCTGTTTCAGGAAT
     TAGCTAGGGCCATGCGACGTCCTATTACAGGCCACAGTACGACGGTGGAAGACGAGACGCCGAAAGACAAAGTCCTTA
                                         261◄ A  A  V  K  Q  E  A  A  K  Q  K  L  F
13◄  D  I  G  T  R  Q  L  I  I  D  P  T  M

859  CCAAGAGCTTTTACTGCTTCGGCCTGTGTCAGTTCTGACGATGCACGAATGTCGCGGCGAAATATCTGGGAACAGAGC
     GGTTCTCGAAAATGACGAAGCCGGACACAGTCAAGACTGCTACGTGCTTACAGCGCCGCTTTATAGACCCTTGTCTCG
247◄ G  L  A  K  V  A  E  A  Q  T  L  E  S  S  A  R  I  D  R  R  F  I  Q  S  C  L

937  GGCAATAAGTCGTCATCCCATGTTTTATCCAGGGCGATCAGCAGAGTGTTAATCTCCTGCATGGTTTCATCGTTAACC
     CCGTTATTCAGCAGTAGGGTACAAAATAGGTCCCGCTAGTCGTCTCACAATTAGAGGACGTACCAAAGTAGCAATTGG
?221◄P  L  L  D  D  D  W  T  K  D  L  A  I  L  L  T  N  I  E  Q  M  T  E  D  N  V

PstI
1015 GGAGTGATGTCGCGTTCCGGCTGACGTTCTGCAGTGTATGCAGTATTTTCGACAATGCGCTCGGCTTCATCCTTGTCA
     CCTCACTACAGCGCAAGGCCGACTGCAAGACGTCACATACGTCATAAAAGCTGTTACGCGAGCCGAAGTAGGAACAGT
195◄P  T  I  D  R  E  P  Q  R  E  A  T  Y  A  T  N  E  V  I  R  E  A  E  D  K  D

BglI
1093 TAGATACCAGCAAATCCGAAGGCCAGACGGGCACACTGAATCATGGCTTTATGACGTAACATCCGTTTGGGATGCGAC
     ATCTATGGTCGTTTAGGCTTCCGGTCTGCCCGTGTGACTTAGTACCGAAATACTGCATTGTAGGCAAACCCTACGCTG
169◄Y  I  G  A  F  G  F  A  L  R  A  C  Q  I  M  A  K  H  R  L  M  R  K  P  H  S

1171 TGCCACGGCCCCGTGATTTCTCTGCCTTCGCGAGTTTTGAATGGTTCGCGGCGGCATTCATCCATCCATTCGGTAACG
     ACGGTGCCGGGGCACTAAAGAGACGGAAGCGCTCAAAACTTACCAAGCGCCGCCGTAAGTAGGTAGGTAAGCCATTGC
143◄Q  W  P  G  T  I  E  R  G  E  R  T  K  F  P  E  R  R  C  E  D  M  W  E  T  V

1249 CAGATCGGATGATTACGGTCCTTGCGGTAAATCCGGCATGTACAGGATTCATTGTCCTGCTCAAAGTCCATGCCATCA
     GTCTAGCCTACTAATGCCAGGAACGCCATTTAGGCCGTACATGTCCTAAGTAACAGGACGAGTTTCAGGTACGGTAGT
117◄C  I  P  H  N  R  D  K  R  Y  I  R  C  T  C  S  E  N  D  Q  E  F  D  M  G  D

1327 AACTGCTGGTTTTCATTGATGATGCGGGACCAGCCATCAACGCCCACCACCGGAACGATGCCATTCTGCTTATCAGGA
     TTGACGACCAAAAGTAACTACTACGCCCTGGTCGGTAGTTGCGGGTGGTGGCCTTGCTACGGTAAGACGAATAGTCCT
91◄F  Q  Q  N  E  N  I  I  R  S  W  G  D  V  G  V  V  P  V  I  G  N  Q  K  D  P

1405 AAGGCGTAAATTTCTTTCGTCCACGGATTAAGGCCGTACTGGTTGGCAACGATCAGTAATGCGATGAACTGCGCATCG
     TTCCGCATTTAAAGAAAGCAGGTGCCTAATTCCGGCATGACCAACCGTTGCTAGTCATTACGCTACTTGACGCGTAGC
65◄F  A  Y  I  E  K  T  W  P  N  L  G  Y  Q  N  A  V  I  L  L  A  I  F  Q  A  D

SalI
1483 CTGGCATCACCTTTAAATGCCGTCTGGCGAAGAGTGGTGATCAGTTCCTGTGGGTCGACAGAATCCATGCCGACACGT
     GACCGTAGTGGAAATTTACGGCAGACCGCTTCTCACCACTAGTCAAGGACACCCAGCTGTCTTAGGTACGGCTGTGCA
39◄S  A  D  G  K  F  A  T  Q  R  L  T  T  I  L  E  Q  P  D  V  S  D  M  G  V  R

Bet
1561 TCAGCCAGCTTCCCAGCCAGCGTTGCGAGTGCAGTACTCATTCGTTTTATACCTCTGAATCAATATCAACCTGGTGGT
     AGTCGGTCGAAGGGTCGGTCGCAACGCTCACGTCATGAGTAAGCAAAATATGGAGACTTAGTTATAGTTGGACCACCA
13◄E  A  L  K  G  A  L  T  A  L  A  T  S  M      98◄V  E  S  D  I  D  V  Q  H  H

1639 GAGCAATGGTTTCAACCATGTACCGGATGTGTTCTGCCATGCGCTCCTGAAACTCAACATCGTCATCAAACGCACGGG
     CTCGTTACCAAAGTTGGTACATGGCCTACACAAGACGGTACGCGAGGACTTTGAGTTGTAGCAGTAGTTTGCGTGCCC
88◄  A  I  T  E  V  M  Y  R  I  H  E  A  M  R  E  Q  F  E  V  D  D  D  F  A  R  T
```

FIG. 4B

```
                                            Nsil                                   Stul
1717 TAATGGATTTTTTGCTGGCCCCGTGGCGTTGCAAATGATCGATGCATAGCGATTCAAACAGGTGCTGGGGCAGGCCTTT
     ATTACCTAAAAAACGACCGGGGCACCGCAACGTTTACTAGCTACGTATCGCTAAGTTTGTCCACGACCCCGTCCGGAA
 62◀  I   S   K   K   S   A   G   H   R   Q   L   H   D   I   C   L   S   E   F   L   H   Q   P   L   G   K 1795 TTTCCATGTCGTCTGCCAGTTCTGCCTCTTTCTCTTCACGGGCGAGCTGCTGGTAGTGACGCGCCCAGCTCTGAGCCT
     AAAGGTACAGCAGACGGTCAAGACGGAGAAAGAGAAGTGCCCGCTCGACGACCATCACTGCGCGGGTCGAGACTCGGA
 36◀  E   M   D   D   A   L   E   A   E   K   E   E   R   A   L   Q   Q   Y   H   R   A   W   S   Q   A   E Gam
1873 CAAGACGATCCTGAATGTAATAAGCGTTCATGGCTGAACTCCTGAAATAGCTGTGAAAATATCGCCCGCGAAATGCCG
     GTTCTGCTAGGACTTACATTATTCGCAAGTACCGACTTGAGGACTTTATCGACACTTTTATAGCGGGCGCTTTACGGC
 10◀  L   R   D   Q   I   Y   Y   A   N   M   ═══════════════════════════════════

N -kil del
1951 GGCTGATTAGTAATCCGGAATCGCACTTACGGCCAATGCTTCGTTTCGTATCACACACCCCAAAGCCTTCTGCTTTGA
     CCGACTAATCATTAGGCCTTAGCGTGAATGCCGGTTACGAAGCAAAGCATAGTGTGTGGGGTTTCGGAAGACGAAACT
     ═══════════════════════════════════════════════════════════════════════════

2029 ATGCTGCCCTTCTTCAGGGCTTAATTTTTAAGAGCGTCACCTTCATGGTGGTCAGTGCGTCCTGCTGATGTGCTCAGT
     TACGACGGGAAGAAGTCCCGAATTAAAAATTCTCGCAGTGGAAGTACCACCAGTCACGCAGGACGACTACACGAGTCA

2107 ATCACCGCCAGTGGTATTTATGTCAACACCGCCAGAGATAATTTATCACCGCAGATGGTTATCTGTATGTTTTTTATA
     TAGTGGCGGTCACCATAAATACAGTTGTGGCGGTCTCTATTAAATAGTGGCGTCTACCAATAGACATACAAAAAATAT

2185 TGAATTTATTTTTTGCAGGGGGCATTGTTTGGTAGGTGAGAGATCTGAATTGCTATGTTTAGTGAGTTGTATCTATT
     ACTTAAATAAAAACGTCCCCCCGTAACAAACCATCCACTCTCTAGACTTAACGATACAAATCACTCAACATAGATAA

2263 TATTTTTCAATAAATACAATTGGTTATGTGTTTTGGGGGCGATCGTGAGGCAAAGAAAACCCGGCGCTGAGGCCGGGT
     ATAAAAGTTATTTATGTTAACCAATACACAAAACCCCGCTAGCACTCCGTTTCTTTTGGGCCGCGACTCCGGCCCA
                                                           ═══════════════════════ junction marker
2341 TAAGAGTTGGTAGCTCTTGATCCGGCAAACAAACCACCGCTGGTAGCGGTGGTTTTTTTGTTTGCAAGCAGCAGATTA
     ATTCTCAACCATCGAGAACTAGGCCGTTTGTTTGGTGGCGACCATCGCCACCAAAAAAACAAACGTTCGTCGTCTAAT
         ──────────────────────────────────▶

2419 CGCGCAGAAAAAAGGATCTCAAGAAGATCCTTTGATCTTTTCTACGGGGTCTGACGCTCAGTGGAACGAAAACTCAC
     GCGCGTCTTTTTTTCCTAGAGTTCTTCTAGGAAACTAGAAAAGATGCCCCAGACTGCGAGTCACCTTGCTTTTGAGTG

2497 GTTAAGGGATTTTGGTCATGAGATTATCAAAAAGGATCTTCACCTAGATCCTTTTAAATTAAAAATGAAGTTTTAAAT
     CAATTCCCTAAAACCAGTACTCTAATAGTTTTTCCTAGAAGTGGATCTAGGAAAATTTAATTTTTACTTCAAAATTTA

2575 CAATCTAAAGTATATATGAGTAAACTTGGTCTGACAGTTACCAATGCTTAATCAGTGAGGCACCTATCTCAGCGATCT
     GTTAGATTTCATATATACTCATTTGAACCAGACTGTCAATGGTTACGAATTAGTCACTCCGTGGATAGAGTCGCTAGA
                                                       286◀ W   H   K   I   L   S   A   G   I   E   A   I   Q

2653 GTCTATTTCGTTCATCCATAGTTGCCTGACTCCCCGTCGTGTAGATAACTACGATACGGGAGGGCTTACCATCTGGCC
     CAGATAAAGCAAGTAGGTATCAACGGACTGAGGGGCAGCACATCTATTGATGCTATGCCCTCCCGAATGGTAGACCGG
 273◀ R   N   R   E   D   M   T   A   Q   S   G   T   T   Y   I   V   V   I   R   S   P   K   G   D   P   G

2731 CCAGTGCTGCAATGATACCGCGAGACCCACGCTCACCGGCTCCAGATTTATCAGCAATAAACCAGCCAGCCGGAAGGG
     GGTCACGACGTTACTATGGCGCTCTGGGTGCGAGTGGCCGAGGTCTAAATAGTCGTTATTTGGTCGGTCGGCCTTCCC
 247◀ L   A   A   I   I   G   R   S   G   R   E   G   A   G   S   K   D   A   I   F   W   G   A   P   L   A
```

FIG. 4C

```
2809 CCGAGCGcagaagtggtcctgcaactTTATCCGCCTCCATCCAGTCTATTAATTGTTGCCGGGAAGCTAGAGTAAGTA
     GGCTCGCgtcttcaccaggacgttgaAATAGGCGGAGGTAGGTCAGATAATTAACAACGGCCCTTCGATCTCATTCAT
2214  S  R  L  L  P  G  A  V  K  D  A  E  M  W  D  I  L  Q  Q  R  S  A  L  T  L  L 2887 GTTCGCCAGTTAATAGTTTGCGCAACGTTGTTGCCATTGCTGCAGGCATCGTGGTGTCACGCTCGTCGTTTGGTATGG
     CAAGCGGTCAATTATCAAACGCGTTGCAACAACGGTAACGACGTCCGTAGCACCACAGTGCGAGCAGCAAACCATACC
1954  E  G  T  L  L  K  R  L  T  T  A  M  A  A  P  M  T  T  D  R  E  D  N  P  I  A 2965 CTTCATTCAGCTCCGGTTCCCAACGATCAAGGCGAGTTACATGATCCCCCATGTTGTGCAAAAAGCGGTTAGCTCCT
     GAAGTAAGTCGAGGCCAAGGGTTGCTAGTTCCGCTCAATGTACTAGGGGGTACAACACGTTTTTTCGCCAATCGAGGA
1694  E  N  L  E  P  E  W  R  D  L  R  T  V  H  D  G  M  N  H  L  F  A  T  L  E  K 3043 TCGGTCCTCCGATCGTTGTCAGAAGTAAGTTGGCCGCAGTGTTATCACTCATGGTTATGGCAGCACTGCATAATTCTC
     AGCCAGGAGGCTAGCAACAGTCTTCATTCAACCGGCGTCACAATAGTGAGTACCAATACCGTCGTGACGTATTAAGAG
1434  P  G  G  I  T  T  L  L  L  N  A  A  T  N  D  S  M  T  I  A  A  S  C  L  E  R 3121 TTACTGTCATGCCATCCGTAAGATGCTTTTCTGTGACTggtgagtactcaaccaagtcATTCTGAGAATAGTGTATGC
     AATGACAGTACGGTAGGCATTCTACGAAAAGACACTGAccactcatgagttggttcagTAAGACTCTTATCACATACG
1174  V  T  M  G  D  T  L  H  K  E  T  V  P  S  Y  E  V  L  D  N  Q  S  Y  H  I  R 3199 GGCGACCGAGTTGCTCTTGCCCGGCGTCAACACGGGATAATACCGCGCCACATAGCAGAACTTTAAAAGTGCTCATCA
     CCGCTGGCTCAACGAGAACGGGCCGCAGTTGTGCCCTATTATGGCGCGGTGTATCGTCTTGAAATTTTCACGAGTAGT
914   R  G  L  Q  E  Q  G  A  D  V  R  S  L  V  A  G  C  L  L  V  K  F  T  S  M  M 3277 TTGGAAAACGTTCTTCGGGGCGAAAACTCTCAAGGATCTTACCGCTGTTGAGATCCAGTTCGATGTAACCCACTCGTG
     AACCTTTTGCAAGAAGCCCCGCTTTTGAGAGTTCCTAGAATGGCGACAACTCTAGGTCAAGCTACATTGGGTGAGCAC
654   P  F  R  E  E  P  R  F  S  E  L  I  K  G  S  N  L  D  L  E  I  Y  G  V  R  A 3355 CACCCAACTGATCTTCAGCATCTTTTACTTTCACCAGCGTTTCTGGCTGAGCAAAAACAGGAAGGCAAAATGCCGCAA
     GTGGGTTGACTAGAAGTCGTAGAAAATGAAAGTGGTCGCAAAGACCGACTCGTTTTTGTCCTTCCGTTTTACGGCGTT
394   G  L  Q  D  E  A  D  K  V  K  V  L  T  E  P  H  A  F  V  P  L  C  F  A  A  F
                                                                        amp
3433 AAAAGGGAATAAGGGCGACACGGAAATGTTGAATACTCATACTCTTCCTTTTTCAATATTATTGAAGCATTTATCAGG
     TTTTCCCTTATTCCCGCTGTGCCTTTACAACTTATGAGTATGAGAAGGAAAAAGTTATAATAACTTCGTAAATAGTCC
134   F  P  I  L  A  V  R  F  H  Q  I  S  M
                                                          rexA'
3511 GTTATTGTCTCATGAGCCGATACATATTTGAATGAATTCAATCCATTTACTATGTTATGTTCTGAGGGGAGTGAAAAT
     CAATAACAGAGTACTCGCCTATGTATAAACTTACTTAAGTTAGGTAAATGATACAATACAAGACTCCCCTCACTTTTA
                                                          ◄─────────────────────

3589 TCCCCTAATTCGATGAAGATTCTTGCTCAATTGTTATCAGCTATGCGCCGACCAGAACACCTTGCCGATCAGCCAAAC
     AGGGGATTAAGCTACTTCTAAGAACGAGTTAACAATAGTCGATACGCGGCTGGTCTTGTGGAACGGCTAGTCGGTTTG
     ─────

3667 GTCTCTTCAGGCCACTGACTAGCGATAACTTTCCCCACAACGGAACAACTCTCATTGCATGGGATCATTGGGTACTGT
     CAGAGAAGTCCGGTGACTGATCGCTATTGAAAGGGGTGTTGCCTTGTTGAGAGTAACGTACCCTAGTAACCCATGACA

3745 GGGTTTAGTGGTTGTAAAAACACCTGACCGCTATCCCTGATCAGTTTCTTGAAGGTAAACTCATCACCCCCAACTCTG
     CCCAAATCACCAACATTTTTGTGGACTGGCGATAGGGACTAGTCAAAGAACTTCCATTTGAGTAGTGGGGGTTGAGAC
                                                                              HindIII
3823 GCTATGCAGAAATCACCTGGCTCAACAGCCTGCTCAGGGTCAACGAGAATTAACATTCCGTCAGGAAAGCTTGGCTTG
     CGATACGTCTTTAGTGGACCGAGTTGTCGGACGAGTCCCAGTTGCTCTTAATTGTAAGGCAGTCCTTTCGAACCGAAC
```

FIG. 4D

```
3901 GAGCCTGTTGGTGCGGTCATGGAATTACCTTCAACCTCAAGCCAGAATGCAGAATCACTGGCTTTTTTGGTTGTGCTT
     CTCGGACAACCACGCCAGTACCTTAATGGAAGTTGGAGTTCGGTCTTACGTCTTAGTGACCGAAAAAACCAACACGAA

HindIII
3979 ACCCATCTCTCCGCATCACCTTTGGTAAAGGTTCTAAGCTTAGGTGAGAACATCCCTGCCTGAACATGAGAAAAAACA
     TGGGTAGAGAGGCGTAGTGGAAACCATTTCCAAGATTCGAATCCACTCTTGTAGGGACGGACTTGTACTCTTTTTTGT 4057 GGGTACTCATACTCACTTCTAAGTGACGGCTGCATACTAACCGCTTCATACATCTCGTAGATTTCTCTGGCGATTGAA
     CCCATGAGTATGAGTGAAGATTCACTGCCGACGTATGATTGGCGAAGTATGTAGAGCATCTAAAGAGACCGCTAACTT NsiI
4135 GGGCTAAATTCTTCAACGCTAACTTTGAGAATTTTTGTAAGCAATGCGGCGTTATAAGCATTTAATGCATTGATGCCA
     CCCGATTTAAGAAGTTGCGATTGAAACTCTTAAAAACATTCGTTACGCCGCAATATTCGTAAATTACGTAACTACGGT 4213 TTAAATAAAGCACCAACGCCTGACTGCCCCATCCCCATCTTGTCTGCGACAGATTCCTGGGATAAGCCAAGTTCATTT
     AATTTATTTCGTGGTTGCGGACTGACGGGGTAGGGGTAGAACAGACGCTGTCTAAGGACCCTATTCGGTTCAAGTAAA 4291 TTCTTTTTTTCATAAATTGCTTTAAGGCGACGTGCGTCCTCAAGCTGCTCTTGTGTTAATGGTTTCTTTTTTGTGCTC
     AAGAAAAAAAGTATTTAACGAAATTCCGCTGCACGCAGGAGTTCGACGAGAACACAATTACCAAAGAAAAAACACGAG cI
4369 ATACGTTAAATCTATCACCGCAAGGGATAAATATCTAACACCGTGCGTGTTGACTATTTTACCTCTGGCGGTGATAAT
     TATGCAATTTAGATAGTGGCGTTCCCTATTTATAGATTGTGGCACGCACAACTGATAAAATGGAGACCGCCACTATTA cro'                        PvuII
4447 GGTTGCATGTACTAAGGAGGTTGTATGGAACAACGAGATGTGTATAAGAGACAGCTGGCGCTCTTCCGCTTCCTCGCT
     CCAACGTACATGATTCCTCCAACATACCTTGTTGCTCTACACATATTCTCTGTCGACCGCGAGAAGGCGAAGGAGCGA
     ═══════════════════════════════════════════════════════════════════════════════▶

4525 CACTGACTCGCTGCGCTCGGTCGTTCGGCTGCGGCGAGCGGTATCAGCTCACTCAAAGGCGGTAATACGGTTATCCAC
     GTGACTGAGCGACGCGAGCCAGCAAGCCGACGCCGCTCGCCATAGTCGAGTGAGTTTCCGCCATTATGCCAATAGGTG

4603 AGAATCAGGGGATAACGCAGGAAAGAACATGTGAGCAAAAGGCCAGCAAAAGGCCAGGAACCGTAAAAAGGCCGCGTT
     TCTTAGTCCCCTATTGCGTCCTTTCTTGTACACTCGTTTTCCGGTCGTTTTCCGGTCCTTGGCATTTTTCCGGCGCAA

4681 GCTGGCGTTTTTCCATAGGCTCCGCCCCCCTGACGAGCATCACAAAAATCGACGCTCAAGTCAGAGGTGGCGAAACCC
     CGACCGCAAAAAGGTATCCGAGGCGGGGGGACTGCTCGTAGTGTTTTTAGCTGCGAGTTCAGTCTCCACCGCTTTGGG

4759 GACAGGACTATAAAGATACCAGGCGTTTCCCCCTGGAAGCTCCCTCGTGCGCTCTCCTGTTCCGACCCTGCCGCTTAC
     CTGTCCTGATATTTCTATGGTCCGCAAAGGGGGACCTTCGAGGGAGCACGCGAGAGGACAAGGCTGGGACGGCGAATG

4837 CGGATACCTGTCCGCCTTTCTCCCTTCGGGAAGCGTGGCGCTTTCTCATAGCTCACGCTGTAGGTATCTCAGTTCGGT
     GCCTATGGACAGGCGGAAAGAGGGAAGCCCTTCGCACCGCGAAAGAGTATCGAGTGCGACATCCATAGAGTCAAGCCA

4915 GTAGGTCGTTCGCTCCAAGCTGGGCTGTGTGCACGAACCCCCCGTTCAGCCCGACCGCTGCGCCTTATCCGGTAACTA
     CATCCAGCAAGCGAGGTTCGACCCGACACACGTGCTTGGGGGGCAAGTCGGGCTGGCGACGCGGAATAGGCCATTGAT

4993 TCGTCTTGAGTCCAACCCGGTAAGACACGACTTATCGCCACTGGCAGCAGCCACTGGTAACAGGATTAGCAGAGCGAG
     AGCAGAACTCAGGTTGGGCCATTCTGTGCTGAATAGCGGTGACCGTCGTCGGTGACCATTGTCCTAATCGTCTCGCTC

5071 GTATGTAGGCGGTGCTACAGAGTTCTTGAAGTGGTGGCCTAACTACGGCTACACTAGAAGGACAGTATTTGGTATCTG
     CATACATCCGCCACGATGTCTCAAGAACTTCACCACCGGATTGATGCCGATGTGATCTTCCTGTCATAAACCATAGAC

5149 CGCTCTGCTGAAGCCAGTTACCTTCGGAAAAAGAGTTGGTAGCTCTTGATCCGGCAAACAAACCACCGCTGGTAGCGG
     GCGAGACGACTTCGGTCAATGGAAGCCTTTTTCTCAACCATCGAGAACTAGGCCGTTTGTTTGGTGGCGACCATCGCC
```

FIG. 4E

```
       PvuII    Tn5 site         tL3
  1  CAGCTGTCTCTTATACACATCTCCGCTGTGCTTTCAGTGGATTTCGGATAACAGAAAGGCCGGGAAATACCCAGCCTCG
     GTCGACAGAGAATATGTGTAGAGGCGACACGAAAGTCACCTAAAGCCTATTGTCTTTCCGGCCCTTTATGGGTCGGAGC 80  CTTTGTAACGGAGTAGACGAAAGTGATTGCGCCTACCCGGATATTATCGTGAGGATGCGTCATCGCCATTGCTCCCCAA
     GAAACATTGCCTCATCTGCTTTCACTAACGCGGATGGGCCTATAATAGCACTCCTACGCAGTAGCGGTAACGAGGGGTT

226▸ R  W  Q  E  G  F

159  ATACAAAACCAATTTCAGCCAGTGCCTCGTCCATTTTTTCGATGAACTCCGGCACGATCTCGTCAAAACTCGCCATGTA
     TATGTTTTGGTTAAAGTCGGTCACGGAGCAGGTAAAAAAGCTACTTGAGGCCGTGCTAGAGCAGTTTTGAGCGGTACAT

220▸  V  F  G  I  E  A  L  A  E  D  M  K  E  I  F  E  P  V  I  E  D  F  S  A  M  Y

StuI
238  CTTTTCATCCGCTCAATCACGACATAATGCAGGCCTTCACGCTTCATACGCGGGTCATAGTTGGCAAAGTACCAGGCA
     GAAAAGTAGGGCGAGTTAGTGCTGTATTACGTCCGGAAGTGCGAAGTATGCGCCCAGTATCAACCGTTTCATGGTCCGT

194▸ K  E  D  R  E  I  V  V  Y  H  L  G  E  R  K  M  R  P  D  Y  N  A  F  Y  W  A

317  TTTTTTCGCGTCACCCACATGCTGTACTGCACCTGGGCCATGTAAGCTGACTTTATGGCCTCGAAACCACCGAGCCGGA
     AAAAAAGCGCAGTGGGTGTACGACATGACGTGGACCCGGTACATTCGACTGAAATACCGGAGCTTTGGTGGCTCGGCCT

167▸N  K  R  T  V  W  M  S  Y  Q  V  Q  A  M  Y  A  S  K  I  A  E  F  G  G  L  R  F

SmaI
396  ACTTCATGAAATCCCGGGAGGTAAACGGGCATTTCAGTTCAAGGCCGTTGCCGTCACTGCATAAACCATCGGGAGAGCA
     TGAAGTACTTTAGGGCCCTCCATTTGCCCGTAAAGTCAAGTTCCGGCAACGGCAGTGACGTATTTGGTAGCCCTCTCGT

141▸ K  M  F  D  R  S  T  F  P  C  K  L  E  L  G  N  G  D  S  C  L  G  D  P  S  C

475  GGCGGTACGCATACTTTCGTCGCGATAGATGATCGGGGATTCAGTAACATTCACGCCGGAAGTGAAcTCAAACAGGGTT
     CCGCCATGCGTATGAAAGCAGCGCTATCTACTAGCCCCTAAGTCATTGTAAGTGCGGCCTTCACTTgAGTTTGTCCCAA

115▸ A  T  R  M  S  E  D  R  Y  I  I  P  S  E  T  V  N  V  G  S  T  F  E  F  L  T

554  CTGGCGTCGTTCTCGTACTGTTTTCCCCAGGCCAGTGCTTTAGCGTTAACTTCCGGAGCCACACCGGTGCAAACCTCAG
     GACCGCAGCAAGAGCATGACAAAAGGGGTCCGGTCACGAAATCGCAATTGAAGGCCTCGGTGTGGCCACGTTTGGAGTC

88▸R  A  D  N  E  Y  Q  K  G  W  A  L  A  K  A  N  V  E  P  A  V  G  T  C  V  E  A

633  CAAGCAGGGTGTGGAAGTAGGACATTTTCATGTCAGGCCACTTCTTTCCGGAGCGGGGTTTTGCTATCACGTTGTGAAC
     GTTCGTCCCACACCTTCATCCTGTAAAAGTACAGTCCGGTGAAGAAAGGCCTCGCCCCAAAACGATAGTGCAACACTTG

62▸ L  L  T  H  F  Y  S  M  K  M  D  P  W  K  K  G  S  R  P  K  A  I  V  N  H  V

712  TTCTGAAGCGGTGATGACGCCGAGCCGTAATTTGTGCCACGCATCATCCCCCTGTTCGACAGCTCTCACATCGATCCCG
     AAGACTTCGCCACTACTGCGGCTCGGCATTAAACACGGTGCGTAGTAGGGGGACAAGCTGTCGAGAGTGTAGCTAGGGC

36▸ E  S  A  T  I  V  G  L  R  L  K  H  W  A  D  D  G  Q  E  V  A  R  V  D  I  G

PstI                   Exo
791  GTACGCTGCAGGATAATGTCCGGTGTCATGCTGCCACCTTCTGCTCTGCGGCTTTCTGTTTCAGGAATCCAAGAGCTTT
     CATGCGACGTCCTATTACAGGCCACAGTACGACGGTGGAAGACGAGACGCCGAAAGACAAAGTCCTTAGGTTCTCGAAA
                                  261▸ A  A  V  K  Q  E  A  A  K  Q  K  L  F  G  L  A  K
      9▸T R Q L I I D P T M
```

```
 870 TACTGCTTCGGCCTGTGTCAGTTCTGACGATGCACGAATGTCGCGGCGAAATATCTGGGAACAGAGCGGCAATAAGTCG
     ATGACGAAGCCGGACACAGTCAAGACTGCTACGTGCTTACAGCGCCGCTTTATAGACCCTTGTCTCGCCGTTATTCAGC
244◄ V  A  E  A  Q  T  L  E  S  S  A  R  I  D  R  R  F  I  Q  S  C  L  P  L  L  D

949 TCATCCCATGTTTTATCCAGGGCGATCAGCAGAGTGTTAATCTCCTGCATGGTTTCATCGTTAACCGGAGTGATGTCGC
     AGTAGGGTACAAAATAGGTCCCGCTAGTCGTCTCACAATTAGAGGACGTACCAAAGTAGCAATTGGCCTCACTACAGCG
217◄D  D  W  T  K  D  L  A  I  L  L  T  N  I  E  Q  M  T  E  D  N  V  P  T  I  D  R

PstI
1028 GTTCCGGCTGACGTTCTGCAGTGTATGCAGTATTTTCGACAATGCGCTCGGCTTCATCCTTGTCATAGATACCAGCAAA
     CAAGGCCGACTGCAAGACGTCACATACGTCATAAAAGCTGTTACGCGAGCCGAAGTAGGAACAGTATCTATGGTCGTTT
191◄ E  P  Q  R  E  A  T  Y  /  T  N  E  V  I  R  E  A  E  D  K  D  Y  I  G  A  F

BglI
1107 TCCGAAGGCCAGACGGGCACACTGAATCATGGCTTTATGACGTAACATCCGTTTGGGATGCGACTGCCACGGCCCCGTG
     AGGCTTCCGGTCTGCCCGTGTGACTTAGTACCGAAATACTGCATTGTAGGCAAACCCTACGCTGACGGTGCCGGGGCAC
165◄ G  F  A  L  R  A  C  Q  I  M  A  K  H  R  L  M  R  K  P  H  S  Q  W  P  G  T

1186 ATTTCTCTGCCTTCGCGAGTTTTGAATGGTTCGCGGCGGCATTCATCCATCCATTCGGTAACGCAGATCGGATGATTAC
     TAAAGAGACGGAAGCGCTCAAAACTTACCAAGCGCCGCCGTAAGTAGGTAGGTAAGCCATTGCGTCTAGCCTACTAATG
138◄I  E  R  G  E  R  T  K  F  P  E  R  R  C  E  D  M  W  E  T  V  C  I  P  H  N  R

1265 GGTCCTTGCGGTAAATCCGGCATGTACAGGATTCATTGTCCTGCTCAAAGTCCATGCCATCAAACTGCTGGTTTTCATT
     CCAGGAACGCCATTTAGGCCGTACATGTCCTAAGTAACAGGACGAGTTTCAGGTACGGTAGTTTGACGACCAAAAGTAA
112◄ D  K  R  Y  I  R  C  T  C  S  E  N  D  Q  E  F  D  M  G  D  F  Q  Q  N  E  N

1344 GATGATGCGGGACCAGCCATCAACGCCCACCACCGGAACGATGCCATTCTGCTTATCAGGAAAGGCGTAAATTTCTTTC
     CTACTACGCCCTGGTCGGTAGTTGCGGGTGGTGGCCTTGCTACGGTAAGACGAATAGTCCTTTCCGCATTTAAAGAAAG
 86◄ I  I  R  S  W  G  D  V  G  V  V  P  V  I  G  N  Q  K  D  P  F  A  Y  I  E  K

1423 GTCCACGGATTAAGGCCGTACTGGTTGGCAACGATCAGTAATGCGATGAACTGCGCATCGCTGGCATCACCTTTAAATG
     CAGGTGCCTAATTCCGGCATGACCAACCGTTGCTAGTCATTACGCTACTTGACGCGTAGCGACCGTAGTGGAAATTTAC
 59◄T  W  P  N  L  G  Y  Q  N  A  V  I  L  L  A  I  F  Q  A  D  S  A  D  G  K  F  A

SalI
1502 CCGTCTGGCGAAGAGTGGTGATCAGTTCCTGTGGGTCGACAGAATCCATGCCGACACGTTCAGCCAGCTTCCCAGCCAG
     GGCAGACCGCTTCTCACCACTAGTCAAGGACACCCAGCTGTCTTAGGTACGGCTGTGCAAGTCGGTCGAAGGGTCGGTC
 33◄ T  Q  R  L  T  T  I  L  E  Q  P  D  V  S  D  M  G  V  R  E  A  L  K  G  A  L

Bet
1581 CGTTGCGAGTGCAGTACTCATTCGTTTTATACCTCTGAATCAATATCAACCTGGTGGTGAGCAATGGTTTCAACCATGT
     GCAACGCTCACGTCATGAGTAAGCAAAATATGGAGACTTAGTTATAGTTGGACCACCACTCGTTACCAAAGTTGGTACA
  7◄ T  A  L  A  T  S  M        98◄V  E  S  D  I  D  V  Q  H  H  A  I  T  E  V  M  Y

1660 ACCGGATGTGTTCTGCCATGCGCTCCTGAAACTCAACATCGTCATCAAACGCACGGGTAATGGATTTTTTGCTGGCCCC
     TGGCCTACACAAGACGGTACGCGAGGACTTTGAGTTGTAGCAGTAGTTTGCGTGCCCATTACCTAAAAAACGACCGGGG
 81◄ R  I  H  E  A  M  R  E  Q  F  E  V  D  D  D  F  A  R  T  I  S  K  K  S  A  G

StuI
1739 GTGGCGTTGCAAATGATCGATGCATAGCGATTCAAACAGGTGCTGGGGCAGGCCTTTTTCCATGTCGTCTGCCAGTTCT
     CACCGCAACGTTTACTAGCTACGTATCGCTAAGTTTGTCCACGACCCCGTCCGGAAAAAGGTACAGCAGACGGTCAAGA
 55◄ H  R  Q  L  H  D  I  C  L  S  E  F  L  H  Q  P  L  G  K  E  M  D  D  A  L  E

1818 GCCTCTTTCTCTTCACGGGCGAGCTGCTGGTAGTGACGCGCCCAGCTCTGAGCCTCAAGACGATCCTGAATGTAATAAG
     CGGAGAAAGAGAAGTGCCCGCTCGACGACCATCACTGCGCGGGTCGAGACTCGGAGTTCTGCTAGGACTTACATTATTC
 28◄A  E  K  E  E  R  A  L  Q  Q  Y  H  R  A  W  S  Q  A  E  L  R  D  Q  I  Y  Y  A
```

```
                        Gam                                                           N-kil del
1897 CGTTCATGGCTGAACTCCTGAAATAGCTGTGAAAATATCGCCCGCGAAATGCCGGGCTGATTAGTAATCCGGAATCGCA
     GCAAGTACCGACTTGAGGACTTTATCGACACTTTTATAGCGGGCGCTTTACGGCCCGACTAATCATTAGGCCTTAGCGT
      2◀ N  M 1976 CTTACGGCCAATGCTTCGTTTCGTATCACACACCCCAAAGCCTTCTGCTTTGAATGCTGCCCTTCTTCAGGGCTTAATT
     GAATGCCGGTTACGAAGCAAAGCATAGTGTGTGGGGTTTCGGAAGACGAAACTTACGACGGGAAGAAGTCCCGAATTAA 2055 TTTAAGAGCGTCACCTTCATGGTGGTCAGTGCGTCCTGCTGATGTGCTCAGTATCACCGCCAGTGGTATTTATGTCAAC
     AAATTCTCGCAGTGGAAGTACCACCAGTCACGCAGGACGACTACACGAGTCATAGTGGCGGTCACCATAAATACAGTTG 2134 ACCGCCAGAGATAATTTATCACCGCAGATGGTTATCTGTATGTTTTTTATATGAATTTATTTTTTGCAGGGGGGCATTG
     TGGCGGTCTCTATTAAATAGTGGCGTCTACCAATAGACATACAAAAAATATACTTAAATAAAAAACGTCCCCCCGTAAC 2213 TTTGGTAGGTGAGAGATCTGAATTGCTATGTTTAGTGAGTTGTATCTATTTATTTTTCAATAAATACAATTGGTTATGT
     AAACCATCCACTCTCTAGACTTAACGATACAAATCACTCAACATAGATAAATAAAAAGTTATTTATGTTAACCAATACA 2292 GTTTTGGGGGCGATCGTGAGGCAAAGAAAACCCGGCGCTGAGGCCGGGTTACGCCCCGCCCTGCCACTCATCGCAGTAC
     CAAAACCCCCGCTAGCACTCCGTTTCTTTTGGGCCGCGACTCCGGCCCAATGCGGGGCGGGACGGTGAGTAGCGTCATG
                                                  219◀ A  G  G  Q  W  E  D  C  Y 2371 TGTTGTAATTCATTAAGCATTCTGCCGACATGGAAGCCATCACAGACGGCATGATGAACCTGAATCGCCAGCGGCATCA
     ACAACATTAAGTAATTCGTAAGACGGCTGTACCTTCGGTAGTGTCTGCCGTACTACTTGGACTTAGCGGTCGCCGTAGT
     209◀Q  Q  L  E  N  L  M  R  G  V  H  F  G  D  C  V  A  H  H  V  Q  I  A  L  P  M  L
                       NcoI
2450 GCACCTTGTCGCCTTGCGTATAATATTTGCCCATGGTGAAAACGGGGGCGAAGAAGTTGTCCATATTGGCCACGTTTAA
     CGTGGAACAGCGGAACGCATATTATAAACGGGTACCACTTTTGCCCCCGCTTCTTCAACAGGTATAACCGGTGCAAATT
     183◀ V  K  D  G  Q  T  Y  Y  K  G  M  T  F  V  P  A  F  F  N  D  M  N  A  V  N  L 2529 ATCAAAACTGGTGAAACTCACCCAGGGATTGGCTGAGACGAAAAACATATTCTCAATAAACCCTTTAGGGAAATAGGCC
     TAGTTTTGACCACTTTGAGTGGGTCCCTAACCGACTCTGCTTTTTGTATAAGAGTTATTTGGGAAATCCCTTTATCCGG
     157◀ D  F  S  T  F  S  V  W  P  N  A  S  V  F  F  M  N  E  I  F  G  K  P  F  Y  A 2608 AGGTTTTCACCGTAACACGCCACATCTTGCGAATATATGTGTAGAAACTGCCGGAAATCGTCGTGGTATTCACTCCAGA
     TCCAAAAGTGGCATTGTGCGGTGTAGAACGCTTATATACACATCTTTGACGGCCTTTAGCAGCACCATAAGTGAGGTCT
     130◀L  N  E  G  Y  C  A  V  D  Q  S  Y  I  H  L  F  Q  R  F  D  D  H  Y  E  S  W  L 2687 GCGATGAAAACGTTTCAGTTTGCTCATGGAAAACGGTGTAACAAGGGTGAACACTATCCATATCACCAGCTCACCGTC
     CGCTACTTTTGCAAAGTCAAACGAGTACCTTTTGCCACATTGTTCCCACTTGTGATAGGGTATAGTGGTCGAGTGGCAG
     104◀ S  S  F  T  E  T  Q  E  H  F  V  T  Y  C  P  H  V  S  D  W  I  V  L  E  G  D
              EcoRI
2766 TTTCATTGCCATACGGAATTCCGGATGAGCATTCATCAGGCGGGCAAGAATGTGAATAAAGGCCGGATAAAACTTGTGC
     AAAGTAACGGTATGCCTTAAGGCCTACTCGTAAGTAGTCCGCCCGTTCTTACACTTATTTCCGGCCTATTTTGAACACG
     78◀ K  M  A  M  R  F  E  P  H  A  N  M  L  R  A  L  I  H  I  F  A  P  Y  F  K  H
              PvuII
2845 TTATTTTTCTTTACGGTCTTTAAAAAGGCCGTAATATCCAGCTGAACGGTCTGGTTATAGGTACATTGAGCAACTGACT
     AATAAAAAGAAATGCCAGAAATTTTTCCGGCATTATAGGTCGACTTGCCAGACCAATATCCATGTAACTCGTTGACTGA
     51◀K  N  K  K  V  T  K  L  F  A  T  I  D  L  Q  V  T  Q  N  Y  T  C  Q  A  V  S  Q
```

```
                                                                                    rexA'
                                                                                     cat
2924 GAAATGCCTCAAAATGTTCTTTACGATGCCATTGGGATATATCAACGGTGGTATATCCAGTGATTTTTTTCTCCATAAT
     CTTTACGGAGTTTTACAAGAAATGCTACGGTAACCCTATATAGTTGCCACCATATAGGTCACTAAAAAAAGAGGTATTA
  254 F  A  E  F  H  E  K  R  H  W  Q  S  I  D  V  T  T  Y  G  T  I  K  K  E  M
                                                                         ←

3003 TCAATCCATTTACTATGTTATGTTCTGAGGGGAGTGAAAATTCCCCTAATTCGATGAAGATTCTTGCTCAATTGTTATC
     AGTTAGGTAAATGATACAATACAAGACTCCCCTCACTTTTAAGGGGATTAAGCTACTTCTAAGAACGAGTTAACAATAG
     _____

3082 AGCTATGCGCCGACCAGAACACCTTGCCGATCAGCCAAACGTCTCTTCAGGCCACTGACTAGCGATAACTTTCCCCACA
     TCGATACGCGGCTGGTCTTGTGGAACGGCTAGTCGGTTTGCAGAGAAGTCCGGTGACTGATCGCTATTGAAAGGGGTGT
  237 G  F  T  E  E  P  W  Q  S  A  I  V  K  G  V

3161 ACGGAACAACTCTCATTGCATGGGATCATTGGGTACTGTGGGTTTAGTGGTTGTAAAAACACCTGACCGCTATCCCTGA
     TGCCTTGTTGAGAGTAACGTACCCTAGTAACCCATGACACCCAAATCACCAACATTTTTGTGGACTGGCGATAGGGACT
  221 V  S  C  S  E  N  C  P  I  M  P  Y  Q  P  N  L  P  Q  L  F  V  Q  G  S  D  R  I

3240 TCAGTTTCTTGAAGGTAAACTCATCACCCCCAAGTCTGGCTATGCAGAAATCACCTGGCTCAACAGCCTGCTCAGGGTC
     AGTCAAAGAACTTCCATTTGAGTAGTGGGGGTTCAGACCGATACGTCTTTAGTGGACCGAGTTGTCGGACGAGTCCCAG
  195 L  K  K  F  T  F  E  D  G  G  L  R  A  I  C  F  D  G  P  E  V  A  Q  E  P  D
                                                          HindIII
3319 AACGAGAATTAACATTCCGTCAGGAAAGCTTGGCTTGGAGCCTGTTGGTGCGGTCATGGAATTACCTTCAACCTCAAGC
     TTGCTCTTAATTGTAAGGCAGTCCTTTCGAACCGAACCTCGGACAACCACGCCAGTACCTTAATGGAAGTTGGAGTTCG
  169 V  L  I  L  M  G  D  P  F  S  P  K  S  G  T  P  A  T  M  S  N  G  E  V  E  L
                                                                                HindIII
3398 CAGAATGCAGAATCACTGGCTTTTTTGGTTGTGCTTACCCATCTCTCCGCATCACCTTTGGTAAAGGTTCTAAGCTTAG
     GTCTTACGTCTTAGTGACCGAAAAAACCAACACGAATGGGTAGAGAGGCGTAGTGGAAACCATTTCCAAGATTCGAATC
  142 W  F  A  S  D  S  A  K  K  T  T  S  V  W  R  E  A  D  G  K  T  F  T  R  L  K  P 3477 GTGAGAACATCCCTGCCTGAACATGAGAAAAAACAGGGTACTCATACTCACTTCTAAGTGACGGCTGCATACTAACCGC
     CACTCTTGTAGGGACGGACTTGTACTCTTTTTTGTCCCATGAGTATGAGTGAAGATTCACTGCCGACGTATGATTGGCG
  116 S  F  M  G  A  Q  V  H  S  F  V  P  Y  E  Y  E  S  R  L  S  P  Q  M  S  V  A 3556 TTCATACATCTCGTAGATTTCTCTGGCGATTGAAGGGCTAAATTCTTCAACGCTAACTTTGAGAATTTTTGTAAGCAAT
     AAGTATGTAGAGCATCTAAAGAGACCGCTAACTTCCCGATTTAAGAAGTTGCGATTGAAACTCTTAAAAACATTCGTTA
   90 E  Y  M  E  Y  I  E  R  A  I  S  P  S  F  E  E  V  S  V  K  L  I  K  T  L  L 3635 GCGGCGTTATAAGCATTTAATGCATTGATGCCATTAAATAAAGCACCAACGCCTGACTGCCCCATCCCCATCTTGTCTG
     CGCCGCAATATTCGTAAATTACGTAACTACGGTAATTTATTTCGTGGTTGCGGACTGACGGGGTAGGGGTAGAACAGAC
   63 A  A  N  Y  A  N  L  A  N  I  G  N  F  L  A  G  V  G  S  Q  G  M  G  M  K  D  A 3714 CGACAGATTCCTGGGATAAGCCAAGTTCATTTTTCTTTTTTTCATAAATTGCTTTAAGGCGACGTGCGTCCTCAAGCTG
     GCTGTCTAAGGACCCTATTCGGTTCAAGTAAAAAGAAAAAAAGTATTTAACGAAATTCCGCTGCACGCAGGAGTTCGAC
   37 V  S  E  Q  S  L  G  L  E  N  K  K  K  E  Y  I  A  K  L  R  R  A  D  E  L  Q
                                            cl 857
3793 CTCTTGTGTTAATGGTTTCTTTTTTGTGCTCATACGTTAAATCTATCACCGCAAGGGATAAATATCTAACACCGTGCGT
     GAGAACACAATTACCAAAGAAAAAACACGAGTATGCAATTTAGATAGTGGCGTTCCCTATTTATAGATTGTGGCACGCA
   11 E  Q  T  L  P  K  K  K  T  S  M
```

```
                                                                    cro'
3872 GTTGACTATTTTACCTCTGGCGGTGATAATGGTTGCATGTACTAAGGAGGTTGTATGGAACAACGAGATGTGTATAAGA
     CAACTGATAAAATGGAGACCGCCACTATTACCAACGTACATGATTCCTCCAACATACCTTGTTGCTCTACACATATTCT PvuII
3951 GACAGCTGACGGGTTTTGCTGCCCGCAAACGGGCTGTTCTGGTGTTGCTAGTTTGTTATCAGAATCGCAGATCCGGCTT
     CTGTCGACTGCCCAAAACGACGGGCGTTTGCCCGACAAGACCACAACGATCAAACAATAGTCTTAGCGTCTAGGCCGAA 4030 CAGGTTTGCCGGCTGAAAGCGCTATTTCTTCCAGAATTGCCATGATTTTTTCCCCACGGGAGGCGTCACTGGCTCCCGT
     GTCCAAACGGCCGACTTTCGCGATAAAGAAGGTCTTAACGGTACTAAAAAAGGGGTGCCCTCCGCAGTGACCGAGGGCA
                      137◄ K K W F Q W S K K G V P P T V P E R 4109 GTTGTCGGCAGCTTTGATTCGATAAGCAGCATCGCCTGTTTCAGGCTGTCTATGTGTGACTGTTGAGCTGTAACAAGTT
     CAACAGCCGTCGAAACTAAGCTATTCGTCGTAGCGGACAAAGTCCGACAGATACACACTGACAACTCGACATTGTTCAA
     118◄ T T P L K S E I L L M A Q K L S D I H S Q Q A T V L Q 4188 GTCTCAGGTGTTCAATTTCATGTTCTAGTTGCTTTGTTTACTGGTTTCACCTGTTCTATTAGGTGTTACATGCTGTTC
     CAGAGTCCACAAGTTAAAGTACAAGATCAACGAAACAAAATGACCAAAGTCGACAAGATAATCCACAATGTACGACAAG
     92◄ R L H E I E H E L Q K T K S T E G T R N P T V H Q E 4267 ATCTGTTACATTGTCGATCTGTTCATGGTGAACAGCTTTGAATGCACCAAAAACTCGTAAAAGCTCTGATGTATCTATC
     TAGACAATGTAACAGCTAGACAAGTACCACTTGTCGAAACTTACGTGGTTTTTGAGCATTTTCGAGACTACATAGATAG
     66◄ D T V N D I Q E H H V A K F A G F V R L L E S T D I 4346 TTTTTTACACCGTTTTCATCTGTGCATATGGACAGTTTTCCCTTTGATATGTAACGGTGAACAGTTGTTCTACTTTTGT
     AAAAAATGTGGCAAAAGTAGACACGTATACCTGTCAAAAGGGAAACTATACATTGCCACTTGTCAACAAGATGAAAACA
     39◄ K K V G N E D T C I S L K G K S I Y R H V T T R S K N 4425 TTCTTAGTCTTGATGCTTCACTGATAGATACAAGAGCCATAAGAACCTCAGATCCTTCCGTATTTAGCCAGTATGTTCT
     AAGAATCAGAACTACGAAGTGACTATCTATGTTCTCGGTATTCTTGGAGTCTAGGAAGGCATAAATCGGTCATACAAGA
     13◄ T L R S A E S I S V L A M     316◄ I R G Y F A L I N E 4504 CTAGTGTGGTTCGTTGTTTTTGCGTGAGCCATGAGAACGAACCATTGAGATCATACTTACTTTGCATGTCACTCAAAAA
     GATCACACCAAGCAACAAAAACGCACTCGGTACTCTTGCTTGGTAACTCTAGTATGAATGAAACGTACAGTGAGTTTTT
     390◄ L T T R Q K Q T L W S F S G N L D Y K S Q M D S L F 4583 TTTTGCCTCAAAACTGGTGAGCTGAATTTTTGCAGTTAAAGCATCGTGTAGTGTTTTCTTAGTCCGTTATGTAGGTAG
     AAAACGGAGTTTTGACCACTCGACTTAAAAACGTCAATTTCGTAGCACATCACAAAAAGAATCAGGCAATACATCCATC
     280◄ K A E F S T L Q I K A T L A D H L T K R L G N H L Y 4662 GAATCTGATGTAATGGTTGTTGGTATTTTGTCACCATTCATTTTTATCTGGTTGTTCTCAAGTTCGGTTACGAGATCCA
     CTTAGACTACATTACCAACAACCATAAAACAGTGGTAAGTAAAAATAGACCAACAAGAGTTCAAGCCAATGCTCTAGGT
     253◄ S D S T I T T P I K D G N M K I Q N N E L E T V L D M 4741 TTTGTCTATCTAGTTCAACTTGGAAAATCAACGTATCAGTCGGGCGGCCTCGCTTATCAACCACCAATTTCATATTGCT
     AAACAGATAGATCAAGTTGAACCTTTTAGTTGCATAGTCAGCCCGCCGGAGCGAATAGTTGGTGGTTAAAGTATAACGA
     227◄ Q R D L E V Q F I L T D P R G R K D V V L K M N S 4820 GTAAGTGTTTAAATCTTTACTTATTGGTTTCAAAACCCATTGGTTAAGCCTTTTAAACTCATGGTAGTTATTTTCAAGC
     CATTCACAAATTTAGAAATGAATAACCAAAGTTTTGGGTAACCAATTCGGAAAATTTGAGTACCATCAATAAAAGTTCG
     201◄ Y T N L D K S I P K L V W Q N L R K F E H Y N N E L 4899 ATTAACATGAACTTAAATTCATCAAGGCTAATCTCTATATTTGCCTTGTGAGTTTTCTTTTGTGTTAGTTCTTTTAATA
     TAATTGTACTTGAATTTAAGTAGTTCCGATTAGAGATATAAACGGAACACTCAAAAGAAAACACAATCAAGAAAATTAT
     174◄ M L M F K F E D L S I E I N A K H T K E Q T L E K L L
```

```
4978 ACCACTCATAAATCCTCATAGAGTATTTGTTTTCAAAAGACTTAACATGTTCCAGATTATATTTTATGAATTTTTTTAA
     TGGTGAGTATTTAGGAGTATCTCATAAACAAAAGTTTTCTGAATTGTACAAGGTCTAATATAAAATACTTAAAAAAATT
 148◄ W  E  Y  I  R  M  S  Y  K  N  E  F  S  K  V  H  E  L  N  Y  K  I  F  K  K  L

5057 CTGGAAAAGATAAGGCAATATCTCTTCACTAAAAACTAATTCTAATTTTTCGCTTGAGAACTTGGCATAGTTTGTCCAC
     GACCTTTTCTATTCCGTTATAGAGAAGTGATTTTTGATTAAGATTAAAAAGCGAACTCTTGAACCGTATCAAACAGGTG
 122◄ Q  F  L  Y  P  L  I  E  E  S  F  V  L  E  L  K  E  S  S  F  K  A  Y  N  T  W

5136 TGGAAAATCTCAAAGCCTTTAACCAAAGGATTCCTGATTTCCACAGTTCTCGTCATCAGCTCTCTGGTTGCTTTAGCTA
     ACCTTTTAGAGTTTCGGAAATTGGTTTCCTAAGGACTAAAGGTGTCAAGAGCAGTAGTCGAGAGACCAACGAAATCGAT
  95◄Q  F  I  E  F  G  K  V  L  P  N  R  I  C  V  T  R  T  M  L  E  R  T  A  K  A  L

5215 ATACACCATAAGCATTTTCCCTACTGATGTTCATCATCTGAGCGTATTGGTTATAAGTGAACGATACCGTCCGTTCTTT
     TATGTGGTATTCGTAAAAGGGATGACTACAAGTAGTAGACTCGCATAACCAATATTCACTTGCTATGGCAGGCAAGAAA
  69◄ V  G  Y  A  N  E  R  S  I  N  M  M  Q  A  Y  Q  N  Y  T  F  S  V  T  R  E  K

5294 CCTTGTAGGGTTTTCAATCGTGGGGTTGAGTAGTGCCACACAGCATAAAATTAGCTTGGTTTCATGCTCCGTTAAGTCA
     GGAACATCCCAAAAGTTAGCACCCCAACTCATCACGGTGTGTCGTATTTTAATCGAACCAAAGTACGAGGCAATTCAGT
  43◄ R  T  P  N  E  I  T  P  N  L  L  A  V  C  C  L  I  L  K  T  E  H  E  T  L  D

5373 TAGCGACTAATCGCTAGTTCATTTGCTTTGAAAACAACTAATTCAGACATACATCTCAATTGGTCTAGGTGATTTTAAT
     ATCGCTGATTAGCGATCAAGTAAACGAAACTTTTGTTGATTAAGTCTGTATGTAGAGTTAACCAGATCCACTAAAATTA
  16◄Y  R  S  I  A  L  E  N  A  K  F  V  V  L  E  S  M

5452 CACTATACCAATTGAGATGGGCTAGTCAATGATAATTACTAGTCCTTTTCCTTTGAGTTGTGGGTATCTGTAAATTCTG
     GTGATATGGTTAACTCTACCCGATCAGTTACTATTAATGATCAGGAAAAGGAAACTCAACACCCATAGACATTTAAGAC

5531 CTAGACCTTTGCTGGAAAACTTGTAAATTCTGCTAGACCCTCTGTAAATTCCGCTAGACCTTTGTGTGTTTTTTTTGTT
     GATCTGGAAACGACCTTTTGAACATTTAAGACGATCTGGGAGACATTTAAGGCGATCTGGAAACACACAAAAAAAACAA

5610 TATATTCAAGTGGTTATAATTTATAGAATAAAGAAAGAATAAAAAAAAGATAAAAAGAATAGATCCCAGCCCTGTGTATA
     ATATAAGTTCACCAATATTAAATATCTTATTTCTTTCTTATTTTTTTCTATTTTTCTTATCTAGGGTCGGGACACATAT

5689 ACTCACTACTTTAGTCAGTTCCGCAGTATTACAAAAGGATGTCGCAAACGCTGTTTGCTCCTCTACAAAACAGACCTTA
     TGAGTGATGAAATCAGTCAAGGCGTCATAATGTTTTCCTACAGCGTTTGCGACAAACGAGGAGATGTTTTGTCTGGAAT
                                                                          ori 101
5768 AAACCCTAAAGGCTTAAGTAGCACCCTCGCAAGCTCGGGCAAATCGCTGAATATTCCTTTTGTCTCCGACCATCAGGCA
     TTTGGGATTTCCGAATTCATCGTGGGAGCGTTCGAGCCCGTTTAGCGACTTATAAGGAAAACAGAGGCTGGTAGTCCGT 5847 CCTGAGTCGCTGTCTTTTTCGTGACATTCAGTTCGCTGCGCTCACGGCTCTGGCAGTGAATGGGGGTAAATGGCACTAC
     GGACTCAGCGACAGAAAAAGCACTGTAAGTCAAGCGACGCGAGTGCCGAGACCGTCACTTACCCCCATTTACCGTGATG 5926 AGGCGCCTTTTATGGATTCATGCAAGGAAACTACCCATAATACAAGAAAAGCCCGTCACGGGCTTCTCAGGGCGTTTTA
     TCCGCGGAAAATACCTAAGTACGTTCCTTTGATGGGTATTATGTTCTTTTCGGGCAGTGCCCGAAGAGTCCCGCAAAAT 6005 TGGCGGGTCTGCTATGTGGTGCTATCTGACTTTTTGCTGTTCAGCAGTTCCTGCCCTCTGATTTTCCAGTCTGACCACT
     ACCGCCCAGACGATACACCACGATAGACTGAAAAACGACAAGTCGTCAAGGACGGGAGACTAAAAGGTCAGACTGGTGA 6084 TCGGATTATCCCGTGACAGGTCATTCAGACTGGCTAATGCACCCAGTAAGGCAGCGGTATCATCAACAGGCTTACCCGT
     AGCCTAATAGGGCACTGTCCAGTAAGTCTGACCGATTACGTGGGTCATTCCGTCGCCATAGTAGTTGTCCGAATGGGCA
```

```
                  pSC101
6163 CTTACTGTC
     GAATGACAG
     ─────────
```

```
     PvuII    Tn5 site         tL3
  1  CAGCTGTCTCTTATACACATCTCCGCTGTGCTTTCAGTGGATTTCGGATAACAGAAAGGCCGGGAAATACCCAGCCTCG
     GTCGACAGAGAATATGTGTAGAGGCGACACGAAAGTCACCTAAAGCCTATTGTCTTTCCGGCCCTTTATGGGTCGGAGC 80  CTTTGTAACGGAGTAGACGAAAGTGATTGCGCCTACCCGGATATTATCGTGAGGATGCGTCATCGCCATTGCTCCCCAA
     GAAACATTGCCTCATCTGCTTTCACTAACGCGGATGGGCCTATAATAGCACTCCTACGCAGTAGCGGTAACGAGGGGTT
                                                                226◄  R  W  Q  E  G  F 159  ATACAAAACCAATTTCAGCCAGTGCCTCGTCCATTTTTTCGATGAACTCCGGCACGATCTCGTCAAAACTCGCCATGTA
     TATGTTTTGGTTAAAGTCGGTCACGGAGCAGGTAAAAAAGCTACTTGAGGCCGTGCTAGAGCAGTTTTGAGCGGTACAT 220◄ V  F  G  I  E  \  !  A  E  D  M  K  E  I  F  Ē  P  V  I  E  D  F  S  A  M  Y
                                         StuI
238  CTTTTCATCCCGCTCAATCACGACATAATGCAGGCCTTCACGCTTCATACGCGGGTCATAGTTGGCAAAGTACCAGGCA
     GAAAAGTAGGGCGAGTTAGTGCTGTATTACGTCCGGAAGTGCGAAGTATGCGCCCAGTATCAACCGTTTCATGGTCCGT 194◄ K  E  D  R  E  I  V  V  Y  H  L  G  E  R  K  M  R  P  D  Y  N  A  F  Y  W  A 317  TTTTTTCGCGTCACCCACATGCTGTACTGCACCTGGGCCATGTAAGCTGACTTTATGGCCTCGAAACCACCGAGCCGGA
     AAAAAAGCGCAGTGGGTGTACGACATGACGTGGACCCGGTACATTCGACTGAAATACCGGAGCTTTGGTGGCTCGGCCT 167◄N  K  R  T  V  W  M  S  Y  Q  V  Q  A  M  Y  A  S  K  I  A  E  F  G  G  L  R  F
             SmaI
396  ACTTCATGAAATCCCGGGAGGTAAACGGGCATTTCAGTTCAAGGCCGTTGCCGTCACTGCATAAACCATCGGGAGAGCA
     TGAAGTACTTTAGGGCCCTCCATTTGCCCGTAAAGTCAAGTTCCGGCAACGGCAGTGACGTATTTGGTAGCCCTCTCGT

141◄ K  M  F  D  R  S  T  F  P  C  K  L  E  L  G  N  D  S  C  L  G  D  P  S  C

475  GGCGGTACGCATACTTTCGTCGCGATAGATGATCGGGGATTCAGTAACATTCACGCCGGAAGTGAAcTCAAACAGGGTT
     CCGCCATGCGTATGAAAGCAGCGCTATCTACTAGCCCCTAAGTCATTGTAAGTGCGGCCTTCACTTgAGTTTGTCCCAA

115◄ A  T  R  M  S  E  D  R  Y  I  I  P  S  E  T  V  N  V  G  S  T  F  E  F  L  T

554  CTGGCGTCGTTCTCGTACTGTTTTCCCCAGGCCAGTGCTTTAGCGTTAACTTCCGGAGCCACACCGGTGCAAACCTCAG
     GACCGCAGCAAGAGCATGACAAAAGGGGTCCGGTCACGAAATCGCAATTGAAGGCCTCGGTGTGGCCACGTTTGGAGTC

88◄R  A  D  N  E  Y  Q  K  G  W  A  L  A  K  A  N  V  E  P  A  V  G  T  C  V  E  A

633  CAAGCAGGGTGTGGAAGTAGGACATTTTCATGTCAGGCCACTTCTTTCCGGAGCGGGGTTTTGCTATCACGTTGTGAAC
     GTTCGTCCCACACCTTCATCCTGTAAAAGTACAGTCCGGTGAAGAAAGGCCTCGCCCCAAAACGATAGTGCAACACTTG

62◄  L  L  T  H  F  Y  S  M  K  M  D  P  W  K  K  G  S  R  P  K  A  I  V  N  H  V

712  TTCTGAAGCGGTGATGACGCCGAGCCGTAATTTGTGCCACGCATCATCCCCCTGTTCGACAGCTCTCACATCGATCCCG
     AAGACTTCGCCACTACTGCGGCTCGGCATTAAACACGGTGCGTAGTAGGGGGACAAGCTGTCGAGAGTGTAGCTAGGGC

36◄ E  S  A  T  I  V  G  L  R  L  K  H  W  A  D  D  G  Q  E  V  A  R  V  D  I  G
         PstI                       Exo
791  GTACGCTGCAGGATAATGTCCGGTGTCATGCTGCCACCTTCTGCTCTGCGGCTTTCTGTTTCAGGAATCCAAGAGCTTT
     CATGCGACGTCCTATTACAGGCCACAGTACGACGGTGGAAGACGAGACGCCGAAAGACAAAGTCCTTAGGTTCTCGAAA
                                        261◄ A  A  V  K  Q  E  A  A  K  Q  K  L  F  G  L  A  K
  9◄T  R  Q  L  I  I  D  P  T  M

870  TACTGCTTCGGCCTGTGTCAGTTCTGACGATGCACGAATGTCGCGGCGAAATATCTGGGAACAGAGCGGCAATAAGTCG
     ATGACGAAGCCGGACACAGTCAAGACTGCTACGTGCTTACAGCGCCGCTTTATAGACCCTTGTCTCGCCGTTATTCAGC
244◄ V  A  E  A  Q  T  L  E  S  S  A  R  I  D  R  R  F  I  Q  S  C  L  P  L  L  D
```

FIG. 8B

```
 949 TCATCCCATGTTTTATCCAGGGCGATCAGCAGAGTGTTAATCTCCTGCATGGTTTCATCGTTAACCGGAGTGATGTCGC
     AGTAGGGTACAAAATAGGTCCCGCTAGTCGTCTCACAATTAGAGGACGTACCAAAGTAGCAATTGGCCTCACTACAGCG
217◄ D  D  W  T  K  D  L  A  I  L  L  T  N  I  E  Q  M  T  E  D  N  V  P  T  I  D  R

PstI
1028 GTTCCGGCTGACGTTCTGCAGTGTATGCAGTATTTTCGACAATGCGCTCGGCTTCATCCTTGTCATAGATACCAGCAAA
     CAAGGCCGACTGCAAGACGTCACATACGTCATAAAAGCTGTTACGCGAGCCGAAGTAGGAACAGTATCTATGGTCGTTT
191◄ E  P  Q  R  E  A  T  Y  A  T  N  E  V  I  R  E  A  E  D  K  D  Y  I  G  A  F

BglI
1107 TCCGAAGGCCAGACGGGCACACTGAATCATGGCTTTATGACGTAACATCCGTTTGGGATGCGACTGCCACGGCCCCGTG
     AGGCTTCCGGTCTGCCCGTGTGACTTAGTACCGAAATACTGCATTGTAGGCAAACCCTACGCTGACGGTGCCGGGGCAC
165◄ G  F  A  L  R  A  C  Q  I  M  A  K  H  R  L  M  R  K  P  H  S  Q  W  P  G  T

1186 ATTTCTCTGCCTTCGCGAGTTTTGAATGGTTCGCGGCGGCATTCATCCATCCATTCGGTAACGCAGATCGGATGATTAC
     TAAAGAGACGGAAGCGCTCAAAACTTACCAAGCGCCGCCGTAAGTAGGTAGGTAAGCCATTGCGTCTAGCCTACTAATG
138◄ I  E  R  G  E  R  T  K  F  P  E  R  R  C  E  D  M  W  E  T  V  C  I  P  H  N  R

1265 GGTCCTTGCGGTAAATCCGGCATGTACAGGATTCATTGTCCTGCTCAAAGTCCATGCCATCAAACTGCTGGTTTTCATT
     CCAGGAACGCCATTTAGGCCGTACATGTCCTAAGTAACAGGACGAGTTTCAGGTACGGTAGTTTGACGACCAAAAGTAA
112◄ D  K  R  Y  I  R  C  T  C  S  E  N  D  Q  E  F  D  M  G  D  F  Q  Q  N  E  N

1344 GATGATGCGGGACCAGCCATCAACGCCCACCACCGGAACGATGCCATTCTGCTTATCAGGAAAGGCGTAAATTTCTTTC
     CTACTACGCCCTGGTCGGTAGTTGCGGGTGGTGGCCTTGCTACGGTAAGACGAATAGTCCTTTCCGCATTTAAAGAAAG
 86◄ I  I  R  S  W  G  D  V  G  V  V  P  V  I  G  N  Q  K  D  P  F  A  Y  I  E  K

1423 GTCCACGGATTAAGGCCGTACTGGTTGGCAACGATCAGTAATGCGATGAACTGCGCATCGCTGGCATCACCTTTAAATG
     CAGGTGCCTAATTCCGGCATGACCAACCGTTGCTAGTCATTACGCTACTTGACGCGTAGCGACCGTAGTGGAAATTTAC
 59◄ T  W  P  N  L  G  Y  Q  N  A  V  I  L  L  A  I  F  Q  A  D  S  A  D  G  K  F  A

SalI
1502 CCGTCTGGCGAAGAGTGGTGATCAGTTCCTGTGGGTCGACAGAATCCATGCCGACACGTTCAGCCAGCTTCCCAGCCAG
     GGCAGACCGCTTCTCACCACTAGTCAAGGACACCCAGCTGTCTTAGGTACGGCTGTGCAAGTCGGTCGAAGGGTCGGTC
 33◄ T  Q  R  L  T  T  I  L  E  Q  P  D  V  S  D  M  G  V  R  E  A  L  K  G  A  L

Bet
1581 CGTTGCGAGTGCAGTACTCATTCGTTTTATACCTCTGAATCAATATCAACCTGGTGGTGAGCAATGGTTTCAACCATGT
     GCAACGCTCACGTCATGAGTAAGCAAAATATGGAGACTTAGTTATAGTTGGACCACCACTCGTTACCAAAGTTGGTACA
  7◄ T  A  L  A  T  S  M         98◄ V  E  S  D  I  D  V  Q  H  H  A  I  T  E  V  M  Y

1660 ACCGGATGTGTTCTGCCATGCGCTCCTGAAACTCAACATCGTCATCAAACGCACGGGTAATGGATTTTTTGCTGGCCCC
     TGGCCTACACAAGACGGTACGCGAGGACTTTGAGTTGTAGCAGTAGTTTGCGTGCCCATTACCTAAAAAACGACCGGGG
 81◄ R  I  H  E  A  M  R  E  Q  F  E  V  D  D  D  F  A  R  T  I  S  K  K  S  A  G

StuI
1739 GTGGCGTTGCAAATGATCGATGCATAGCGATTCAAACAGGTGCTGGGGCAGGCCTTTTTCCATGTCGTCTGCCAGTTCT
     CACCGCAACGTTTACTAGCTACGTATCGCTAAGTTTGTCCACGACCCCGTCCGGAAAAAGGTACAGCAGACGGTCAAGA
 55◄ H  R  Q  L  H  D  I  C  L  S  E  F  L  H  Q  P  L  G  K  E  M  D  D  A  L  E

1818 GCCTCTTTCTCTTCACGGGCGAGCTGCTGGTAGTGACGCGCCCAGCTCTGAGCCTCAAGACGATCCTGAATGTAATAAG
     CGGAGAAAGAGAAGTGCCCGCTCGACGACCATCACTGCGCGGGTCGAGACTCGGAGTTCTGCTAGGACTTACATTATTC
 28◄ A  E  K  E  E  R  A  L  Q  Q  Y  H  R  A  W  S  Q  A  E  L  R  D  Q  I  Y  Y  A

Gam                                                              N-kil del
1897 CGTTCATGGCTGAACTCCTGAAATAGCTGTGAAAATATCGCCCGCGAAATGCCGGGCTGATTAGTAATCCGGAATCGCA
     GCAAGTACCGACTTGAGGACTTTATCGACACTTTTATAGCGGGCGCTTTACGGCCCGACTAATCATTAGGCCTTAGCGT
  2◄ N  M                                            ─────────────────────────────

1976 CTTACGGCCAATGCTTCGTTTCGTATCACACACCCCAAAGCCTTCTGCTTTGAATGCTGCCCTTCTTCAGGGCTTAATT
     GAATGCCGGTTACGAAGCAAAGCATAGTGTGTGGGGTTTCGGAAGACGAAACTTACGACGGGAAGAAGTCCCGAATTAA
     ───────────────────────────────────────────────────────────────────────────────
```

FIG. 8C

```
2055 TTTAAGAGCGTCACCTTCATGGTGGTCAGTGCGTCCTGCTGATGTGCTCAGTATCACCGCCAGTGGTATTTATGTCAAC
     AAATTCTCGCAGTGGAAGTACCACCAGTCACGCAGGACGACTACACGAGTCATAGTGGCGGTCACCATAAATACAGTTG

2134 ACCGCCAGAGATAATTTATCACCGCAGATGGTTATCTGTATGTTTTTTATATGAATTTATTTTTTGCAGGGGGGCATTG
     TGGCGGTCTCTATTAAATAGTGGCGTCTACCAATAGACATACAAAAAATATACTTAAATAAAAAACGTCCCCCCGTAAC

2213 TTTGGTAGGTGAGAGATCTGAATTGCTATGTTTAGTGAGTTGTATCTATTTATTTTTCAATAAATACAATTGGTTATGT
     AAACCATCCACTCTCTAGACTTAACGATACAAATCACTCAACATAGATAAATAAAAAGTTATTTATGTTAACCAATACA ◂ junction marker
2292 GTTTTGGGGGCGATCGTGAGGCAAAGAAAACCCGGCGCTGAGGCCGGGTTAAGAGTTGGTAGCTCTTGATCCGGCAAAC
     CAAAACCCCCGCTAGCACTCCGTTTCTTTTGGGCCGCGACTCCGGCCCAATTCTCAACCATCGAGAACTAGGCCGTTTG
     ────────────────────────────────────────────────────────────────────────────────▶

2371 AAACCACCGCTGGTAGCGGTGGTTTTTTTGTTTGCAAGCAGCAGATTACGCGCAGAAAAAAAGGATCTCAAGAAGATCC
     TTTGGTGGCGACCATCGCCACCAAAAAAACAAACGTTCGTCGTCTAATGCGCGTCTTTTTTTCCTAGAGTTCTTCTAGG

2450 TTTGATCTTTTCTACGGGGTCTGACGCTCAGTGGAACGAAAACTCACGTTAAGGGATTTTGGTCATGAGATTATCAAAA
     AAACTAGAAAAGATGCCCCAGACTGCGAGTCACCTTGCTTTTGAGTGCAATTCCCTAAAACCAGTACTCTAATAGTTTT

2529 AGGATCTTCACCTAGATCCTTTTAAATTAAAAATGAAGTTTTAAATCAATCTAAAGTATATATGAGTAAACTTGGTCTG
     TCCTAGAAGTGGATCTAGGAAAATTTAATTTTTACTTCAAAATTTAGTTAGATTTCATATATACTCATTTGAACCAGAC

2608 ACAGTTACCAATGCTTAATCAGTGAGGCACCTATCTCAGCGATCTGTCTATTTCGTTCATCCATAGTTGCCTGACTCCC
     TGTCAATGGTTACGAATTAGTCACTCCGTGGATAGAGTCGCTAGACAGATAAAGCAAGTAGGTATCAACGGACTGAGGG
        286◂ W  H  K  I  L  S  A  G  I  E  A  I  Q  R  N  R  E  D  M  T  A  Q  S  G

2687 CGTCGTGTAGATAACTACGATACGGGAGGGCTTACCATCTGGCCCCAGTGCTGCAATGATACCGCGAGACCCACGCTCA
     GCAGCACATCTATTGATGCTATGCCCTCCCGAATGGTAGACCGGGGTCACGACGTTACTATGGCGCTCTGGGTGCGAGT
     262◂ T  T  Y  I  V  V  I  R  S  P  K  G  D  P  G  L  A  A  I  I  G  R  S  G  R  E

2766 CCGGCTCCAGATTTATCAGCAATAAACCAGCCAGCCGGAAGGGCCGAGCGcagaagtggtcctgcaactTTATCCGCCT
     GGCCGAGGTCTAAATAGTCGTTATTTGGTCGGTCGGCCTTCCCGGCTCGCgtcttcaccaggacgttgaAATAGGCGGA
     235◂ G  A  G  S  K  D  A  I  F  W  G  A  P  L  A  S  R  L  L  P  G  A  V  K  D  A  E 2845 CCATCCAGTCTATTAATTGTTGCCGGGAAGCTAGAGTAAGTAGTTCGCCAGTTAATAGTTTGCGCAACGTTGTTGCCAT
     GGTAGGTCAGATAATTAACAACGGCCCTTCGATCTCATTCATCAAGCGGTCAATTATCAAACGCGTTGCAACAACGGTA
     209◂ M  W  D  I  L  Q  Q  R  S  A  L  T  L  L  E  G  T  L  L  K  R  L  T  T  A  M 2924 TGCTGCAGGCATCGTGGTGTCACGCTCGTCGTTTGGTATGGCTTCATTCAGCTCCGGTTCCCAACGATCAAGGCGAGTT
     ACGACGTCCGTAGCACCACAGTGCGAGCAGCAAACCATACCGAAGTAAGTCGAGGCCAAGGGTTGCTAGTTCCGCTCAA
     183◂ A  A  P  M  T  T  D  R  E  D  N  P  I  A  E  N  L  E  P  E  W  R  D  L  R  T 3003 ACATGATCCCCCATGTTGTGCAAAAAAGCGGTTAGCTCCTTCGGTCCTCCGATCGTTGTCAGAAGTAAGTTGGCCGCAG
     TGTACTAGGGGTACAACACGTTTTTTCGCCAATCGAGGAAGCCAGGAGGCTAGCAACAGTCTTCATTCAACCGGCGTC
     156◂ V  H  D  G  M  N  H  L  F  A  T  L  E  K  P  G  G  I  T  T  L  L  L  N  A  A  T 3082 TGTTATCACTCATGGTTATGGCAGCACTGCATAATTCTCTTACTGTCATGCCATCCGTAAGATGCTTTTCTGTGACTgg
     ACAATAGTGAGTACCAATACCGTCGTGACGTATTAAGAGAATGACAGTACGGTAGGCATTCTACGAAAAGACACTGAcc
     130◂ N  D  S  M  T  I  A  A  S  C  L  E  R  V  T  M  G  D  T  L  H  K  E  T  V  P 3161 tgagtactcaaccaagtcATTCTGAGAATAGTGTATGCGGCGACCGAGTTGCTCTTGCCCGGCGTCAACACGGGATAAT
     actcatgagttggttcagTAAGACTCTTATCACATACGCCGCTGGCTCAACGAGAACGGGCCGCAGTTGTGCCCTATTA
     104◂ S  Y  E  V  L  D  N  Q  S  Y  H  I  R  R  G  L  Q  E  Q  G  A  D  V  R  S  L 3240 ACCGCGCCACATAGCAGAACTTTAAAAGTGCTCATCATTGGAAAACGTTCTTCGGGGCGAAAACTCTCAAGGATCTTAC
     TGGCGCGGTGTATCGTCTTGAAATTTTCACGAGTAGTAACCTTTTGCAAGAAGCCCCGCTTTTGAGAGTTCCTAGAATG
     77◂ V  A  G  C  L  L  V  K  F  T  S  M  M  P  F  R  E  E  P  R  F  S  E  L  I  K  G 3319 CGCTGTTGAGATCCAGTTCGATGTAACCCACTCGTGCACCCAACTGATCTTCAGCATCTTTTACTTTCACCAGCGTTTC
     GCGACAACTCTAGGTCAAGCTACATTGGGTGAGCACGTGGGTTGACTAGAAGTCGTAGAAAATGAAAGTGGTCGCAAAG
     51◂ S  N  L  D  L  E  I  Y  G  V  R  A  G  L  Q  D  E  A  D  K  V  K  V  L  T  E
```

FIG. 8D

```
                                                                                              amp
3398 TGGGTGAGCAAAAACAGGAAGGCAAAATGCCGCAAAAAAGGGAATAAGGGCGACACGGAAATGTTGAATACTCATACTC
     ACCCACTCGTTTTTGTCCTTCCGTTTTACGGCGTTTTTTCCCTTATTCCCGCTGTGCCTTTACAACTTATGAGTATGAG
  254 P  H  A  F  V  P  L  C  F  A  A  F  F  P  I  L  A  V  R  F  H  Q  I  S  M rexA'
3477 TTCCTTTTTCAATATTATTGAAGCATTTATCAGGGTTATTGTCTCATGAGCGGATACATATTTGAATGAATTCAATCCA
     AAGGAAAAAGTTATAATAACTTCGTAAATAGTCCCAATAACAGAGTACTCGCCTATGTATAAACTTACTTAAGTTAGGT
                                                       ◄─────────────────────────────

3556 TTTACTATGTTATGTTCTGAGGGGAGTGAAAATTCCCCTAATTCGATGAAGATTCTTGCTCAATTGTTATCAGCTATGC
     AAATGATACAATACAAGACTCCCCTCACTTTTAAGGGGATTAAGCTACTTCTAAGAACGAGTTAACAATAGTCGATACG
     ──────────────────────────────────────

3635 GCCGACCAGAACACCTTGCCGATCAGCCAAACGTCTCTTCAGGCCACTGACTAGCGATAACTTTCCCCACAACGGAACA
     CGGCTGGTCTTGTGGAACGGCTAGTCGGTTTGCAGAGAAGTCCGGTGACTGATCGCTATTGAAAGGGGTGTTGCCTTGT
                       2374 G  F  T  E  E  P  W  Q  S  A  I  V  K  G  V  V  S  C

3714 ACTCTCATTGCATGGGATCATTGGGTACTGTGGGTTTAGTGGTTGTAAAAACACCTGACCGCTATCCCTGATCAGTTTC
     TGAGAGTAACGTACCCTAGTAACCCATGACACCCAAATCACCAACATTTTTGTGGACTGGCGATAGGGACTAGTCAAAG
  2194 S  E  N  C  P  I  M  P  Y  Q  P  N  L  P  Q  L  F  V  Q  G  S  D  R  I  L  K

3793 TTGAAGGTAAACTCATCACCCCCAAGTCTGGCTATGCAGAAATCACCTGGCTCAACAGCCTGCTCAGGGTCAACGAGAA
     AACTTCCATTTGAGTAGTGGGGGTTCAGACCGATACGTCTTTAGTGGACCGAGTTGTCGGACGAGTCCCAGTTGCTCTT
  1924 K  F  T  F  E  D  G  G  L  R  A  I  C  F  D  G  P  E  V  A  Q  E  P  D  V  L  I
                HindIII
3872 TTAACATTCCGTCAGGAAAGCTTGGCTTGGAGCCTGTTGGTGCGGTCATGGAATTACCTTCAACCTCAAGCCAGAATGC
     AATTGTAAGGCAGTCCTTTCGAACCGAACCTCGGACAACCACGCCAGTACCTTAATGGAAGTTGGAGTTCGGTCTTACG
  1664 L  M  G  D  P  F  S  P  K  S  G  T  P  A  T  M  S  N  G  E  V  E  L  W  F  A
                                                                    HindIII
3951 AGAATCACTGGCTTTTTTGGTTGTGCTTACCCATCTCTCCGCATCACCTTTGGTAAAGGTTCTAAGCTTAGGTGAGAAC
     TCTTAGTGACCGAAAAAACCAACACGAATGGGTAGAGAGGCGTAGTGGAAACCATTTCCAAGATTCGAATCCACTCTTG
  1404 S  D  S  A  K  K  T  T  S  V  W  R  E  A  D  G  K  T  F  T  R  L  K  P  S  F 4030 ATCCCTGCCTGAACATGAGAAAAAACAGGGTACTCATACTCACTTCTAAGTGACGGCTGCATACTAACCGCTTCATACA
     TAGGGACGGACTTGTACTCTTTTTTGTCCCATGAGTATGAGTGAAGATTCACTGCCGACGTATGATTGGCGAAGTATGT
  1134 M  G  A  Q  V  H  S  F  V  P  Y  E  Y  E  S  R  L  S  P  Q  M  S  V  A  E  Y  M 4109 TCTCGTAGATTTCTCTGGCGATTGAAGGGCTAAATTCTTCAACGCTAACTTTGAGAATTTTTGTAAGCAATGCGGCGTT
     AGAGCATCTAAAGAGACCGCTAACTTCCCGATTTAAGAAGTTGCGATTGAAACTCTTAAAAACATTCGTTACGCCGCAA
   874 E  Y  I  E  R  A  I  S  P  S  F  E  E  V  S  V  K  L  I  K  T  L  L  A  A  N 4188 ATAAGCATTTAATGCATTGATGCCATTAAATAAAGCACCAACGCCTGACTGCCCCATCCCCATCTTGTCTGCGACAGAT
     TATTCGTAAATTACGTAACTACGGTAATTTATTTCGTGGTTGCGGACTGACGGGGTAGGGGTAGAACAGACGCTGTCTA
   614 Y  A  N  L  A  N  I  G  N  F  L  A  G  V  G  S  Q  G  M  G  M  K  D  A  V  S 4267 TCCTGGGATAAGCCAAGTTCATTTTTCTTTTTTTCATAAATTGCTTTAAGGCGACGTGCGTCCTCAAGCTGCTCTTGTG
     AGGACCCTATTCGGTTCAAGTAAAAAGAAAAAAAGTATTTAACGAAATTCCGCTGCACGCAGGAGTTCGACGAGAACAC
   344 E  Q  S  L  G  L  E  N  K  K  K  E  Y  I  A  K  L  R  R  A  D  E  L  Q  E  Q  T cI 857
4346 TTAATGGTTTCTTTTTTGTGCTCATACGTTAAATCTATCACCGCAAGGGATAAATATCTAACACCGTGCGTGTTGACTA
     AATTACCAAAGAAAAAACACGAGTATGCAATTTAGATAGTGGCGTTCCCTATTTATAGATTGTGGCACGCACAACTGAT
    84 L  P  K  K  K  T  S  M
                                                        cro'                     PvuII
4425 TTTTACCTCTGGCGGTGATAATGGTTGCATGTACTAAGGAGGTTGTATGGAACAACGAGATGTGTATAAGAGACAGCTG
     AAAATGGAGACCGCCACTATTACCAACGTACATGATTCCTCCAACATACCTTGTTGCTCTACACATATTCTCTGTCGAC
```

FIG. 8E

```
4504 ACGGGTTTTGCTGCCCGCAAACGGGCTGTTCTGGTGTTGCTAGTTTGTTATCAGAATCGCAGATCCGGCTTCAGGTTTG
     TGCCCAAAACGACGGGCGTTTGCCCGACAAGACCACAACGATCAAACAATAGTCTTAGCGTCTAGGCCGAAGTCCAAAC

4583 CCGGCTGAAAGCGCTATTTCTTCCAGAATTGCCATGATTTTTTCCCCACGGGAGGCGTCACTGGCTCCCGTGTTGTCGG
     GGCCGACTTTCGCGATAAAGAAGGTCTTAACGGTACTAAAAAAGGGGTGCCCTCCGCAGTGACCGAGGGCACAACAGCC
              1374 K K W F Q W S K K G V P P T V P E R T T P pKO3 homol starts (4694)
4662 CAGCTTTGATTCGATAAGCAGCATCGCCTGTTTCAGGCTGTCTATGTGTGACTGTTGAGCTGTAACAAGTTGTCTCAGG
     GTCGAAACTAAGCTATTCGTCGTAGCGGACAAAGTCCGACAGATACACACTGACAACTCGACATTGTTCAACAGAGTCC
     1164 L K S E I L L M A Q K L S D I H S Q Q A T V L Q R L 4741 TGTTCAATTTCATGTTCTAGTTGCTTTGTTTTACTGGTTTCACCTGTTCTATTAGGTGTTACATGCTGTTCATCTGTTA
     ACAAGTTAAAGTACAAGATCAACGAAACAAAATGACCAAAGTGGACAAGATAATCCACAATGTACGACAAGTAGACAAT
      894 H E I E H E L Q K T K S T E G T R N P T V H Q E D T V 4820 CATTGTCGATCTGTTCATGGTGAACAGCTTTGAATGCACCAAAAACTCGTAAAAGCTCTGATGTATCTATCTTTTTTAC
     GTAACAGCTAGACAAGTACCACTTGTCGAAACTTACGTGGTTTTTGAGCATTTTCGAGACTACATAGATAGAAAAAATG
      634 N D I Q E H H V A K F A G F V R L L E S T D I K K V 4899 ACCGTTTTCATCTGTGCATATGGACAGTTTTCCCTTTGATATGTAACGGTGAACAGTTGTTCTACTTTTGTTTGTTAGT
     TGGCAAAAGTAGACACGTATACCTGTCAAAAGGGAAACTATACATTGCCACTTGTCAACAAGATGAAAACAAACAATCA
      374 G N E D T C I S L K G K S I Y R H V T T R S K N T L 4978 CTTGATGCTTCACTGATAGATACAAGAGCCATAAGAACCTCAGATCCTTCCGTATTTAGCCAGTATGTTCTCTAGTGTG
     GAACTACGAAGTGACTATCTATGTTCTCGGTATTCTTGGAGTCTAGGAAGGCATAAATCGGTCATACAAGAGATCACAC
      104 R S A E S I S V L A M    3164 I R G Y K A L I N E L T 5057 GTTCGTTGTTTTTGCGTGAGCCATGAGAACGAACCATTGAGATCATACTTACTTTGCATGTCACTCAAAAATTTTGCCT
     CAAGCAACAAAAACGCACTCGGTACTCTTGCTTGGTAACTCTAGTATGAATGAAACGTACAGTGAGTTTTTAAAACGGA
     3034 T R Q K Q T L W S F S G N L D Y K S Q M D S L F K A E 5136 CAAAACTGGTGAGCTGAATTTTTGCAGTTAAAGCATCGTGTAGTGTTTTTCTTAGTCCGTTATGTAGGTAGGAATCTGA
     GTTTTGACCACTCGACTTAAAAACGTCAATTTCGTAGCACATCACAAAAAGAATCAGGCAATACATCCATCCTTAGACT
     2774 F S T L Q I K A T L A D H L T K R L G N H L Y S D S 5215 TGTAATGGTTGTTGGTATTTTGTCACCATTCATTTTTATCTGGTTGTTCTCAAGTTCGGTTACGAGATCCATTTGTCTA
     ACATTACCAACAACCATAAAACAGTGGTAAGTAAAAATAGACCAACAAGAGTTCAAGCCAATGCTCTAGGTAAACAGAT
     2514 T I T T P I K D G N M K I Q N N E L E T V L D M Q R 5294 TCTAGTTCAACTTGGAAAATCAACGTATCAGTCGGGCGGCCTCGCTTATCAACCACCAATTTCATATTGCTGTAAGTGT
     AGATCAAGTTGAACCTTTTAGTTGCATAGTCAGCCCGCCGGAGCGAATAGTTGGTGGTTAAAGTATAACGACATTCACA
     2244 D L E V Q F I L T D T P R G R K D V V L K M N S Y T N 5373 TTAAATCTTTACTTATTGGTTTCAAAACCCATTGGTTAAGCCTTTTAAACTCATGGTAGTTATTTTCAAGCATTAACAT
     AATTTAGAAATGAATAACCAAAGTTTTGGGTAACCAATTCGGAAAATTTGAGTACCATCAATAAAAGTTCGTAATTGTA
     1984 L D K S I P K L V W Q N L R K F E H Y N N E L M L M 5452 GAACTTAAATTCATCAAGGCTAATCTCTATATTTGCCTTGTGAGTTTTCTTTTGTGTTAGTTCTTTTAATAACCACTCA
     CTTGAATTTAAGTAGTTCCGATTAGAGATATAAACGGAACACTCAAAAGAAAACACAATCAAGAAATTATTGGTGAGT
     1724 F K F E D L S I E I N A K H T K K Q T L E K L L W E 5531 TAAATCCTCATAGAGTATTTGTTTTCAAAAGACTTAACATGTTCCAGATTATATTTTATGAATTTTTTTAACTGGAAAA
     ATTTAGGAGTATCTCATAAACAAAAGTTTTCTGAATTGTACAAGGTCTAATATAAAATACTTAAAAAAATTGACCTTTT
     1454 Y I R M S Y K N E F S K V H E L N Y K I F K K L Q F L 5610 GATAAGGCAATATCTCTTCACTAAAAACTAATTCTAATTTTTCGCTTGAGAACTTGGCATAGTTTGTCCACTGGAAAAT
     CTATTCCGTTATAGAGAAGTGATTTTTGATTAAGATTAAAAAGCGAACTCTTGAACCGTATCAAACAGGTGACCTTTTA
     1194 Y P L I E E S F V L E L K E S S F K A Y N T W Q F I
```

```
5689 CTCAAAGCCTTTAACCAAAGGATTCCTGATTTCCACAGTTCTCGTCATCAGCTCTCTGGTTGCTTTAGCTAATACACCA
     GAGTTTCGGAAATTGGTTTCCTAAGGACTAAAGGTGTCAAGAGCAGTAGTCGAGAGACCAACGAAATCGATTATGTGGT
  93* E  F  G  K  V  L  P  N  R  I  E  V  T  R  T  M  L  E  R  T  A  K  A  L  V  G

5768 TAAGCATTTTCCCTACTGATGTTCATCATCTGAGCGTATTGGTTATAAGTGAACGATACCGTCCGTTCTTTCCTTGTAG
     ATTCGTAAAAGGGATGACTACAAGTAGTAGACTCGCATAACCAATATTCACTTGCTATGGCAGGCAAGAAAGGAACATC
  66*Y  A  N  E  R  S  I  N  M  M  Q  A  Y  Q  N  Y  T  F  S  V  T  R  E  K  R  T  P

5847 GGTTTTCAATCGTGGGGTTGAGTAGTGCCACACAGCATAAAATTAGCTTGGTTTCATGCTCCGTTAAGTCATAGCGACT
     CCAAAAGTTAGCACCCCAACTCATCACGGTGTGTCGTATTTTAATCGAACCAAAGTACGAGGCAATTCAGTATCGCTGA
  40* N  E  I  T  P  N  L  L  A  V  C  C  L  I  L  K  T  E  H  E  T  L  D  Y  R  S

5926 AATCGCTAGTTCATTTGCTTTGAAAACAACTAATTCAGACATACATCTCAATTGGTCTAGGTGATTTTAATCACTATAC
     TTAGCGATCAAGTAAACGAAACTTTTGTTGATTAAGTCTGTATGTAGAGTTAACCAGATCCACTAAAATTAGTGATATG
  14* I  A  L  E  N  A  K  F  V  V  L  E  S  M

6005 CAATTGAGATGGGCTAGTCAATGATAATTACTAGTCCTTTTCCTTTGAGTTGTGGGTATCTGTAAATTCTGCTAGACCT
     GTTAACTCTACCCGATCAGTTACTATTAATGATCAGGAAAAGGAAACTCAACACCCATAGACATTTAAGACGATCTGGA

6084 TTGCTGGAAAACTTGTAAATTCTGCTAGACCCTCTGTAAATTCCGCTAGACCTTTGTGTGTTTTTTTTGTTTATATTCA
     AACGACCTTTTGAACATTTAAGACGATCTGGGAGACATTTAAGGCGATCTGGAAACACACAAAAAAAACAAATATAAGT

6163 AGTGGTTATAATTTATAGAATAAAGAAAGAATAAAAAAAGATAAAAAGAATAGATCCCAGCCCTGTGTATAACTCACTA
     TCACCAATATTAAATATCTTATTTCTTTCTTATTTTTTCTATTTTTCTTATCTAGGGTCGGGACACATATTGAGTGAT

6242 CTTTAGTCAGTTCCGCAGTATTACAAAAGGATGTCGCAAACGCTGTTTGCTCCTCTACAAAACAGACCTTAAAACCCTA
     GAAATCAGTCAAGGCGTCATAATGTTTTCCTACAGCGTTTGCGACAAACGAGGAGATGTTTTGTCTGGAATTTTGGGAT
                                                                         ori 101
6321 AAGGCTTAAGTAGCACCCTCGCAAGCTCGGGCAAATCGCTGAATATTCCTTTTGTCTCCGACCATCAGGCACCTGAGTC
     TTCCGAATTCATCGTGGGAGCGTTCGAGCCCGTTTAGCGACTTATAAGGAAAACAGAGGCTGGTAGTCCGTGGACTCAG 6400 GCTGTCTTTTTCGTGACATTCAGTTCGCTGCGCTCACGGCTCTGGCAGTGAATGGGGGTAAATGGCACTACAGGCGCCT
     CGACAGAAAAAGCACTGTAAGTCAAGCGACGCGAGTGCCGAGACCGTCACTTACCCCCATTTACCGTGATGTCCGCGGA 6479 TTTATGGATTCATGCAAGGAAACTACCCATAATACAAGAAAAGCCCGTCACGGGCTTCTCAGGGCGTTTTATGGCGGGT
     AAATACCTAAGTACGTTCCTTTGATGGGTATTATGTTCTTTTCGGGCAGTGCCCGAAGAGTCCCGCAAAATACCGCCCA 6558 CTGCTATGTGGTGCTATCTGACTTTTTGCTGTTCAGCAGTTCCTGCCCTCTGATTTTCCAGTCTGACCACTTCGGATTA
     GACGATACACCACGATAGACTGAAAAACGACAAGTCGTCAAGGACGGGAGACTAAAAGGTCAGACTGGTGAAGCCTAAT 6637 TCCCGTGACAGGTCATTCAGACTGGCTAATGCACCCAGTAAGGCAGCGGTATCATCAACAGGCTTACCCGTCTTACTGT
     AGGGCACTGTCCAGTAAGTCTGACCGATTACGTGGGTCATTCCGTCGCCATAGTAGTTGTCCGAATGGGCAGAATGACA pSC101
6716 C
     G
```

FIG. 8F

```
      PvuII    Tn5 site          tL3
  1 CAGCTGTCTCTTATACACATCTCCGCTGTGCTTTCAGTGGATTTCGGATAACAGAAAGGCCGGGAAATACCCAGCCTCGC
    GTCGACAGAGAATATGTGTAGAGGCGACACGAAAGTCACCTAAAGCCTATTGTCTTTCCGGCCCTTTATGGGTCGGAGCG
    _____

81 TTTGTAACGGAGTAGACGAAAGTGATTGCGCCTACCCGGATATTATCGTGAGGATGCGTCATCGCCATTGCTCCCCAAAT
    AAACATTGCCTCATCTGCTTTCACTAACGCGGATGGGCCTATAATAGCACTCCTACGCAGTAGCGGTAACGAGGGGTTTA

226◀ R  W  Q  E  G  F
161 ACAAAACCAATTTCAGCCAGTGCCTCGTCCATTTTTTCGATGAACTCCGGCACGATCTCGTCAAAACTCGCCATGTACTT
    TGTTTTGGTTAAAGTCGGTCACGGAGCAGGTAAAAAAGCTACTTGAGGCCGTGCTAGAGCAGTTTTGAGCGGTACATGAA

219◀V  F  G  I  E  A  L  A  E  D  M  K  E  I  F  E  P  V  I  E  D  F  S  A  M  Y  K
                                                Stul
241 TTCATCCCGCTCAATCACGACATAATGCAGGCCTTCACGCTTCATACGCGGGTCATAGTTGGCAAAGTACCAGGCATTTT
    AAGTAGGGCGAGTTAGTGCTGTATTACGTCCGGAAGTGCGAAGTATGCGCCCAGTATCAACCGTTTCATGGTCCGTAAAA 193◀E  D  R  E  I  V  V  Y  H  L  G  E  R  K  M  R  P  D  Y  N  A  F  Y  W  A  N  K
321 TTCGCGTCACCCACATGCTGTACTGCACCTGGCCATGTAAGCTGACTTTATGGCCTCGAAACCACCGAGCCGGAACTTC
    AAGCGCAGTGGGTGTACGACATGACGTGGACCCGGTACATTCGACTGAAATACCGGAGCTTTGGTGGCTCGGCCTTGAAG 166◀ R  T  V  W  M  S  Y  Q  V  Q  A  M  Y  A  S  K  I  A  E  F  G  G  L  R  F  K
       Smal
401 ATGAAATCCCGGGAGGTAAACGGGCATTTCAGTTCAAGGCCGTTGCCGTCACTGCATAAACCATCGGGAGAGCAGGCGGT
    TACTTTAGGGCCCTCCATTTGCCCGTAAAGTCAAGTTCCGGCAACGGCAGTGACGTATTTGGTAGCCCTCTCGTCCGCCA 139◀M  F  D  R  S  T  F  P  C  K  L  E  L  G  N  G  D  S  C  L  G  D  P  S  C  A  T
481 ACGCATACTTTCGTCGCGATAGATGATCGGGATTCAGTAACATTCACGCCGGAAGTGAACTCAAACAGGGTTCTGGCGT
    TGCGTATGAAAGCAGCGCTATCTACTAGCCCTAAGTCATTGTAAGTGCGGCCTTCACTTgAGTTTGTCCCAAGACCGCA 113◀ R  M  S  E  D  R  Y  I  I  P  S  E  T  V  N  V  G  S  T  F  E  F  L  T  R  A  D
561 CGTTCTCGTACTGTTTTCCCCAGGCCAGTGCTTTAGCGTTAACTTCCGGAGCCACACCGGTGCAAACCTCAGCAAGCAGG
    GCAAGAGCATGACAAAAGGGGTCCGGTCACGAAATCGCAATTGAAGGCCTCGGTGTGGCCACGTTTGGAGTCGTTCGTCC 86◀  N  E  Y  Q  K  G  W  A  L  A  K  A  N  V  E  P  A  V  G  T  C  V  E  A  L  L
641 GTGTGGAAGTAGGACATTTTCATGTCAGGCCACTTCTTTCCGGAGCGGGGTTTTGCTATCACGTTGTGAACTTCTGAAGC
    CACACCTTCATCCTGTAAAAGTACAGTCCGGTGAAGAAAGGCCTCGCCCCAAAACGATAGTGCAACACTTGAAGACTTCG 59◀T  H  F  Y  S  M  K  M  D  P  W  K  K  G  S  R  P  K  A  I  V  N  H  V  E  S  A
                                                                                    PstI
721 GGTGATGACGCCGAGCCGTAATTTGTGCCACGCATCATCCCCCTGTTCGACAGCTCTCACATCGATCCCGGTACGCTGCA
    CCACTACTGCGGCTCGGCATTAAACACGGTGCGTAGTAGGGGGACAAGCTGTCGAGAGTGTAGCTAGGGCCATGCGACGT 33◀ T  I  V  G  L  R  L  K  H  W  A  D  D  G  Q  E  V  A  R  V  D  I  G  T  R  Q  L
```

FIG. 10A

```
                           Exo
801  GGATAATGTCCGGTGTCATGCTGCCACCTTCTGCTCTGCGGCTTTCTGTTTCAGGAATCCAAGAGCTTTTACTGCTTCGG
     CCTATTACAGGCCACAGTACGACGGTGGAAGACGAGACGCCGAAAGACAAAGTCCTTAGGTTCTCGAAAATGACGAAGCC
                    261◄ A  A  V  K  Q  E  A  A  K  Q  K  L  F  G  L  A  K  V  A  E  A
      6◄ I  I  D  P  T  M

881  CCTGTGTCAGTTCTGACGATGCACGAATGTCGCGGCGAAATATCTGGGAACAGAGCGGCAATAAGTCGTCATCCATGTT
     GGACACAGTCAAGACTGCTACGTGCTTACAGCGCCGCTTTATAGACCCTTGTCTCGCCGTTATTCAGCAGTAGGGTACAA
    240◄ Q  T  L  E  S  S  A  R  I  D  R  R  F  I  Q  S  C  L  P  L  L  D  D  D  W  T

961  TTATCCAGGGCGATCAGCAGAGTGTTAATCTCCTGCATGGTTTCATCGTTAACCGGAGTGATGTCGCGTTCCGGCTGACG
     AATAGGTCCCGCTAGTCGTCTCACAATTAGAGGACGTACCAAAGTAGCAATTGGCCTCACTACAGCGCAAGGCCGACTGC
    213◄ K  D  L  A  I  L  L  T  N  I  E  Q  M  T  E  D  N  V  P  T  I  D  R  E  P  Q  R

PstI                                                                        BglI
1041 TTCTGCAGTGTATGCAGTATTTTCGACAATGCGCTCGGCTTCATCCTTGTCATAGATACCAGCAAATCCGAAGGCCAGAC
     AAGACGTCACATACGTCATAAAAGCTGTTACGCGAGCCGAAGTAGGAACAGTATCTATGGTCGTTTAGGCTTCCGGTCTG
    187◄ E  A  T  Y  A  T  N  E  V  I  R  E  A  E  D  K  D  Y  I  G  A  F  G  F  A  L  R

1121 GGGCACACTGAATCATGGCTTTATGACGTAACATCCGTTTGGGATGCGACTGCCACGGCCCCTGATTTCTCTGCCTTCG
     CCCGTGTGACTTAGTACCGAAATACTGCATTGTAGGCAAACCCTACGCTGACGGTGCCGGGGCACTAAAGAGACGGAAGC
    160◄ A  C  Q  I  M  A  K  H  R  L  M  R  K  P  H  S  Q  W  P  G  T  I  E  R  G  E

1201 CGAGTTTTGAATGGTTCGCGGCGGCATTCATCCATCCATTCGGTAACGCAGATCGGATGATTACGGTCCTTGCGGTAAAT
     GCTCAAAACTTACCAAGCGCCGCCGTAAGTAGGTAGGTAAGCCATTGCGTCTAGCCTACTAATGCCAGGAACGCCATTTA
    133◄ R  T  K  F  P  E  R  R  C  E  D  M  W  E  T  V  C  I  P  H  N  R  D  K  R  Y  I

1281 CCGGCATGTACAGGATTCATTGTCCTGCTCAAAGTCCATGCCATCAAACTGCTGGTTTTCATTGATGATGCGGGACCAGC
     GGCCGTACATGTCCTAAGTAACAGGACGAGTTTCAGGTACGGTAGTTTGACGACCAAAAGTAACTACTACGCCCTGGTCG
    107◄ R  C  T  C  S  E  N  D  Q  E  F  D  M  G  D  F  Q  Q  N  E  N  I  I  R  S  W  G

1361 CATCAACGCCCACCACCGGAACGATGCCATTCTGCTTATCAGGAAAGGCGTAAATTTCTTTCGTCCACGGATTAAGGCCG
     GTAGTTGCGGGTGGTGGCCTTGCTACGGTAAGACGAATAGTCCTTTCCGCATTTAAAGAAAGCAGGTGCCTAATTCCGGC
     80◄ D  V  G  V  V  P  V  I  G  N  Q  K  D  P  F  A  Y  I  E  K  T  W  P  N  L  G

1441 TACTGGTTGGCAACGATCAGTAATGCGATGAACTGCGCATCGCTGGCATCACCTTTAAATGCCGTCTGGCGAAGAGTGGT
     ATGACCAACCGTTGCTAGTCATTACGCTACTTGACGCGTAGCGACCGTAGTGGAAATTTACGGCAGACCGCTTCTCACCA
     53◄ Y  Q  N  A  V  I  L  L  A  I  F  Q  A  D  S  A  D  G  K  F  A  T  Q  R  L  T  T

SalI
1521 GATCAGTTCCTGTGGGTCGACAGAATCCATGCCGACACGTTCAGCCAGCTTCCCAGCCAGCGTTGCGAGTGCAGTACTCA
     CTAGTCAAGGACACCCAGCTGTCTTAGGTACGGCTGTGCAAGTCGGTCGAAGGGTCGGTCGCAACGCTCACGTCATGAGT
     27◄ I  L  E  Q  P  D  V  S  D  M  G  V  R  E  A  L  K  G  A  L  T  A  L  A  T  S  M

Bcl
1601 TTCGTTTTATACCTCTGAATCAATATCAACCTGGTGGTGAGCAATGGTTTCAACCATGTACCGGATGTGTTCTGCCATGC
     AAGCAAAATATGGAGACTTAGTTATAGTTGGACCACCACTCGTTACCAAAGTTGGTACATGGCCTACACAAGACGGTACG
      0◄        98◄ V  E  S  D  I  D  V  Q  H  H  A  I  T  E  V  M  Y  R  I  H  E  A  M  R

NsiI
1681 GCTCCTGAAACTCAACATCGTCATCAAACGCACGGGTAATGGATTTTTTGCTGGCCCCGTGGCGTTGCAAATGATCGATG
     CGAGGACTTTGAGTTGTAGCAGTAGTTTGCGTGCCCATTACCTAAAAAACGACCGGGGCACCGCAACGTTTACTAGCTAC
     74◄ E  Q  F  E  V  D  D  D  F  A  R  T  I  S  K  K  S  A  G  H  R  Q  L  H  D  I
```

FIG. 10B

```
                                        StuI
1761  CATAGCGATTCAAACAGGTGCTGGGGCAGGCCTTTTTCCATGTCGTCTGCCAGTTCTGCCTCTTTCTCTTCACGGGCGAG
      GTATCGCTAAGTTTGTCCACGACCCCGTCCGGAAAAAGGTACAGCAGACGGTCAAGACGGAGAAAGAGAAGTGCCCGCTC
 474◀  C  L  S  E  F  L  H  Q  P  L  G  K  E  M  D  D  A  L  E  A  E  K  E  E  R  A  L

Gam
1841  CTGCTGGTAGTGACGCGCCCAGCTCTGAGCCTCAAGACGATCCTGAATGTAATAAGCGTTCATGGCTGAACTCCTGAAAT
      GACGACCATCACTGCGCGGGTCGAGACTCGGAGTTCTGCTAGGACTTACATTATTCGCAAGTACCGACTTGAGGACTTTA
 214◀  Q  Q  Y  H  R  A  W  S  Q  A  E  L  R  D  Q  I  Y  Y  A  N  M

N -kil del
1921  AGCTGTGAAAATATCGCCCGCGAAATGCCGGGCTGATTAGTAATCCGGAATCGCACTTACGGCCAATGCTTCGTTTCGTA
      TCGACACTTTTATAGCGGGCGCTTTACGGCCCGACTAATCATTAGGCCTTAGCGTGAATGCCGGTTACGAAGCAAAGCAT 2001  TCACACACCCCAAAGCCTTCTGCTTTGAATGCTGCCCTTCTTCAGGGCTTAATTTTTAAGAGCGTCACCTTCATGGTGGT
      AGTGTGTGGGGTTTCGGAAGACGAAACTTACGACGGGAAGAAGTCCCGAATTAAAAATTCTCGCAGTGGAAGTACCACCA 2081  CAGTGCGTCCTGCTGATGTGCTCAGTATCACCGCCAGTGGTATTTATGTCAACACCGCCAGAGATAAATTTATCACCGCAG
      GTCACGCAGGACGACTACACGAGTCATAGTGGCGGTCACCATAAATACAGTTGTGGCGGTCTCTATTAAATAGTGGCGTC 2161  ATGGTTATCTGTATGTTTTTTATATGAATTTATTTTTTGCAGGGGGGCATTGTTTGGTAGGTGAGAGATCTGAATTGCTA
      TACCAATAGACATACAAAAAATATACTTAAATAAAAAACGTCCCCCCGTAACAAACCATCCACTCTCTAGACTTAACGAT 2241  TGTTTAGTGAGTTGTATCTATTTATTTTTCAATAAATACAATTGGTTATGTGTTTTGGGGCGATCGTGAGGCAAAGAAA
      ACAAATCACTCAACATAGATAAATAAAAAGTTATTTATGTTAACCAATACACAAAACCCCCGCTAGCACTCCGTTTCTTT
                                                           ◀───────────────────────── junction marker
2321  ACCCGGCGCTGAGGCCGGGTTAAGAGTTGGTAGCTCTTGATCCGGCAAACAAACCACCGCTGGTAGCGGTGGTTTTTTTG
      TGGGCCGCGACTCCGGCCCAATTCTCAACCATCGAGAACTAGGCCGTTTGTTTGGTGGCGACCATCGCCACCAAAAAAAC
      ─────────────────────────▶

2401  TTTGCAAGCAGCAGATTACGCGCAGAAAAAAAGGATCTCAAGAAGATCCTTTGATCTTTTCTACGGGGTCTGACGCTCAG
      AAACGTTCGTCGTCTAATGCGCGTCTTTTTTTCCTAGAGTTCTTCTAGGAAACTAGAAAAGATGCCCCAGACTGCGAGTC

2481  TGGAACGAAAACTCACGTTAAGGGATTTTGGTCATGAGATTATCAAAAAGGATCTTCACCTAGATCCTTTTAAATTAAAA
      ACCTTGCTTTTGAGTGCAATTCCCTAAAACCAGTACTCTAATAGTTTTTCCTAGAAGTGGATCTAGGAAAATTTAATTTT

2561  ATGAAGTTTTAAATCAATCTAAAGTATATATGAGTAAACTTGGTCTGACAGTTACCAATGCTTAATCAGTGAGGCACCTA
      TACTTCAAAATTTAGTTAGATTTCATATATACTCATTTGAACCAGACTGTCAATGGTTACGAATTAGTCACTCCGTGGAT
                                                      2864◀  W  H  K  I  L  S  A  G  I

2641  TCTCAGCGATCTGTCTATTTCGTTCATCCATAGTTGCCTGACTCCCCGTCGTGTAGATAACTACGATACGGGAGGGCTTA
      AGAGTCGCTAGACAGATAAAGCAAGTAGGTATCAACGGACTGAGGGGCAGCACATCTATTGATGCTATGCCCTCCCGAAT
 277◀  E  A  I  Q  R  N  R  E  D  M  T  A  Q  S  G  T  T  Y  I  V  V  I  R  S  P  K

2721  CCATCTGGCCCCAGTGCTGCAATGATACCGCGAGACCCACGCTCACCGGCTCCAGATTTATCAGCAATAAACCAGCCAGC
      GGTAGACCGGGGTCACGACGTTACTATGGCGCTCTGGGTGCGAGTGGCCGAGGTCTAAATAGTCGTTATTTGGTCGGTCG
 250◀  G  D  P  G  L  A  A  I  I  G  R  S  G  R  E  G  A  G  S  K  D  A  I  F  W  G  A

2801  CGGAAGGGCCGAGCGcagaagtggtcctgcaactTTATCCGCCTCCATCCAGTCTATTAATTGTTGCCGGGAAGCTAGAG
      GCCTTCCCGGCTCGCgtcttcaccaggacgttgaAATAGGCGGAGGTAGGTCAGATAATTAACAACGGCCCTTCGATCTC
 224◀  P  L  A  S  R  L  L  P  G  A  V  K  D  A  E  M  W  D  I  L  Q  Q  R  S  A  L  T
```

FIG. 10C

```
2881 TAAGTAGTTCGCCAGTTAATAGTTTGCGCAACGTTGTTGCCATTGCTGCAGGCATCGTGGTGTCACGCTCGTCGTTTGGT
     ATTCATCAAGCGGTCAATTATCAAACGCGTTGCAACAACGGTAACGACGTCCGTAGCACCACAGTGCGAGCAGCAAACCA
1974  L  L  E  G  T  L  L  K  R  L  T  T  A  M  A  A  P  M  T  T  D  R  E  D  N  P

2961 ATGGCTTCATTCAGCTCCGGTTCCCAACGATCAAGGCGAGTTACATGATCCCCCATGTTGTGCAAAAAGCGGTTAGCTC
     TACCGAAGTAAGTCGAGGCCAAGGGTTGCTAGTTCCGCTCAATGTACTAGGGGGTACAACACGTTTTTTCGCCAATCGAG
1704 I  A  E  N  L  E  P  E  W  R  D  L  R  T  V  H  D  G  M  N  H  L  F  A  T  L  E

3041 CTTCGGTCCTCCGATCGTTGTCAGAAGTAAGTTGGCCGCAGTGTTATCACTCATGGTTATGGCAGCACTGCATAATTCTC
     GAAGCCAGGAGGCTAGCAACAGTCTTCATTCAACCGGCGTCACAATAGTGAGTACCAATACCGTCGTGACGTATTAAGAG
1444  K  P  G  G  I  T  T  L  L  L  N  A  A  T  N  D  S  M  T  I  A  A  S  C  L  E  R

3121 TTACTGTCATGCCATCCGTAAGATGCTTTTCTGTGACTggtgagtactcaaccaagtcATTCTGAGAATAGTGTATGCGG
     AATGACAGTACGGTAGGCATTCTACGAAAAGACACTGAccactcatgagttggttcagTAAGACTCTTATCACATACGCC
1174  V  T  M  G  D  T  L  H  K  E  T  V  P  S  Y  E  V  L  D  N  Q  S  Y  H  I  R 3201 CGACCGAGTTGCTCTTGCCCGGCGTCAACACGGGATAATACCGCGCCACATAGCAGAACTTTAAAAGTGCTCATCATTGG
     GCTGGCTCAACGAGAACGGGCCGCAGTTGTGCCCTATTATGGCGCGGTGTATCGTCTTGAAATTTTCACGAGTAGTAACC
904 R  G  L  Q  E  Q  G  A  D  V  R  S  L  V  A  G  C  L  L  V  K  F  T  S  M  M  P 3281 AAAACGTTCTTCGGGGCGAAAACTCTCAAGGATCTTACCGCTGTTGAGATCCAGTTCGATGTAACCCACTCGTGCACCCA
     TTTTGCAAGAAGCCCCGCTTTTGAGAGTTCCTAGAATGGCGACAACTCTAGGTCAAGCTACATTGGGTGAGCACGTGGGT
644  F  R  E  E  P  R  F  S  E  L  I  K  G  S  N  L  D  L  E  I  Y  G  V  R  A  G  L 3361 ACTGATCTTCAGCATCTTTTACTTTCACCAGCGTTTCTGGGTGAGCAAAAACAGGAAGCAAAATGCCCAAAAAAGGGA
     TGACTAGAAGTCGTAGAAAATGAAAGTGGTCGCAAAGACCCACTCGTTTTTGTCCTTCCGTTTTACGGGTTTTTTCCCT
374  Q  D  E  A  D  K  V  K  V  L  T  E  P  H  A  F  V  P  L  C  F  A  A  F  F  P amp
3441 ATAAGGGCGACACGGAAATGTTGAATACTCATACTCTTCCTTTTTCAATATTATTGAAGCATTTATCAGGGTTATTGTCT
     TATTCCCGCTGTGCCTTTACAACTTATGAGTATGAGAAGGAAAAAGTTATAATAACTTCGTAAATAGTCCCAATAACAGA
104 I  L  A  V  R  F  H  Q  I  S  M rexA'
3521 CATGAGCGGATACATATTTGAATGAATTCAATCCATTTACTATGTTATGTTCTGAGGGGAGTGAAAATTCCCCTAATTCG
     GTACTCGCCTATGTATAAACTTACTTAAGTTAGGTAAATGATACAATACAAGACTCCCCTCACTTTTAAGGGGATTAAGC
                            ←――――――――――――――――――――――――――――――――――――――――――――――――

3601 ATGAAGATTCTTGCTCAATTGTTATCAGCTATGCGCCGACCAGAACACCTTGCCGATCAGCCAAACGTCTCTTCAGGCCA
     TACTTCTAAGAACGAGTTAACAATAGTCGATACGCGGCTGGTCTTGTGGAACGGCTAGTCGGTTTGCAGAGAAGTCCGGT
                                                                     2374  G  F  T  E  E  P  W

3681 CTGACTAGCGATAACTTTCCCCACAACGGAACAACTCTCATTGCATGGGATCATTGGGTACTGTGGGTTTAGTGGTTGTA
     GACTGATCGCTATTGAAAGGGGTGTTGCCTTGTTGAGAGTAACGTACCCTAGTAACCCATGACACCCAAATCACCAACAT
2304  Q  S  A  I  V  K  G  V  V  S  C  S  E  N  C  P  I  M  P  Y  Q  P  N  L  P  Q  L

3761 AAAACACCTGACCGCTATCCCTGATCAGTTTCTTGAAGGTAAACTCATCACCCCCAAGTCTGGCTATGCAGAAATCACCT
     TTTTGTGGACTGGCGATAGGGACTAGTCAAAGAACTTCCATTTGAGTAGTGGGGGTTCAGACCGATACGTCTTTAGTGGA
2034  F  V  Q  G  S  D  R  I  L  K  K  F  T  F  E  D  G  G  L  R  A  I  C  F  D  G

HindIII
3841 GGCTCAACAGCCTGCTCAGGGTCAACGAGAATTAACATTCCGTCAGGAAAGCTTGGCTTGGAGCCTGTTGGTGCGGTCAT
     CCGAGTTGTCGGACGAGTCCCAGTTGCTCTTAATTGTAAGGCAGTCCTTTCGAACCGAACCTCGGACAACCACGCCAGTA
1764 P  E  V  A  Q  E  P  D  V  L  I  L  M  G  D  P  F  S  P  K  S  G  T  P  A  T  M
```

```
3921 GGAATTACCTTCAACCTCAAGCCAGAATGCAGAATCACTGGCTTTTTTGGTTGTGCTTACCCATCTCTCCGCATCACCTT
     CCTTAATGGAAGTTGGAGTTCGGTCTTACGTCTTAGTGACCGAAAAAACCAACACGAATGGGTAGAGAGGCGTAGTGGAA
150◄  S  N  G  E  V  E  L  W  F  A  S  D  S  A  K  K  T  T  S  V  W  R  E  A  D  G  K

HindIII
4001 TGGTAAAGGTTCTAAGCTTAGGTGAGAACATCCCTGCCTGAACATGAGAAAAAACAGGGTACTCATACTCACTTCTAAGT
     ACCATTTCCAAGATTCGAATCCACTCTTGTAGGGACGGACTTGTACTCTTTTTTGTCCCATGAGTATGAGTGAAGATTCA
123◄  T  F  T  R  L  K  P  S  F  M  G  A  Q  V  H  S  F  V  P  Y  E  Y  E  S  R  L 4081 GACGGCTGCATACTAACCGCTTCATACATCTCGTAGATTTCTCTGGCGATTGAAGGGCTAAATTCTTCAACGCTAACTTT
     CTGCCGACGTATGATTGGCGAAGTATGTAGAGCATCTAAAGAGACCGCTAACTTCCCGATTTAAGAAGTTGCGATTGAAA
96◄ S  P  Q  M  S  V  A  E  Y  M  E  Y  !  E  R  A  I  S  P  S  F  E  E  V  S  V  K NsiI
4161 GAGAATTTTTGTAAGCAATGCGGCGTTATAAGCATTTAATGCATTGATGCCATTAAATAAAGCACCAACGCCTGACTGCC
     CTCTTAAAAACATTCGTTACGCCGCAATATTCGTAAATTACGTAACTACGGTAATTTATTTCGTGGTTGCGGACTGACGG
70◄  L  I  K  T  L  L  A  A  N  Y  A  N  L  A  N  I  G  N  F  L  A  G  V  G  S  Q  G 4241 CCATCCCCATCTTGTCTGCGACAGATTCCTGGGATAAGCCAAGTTCATTTTTCTTTTTTTCATAAATTGCTTTAAGGCGA
     GGTAGGGGTAGAACAGACGCTGTCTAAGGACCCTATTCGGTTCAAGTAAAAAGAAAAAAAGTATTTAACGAAATTCCGCT
43◄  M  G  M  K  D  A  V  S  E  Q  S  L  G  L  E  N  K  K  K  E  Y  I  A  K  L  R cI
4321 CGTGCGTCCTCAAGCTGCTCTTGTGTTAATGGTTTCTTTTTTGTGCTCATACGTTAAATCTATCACCGCAAGGGATAAAT
     GCACGCAGGAGTTCGACGAGAACACAATTACCAAAGAAAAAACACGAGTATGCAATTTAGATAGTGGCGTTCCCTATTTA
16◄ R  A  D  E  L  Q  E  Q  T  L  P  K  K  K  T  S  M cro'
4401 ATCTAACACCGTGCGTGTTGACTATTTTACCTCTGGCGGTGATAATGGTTGCATGTACTAAGGAGGTTGTATGGAACAAC
     TAGATTGTGGCACGCACAACTGATAAAATGGAGACCGCCACTATTACCAACGTACATGATTCCTCCAACATACCTTGTTG
```

```
          PvuII   ori/pBBR1
4481 GAGATGTGTATAAGAGACAGCTGGCCTGCCCCTCCCTTTTGGTGTCCAACCGGCTCGACGGGGGCAGCGCAAGGCGGTGC
     CTCTACACATATTCTCTGTCGACCGGACGGGGAGGGAAAACCACAGGTTGGCCGAGCTGCCCCCGTCGCGTTCCGCCACG
```

```
4561 CTCCGGCGGGCCACTCAATGCTTGAGTATACTCACTAGACTTTGCTTCGCAAAGTCGTGACCGCCTACGGCGGCTGCGGC
     GAGGCCGCCCGGTGAGTTACGAACTCATATGAGTGATCTGAAACGAAGCGTTTCAGCACTGGCGGATGCCGCCGACGCCG
```

```
4641 GCCCTACGGGCTTGCTCTCCGGGCTTCGCCCTGCGCGGTCGCTGCGCTCCCTTGCCAGCCCGTGGATATGTGGACGATGG
     CGGGATGCCCGAACGAGAGGCCCGAAGCGGGACGCGCCAGCGACGCGAGGGAACGGTCGGGCACCTATACACCTGCTACC
```

```
4721 CCGCGAGCGGCCACCGGCTGGCTCGCTTCGCTCGGCCCGTGGACAACCCTGCTGGACAAGCTGATGGACAGGCTGCGCCT
     GGCGCTCGCCGGTGGCCGACCGAGCGAAGCGAGCCGGGCACCTGTTCGACCTGTTCGACTACCTGTCCGACGCGGA
```

```
4801 GCCCACGAGCTTGACCACAGGGATTGCCCACCGGCTACCCAGCCTTCGACCACATACCCACCGGCTCCAACTGCGCGGCC
     CGGGTGCTCGAACTGGTGTCCCTAACGGGTGGCCGATGGGTCGGAAGCTGGTGTATGGGTGGCCGAGGTTGACGCGCCGG
```

FIG. 10F

```
4881 TGCGGCCTTGCCCCATCAATTTTTTTAATTTTCTCTGGGGAAAAGCCTCCGGCCTGCGGCCTGCGCGCTTCGCTTGCCGG
     ACGCCGGAACGGGGTAGTTAAAAAAATTAAAAGAGACCCCTTTTCGGAGGCCGGACGCCGGACGCGCGAAGCGAACGGCC

4961 TTGGACACCAAGTGGAAGGCGGGTCAAGGCTCGCGCAGCGACCGCGCAGCGGCTTGGCCTTGACGCGCCTGGAACGACCC
     AACCTGTGGTTCACCTTCCGCCCAGTTCCGAGCGCGTCGCTGGCGCGTCGCCGAACCGGAACTGCGCGGACCTTGCTGGG

5041 AAGCCTATGCGAGTGGGGGCAGTCGAAGGCGAAGCCCGCCCGCCTGCCCCCCGAGCCTCACGGCGGCGAGTGCGGGGGTT
     TTCGGATACGCTCACCCCCGTCAGCTTCCGCTTCGGGCGGGCGGACGGGGGGCTCGGAGTGCCGCCGCTCACGCCCCCAA

5121 CCAAGGGGGCAGCGCCACCTTGGGCAAGGCCGAAGGCCGCGCAGTCGATCAACAAGCCCCGGAGGGGCCACTTTTTGCCG
     GGTTCCCCCGTCGCGGTGGAACCCGTTCCGGCTTCCGGCGCGTCAGCTAGTTGTTCGGGGCCTCCCCGGTGAAAAACGGC

5201 GAGGGGGAGCCGCGCCGAAGGCGTGGGGGAACCCCGCAGGGGTGCCCTTCTTTGGGCACCAAAGAACTAGATATAGGGCG
     CTCCCCCTCGGCGCGGCTTCCGCACCCCCTTGGGGCGTCCCCACGGGAAGAAACCCGTGGTTTCTTGATCTATATCCCGC

5281 AAATGCGAAAGACTTAAAAAATCAACAACTTAAAAAAGGGGGGTACGCAACAGCTCATTGCGGCACCCCCCGCAATAGCTC
     TTTACGCTTTCTGAATTTTTAGTTGTTGAATTTTTTCCCCCCATGCGTTGTCGAGTAACGCCGTGGGGGCGTTATCGAG

5361 ATTGCGTAGGTTAAAGAAAATCTGTAATTGACTGCCACTTTTACGCAACGCATAATTGTTGTCGCGCTGCCGAAAAGTTG
     TAACGCATCCAATTTCTTTTAGACATTAACTGACGGTGAAAATGCGTTGCGTATTAACAACAGCGCGACGGCTTTTCAAC

Rep
5441 CAGCTGATTGCGCATGGTGCCGCAACCGTGCGGCACCCTACCGCATGGAGATAAGCATGGCCACGCAGTCCAGAGAAATC
     GTCGACTAACGCGTACCACGGCGTTGGCACGCCGTGGGATGGCGTACCTCTATTCGTACCGGTGCGTCAGGTCTCTTTAG
                                                       1▶ M  A  T  Q  S  R  E  I

5521 GGCATTCAAGCCAAGAACAAGCCCGGTCACTGGGTGCAAACGGAACGCAAAGCGCATGAGGCGTGGGCCGGGCTTATTGC
     CCGTAAGTTCGGTTCTTGTTCGGGCCAGTGACCCACGTTTGCCTTGCGTTTCGCGTACTCCGCACCCGGCCCGAATAACG
     9▶ G  I  Q  A  K  N  K  P  G  H  W  V  Q  T  E  R  K  A  H  E  A  W  A  G  L  I  A

5601 GAGGAAACCCACGGCGGCAATGCTGCTGCATCACCTCGTGGCGCAGATGGGCCACCAGAACGCCGTGGTGGTCAGCCAGA
     CTCCTTTGGGTGCCGCCGTTACGACGACGTAGTGGAGCACCGCGTCTACCCGGTGGTCTTGCGGCACCACCAGTCGGTCT
     35▶ R  K  P  T  A  A  M  L  L  H  H  L  V  A  Q  M  G  H  Q  N  A  V  V  V  S  Q

5681 AGACACTTTCCAAGCTCATCGGACGTTCTTTGCGGACGGTCCAATACGCAGTCAAGGACTTGGTGGCCGAGCGCTGGATC
     TCTGTGAAAGGTTCGAGTAGCCTGCAAGAAACGCCTGCCAGGTTATGCGTCAGTTCCTGAACCACCGGCTCGCGACCTAG
     62▶ K  T  L  S  K  L  I  G  R  S  L  R  T  V  Q  Y  A  V  K  D  L  V  A  E  R  W  I
```

```
5761  TCCGTCGTGAAGCTCAACGGCCCCGGCACCGTGTCGGCCTACGTGGTCAATGACCGCGTGGCGTGGGGCCAGCCCCGCGA
      AGGCAGCACTTCGAGTTGCCGGGGCCGTGGCACAGCCGGATGCACCAGTTACTGGCGCACCGCACCCCGGTCGGGCGCT
  89▶ S   V   V   K   L   N   G   P   G   T   V   S   A   Y   V   V   N   D   R   V   A   W   G   Q   P   R   D

5841  CCAGTTGCGCCTGTCGGTGTTCAGTGCCGCCGTGGTGGTGATCACGACGACCAGGACGAATCGCTGCTGGGCCATGGCG
      GGTCAACGCGGACAGCCACAAGTCACGGCGGCACCACCAACTAGTGCTGCTGGTCCTGCTTAGCGACGACCCCGTACCGC
 115▶ Q   L   R   L   S   V   F   S   A   A   V   V   V   D   H   D   D   Q   D   E   S   L   L   G   H   G

5921  ACCTGCGCCGCATCCCGACCCTGTATCCGGGCGAACAGCAACTACCGACGGGCCCGGCGAGGAGCCGCCCAGCCAGCTC
      TGGACGCGGCGTAGGGCTGGGACATAGGCCCGCTTGTCGTTGATGGCTGCCCGGGCCGCTCCTCGGCGGGTCGGTCGAG
 142▶ D   L   R   R   I   P   T   L   Y   P   G   E   Q   Q   L   P   T   G   P   G   E   E   P   P   S   Q   P

6001  GGCATTCCGGGCATGGAACCAGACCTGCCAGCCTTGACCGAAACGGAGGAATGGGAACGGCGCGGGCAGCAGCGCCTGC
      CCGTAAGGCCCGTACCTTGGTCTGGACGGTCGGAACTGGCTTTGCCTCCTTACCCTTGCCGCGCCCGTCGTCGCGGACG
 169▶ G   I   P   G   M   E   P   D   L   P   A   L   T   E   T   E   E   W   E   R   R   G   Q   Q   R   L   P

6081  GATGCCCGATGAGCCGTGTTTTCTGGACGATGGCGAGCCATTGGAGCCGCCGACAGGGTCACGCTGCCGCGCCAGTAGC
      CTACGGGCTACTCGGCACAAAAGACCTGCTACCGCTCGGCAACCTCGGCGGCTGTGCCAGTGCGACGGCGCGGTCATCG
 195▶ M   P   D   E   P   C   F   L   D   D   G   E   P   L   E   P   P   T   R   V   T   L   P   R   R

6161  ACTTGGGTTGCGCAGCAACCCGTAAGTGGCCTGTTCCAGACTATCGGCGTGTAGCCGCCTCG
      TGAACCCAACGCGTCGTTGGGCATTCACCGGACAAGGTCTGATAGCCGCACATCGGCGGAGC
                                                    ◀
```

FIG. 10G

```
     PvuII     Tn5 site          tL3
  1  CAGCTGTCTCTTATACACATCTCCGCTGTGCTTTCAGTGGATTTCGGATAACAGAAAGGCCGGGAAATACCCAGCCTCGC
     GTCGACAGAGAATATGTGTAGAGGCGACACGAAAGTCACCTAAAGCCTATTGTCTTTCCGGCCCTTTATGGGTCGGAGCG 81  TTTGTAACGGAGTAGACGAAAGTGATTGCGCCTACCCGGATATTATCGTGAGGATGCGTCATCGCCATTGCTCCCCAAAT
     AAACATTGCCTCATCTGCTTTCACTAACGCGGATGGGCCTATAATAGCACTCCTACGCAGTAGCGGTAACGAGGGGTTTA 226◀ R  W  Q  E  G  F
161  ACAAAACCAATTTCAGCCAGTGCCTCGTCCATTTTTTCGATGAACTCCGGCACGATCTCGTCAAAACTCGCCATGTACTT
     TGTTTTGGTTAAAGTCGGTCACGGAGCAGGTAAAAAAGCTACTTGAGGCCGTGCTAGAGCAGTTTTGAGCGGTACATGAA 219◀ V  F  G  I  E  A  L  A  E  D  M  K  E  I  F  E  P  V  I  E  D  F  S  A  M  Y  K
                                            StuI
241  TTCATCCCGCTCAATCACGACATAATGCAGGCCTTCACGCTTCATACGCGGGTCATAGTTGGCAAAGTACCAGGCATTTT
     AAGTAGGGCGAGTTAGTGCTGTATTACGTCCGGAAGTGCGAAGTATGCGCCCAGTATCAACCGTTTCATGGTCCGTAAAA 193◀ E  D  R  E  I  V  V  Y  H  L  G  E  R  K  M  R  P  D  Y  N  A  F  Y  W  A  N  K 321  TTCGCGTCACCCACATGCTGTACTGCACCTGGGCCATGTAAGCTGACTTTATGGCCTCGAAACCACCGAGCCGGAACTTC
     AAGCGCAGTGGGTGTACGACATGACGTGGACCCGGTACATTCGACTGAAATACCGGAGCTTTGGTGGCTCGGCCTTGAAG 166◀ R  T  V  W  M  S  Y  Q  V  Q  A  M  Y  A  S  K  I  A  E  F  G  G  L  R  F  K
             SmaI
401  ATGAAATCCCGGGAGGTAAACGGGCATTTCAGTTCAAGGCCGTTGCCGTCACTGCATAAACCATCGGGAGAGCAGGCGGT
     TACTTTAGGGCCCTCCATTTGCCCGTAAAGTCAAGTTCCGGCAACGGCAGTGACGTATTTGGTAGCCCTCTCGTCCGCCA 139◀ M  F  D  R  S  T  F  P  C  K  L  E  L  G  N  D  S  C  L  G  D  P  S  C  A  T 481  ACGCATACTTTCGTCGCGATAGATGATCCGGGATTCAGTAACATTCACGCCGGAAGTGAAcTCAAACAGGGTTCTGGCGT
     TGCGTATGAAAGCAGCGCTATCTACTAGCCCCTAAGTCATTGTAAGTGCGGCCTTCACTTgAGTTTGTCCCAAGACCGCA 113◀ R  M  S  E  D  R  Y  I  I  P  S  E  T  V  N  V  G  S  T  F  E  F  L  T  R  A  D 561  CGTTCTCGTACTGTTTTCCCCAGGCCAGTGCTTTAGCGTTAACTTCCGGAGCCACACCGGTGCAAACCTCAGCAAGCAGG
     GCAAGAGCATGACAAAAGGGGTCCGGTCACGAAATCGCAATTGAAGGCCTCGGTGTGGCCACGTTTGGAGTCGTTCGTCC

86◀ N  E  Y  Q  K  G  W  A  L  A  K  A  N  V  E  P  A  V  G  T  C  V  E  A  L  L

641  GTGTGGAAGTAGGACATTTTCATGTCAGGCCACTTCTTTCCGGAGCGGGGTTTTGCTATCACGTTGTGAACTTCTGAAGC
     CACACCTTCATCCTGTAAAAGTACAGTCCGGTGAAGAAAGGCCTCGCCCAAAACGATAGTGCAACACTTGAAGACTTCG

59◀ T  H  F  Y  S  M  K  M  D  P  W  K  K  G  S  R  P  K  A  I  V  N  H  V  E  S  A
                                                                                PstI
721  GGTGATGACGCCGAGCCGTAATTTGTGCCACGCATCATCCCCCTGTTCGACAGCTCTCACATCGATCCGGTACGCTGCA
     CCACTACTGCGGCTCGGCATTAAACACGGTGCGTAGTAGGGGGACAAGCTGTCGAGAGTGTAGCTAGGGCCATGCGACGT

```
                          Exo
 801 GGATAATGTCCGGTGTCATGCTGCCACCTTCTGCTCTGCGGCTTTCTGTTTCAGGAATCCAAGAGCTTTTACTGCTTCGG
     CCTATTACAGGCCACAGTACGACGGTGGAAGACGAGACGCCGAAAGACAAAGTCCTTAGGTTCTCGAAAATGACGAAGCC
                    261◄  A  A  V  K  Q  E  A  A  K  Q  K  L  F  G  L  A  K  V  A  E  A
       6◄ I  I  D  P  T  M

881 CCTGTGTCAGTTCTGACGATGCACGAATGTCGCGGCGAAATATCTGGGAACAGAGCGGCAATAAGTCGTCATCCCATGTT
     GGACACAGTCAAGACTGCTACGTGCTTACAGCGCCGCTTTATAGACCCTTGTCTCGCCGTTATTCAGCAGTAGGGTACAA
     240◄ Q  T  L  E  S  S  A  R  I  D  R  R  F  I  Q  S  C  L  P  L  L  D  D  D  W  T

961 TTATCCAGGGCGATCAGCAGAGTGTTAATCTCCTGCATGGTTTCATCGTTAACCGGAGTGATGTCGCGTTCCGGCTGACG
     AATAGGTCCCGCTAGTCGTCTCACAATTAGAGGACGTACCAAAGTAGCAATTGGCCTCACTACAGCGCAAGGCCGACTGC
     213◄ K  D  L  A  I  L  L  T  N  I  E  Q  M  T  E  D  N  V  P  T  I  D  R  E  P  Q  R

PstI                                                                         BglI
1041 TTCTGCAGTGTATGCAGTATTTTCGACAATGCGCTCGGCTTCATCCTTGTCATAGATACCAGCAAATCCGAAGGCCAGAC
     AAGACGTCACATACGTCATAAAAGCTGTTACGCGAGCCGAAGTAGGAACAGTATCTATGGTCGTTTAGGCTTCCGGTCTG
     187◄ E  A  T  Y  A  T  N  E  V  I  R  E  A  E  D  K  D  Y  I  G  A  F  G  F  A  L  R

1121 GGGCACACTGAATCATGGCTTTATGACGTAACATCCGTTTGGGATGCGACTGCCACGGCCCCGTGATTTCTCTGCCTTCG
     CCCGTGTGACTTAGTACCGAAATACTGCATTGTAGGCAAACCCTACGCTGACGGTGCCGGGGCACTAAAGAGACGGAAGC
     160◄ A  C  Q  I  M  A  K  H  R  L  M  R  K  P  H  S  Q  W  P  G  T  I  E  R  G  E

1201 CGAGTTTTGAATGGTTCGCGGCGGCATTCATCCATCCATTCGGTAACGCAGATCGGATGATTACGGTCCTTGCGGTAAAT
     GCTCAAAACTTACCAAGCGCCGCCGTAAGTAGGTAGGTAAGCCATTGCGTCTAGCCTACTAATGCCAGGAACGCCATTTA
     133◄ R  T  K  F  P  E  R  R  C  E  D  M  W  E  T  V  C  I  P  H  N  R  D  K  R  Y  I

1281 CCGGCATGTACAGGATTCATTGTCCTGCTCAAAGTCCATGCCATCAAACTGCTGGTTTTCATTGATGATGCGGGACCAGC
     GGCCGTACATGTCCTAAGTAACAGGACGAGTTTCAGGTACGGTAGTTTGACGACCAAAAGTAACTACTACGCCCTGGTCG
     107◄ R  C  T  C  S  E  N  D  Q  E  F  D  M  G  D  F  Q  Q  N  E  N  I  I  R  S  W  G

1361 CATCAACGCCCACCACCGGAACGATGCCATTCTGCTTATCAGGAAAGGCGTAAATTTCTTTCGTCCACGGATTAAGGCCG
     GTAGTTGCGGGTGGTGGCCTTGCTACGGTAAGACGAATAGTCCTTTCCGCATTTAAAGAAAGCAGGTGCCTAATTCCGGC
      80◄ D  V  G  V  V  P  V  I  G  N  Q  K  D  P  F  A  Y  I  E  K  T  W  P  N  L  G

1441 TACTGGTTGGCAACGATCAGTAATGCGATGAACTGCGCATCGCTGGCATCACCTTTAAATGCCGTCTGGCGAAGAGTGGT
     ATGACCAACCGTTGCTAGTCATTACGCTACTTGACGCGTAGCGACCGTAGTGGAAATTTACGGCAGACCGCTTCTCACCA
      53◄ Y  Q  N  A  V  I  L  L  A  I  F  Q  A  D  S  A  D  G  K  F  A  T  Q  R  L  T  T

SalI
1521 GATCAGTTCCTGTGGGTCGACAGAATCCATGCCGACACGTTCAGCCAGCTTCCCAGCCAGCGTTGCGAGTGCAGTACTCA
     CTAGTCAAGGACACCCAGCTGTCTTAGGTACGGCTGTGCAAGTCGGTCGAAGGGTCGGTCGCAACGCTCACGTCATGAGT
      27◄ I  L  E  Q  P  D  V  S  D  M  G  V  R  E  A  L  K  G  A  L  T  A  L  A  T  S  M

Bet
1601 TTCGTTTTATACCTCTGAATCAATATCAACCTGGTGGTGAGCAATGGTTTCAACCATGTACCGGATGTGTTCTGCCATGC
     AAGCAAAATATGGAGACTTAGTTATAGTTGGACCACCACTCGTTACCAAAGTTGGTACATGGCCTACACAAGACGGTACG
       0◄              98◄ V  E  S  D  I  D  V  Q  H  H  A  I  T  E  V  M  Y  R  I  H  E  A  M  R

NsiI
1681 GCTCCTGAAACTCAACATCGTCATCAAACGCACGGGTAATGGATTTTTTGCTGGCCCCGTGGCGTTGCAAATGATCGATG
     CGAGGACTTTGAGTTGTAGCAGTAGTTTGCGTGCCCATTACCTAAAAAACGACCGGGGCACCGCAACGTTTACTAGCTAC
      74◄ E  Q  F  E  V  D  D  D  F  A  R  T  I  S  K  K  S  A  G  H  R  Q  L  H  D  I
```

FIG. 12B

```
                                    StuI
1761 CATAGCGATTCAAACAGGTGCTGGGGCAGGCCTTTTTCCATGTCGTCTGCCAGTTCTGCCTCTTTCTCTTCACGGGCGAG
     GTATCGCTAAGTTTGTCCACGACCCCGTCCGGAAAAAGGTACAGCAGACGGTCAAGACGGAGAAAGAGAAGTGCCCGCTC
 474 C  L  S  E  F  L  H  Q  P  L  G  K  E  M  D  D  A  L  E  A  E  K  E  E  R  A  L

GsrI
1841 CTGCTGGTAGTGACGCGCCCAGCTCTGAGCCTCAAGACGATCCTGAATGTAATAAGCGTTCATGGCTGAACTCCTGAAAT
     GACGACCATCACTGCGCGGGTCGAGACTCGGAGTTCTGCTAGGACTTACATTATTCGCAAGTACCGACTTGAGGACTTTA
 214 Q  Q  Y  H  R  A  W  S  Q  A  E  L  R  D  Q  I  Y  Y  A  N  M

N-kil del
1921 AGCTGTGAAAATATCGCCCGCGAAATGCCGGGCTGATTAGTAATCCGGAATCGCACTTACGGCCAATGCTTCGTTTCGTA
     TCGACACTTTTATAGCGGGCGCTTTACGGCCCGACTAATCATTAGGCCTTAGCGTGAATGCCGGTTACGAAGCAAAGCAT 2001 TCACACACCCCAAAGCCTTCTGCTTTGAATGCTGCCCTTCTTCAGGGCTTAATTTTTAAGAGCGTCACCTTCATGGTGGT
     AGTGTGTGGGGTTTCGGAAGACGAAACTTACGACGGGAAGAAGTCCCGAATTAAAAATTCTCGCAGTGGAAGTACCACCA 2081 CAGTGCGTCCTGCTGATGTGCTCAGTATCACCGCCAGTGGTATTTATGTCAACACCGCCAGAGATAATTTATCACCGCAG
     GTCACGCAGGACGACTACACGAGTCATAGTGGCGGTCACCATAAATACAGTTGTGGCGGTCTCTATTAAATAGTGGCGTC 2161 ATGGTTATCTGTATGTTTTTTATATGAATTTATTTTTTGCAGGGGGGCATTGTTTGGTAGGTGAGAGATCTGAATTGCTA
     TACCAATAGACATACAAAAAATATACTTAAATAAAAAACGTCCCCCCGTAACAAACCATCCACTCTCTAGACTTAACGAT 2241 TGTTTAGTGAGTTGTATCTATTTATTTTTTCAATAAATACAATTGGTTATGTGTTTTGGGGCGATCGTGAGGCAAAGAAA
     ACAAATCACTCAACATAGATAAATAAAAGTTATTTATGTTAACCAATACACAAAACCCCGCTAGCACTCCGTTTCTTT 2321 ACCCGGCGCTGAGGCCGGGTTACGCCCCGCCCTGCCACTCATCGCAGTACTGTTGTAATTCATTAAGCATTCTGCCGACA
     TGGGCCGCGACTCCGGCCCAATGCGGGGCGGGACGGTGAGTAGCGTCATGACAACATTAAGTAATTCGTAAGACGGCTGT
                                      219 A  G  G  Q  W  E  D  C  Y  Q  Q  L  E  N  L  M  R  G  V NcoI
2401 TGGAAGCCATCACAGACGGCATGATGAACCTGAATCGCCAGCGGCATCAGCACCTTGTCGCCTTGCGTATAATATTTGCC
     ACCTTCGGTAGTGTCTGCCGTACTACTTGGACTTAGCGGTCGCCGTAGTCGTGGAACAGCGGAACGCATATTATAAACGG
 199 H  F  G  D  C  V  A  H  H  V  Q  I  A  L  P  M  L  V  K  D  G  Q  T  Y  Y  K  G 2481 CATGGTGAAAACGGGGGCGAAGAAGTTGTCCATATTGGCCACGTTTAAATCAAAACTGGTGAAACTCACCCAGGGATTGG
     GTACCACTTTTGCCCCGCTTCTTCAACAGGTATAACCGGTGCAAATTTAGTTTTGACCACTTTGAGTGGGTCCCTAACC
 173 M  T  F  V  P  A  F  F  N  D  M  N  A  V  N  L  D  F  S  T  F  S  V  W  P  N  A 2561 CTGAGACGAAAAACATATTCTCAATAAACCCTTTAGGGAAATAGGCCAGGTTTTCACCGTAACACGCCACATCTTGCGAA
     GACTCTGCTTTTTGTATAAGAGTTATTTGGGAAATCCCTTTATCCGGTCCAAAAGTGGCATTGTGCGGTGTAGAACGCTT
 146 S  V  F  F  M  N  E  I  F  G  K  P  F  Y  A  L  N  E  G  Y  C  A  V  D  Q  S 2641 TATATGTGTAGAAACTGCCGGAAATCGTCGTGGTATTCACTCCAGAGCGATGAAAACGTTTCAGTTTGCTCATGGAAAAC
     ATATACACATCTTTGACGGCCTTTAGCAGCACCATAAGTGAGGTCTCGCTACTTTTGCAAAGTCAAACGAGTACCTTTTG
 119 Y  I  H  L  F  Q  R  F  D  D  H  Y  E  S  W  L  S  S  F  T  E  T  Q  E  H  F  V EcoRI
2721 GGTGTAACAAGGGTGAACACTATCCCATATCACCAGCTCACCGTCTTTCATTGCCATACGGAATTCCGGATGAGCATTCA
     CCACATTGTTCCCACTTGTGATAGGGTATAGTGGTCGAGTGGCAGAAAGTAACGGTATGCCTTAAGGCCTACTCGTAAGT
  93 T  Y  C  P  H  V  S  D  W  I  V  L  E  G  D  K  M  A  M  R  F  E  P  H  A  N  M
```

FIG. 12C

```
2801 TCAGGCGGGCAAGAATGTGAATAAAGCCGGATAAAACTTGTGCTTATTTTTCTTTACGGTCTTTAAAAAGGCCGTAATA
     AGTCCGCCCGTTCTTACACTTATTTCCGGCCTATTTTGAACACGAATAAAAGAAATGCCAGAAATTTTTCCGGCATTAT
 66◀ L  R  A  L  I  H  I  F  A  P  Y  F  K  H  K  N  K  K  V  T  K  L  F  A  T  I

PvuII
2881 TCCAGCTGAACGGTCTGGTTATAGGTACATTGAGCAACTGACTGAAATGCCTCAAAATGTTCTTTACGATGCCATTGGGA
     AGGTCGACTTGCCAGACCAATATCCATGTAACTCGTTGACTGACTTTACGGAGTTTTACAAGAAATGCTACGGTAACCCT
 39◀ D  L  Q  V  T  Q  N  Y  T  C  Q  A  V  S  Q  F  A  E  F  H  E  K  R  H  W  Q  S rexA'
                                      cat
2961 TATATCAACGGTGGTATATCCAGTGATTTTTTTCTCCATAATTCAATCCATTTACTATGTTATGTTCTGAGGGGACTGAA
     ATATAGTTGCCACCATATAGGTCACTAAAAAAGAGGTATTAAGTTAGGTAAATGATACAATACAAGACTCCCCTGACTT
 13◀ I  D  V  T  T  Y  G  T  I  K  K  E  M
        ◀━━━━━━━━━━━━━━━━━━━━━━━━━━━━━━━━━━━━━━━━━━━━━━━━━━━━━━━━━━━━━━━━━━━━━━━━━━━

3041 AATTCCCCTAATTCGATGAAGATTCTTGCTCAATTGTTATCAGCTATGCGCCGACCAGAACACCTTGCCGATCAGCCAAA
     TTAAGGGGATTAAGCTACTTCTAAGAACGAGTTAACAATAGTCGATACGCGGCTGGTCTTGTGGAACGGCTAGTCGGTTT
                                                                             237◀ G  F
     ━━━━━━━━━━━━━━━━

3121 CGTCTCTTCAGGCCACTGACTAGCGATAACTTTCCCCACAACGGAACAACTCTCATTGCATGGGATCATTGGGTACTGTG
     GCAGAGAAGTCCGGTGACTGATCGCTATTGAAAGGGGTGTTGCCTTGTTGAGAGTAACGTACCCTAGTAACCCATGACAC
 235◀ T  E  E  P  W  Q  S  A  I  V  K  G  V  V  S  C  S  E  N  C  P  I  M  P  Y  Q  P

3201 GGTTTAGTGGTTGTAAAAACACCTGACCGCTATCCCTGATCAGTTTCTTGAAGGTAAACTCATCACCCCCAAGTCTGGCT
     CCAAATCACCAACATTTTTGTGGACTGGCGATAGGGACTAGTCAAAGAACTTCCATTTGAGTAGTGGGGGTTCAGACCGA
 208◀ N  L  P  Q  L  F  V  Q  G  S  D  R  I  L  K  K  F  T  F  E  D  G  G  L  R  A

HindIII
3281 ATGCAGAAATCACCTGGCTCAACAGCCTGCTCAGGGTCAACGAGAATTAACATTCCGTCAGGAAAGCTTGGCTTGGAGCC
     TACGTCTTTAGTGGACCGAGTTGTCGGACGAGTCCCAGTTGCTCTTAATTGTAAGGCAGTCCTTTCGAACCGAACCTCGG
 181◀ I  C  F  D  G  P  E  V  A  Q  E  P  D  V  L  I  L  M  G  D  P  F  S  P  K  S  G 3361 TGTTGGTGCGGTCATGGAATTACCTTCAACCTCAAGCCAGAATGCAGAATCACTGGCTTTTTTGGTTGTGCTTACCCATC
     ACAACCACGCCAGTACCTTAATGGAAGTTGGAGTTCGGTCTTACGTCTTAGTGACCGAAAAAACCAACACGAATGGGTAG
 155◀ T  P  A  T  M  S  N  G  E  V  E  L  W  F  A  S  D  S  A  K  K  T  T  S  V  W  R HindIII
3441 TCTCCGCATCACCTTTGGTAAAGGTTCTAAGCTTAGGTGAGAACATCCCTGCCTGAACATGAGAAAAAACAGGGTACTCA
     AGAGGCGTAGTGGAAACCATTTCCAAGATTCGAATCCACTCTTGTAGGGACGGACTTGTACTCTTTTTTGTCCCATGAGT
 128◀ E  A  D  G  K  T  F  T  R  L  K  P  S  F  M  G  A  Q  V  H  S  F  V  P  Y  E 3521 TACTCACTTCTAAGTGACGGCTGCATACTAACCGCTTCATACATCTCGTAGATTTCTCTGGCGATTGAAGGGCTAAATTC
     ATGAGTGAAGATTCACTGCCGACGTATGATTGGCGAAGTATGTAGAGCATCTAAAGAGACCGCTAACTTCCCGATTTAAG
 101◀ Y  E  S  R  L  S  P  Q  M  S  V  A  E  Y  M  E  Y  I  E  R  A  I  S  P  S  F  E NsiI
3601 TTCAACGCTAACTTTGAGAATTTTTGTAAGCAATGCGGCGTTATAAGCATTTAATGCATTGATGCCATTAAATAAAGCAC
     AAGTTGCGATTGAAACTCTTAAAAACATTCGTTACGCCGCAATATTCGTAAATTACGTAACTACGGTAATTTATTTCGTG
  75◀ E  V  S  V  K  L  I  K  T  L  L  A  A  N  Y  A  N  L  A  N  I  G  N  F  L  A  G 3681 CAACGCCTGACTGCCCCATCCCCATCTTGTCTGCGACAGATTCCTGGGATAAGCCAAGTTCATTTTTCTTTTTTTCATAA
     GTTGCGGACTGACGGGGTAGGGGTAGAACAGACGCTGTCTAAGGACCCTATTCGGTTCAAGTAAAAAGAAAAAAGTATT
  48◀ V  G  S  Q  G  M  G  M  K  D  A  V  S  E  Q  S  L  G  L  E  N  K  K  K  E  Y
```

```
                                                                          cI
3761 ATTGCTTTAAGGCGACGTGCGTCCTCAAGCTGCTCTTGTGTTAATGGTTTCTTTTTTGTGCTCATACGTTAAATCTATCA
     TAACGAAATTCCGCTGCACGCAGGAGTTCGACGAGAACACAATTACCAAAGAAAAAACACGAGTATGCAATTTAGATAGT
  214 I  A  K  L  R  R  A  D  E  L  Q  E  Q  T  L  P  K  K  K  T  S  M

3841 CCGCAAGGGATAAATATCTAACACCGTGCGTGTTGACTATTTTACCTCTGGCGGTGATAATGGTTGCATGTACTAAGGAG
     GGCGTTCCCTATTTATAGATTGTGGCACGCACAACTGATAAAATGGAGACCGCCACTATTACCAACGTACATGATTCCTC
                                                                    _____ cro'                         PvuII
3921 GTTGTATGGAACAACGAGATGTGTATAAGAGACAGCTGGCGCTCTTCCGCTTCCTCGCTCACTGACTCGCTGCGCTCGGT
     CAT ATA CTTGTTGCTCTACACATATTCTCTGTCGACCGCGAGAAGGCG AGGAGCGAGTGACTGAGCGACGCGAGCCA
     _____→

4001 CGTTCGGCTGCGGCGAGCGGTATCAGCTCACTCAAAGGCGGTAATACGGTTATCCACAGAATCAGGGGATAACGCAGGAA
     GCAAGCCGACGCCGCTCGCCATAGTCGAGTGAGTTTCCGCCATTATGCCAATAGGTGTCTTAGTCCCCTATTGCGTCCTT

4081 AGAACATGTGAGCAAAAGGCCAGCAAAAGGCCAGGAACCGTAAAAAGGCCGCGTTGCTGGCGTTTTTCCATAGGCTCCGC
     TCTTGTACACTCGTTTTCCGGTCGTTTTCCGGTCCTTGGCATTTTTCCGGCGCAACGACCGCAAAAAGGTATCCGAGGCG

4161 CCCCCTGACGAGCATCACAAAAATCGACGCTCAAGTCAGAGGTGGCGAAACCCGACAGGACTATAAAGATACCAGGCGTT
     GGGGGACTGCTCGTAGTGTTTTAGCTGCGAGTTCAGTCTCCACCGCTTTGGGCTGTCCTGATATTTCTATGGTCCGCAA

4241 TCCCCCTGGAAGCTCCCTCGTGCGCTCTCCTGTTCCGACCCTGCCGCTTACCGGATACCTGTCCGCCTTTCTCCCTTCGG
     AGGGGGACCTTCGAGGGAGCACGCGAGAGGACAAGGCTGGGACGGCGAATGGCCTATGGACAGGCGGAAAGAGGGAAGCC

4321 GAAGCGTGGCGCTTTCTCATAGCTCACGCTGTAGGTATCTCAGTTCGGTGTAGGTCGTTCGCTCCAAGCTGGGCTGTGTG
     CTTCGCACCGCGAAAGAGTATCGAGTGCGACATCCATAGAGTCAAGCCACATCCAGCAAGCGAGGTTCGACCCGACACAC

4401 CACGAACCCCCCGTTCAGCCCGACCGCTGCGCCTTATCCGGTAACTATCGTCTTGAGTCCAACCCGGTAAGACACGACTT
     GTGCTTGGGGGGCAAGTCGGGCTGGCGACGCGGAATAGGCCATTGATAGCAGAACTCAGGTTGGGCCATTCTGTGCTGAA

4481 ATCGCCACTGGCAGCAGCCACTGGTAACAGGATTAGCAGAGCGAGGTATGTAGGCGGTGCTACAGAGTTCTTGAAGTGGT
     TAGCGGTGACCGTCGTCGGTGACCATTGTCCTAATCGTCTCGCTCCATACATCCGCCACGATGTCTCAAGAACTTCACCA

4561 GGCCTAACTACGGCTACACTAGAAGGACAGTATTTGGTATCTGCGCTCTGCTGAAGCCAGTTACCTTCGGAAAAAGAGTT
     CCGGATTGATGCCGATGTGATCTTCCTGTCATAAACCATAGACGCGAGACGACTTCGGTCAATGGAAGCCTTTTTCTCAA

4641 GGTAGCTCTTGATCCGGCAAACAAACCACCGCTGGTAGCGGTGGTTTTTTTGTTTGCAAGCAGCAGATTACGCGCAGAAA
     CCATCGAGAACTAGGCCGTTTGTTTGGTGGCGACCATCGCCACCAAAAAAACAAACGTTCGTCGTCTAATGCGCGTCTTT

4721 AAAAGGATCTCAAGAAGATCCTTTGATCTTTTCTACGGGGTCTGACGCTCAGTGGAACGAAAACTCACGTTAAGGGATTT
     TTTTCCTAGAGTTCTTCTAGGAAACTAGAAAAGATGCCCCAGACTGCGAGTCACCTTGCTTTTGAGTGCAATTCCCTAAA

4801 TGGTCATGAGATTATCAAAAAGGATCTTCACCCTAGATCCTTTTAAATTAAAAATGAAGTTTTAAATCAATCTAAAGTATA
     ACCAGTACTCTAATAGTTTTTCCTAGAAGTGGATCTAGGAAAATTTAATTTTTACTTCAAAATTTAGTTAGATTTCATAT ori,colE1
4881 TATGAGTAAACTTGGTCTGACAGTTAC
     ATACTCATTTGAACCAGACTGTCAATG
     ←_____
```

```
       PvuII   Tn5 site         tL3
  1  CAGCTGTCTCTTATACACATCTCCGCTGTGCTTTCAGTGGATTTCGGATAACAGAAAGGCCGGGAAATACCCAGCCTCGC
     GTCGACAGAGAATATGTGTAGAGGCGACACGAAAGTCACCTAAAGCCTATTGTCTTTCCGGCCCTTTATGGGTCGGAGCG 81  TTTGTAACGGAGTAGACGAAAGTGATTGCGCCTACCCGGATATTATCGTGAGGATGCGTCATCGCCATTGCTCCCCAAAT
     AAACATTGCCTCATCTGCTTTCACTAACGCGGATGGGCCTATAATAGCACTCCTACGCAGTAGCGGTAACGAGGGGTTTA 226◄ R  W  Q  E  G  F
161  ACAAAACCAATTTCAGCCAGTGCCTCGTCCATTTTTTCGATGAACTCCGGCACGATCTCGTCAAAACTCGCCATGTACTT
     TGTTTTGGTTAAAGTCGGTCACGGAGCAGGTAAAAAAGCTACTTGAGGCCGTGCTAGAGCAGTTTTGAGCGGTACATGAA 219◄ V  F  G  I  E  A  L  A  E  D  M  K  E  I  F  E  P  V  I  E  D  F  S  A  M  Y  K StuI
241  TTCATCCCGCTCAATCACGACATAATGCAGGCCTTCACGCTTCATACGCGGGTCATAGTTGGCAAAGTACCAGGCATTTT
     AAGTAGGGCGAGTTAGTGCTGTATTACGTCCGGAAGTGCGAAGTATGCGCCCAGTATCAACCGTTTCATGGTCCGTAAAA 193◄ E  D  R  E  I  V  V  Y  H  L  G  E  R  K  M  R  P  D  Y  N  A  F  Y  W  A  N  K 321  TTCGCGTCACCCACATGCTGTACTGCACCTGGGCCATGTAAGCTGACTTTATGGCCTCGAAACCACCGAGCCGGAACTTC
     AAGCGCAGTGGGTGTACGACATGACGTGGACCCGGTACATTCGACTGAAATACCGGAGCTTTGGTGGCTCGGCCTTGAAG 166◄ R  T  V  W  M  S  Y  Q  V  Q  A  M  Y  A  S  K  I  A  E  F  G  G  L  R  F  K SmaI
401  ATGAAATCCCGGGAGGTAAACGGGCATTTCAGTTCAAGGCCGTTGCCGTCACTGCATAAACCATCGGAGAGCAGGCGGT
     TACTTTAGGGCCCTCCATTTGCCCGTAAAGTCAAGTTCCGGCAACGGCAGTGACGTATTTGGTAGCCCTCTCGTCCGCCA 139◄ M  F  D  R  S  T  F  P  C  K  L  E  L  G  N  G  D  S  C  L  G  D  P  S  C  A  T 481  ACGCATACTTTCGTCGCGATAGATGATCGGGGATTCAGTAACATTCACGCCGGAAGTGAACTCAAACAGGGTTCTGGCGT
     TGCGTATGAAAGCAGCGCTATCTACTAGCCCCTAAGTCATTGTAAGTGCGGCCTTCACTTGAGTTTGTCCCAAGACCGCA 113◄ R  M  S  E  D  R  Y  I  I  P  S  E  T  V  N  V  G  S  T  F  E  F  L  T  R  A  D 561  CGTTCTCGTACTGTTTTCCCCAGGCCAGTGCTTTAGCGTTAACTTCCGGAGCCACACCGGTGCAAACCTCAGCAAGCAGG
     GCAAGAGCATGACAAAAGGGGTCCGGTCACGAAATCGCAATTGAAGGCCTCGGTGTGGCCACGTTTGGAGTCGTTCGTCC

86◄ N  E  Y  Q  K  G  W  A  L  A  K  A  N  V  E  P  A  V  G  T  C  V  E  A  L  L

641  GTGTGGAAGTAGGACATTTTCATGTCAGGCCACTTCTTTCCGGAGCGGGGTTTTGCTATCACGTTGTGAACTTCTGAAGC
     CACACCTTCATCCTGTAAAAGTACAGTCCGGTGAAGAAAGGCCTCGCCCCAAAACGATAGTGCAACACTTGAAGACTTCG

59◄ T  H  F  Y  S  M  K  M  D  P  W  K  K  G  S  R  P  K  A  I  V  N  H  V  E  S  A

PstI
721  GGTGATGACGCCGAGCCGTAATTTGTGCCACGCATCATCCCCCTGTTCGACAGCTCTCACATCGATCCCGGTACGCTGCA
     CCACTACTGCGGCTCGGCATTAAACACGGTGCGTAGTAGGGGGACAAGCTGTCGAGAGTGTAGCTAGGGCCATGCGACGT

```
                        Exo
 801 GGATAATGTCCGGTGTCATGCTGCCACCTTCTGCTCTGCGGCTTTCTGTTTCAGGAATCCAAGAGCTTTTACTGCTTCGG
     CCTATTACAGGCCACAGTACGACGGTGGAAGACGAGACGCCGAAAGACAAAGTCCTTAGGTTCTCGAAAATGACGAAGCC
                    261◀ A  A  V  K  Q  E  A  A  K  Q  K  L  F  G  L  A  K  V  A  E  A
   6◀ I  I  D  P  T  M

881 CCTGTGTCAGTTCTGACGATGCACGAATGTCGCGGCGAAATATCTGGGAACAGAGCGGCAATAAGTCGTCATCCCATGTT
     GGACACAGTCAAGACTGCTACGTGCTTACAGCGCCGCTTTATAGACCCTTGTCTCGCCGTTATTCAGCAGTAGGGTACAA
 240◀ Q  T  L  E  S  S  A  R  I  D  R  R  F  I  Q  S  C  L  P  L  L  D  D  D  W  T

961 TTATCCAGGGCGATCAGCAGAGTGTTAATCTCCTGCATGGTTTCATCGTTAACCGGAGTGATGTCGCGTTCCGGCTGACG
     AATAGGTCCCGCTAGTCGTCTCACAATTAGAGGACGTACCAAAGTAGCAATTGGCCTCACTACAGCGCAAGGCCGACTGC
 213◀ K  D  L  A  I  L  L  T  N  I  E  Q  M  T  E  D  N  V  P  T  I  D  R  E  P  Q  R

PstI                                                                         BgII
1041 TTCTGCAGTGTATGCAGTATTTTCGACAATGCGCTCGGCTTCATCCTTGTCATAGATACCAGCAAATCCGAAGGCCAGAC
     AAGACGTCACATACGTCATAAAAGCTGTTACGCGAGCCGAAGTAGGAACAGTATCTATGGTCGTTTAGGCTTCCGGTCTG
 187◀ E  A  T  Y  A  T  N  E  V  I  R  E  A  E  D  K  D  Y  I  G  A  F  G  F  A  L  R

1121 GGGCACACTGAATCATGGCTTTATGACGTAACATCCGTTTGGGATGCGACTGCCACGGCCCCGTGATTTCTCTGCCTTCG
     CCCGTGTGACTTAGTACCGAAATACTGCATTGTAGGCAAACCCTACGCTGACGGTGCCGGGGCACTAAAGAGACGGAAGC
 160◀ A  C  Q  I  M  A  K  H  R  L  M  R  K  P  H  S  Q  W  P  G  T  I  E  R  G  E

1201 CGAGTTTTGAATGGTTCGCGGCGGCATTCATCCATCCATTCGGTAACGCAGATCGGATGATTACGGTCCTTGCGGTAAAT
     GCTCAAAACTTACCAAGCGCCGCCGTAAGTAGGTAGGTAAGCCATTGCGTCTAGCCTACTAATGCCAGGAACGCCATTTA
 133◀ R  T  K  F  P  E  R  R  C  E  D  M  W  E  T  V  C  I  P  H  N  R  D  K  R  Y  I

1281 CCGGCATGTACAGGATTCATTGTCCTGCTCAAAGTCCATGCCATCAAACTGCTGGTTTTCATTGATGATGCGGGACCAGC
     GGCCGTACATGTCCTAAGTAACAGGACGAGTTTCAGGTACGGTAGTTTGACGACCAAAAGTAACTACTACGCCCTGGTCG
 107◀ R  C  T  C  S  E  N  D  Q  E  F  D  M  G  D  F  Q  Q  N  E  N  I  I  R  S  W  G

1361 CATCAACGCCCACCACCGGAACGATGCCATTCTGCTTATCAGGAAAGGCGTAAATTTCTTTCGTCCACGGATTAAGGCCG
     GTAGTTGCGGGTGGTGGCCTTGCTACGGTAAGACGAATAGTCCTTTCCGCATTTAAAGAAAGCAGGTGCCTAATTCCGGC
  80◀ D  V  G  V  V  P  V  I  G  N  Q  K  D  P  F  A  Y  I  E  K  T  W  P  N  L  G

1441 TACTGGTTGGCAACGATCAGTAATGCGATGAACTGCGCATCGCTGGCATCACCTTTAAATGCCGTCTGGCGAAGAGTGGT
     ATGACCAACCGTTGCTAGTCATTACGCTACTTGACGCGTAGCGACCGTAGTGGAAATTTACGGCAGACCGCTTCTCACCA
  53◀ Y  Q  N  A  V  I  L  L  A  I  F  Q  A  D  S  A  D  G  K  F  A  T  Q  R  L  T  T

SalI
1521 GATCAGTTCCTGTGGGTCGACAGAATCCATGCCGACACGTTCAGCCAGCTTCCCAGCCAGCGTTGCGAGTGCAGTACTCA
     CTAGTCAAGGACACCCAGCTGTCTTAGGTACGGCTGTGCAAGTCGGTCGAAGGGTCGGTCGCAACGCTCACGTCATGAGT
  27◀ I  L  E  Q  P  D  V  S  D  M  G  V  R  E  A  L  K  G  A  L  T  A  L  A  T  S  M

Bet
1601 TTCGTTTTATACCTCTGAATCAATATCAACCTGGTGGTGAGCAATGGTTTCAACCATGTACCGGATGTGTTCTGCCATGC
     AAGCAAAATATGGAGACTTAGTTATAGTTGGACCACCACTCGTTACCAAAGTTGGTACATGGCCTACACAAGACGGTACG
   0◀        98◀ V  E  S  D  I  D  V  Q  H  H  A  I  T  E  V  M  Y  R  I  H  E  A  M  R

NsiI
1681 GCTCCTGAAACTCAACATCGTCATCAAACGCACGGGTAATGGATTTTTTTGCTGGCCCCGTGGCGTTGCAAATGATCGATG
     CGAGGACTTTGAGTTGTAGCAGTAGTTTGCGTGCCCATTACCTAAAAAACGACCGGGGCACCGCAACGTTTACTAGCTAC
  74◀ E  Q  F  E  V  D  D  D  F  A  R  T  I  S  K  K  S  A  G  H  R  Q  L  H  D  I
```

FIG. 14B

```
                                    StuI
1761 CATAGCGATTCAAACAGGTGCTGGGGCAGGCCTTTTTCCATGTCGTCTGCCAGTTCTGCCTCTTTCTCTTCACGGGCGAG
     GTATCGCTAAGTTTGTCCACGACCCCGTCCGGAAAAAGGTACAGCAGACGGTCAAGACGGAGAAAGAGAAGTGCCCGCTC
  474C   L   S   E   F   L   H   Q   P   L   G   K   E   M   D   D   A   L   E   A   E   K   E   E   R   A   L

Gam
1841 CTGCTGGTAGTGACGCGCCCAGCTCTGAGCCTCAAGACGATCCTGAATGTAATAAGCGTTCATGGCTGAACTCCTGAAAT
     GACGACCATCACTGCGCGGGTCGAGACTCGGAGTTCTGCTAGGACTTACATTATTCGCAAGTACCGACTTGAGGACTTTA
  214Q   Q   Y   H   R   A   W   S   Q   A   E   L   R   D   Q   I   Y   Y   A   N   M

N -kil del
1921 AGCTGTGAAAATATCGCCCGCGAAATGCCGGGCTGATTAGTAATCCGGAATCGCACTTACGGCCAATGCTTCGTTTCGTA
     TCGACACTTTTATAGCGGGCGCTTTACGGCCCGACTAATCATTAGGCCTTAGCGTGAATGCCGGTTACGAAGCAAAGCAT 2001 TCACACACCCCAAAGCCTTCTGCTTTGAATGCTGCCCTTCTTCAGGGCTTAATTTTTAAGAGCGTCACCTTCATGGTGGT
     AGTGTGTGGGGTTTCGGAAGACGAAACTTACGACGGGAAGAAGTCCCGAATTAAAAATTCTCGCAGTGGAAGTACCACCA 2081 CAGTGCGTCCTGCTGATGTGCTCAGTATCACCGCCAGTGGTATTTATGTCAACACCGCCAGAGATAATTTATCACCGCAG
     GTCACGCAGGACGACTACACGAGTCATAGTGGCGGTCACCATAAATACAGTTGTGGCGGTCTCTATTAAATAGTGGCGTC 2161 ATGCTTATCTGTATGTTTTTTATATGAATTTATTTTTTTGCAGGGGGGCATTGTTTGGTAGGTGAGAGATCTGAATTGCTA
     TACCAATAGACATACAAAAATATACTTAAATAAAAACGTCCCCCCGTAACAAACCATCCACTCTCTAGACTTAACGAT 2241 TGTTTAGTGAGTTGTATCTATTTATTTTTCAATAAATACAATTGGTTATGTGTTTTGGGGGCGATCGTGAGGCAAAGAAA
     ACAAATCACTCAACATAGATAAATAAAAGTTATTTATGTTAACCAATACACAAAACCCCCGCTAGCACTCCGTTTCTTT 2321 ACCCGGCGCTGAGGCCGGGTTACGCCCCGCCCTGCCACTCATCGCAGTACTGTTGTAATTCATTAAGCATTCTGCCGACA
     TGGGCCGCGACTCCGGCCCAATGCGGGGCGGGACGGTGAGTAGCGTCATGACAACATTAAGTAATTCGTAAGACGGCTGT
                                   2194A   G   G   Q   W   E   D   C   Y   Q   Q   L   E   N   L   M   R   G   V NcoI
2401 TGGAAGCCATCACAGACGGCATGATGAACCTGAATCGCCAGCGGCATCAGCACCTTGTCGCCTTGCGTATAATATTTGCC
     ACCTTCGGTAGTGTCTGCCGTACTACTTGGACTTAGCGGTCGCCGTAGTCGTGGAACAGCGGAACGCATATTATAAACGG
  1994H   F   G   D   C   V   A   H   H   V   Q   I   A   L   P   M   L   V   K   D   G   Q   T   Y   Y   K   G 2481 CATGGTGAAAACGGGGGCGAAGAAGTTGTCCATATTGGCCACGTTTAAATCAAAACTGGTGAAACTCACCCAGGGATTGG
     GTACCACTTTTGCCCCCGCTTCTTCAACAGGTATAACCGGTGCAAATTTAGTTTTGACCACTTTGAGTGGGTCCCTAACC
  1734M   T   F   V   P   A   F   F   N   D   M   N   A   V   N   L   D   F   S   T   F   S   V   W   P   N   A 2561 CTGAGACGAAAAACATATTCTCAATAAACCCTTTAGGGAAATAGGCCAGGTTTTCACCGTAACACGCCACATCTTGCGAA
     GACTCTGCTTTTTGTATAAGAGTTATTTGGGAAATCCCTTTATCCGGTCCAAAAGTGGCATTGTGCGGTGTAGAACGCTT
  1464S   V   F   F   M   N   E   I   F   G   K   P   F   Y   A   L   N   E   G   Y   C   A   V   D   Q   S 2641 TATATGTGTAGAAACTGCCGGAAATCGTCGTGGTATTCACTCCAGAGCGATGAAAACGTTTCAGTTTGCTCATGGAAAAC
     ATATACACATCTTTGACGGCCTTTAGCAGCACCATAAGTGAGGTCTCGCTACTTTTGCAAAGTCAAACGAGTACCTTTTG
  1194Y   I   H   L   F   Q   R   F   D   D   H   Y   E   S   W   L   S   S   F   T   E   T   Q   E   H   F   V EcoRI
2721 GGTGTAACAAGGGTGAACACTATCCCATATCACCAGCTCACCGTCTTTCATTGCCATACGGAATTCCGGATGAGCATTCA
     CCACATTGTTCCCACTTGTGATAGGGTATAGTGGTCGAGTGGCAGAAAGTAACGGTATGCCTTAAGGCCTACTCGTAAGT
   934T   Y   C   P   H   V   S   D   W   I   V   L   E   G   D   K   M   A   M   R   F   E   P   H   A   N   M
```

FIG. 14C

```
2801 TCAGGCGGGCAAGAATGTGAATAAAGGCCGGATAAAACTTGTGCTTATTTTTCTTTACGGTCTTTAAAAAGCCGTAATA
     AGTCCGCCCGTTCTTACACTTATTTCCGGCCTATTTTGAACACGAATAAAAAGAAATGCCAGAAATTTTTCCGGCATTAT
 664 L R A L   I H   F A P Y F K H K N K K V T K L F A T   I

PvuII
2881 TCCAGCTCAACGGTCTCGTTATAGGTACATTGAGCAACTGACTCAAATGCCTCAAAATGTTCTTTACGATGCCATTGGGA
     AGGTCGACTTGCCAGACCAATATCCATGTAACTCGTTGACTGACTTTACGGAGTTTTACAAGAAATGCTACGGTAACCCT
 394 D L Q V T Q N Y T C Q A V S Q F A E F H E K R H W Q S rexA'
                          cat
2961 TATATCAACGGTGGTATATCCAGTGATTTTTTCTCCATAATTCAATCCATTTACTATGTTATGTTCTGAGGGGAGTGAA
     ATATAGTTGCCACCATATAGGTCACTAAAAAAGAGGTATTAAGTTAGGTAAATGATACAATACAAGACTCCCCTCACTT
 134 I D V T T Y G T I K K E M 3041 AATTCCCCTAATTCGATGAAGATTCTTGCTCAATTGTTATCAGCTATGCGCCGACCAGAACACCTTGCCGATCAGCCAAA
     TTAAGGGGATTAAGCTACTTCTAAGAACGAGTTAACAATAGTCGATACGCGGCTGGTCTTGTGGAACGGCTAGTCGGTTT
                                                                             2374 G F 3121 CGTCTCTTCAGGCCACTGACTAGCGATAACTTTCCCCACAACGGAACAACTCTCATTGCATGGGATCATTGGGTACTGTG
     GCAGAGAAGTCCGGTGACTGATCGCTATTGAAAGGGGTGTTGCCTTGTTGAGAGTAACGTACCCTAGTAACCCATGACAC
 2354 T E E P W Q S A I V K G V V S C S E N C P I M P Y Q P 3201 GGTTTAGTGGTTGTAAAAACACCTGACCGCTATCCCTGATCAGTTTCTTGAAGGTAAACTCATCACCCCCAAGTCTGGCT
     CCAAATCACCAACATTTTTGTGGACTGGCGATAGGGACTAGTCAAAGAACTTCCATTTGAGTAGTGGGGGTTCAGACCGA
 2084 N L P Q L F V Q G S D R I L K K F T F E D G G L R A HindIII
3281 ATGCAGAAATCACCCTGGCTCAACAGCCTGCTCAGGGTCAACGAGAATTAACATTCCGTCAGGAAAGCTTGGCTTGGAGCC
     TACGTCTTTAGTGGGACCGAGTTGTCGGACGAGTCCCAGTTGCTCTTAATTGTAAGGCAGTCCTTTCGAACCGAACCTCGG
 1814 I C F D G P E V A Q E P D V L I L M G D P F S P K S G 3361 TGTTGGTGCGGTCATGGAATTACCTTCAACCTCAAGCCAGAATGCAGAATCACTGGCTTTTTTGGTTGTGCTTACCCATC
     ACAACCACGCCAGTACCTTAATGGAAGTTGGAGTTCGGTCTTACGTCTTAGTGACCGAAAAAACCAACACGAATGGGTAG
 1554 T P A T M S N G E V E L W F A S D S A K K T T S V W R HindIII
3441 TCTCCGCATCACCCTTTGGTAAAGGTTCTAAGCTTAGGTGAGAACATCCCTGCCTGAACATGAGAAAAAACAGGGTACTCA
     AGAGGCGTAGTGGGAAACCATTTCCAAGATTCGAATCCACTCTTGTAGGGACGGACTTGTACTCTTTTTTGTCCCATGAGT
 1284 E A D G K T F T R L K P S F M G A Q V H S F V P Y E 3521 TACTCACTTCTAAGTGACGGCTGCATACTAACCGCTTCATACATCTCGTAGATTTCTCTGGCGATTGAAGGGCTAAATTC
     ATGAGTGAAGATTCACTGCCGACGTATGATTGGCGAAGTATGTAGAGCATCTAAAGAGACCGCTAACTTCCCGATTTAAG
 1014 Y E S R L S P Q M S V A E Y M E Y I E R A I S P S F E NsiI
3601 TTCAACGCTAACTTTGAGAATTTTTGTAAGCAATGCGGCGTTATAAGCATTTAATGCATTGATGCCATTAAATAAAGCAC
     AAGTTGCGATTGAAACTCTTAAAAACATTCGTTACGCCGCAATATTCGTAAATTACGTAACTACGGTAATTTATTTCGTG
 754 E V S V K L I K T L L A A N Y A N L A N I G N F L A G 3681 CAACGCCTGACTGCCCCATCCCCATCTTGTCTGCGACAGATTCCTGGGATAAGCCAAGTTCATTTTTCTTTTTTTCATAA
     GTTGCGGACTGACGGGGTAGGGGTAGAACAGACGCTGTCTAAGGACCCTATTCGGTTCAAGTAAAAGAAAAAAGTATT
 484 V G S Q G M G M K D A V S E Q S L G L E N K K K E Y
```

```
                                                                                    cI
3761 ATTGCTTTAAGGCGACGTGCGTCCTCAAGCTGCTCTTGTGTTAATGGTTTCTTTTTTGTGCTCATACGTTAAATCTATCA
     TAACGAAATTCCGCTGCACGCAGGAGTTCGACGAGAACACAATTACCAAAGAAAAAACACGAGTATGCAATTTAGATAGT
  214 I  A  K  L  R  R  A  D  E  L  Q  E  Q  T  L  P  K  K  K  T  S  M

3841 CCGCAAGGGATAAATATCTAACACCGTGCGTGTTGACTATTTTACCTCTGGCGGTGATAATGGTTGCATGTACTAAGGAG
     GGCGTTCCCTATTTATAGATTGTGGCACGCACAACTGATAAAATGGAGACCGCCACTATTACCAACGTACATGATTCCTC cro'                             PvuII   ori/pBBR1
3921 GTTGTATGGAACAACGAGATGTGTATAAGAGACAGCTGGCCTGCCCCTCCCTTTTGGTGTCCAACCGGCTCGACGGGGGC
     CAACATACCTTGTTGCTCTACACATATTCTCTGTCGACCGGACGGGGAGGGAAAACCACAGGTTGGCCGAGCTGCCCCCG 4001 AGCGCAAGGCGGTGCCTCCGGCGGGCCACTCAATGCTTGAGTATACTCACTAGACTTTGCTTCGCAAAGTCGTGACCGCC
     TCGCGTTCCGCCACGGAGGCCGCCCGGTGAGTTACGAACTCATATGAGTGATCTGAAACGAAGCGTTTCAGCACTGGCGG 4081 TACGGCGGCTGCGGCGCCCTACGGGCTTGCTCTCCGGGCTTCGCCCTGCGCGGTCGCTGCGCTCCCTTGCCAGCCCGTGG
     ATGCCGCCGACGCCGCGGGATGCCCGAACGAGAGGCCCGAAGCGGGACGCGCCAGCGACGCGAGGGAACGGTCGGGCACC 4161 ATATGTGGACGATGGCCGCGAGCGGCCACCGGCTGGCTCGCTTCGCTCGGCCCGTGGACAACCCTGCTGGACAAGCTGAT
     TATACACCTGCTACCGGCGCTCGCCGGTGGCCGACCGAGCGAAGCGAGCCGGGCACCTGTTGGGACGACCTGTTCGACTA 4241 GGACAGGCTGCGCCTGCCCACGAGCTTGACCACAGGGATTGCCCACCGGCTACCCAGCCTTCGACCACATACCCACCGGC
     CCTGTCCGACGCGGACGGGTGCTCGAACTGGTGTCCCTAACGGGTGGCCGATGGGTCGGAAGCTGGTGTATGGGTGGCCG 4321 TCCAACTGCGCGGCCTGCGGCCTTGCCCCATCAATTTTTTTAATTTTCTCTGGGGAAAAGCCTCCGGCCTGCGGCCTGCG
     AGGTTGACGCGCCGGACGCCGGAACGGGGTAGTTAAAAAAATTAAAAGAGACCCCTTTTCGGAGGCCGGACGCCGGACGC 4401 CGCTTCGCTTGCCGGTTGGACACCAAGTGGAAGGCGGGTCAAGGCTCGCGCAGCGACCGCGCAGCGGCTTGGCCTTGACG
     GCGAAGCGAACGGCCAACCTGTGGTTCACCTTCCGCCCAGTTCCGAGCGCGTCGCTGGCGCGTCGCCGAACCGGAACTGC 4481 CGCCTGGAACGACCCAAGCCTATGCGAGTGGGGGCAGTCGAAGGCGAAGCCCGCCCGCCTGCCCCCCGAGCCTCACGGCG
     GCGGACCTTGCTGGGTTCGGATACGCTCACCCCCGTCAGCTTCCGCTTCGGGCGGGCGGACGGGGGGCTCGGAGTGCCGC 4561 GCGAGTGCGGGGGTTCCAAGGGGGCAGCGCCACCTTGGGCAAGGCCGAAGGCCGCGCAGTCGATCAACAAGCCCCGGAGG
     CGCTCACGCCCCAAGGTTCCCCCGTCGCGGTGGAACCCGTTCCGGCTTCCGGCGCGTCAGCTAGTTGTTCGGGGCCTCC
```

```
4641  GGCCACTTTTTGCCGGAGGGGGAGCCGCGCCGAAGGCGTGGGGGAACCCCGCAGGGGTGCCCTTCTTTGGGCACCAAAGA
      CCGGTGAAAAACGGCCTCCCCCTCGGCGCGGCTTCCGCACCCCCTTGGGGCGTCCCCACGGGAAGAAACCCGTGGTTTCT

4721  ACTAGATATAGGGCGAAATGCGAAAGACTTAAAAATCAACAACTTAAAAAAGGGGGGTACGCAACAGCTCATTGCGGCAC
      TGATCTATATCCCGCTTTACGCTTTCTGAATTTTTAGTTGTTGAATTTTTTCCCCCCATGCGTTGTCGAGTAACGCCGTG

4801  CCCCCGCAATAGCTCATTGCGTAGGTTAAAGAAAATCTGTAATTGACTGCCACTTTTACGCAACGCATAATTGTTGTCGC
      GGGGGCGTTATCGAGTAACGCATCCAATTTCTTTTAGACATTAACTGACGGTGAAAATGCGTTGCGTATTAACAACAGCG

Rep
4881  GCTGCCGAAAAGTTGCAGCTGATTGCGCATGGTGCCGCAACCGTGCGGCACCCTACCGCATGGAGATAAGCATGGCCACG
      CGACGGCTTTTCAACGTCGACTAACGCGTACCACGGCGTTGGCACGCCGTGGGATGGCGTACCTCTATTCGTACCGGTGC
                                                                           1▶ M  A  T

4961  CAGTCCAGAGAAATCGGCATTCAAGCCAAGAACAAGCCCGGTCACTGGGTGCAAACGGAACGCAAAGCGCATGAGGCGTG
      GTCAGGTCTCTTTAGCCGTAAGTTCGGTTCTTGTTCGGGCCAGTGACCCACGTTTGCCTTGCGTTTCGCGTACTCCGCAC
      4▶ Q  S  R  E  I  G  I  Q  A  K  N  K  P  G  H  W  V  Q  T  E  R  K  A  H  E  A  W

5041  GGCCGGGCTTATTGCGAGGAAACCCACGGCGGCAATGCTGCTGCATCACCTCGTGGCGCAGATGGGCCACCAGAACGCCG
      CCGGCCCGAATAACGCTCCTTTGGGTGCCGCCGTTACGACGACGTAGTGGAGCACCGCGTCTACCCGGTGGTCTTGCGGC
      30▶  A  G  L  I  A  R  K  P  T  A  A  M  L  L  H  H  L  V  A  Q  M  G  H  Q  N  A

5121  TGGTGGTCAGCCAGAAGACACTTTCCAAGCTCATCGGACGTTCTTTGCGGACGGTCCAATACGCAGTCAAGGACTTGGTG
      ACCACCAGTCGGTCTTCTGTGAAAGGTTCGAGTAGCCTGCAAGAAACGCCTGCCAGGTTATGCGTCAGTTCCTGAACCAC
      57▶ V  V  V  S  Q  K  T  L  S  K  L  I  G  R  S  L  R  T  V  Q  Y  A  V  K  D  L  V

5201  GCCGAGCGCTGGATCTCCGTCGTGAAGCTCAACGGCCCCGGCACCGTGTCGGCCTACGTGGTCAATGACCGCGTGGCGTG
      CGGCTCGCGACCTAGAGGCAGCACTTCGAGTTGCCGGGGCCGTGGCACAGCCGGATGCACCAGTTACTGGCGCACCGCAC
      84▶  A  E  R  W  I  S  V  V  K  L  N  G  P  G  T  V  S  A  Y  V  V  N  D  R  V  A  W

5281  GGGCCAGCCCCGCGACCAGTTGCGCCTGTCGGTGTTCAGTGCCGCCGTGGTGGTTGATCACGACGACCAGGACGAATCGC
      CCCGGTCGGGGCGCTGGTCAACGCGGACAGCCACAAGTCACGGCGGCACCACCAACTAGTGCTGCTGGTCCTGCTTAGCG
      110▶  G  Q  P  R  D  Q  L  R  L  S  V  F  S  A  A  V  V  V  D  H  D  D  Q  D  E  S

5361  TGTTGGGGCATGGCGACCTGCGCCGCATCCCGACCCTGTATCCGGGCGAGCAGCAACTACCGACCGGCCCCGGCGAGGAG
      ACAACCCCGTACCGCTGGACGCGGCGTAGGGCTGGGACATAGGCCCGCTCGTCGTTGATGGCTGGCCGGGGCCGCTCCTC
      137▶ L  L  G  H  G  D  L  R  R  I  P  T  L  Y  P  G  E  Q  Q  L  P  T  G  P  G  E  E

5441  CCGCCCAGCCAGCCCGGCATTCCGGGCATGGAACCAGACCTGCCAGCCTTGACCGAAACGGAGGAATGGGAACGGCGCGG
      GGCGGGTCGGTCGGGCCGTAAGGCCCGTACCTTGGTCTGGACGGTCGGAACTGGCTTTGCCTCCTTACCCTTGCCGCGCC
      164▶ P  P  S  Q  P  G  I  P  G  M  E  P  D  L  P  A  L  T  E  T  E  E  W  E  R  R  G
```

```
5521 GCAGCAGCGCCTGCCGATGCCCGATGAGCCGTGTTTTCTGGACGATGGCGAGCCGTTGGAGCCGCCGACACGGGTCACGC
     CGTCGTCGCGGACGGCTACGGGCTACTCGGCACAAAAGACCTGCTACCGCTCGGCAACCTCGGCGGCTGTGCCCAGTGCG
 190▶ Q  Q  R  L  P  M  P  D  E  P  C  F  L  D  D  G  E  P  L  E  P  P  T  R  V  T

5601 TGCCGCGCCGGTAGCACTTGGGTTGCGCAGCAACCCGTAAGTGCGCTGTTCCAGACTATCGGCTGTAGCCGCCTCG
     ACGGCGCGGCCATCGTGAACCCAACGCGTCGTTGGGCATTCACGCGACAAGGTCTGATAGCCGACATCGGCGGAGC
 217▶ L  P  R  R
```

```
        PvuII    Tn5 site            tL3
    1   CAGCTGTCTCTTATACACATCTCCGCTGTGCTTTCAGTGGATTTCGGATAACAGAAAGGCCGGGAAATACCCAGCCTCGC
        GTCGACAGAGAATATGTGTAGAGGCGACACGAAAGTCACCTAAAGCCTATTGTCTTTCCGGCCCTTTATGGGTCGGAGCG 81   TTTGTAACGGAGTAGACGAAAGTGATTGCGCCTACCCGGATATTATCGTGAGGATGCGTCATCGCCATTGCTCCCCAAAT
        AAACATTGCCTCATCTGCTTTCACTAACGCGGATGGGCCTATAATAGCACTCCTACGCAGTAGCGGTAACGAGGGGTTTA

226◄ R  W  Q  E  G  F

161   ACAAAACCAATTTCAGCCAGTGCCTCGTCCATTTTTTCGATGAACTCCGGCACGATCTCGTCAAAACTCGCCATGTACTT
        TGTTTTGGTTAAAGTCGGTCACGGAGCAGGTAAAAAAGCTACTTGAGGCCGTGCTAGAGCAGTTTTGAGCGGTACATGAA

219◄ V  F  G  I  E  A  L  A  E  D  M  K  E  I  F  E  P  V  I  E  D  F  S  A  M  Y  K

StuI
  241   TTCATCCCGCTCAATCACGACATAATGCAGGCCTTCACGCTTCATACGCGGGTCATAGTTGGCAAAGTACCAGGCATTTT
        AAGTAGGGCGAGTTAGTGCTGTATTACGTCCGGAAGTGCGAAGTATGCGCCCAGTATCAACCGTTTCATGGTCCGTAAAA

193◄ E  D  R  E  I  V  V  Y  H  L  G  E  R  K  M  R  P  D  Y  N  A  F  Y  W  A  N  K

321   TTCGCGTCACCCACATGCTGTACTGCACCTGGGCCATGTAAGCTGACTTTATGGCCTCGAAACCACCGAGCCGGAACTTC
        AAGCGCAGTGGGTGTACGACATGACGTGGACCCGGTACATTCGACTGAAATACCGGAGCTTTGGTGGCTCGGCCTTGAAG

166◄  R  T  V  W  M  S  Y  Q  V  Q  A  M  Y  A  S  K  I  A  E  F  G  G  L  R  F  K

SmaI
  401   ATGAAATCCCGGGAGGTAAACGGGCATTTCAGTTCAAGGCCGTTGCCGTCACTGCATAAACCATCGGGAGAGCAGGCGGT
        TACTTTAGGGCCCTCCATTTGCCCGTAAAGTCAAGTTCCGGCAACGGCAGTGACGTATTTGGTAGCCCTCTCGTCCGCCA

139◄ M  F  D  R  S  T  F  P  C  K  L  E  L  G  N  G  D  S  C  L  G  D  P  S  C  A  T

481   ACGCATACTTTCGTCGCGATAGATGATCGGGGATTCAGTAACATTCACGCCGAAGTGAACTCAAACAGGGTTCTGGCGT
        TGCGTATGAAAGCAGCGCTATCTACTAGCCCCTAAGTCATTGTAAGTGCGGCCTTCACTTgAGTTTGTCCCAAGACCGCA

113◄ R  M  S  E  D  R  Y  I  I  P  S  E  T  V  N  V  G  S  T  F  E  F  L  T  R  A  D

561   CGTTCTCGTACTGTTTTCCCCAGGCCAGTGCTTTAGCGTTAACTTCCGGAGCCACACCGGTGCAAACCTCAGCAAGCAGG
        GCAAGAGCATGACAAAAGGGGTCCGGTCACGAAATCGCAATTGAAGGCCTCGGTGTGGCCACGTTTGGAGTCGTTCGTCC

86◄  N  E  Y  Q  K  G  W  A  L  A  K  A  N  V  E  P  A  V  G  T  C  V  E  A  L  L

641   GTGTGGAAGTAGGACATTTTCATGTCAGGCCACTTCTTTCCGGAGCGGGGTTTTGCTATCACGTTGTGAACTTCTGAAGC
        CACACCTTCATCCTGTAAAAGTACAGTCCGGTGAAGAAAGGCCTCGCCCCAAAACGATAGTGCAACACTTGAAGACTTCG

59◄ T  H  F  Y  S  M  K  M  D  P  W  K  K  G  S  R  P  K  A  I  V  N  H  V  E  S  A

PstI
  721   GGTGATGACGCCGAGCCGTAATTTGTGCCACGCATCATCCCCCTGTTCGACAGCTCTCACATCGATCCCGGTACGCTGCA
        CCACTACTGCGGCTCGGCATTAAACACGGTGCGTAGTAGGGGGACAAGCTGTCGAGAGTGTAGCTAGGGCCATGCGACGT

```
                             Exo
 801 GGATAATGTCCGGTGTCATGCTGCCACCTTCTGCTCTGCGGCTTTCTGTTTCAGGAATCCAAGAGCTTTTACTGCTTCGG
     CCTATTACAGGCCACAGTACGACGGTGGAAGACGAGACGCCGAAAGACAAAGTCCTTAGGTTCTCGAAAATGACGAAGCC
                         261◀  A  A  V  K  Q  E  A  A  K  Q  K  L  F  G  L  A  K  V  A  E  A
  6◀  I  I  D  P  T  M

881 CCTGTGTCAGTTCTGACGATGCACGAATGTCGCGGCGAAATATCTGGGAACAGAGCGGCAATAAGTCGTCATCCCATGTT
     GGACACAGTCAAGACTGCTACGTGCTTACAGCGCCGCTTTATAGACCCTTGTCTCGCCGTTATTCAGCAGTAGGGTACAA
 240◀ Q  T  L  E  S  S  A  R  I  D  R  R  F  I  Q  S  C  L  P  L  L  D  D  D  W  T

961 TTATCCAGGGCGATCAGCAGAGTGTTAATCTCCTGCATGGTTTCATCGTTAACCGGAGTGATGTCGCGTTCCGGCTGACG
     AATAGGTCCCGCTAGTCGTCTCACAATTAGAGGACGTACCAAAGTAGCAATTGGCCTCACTACAGCGCAAGGCCGACTGC
 213◀ K  D  L  A  I  L  L  T  N  I  E  Q  M  T  E  D  N  V  P  T  I  D  R  E  P  Q  R

PstI                                                                        BglI
1041 TTCTGCAGTGTATGCAGTATTTTCGACAATGCGCTCGGCTTCATCCTTGTCATAGATACCAGCAAATCCGAAGGCCAGAC
     AAGACGTCACATACGTCATAAAAGCTGTTACGCGAGCCGAAGTAGGAACAGTATCTATGGTCGTTTAGGCTTCCGGTCTG
 187◀ E  A  T  Y  A  T  N  E  V  I  R  E  A  E  D  K  D  Y  I  G  A  F  G  F  A  L  R

1121 GGGCACACTGAATCATGGCTTTATGACGTAACATCCGTTTGGGATGCGACTGCCACGGCCCCGTGATTTCTCTGCCTTCG
     CCCGTGTGACTTAGTACCGAAATACTGCATTGTAGGCAAACCCTACGCTGACGGTGCCGGGGCACTAAAGAGACGGAAGC
 160◀ A  C  Q  I  M  A  K  H  R  L  M  R  K  P  H  S  Q  W  P  G  T  I  E  R  G  E

1201 CGAGTTTTGAATGGTTCGCGGCGGCATTCATCCATCCATTCGGTAACGCAGATCGGATGATTACGGTCCTTGCGGTAAAT
     GCTCAAAACTTACCAAGCGCCGCCGTAAGTAGGTAGGTAAGCCATTGCGTCTAGCCTACTAATGCCAGGAACGCCATTTA
 133◀ R  T  K  F  P  E  R  R  C  E  D  M  W  E  T  V  C  I  P  H  N  R  D  K  R  Y  I

1281 CCGGCATGTACAGGATTCATTGTCCTGCTCAAAGTCCATGCCATCAAACTGCTGGTTTTCATTGATGATGCGGGACCAGC
     GGCCGTACATGTCCTAAGTAACAGGACGAGTTTCAGGTACGGTAGTTTGACGACCAAAAGTAACTACTACGCCCTGGTCG
 107◀ R  C  T  C  S  E  N  D  Q  E  F  D  M  G  D  F  Q  Q  N  E  N  I  I  R  S  W  G

1361 CATCAACGCCCACCACCGGAACGATGCCATTCTGCTTATCAGGAAAGGCGTAAATTTCTTTCGTCCACGGATTAAGGCCG
     GTAGTTGCGGGTGGTGGCCTTGCTACGGTAAGACGAATAGTCCTTTCCGCATTTAAAGAAAGCAGGTGCCTAATTCCGGC
  80◀ D  V  G  V  V  P  V  I  G  N  Q  K  D  P  F  A  Y  I  E  K  T  W  P  N  L  G

1441 TACTGGTTGGCAACGATCAGTAATGCGATGAACTGCGCATCGCTGGCATCACCTTTAAATGCCGTCTGGCGAAGAGTGGT
     ATGACCAACCGTTGCTAGTCATTACGCTACTTGACGCGTAGCGACCGTAGTGGAAATTTACGGCAGACCGCTTCTCACCA
  53◀ Y  Q  N  A  V  I  L  L  A  I  F  Q  A  D  S  A  D  G  K  F  A  T  Q  R  L  T  T

SalI
1521 GATCAGTTCCTGTGGGTCGACAGAATCCATGCCGACACGTTCAGCCAGCTTCCCAGCCAGCGTTGCGAGTGCAGTACTCA
     CTAGTCAAGGACACCCAGCTGTCTTAGGTACGGCTGTGCAAGTCGGTCGAAGGGTCGGTCGCAACGCTCACGTCATGAGT
  27◀ I  L  E  Q  P  D  V  S  D  M  G  V  R  E  A  L  K  G  A  L  T  A  L  A  T  S  M

Bst
1601 TTCGTTTTATACCTCTGAATCAATATCAACCTGGTGGTGAGCAATGGTTTCAACCATGTACCGGATGTGTTCTGCCATGC
     AAGCAAAATATGGAGACTTAGTTATAGTTGGACCACCACTCGTTACCAAAGTTGGTACATGGCCTACACAAGACGGTACG
   0◀          98◀ V  E  S  D  I  D  V  Q  H  H  A  I  T  E  V  M  Y  R  I  H  E  A  M  R

NsiI
1681 GCTCCTGAAACTCAACATCGTCATCAAACGCACGGGTAATGGATTTTTTGCTGGCCCCGTGGCGTTGCAAATGATCCATG
     CGAGGACTTTGAGTTGTAGCAGTAGTTTGCGTGCCCATTACCTAAAAAACGACCGGGGCACCGCAACGTTTACTAGCTAC
  74◀ E  Q  F  E  V  D  D  D  F  A  R  T  I  S  K  K  S  A  G  H  R  Q  L  H  D  I
```

```
2801 TCAGGCGGGCAAGAATGTGAATAAAGGCCGGATAAAACTTGTGCTTATTTTTCTTTACGGTCTTTAAAAAGGCCGTAATA
     AGTCCGCCCGTTCTTACACTTATTTCCGGCCTATTTTGAACACGAATAAAAAGAAATGCCAGAAATTTTTCCGGCATTAT
  66◀ L  R  A  L  I  H  I  F  A  P  Y  F  K  H  K  N  K  K  V  T  K  L  F  A  T  I

PvuII
2881 TCCAGCTGAACGGTCTGGTTATAGGTACATTGAGCAACTGACTGAAATGCCTCAAAATGTTCTTTACGATGCCATTGGGA
     AGGTCGACTTGCCAGACCAATATCCATGTAACTCGTTGACTGACTTTACGGAGTTTTACAAGAAATGCTACGGTAACCCT
  39◀D  L  Q  V  T  Q  N  Y  T  C  Q  A  V  S  Q  F  A  E  F  H  E  K  R  H  W  Q  S rexA' (2999)
                                       cat
2961 TATATCAACGGTGGTATATCCAGTGATTTTTTTCTCCATAATTCAATCCATTTACTATGTTATGTTCTGAGGGGAGTGAA
     ATATAGTTGCCACCATATAGGTCACTAAAAAAGAGGTATTAAGTTAGGTAAATGATACAATACAAGACTCCCCTCACTT
  13◀ I  D  V  T  T  Y  G  T  I  K  K  E  M 3041 AATTCCCCTAATTCGATGAAGATTCTTGCTCAATTGTTATCAGCTATGCGCCGACCAGAACACCTTGCCGATCAGCCAAA
     TTAAGGGGATTAAGCTACTTCTAAGAACGAGTTAACAATAGTCGATACGCGGCTGGTCTTGTGGAACGGCTAGTCGGTTT
                                                                            237◀ G  F 3121 CGTCTCTTCAGGCCACTGACTAGCGATAACTTTCCCCACAACGGAACAACTCTCATTGCATGGGATCATTGGGTACTGTG
     GCAGAGAAGTCCGGTGACTGATCGCTATTGAAAGGGGTGTTGCCTTGTTGAGAGTAACGTACCCTAGTAACCCATGACAC
  235◀ T  E  E  P  W  Q  S  A  I  V  K  G  V  V  S  C  S  C  N  C  P  I  M  P  Y  Q  P 3201 GGTTTAGTGGTTGTAAAAACACCTGACCGCTATCCCTGATCAGTTTCTTGAAGGTAAACTCATCACCCCCAAGTCTGGCT
     CCAAATCACCAACATTTTTGTGGACTGGCGATAGGGACTAGTCAAAGAACTTCCATTTGAGTAGTGGGGTTCAGACCGA
  208◀ N  L  P  Q  L  F  V  Q  G  S  D  R  I  L  K  K  F  T  F  E  D  G  G  L  R  A HindIII
3281 ATGCAGAAATCACCTGGCTCAACAGCCTGCTCAGGGTCAACGAGAATTAACATTCCGTCAGGAAAGCTTGGCTTGGAGCC
     TACGTCTTTAGTGGACCGAGTTGTCGGACGAGTCCCAGTTGCTCTTAATTGTAAGGCAGTCCTTTCGAACCGAACCTCGG
  181◀I  C  F  D  G  P  E  V  A  Q  E  P  D  V  L  I  L  M  G  D  P  F  S  P  K  S  G 3361 TGTTGGTGCGGTCATGGAATTACCTTCAACCTCAAGCCAGAATGCAGAATCACTGGCTTTTTTGGTTGTGCTTACCCATC
     ACAACCACGCCAGTACCTTAATGGAAGTTGGAGTTCGGTCTTACGTCTTAGTGACCGAAAAAACCAACACGAATGGGTAG
  155◀ T  P  A  T  M  S  N  G  E  V  E  L  W  F  A  S  D  S  A  K  K  T  T  S  V  W  R HindIII
3441 TCTCCGCATCACCTTTGGTAAAGGTTCTAAGCTTAGGTGAGAACATCCCTGCCTGAACATGAGAAAAAACAGGGTACTCA
     AGAGGCGTAGTGGAAACCATTTCCAAGATTCGAATCCACTCTTGTAGGGACGGACTTGTACTCTTTTTTGTCCCATGAGT
  128◀ E  A  D  G  K  T  F  T  R  L  K  P  S  F  M  G  A  Q  V  H  S  F  V  P  Y  E 3521 TACTCACTTCTAAGTGACGGCTGCATACTAACCGCTTCATACATCTCGTAGATTTCTCTGGCGATTGAAGGGCTAAATTC
     ATGAGTGAAGATTCACTGCCGACGTATGATTGGCGAAGTATGTAGAGCATCTAAAGAGACCGCTAACTTCCCGATTTAAG
  101◀Y  E  S  R  L  S  P  Q  M  S  V  A  E  Y  M  E  Y  I  E  R  A  I  S  P  S  F  E NsiI
3601 TTCAACGCTAACTTTGAGAATTTTTGTAAGCAATGCGGCGTTATAAGCATTTAATGCATTGATGCCATTAAATAAAGCAC
     AAGTTGCGATTGAAACTCTTAAAAACATTCGTTACGCCGCAATATTCGTAAATTACGTAACTACGGTAATTTATTTCGTG
   75◀ E  V  S  V  K  L  I  K  T  L  L  A  A  N  Y  A  N  L  A  N  I  G  N  F  L  A  G 3681 CAACGCCTGACTGCCCCATCCCCATCTTGTCTGCGACAGATTCCTGGGATAAGCCAAGTTCATTTTTCTTTTTTTCATAA
     GTTGCGGACTGACGGGGTAGGGGTAGAACAGACGCTGTCTAAGGACCCTATTCGGTTCAAGTAAAAAGAAAAAAGTATT
   48◀ V  G  S  Q  G  M  G  M  K  D  A  V  S  E  Q  S  L  G  L  E  N  K  K  K  E  Y
```

FIG. 15D

```
                                                                                  cI
3761 ATTGCTTTAAGGCGACGTGCGTCCTCAAGCTGCTCTTGTGTTAATGGTTTCTTTTTTGTGCTCATACGTTAAATCTATCA
     TAACGAAATTCCGCTGCACGCAGGAGTTCGACGAGAACAATTACCAAAGAAAAAACACGAGTATGCAATTTAGATAGT
 214◄ I  A  K  L  R  R  A  D  E  L  Q  E  Q  T  L  P  K  K  K  T  S  M

3841 CCGCAAGGGATAAATATCTAACACCGTGCGTGTTGACTATTTTACCTCTGGCGGTGATAATGGTTGCATGTACTAAGGAG
     GGCGTTCCCTATTTATAGATTGTGGCACGCACAACTGATAAAATGGAGACCGCCACTATTACCAACGTACATGATTCCTC
                                                                     _____ cro'                           PvuII                                         oriV
3921 GTTGTATGGAACAACGAGATGTGTATAAGAGACAGCTGAAACGCCGTCGAAGCCGTGTGCGAGACACCGCGGCCGCCGGC
     CAACATACCTTGTTGCTCTACACATATTCTCTGTCGACTTTGCGGCAGCTTCGGCACACGCTCTGTGGCGCCGGCGGCCG
     ──────────────────────────────────────────────────────────────────────────────►

4001 GTTGTGGATACCACGCGGAAAACTTGGCCCTCACTGACAGATGAGGGGCGGACGTTGACACTTGAGGGGCCGACTCACCC
     CAACACCTATGGTGCGCCTTTTGAACCGGGAGTGACTGTCTACTCCCCGCCTGCAACTGTGAACTCCCCGGCTGAGTGGG

4081 GGCGCGGCGTTGACAGATGAGGGGCAGGCTCGATTTCGGCCGGCGACGTGGAGCTGGCCAGCCTCGCAAATCGGCGAAAA
     CCGCGCCGCAACTGTCTACTCCCCGTCCGAGCTAAAGCCGGCCGCTGCACCTCGACCGGTCGGAGCGTTTAGCCGCTTTT

4161 CGCCTGATTTTACGCGAGTTTCCCAGACATGATGTGGACAAGCCTGGGGATAAGTGCCCTGCCGGTATTGACACTTGAGG
     GCGGACTAAAATGCGCTCAAAGGGTCTGTACTACACCTGTTCGGACCCCTATTCACGGGACGGCCATAACTGTGAACTCC

4241 GCGCGACTACTGACAGATGAGGGCGCGATCCTTGACACTTGAGGGGCAGAGTGATGACAGATGAGGGGCGCACCTATTG
     CGCGCTGATGACTGTCTACTCCCGCGCTAGGAACTGTGAACTCCCCGTCTCACTACTGTCTACTCCCGCGTGGATAAC

4321 ACATTTGAGGGGCTGTCCACAGGCAGAAAATCCAGCATTTGCAAGGGTTTCCGCCCGTTTTTCGGCCACCGCTAACCTGT
     TGTAAACTCCCCGACAGGTGTCCGTCTTTTAGGTCGTAAACGTTCCCAAAGGCGGGCAAAAAGCCGGTGGCGATTGGACA

4401 CTTTTAACCTGCTTTTAAACCAATATTTATAAACCTTGTTTTTAACCAGGGCTGCGCCCTGGCGCGTGACCGCGCACGCC
     GAAAATTGGACGAAAATTTGGTTATAAATATTTGGAACAAAAATTGGTCCCGACGCGGGACCGCGCACTGGCGCGTGCGG

4481 GAAGGGGGGTGCCCCCCCTTCTCGAACCCTCCCGGCTAACGCGGGCCTCCCATCCCCCGGCTGCGCCCTTCGGCCGCGA
     CTTCCCCCCACGGGGGGGAAGAGCTTGGGAGGGCCGATTGCGCCCGGAGGGTAGGGGGGCCGACGCGGGAAGCCGGCGCT

TelB
4561 ACGGCCTCACCCCAAAAATGGCAGCGCTGGCAGTCCTTGCCATTGCCGGGATCGGGGCAGTAACGGGATGGGCGATCAGC
     TGCCGGAGTGGGGTTTTTACCGTCGCGACCGTCGGAACGGTAACGGCCCTAGCCCCGTCATTGCCCTACCCGCTAGTCG
                      1► M  A  A  L  A  V  L  A  I  A  G  I  G  A  V  T  G  W  A  I  S

4641 CCGAGCGCGACGCCCGGAAGCATTGACGTGCCGCAGGTGCTGGCATCGACATTCAGCGACCAGGTGCCGGGCAGTGAGGG
     GGCTCGCGCTGCGGGCCTTCGTAACTGCACGGCGTCCACGACCGTAGCTGTAAGTCGCTGGTCCACGGCCCGTCACTCCC
  22► P  S  A  T  P  G  S  I  D  V  P  Q  V  L  A  S  T  F  S  D  Q  V  P  G  S  E  G

4721 CGGCGGCCTGGGTGGCGGCCTGCCCTTCACTTCGGCCGTCGGGGCATTCACGGACTTCATGGCGGGCGGGCAATTTTTA
     GCCGCCGGACCCACCGCCGGACGGGAAGTGAAGCCGGCAGCCCCGTAAGTGCCTGAAGTACCGCCCGCCCGTTAAAAAT
  48► G  G  L  G  G  G  L  P  F  T  S  A  V  G  A  F  T  D  F  M  A  G  R  A  I  F

4801 CCTTGGGCATTCTTGGCATAGTGGTCGCGGGTGCCGTGCTCGTGTTCGGGGGTGAATTAATTCCCCGGATCGATCCGTCA
     GGAACCCGTAAGAACCGTATCACCAGCGCCCACGGCACGAGCACAAGCCCCCACTTAATTAAGGGGCCTAGCTAGGCAGT
  75► T  L  G  I  L  G  I  V  V  A  G  A  V  L  V  F  G  G  E  L  I  P  R  I  D  P  S

4881 GCTTCACGCTGCCGCAAGCACTCAGGGCGCAAGGGCTGCTAAAGGAAGCGGAACACGTAGAAAGCCAGTCCGCAGAAACG
     CGAAGTGCGACGGCGTTCGTGAGTCCCGCGTTCCCGACGATTTCCTTCGCCTTGTGCATCTTTCGGTCAGGCGTCTTTGC
 102► A  S  R  C  R  K  H  S  G  R  K  G  C
                               119◄ L  F  R  F  V  Y  F  A  L  G  C  F  R
```

FIG. 15E

```
4961 GTGCTGACCCCGGATGAATGTCACGTACTGGGCTATCTGGACAAGGGAAAACGCAAGCGCAAACACAAACGACCTAGCTT
     CACGACTGGGGCCTACTTACAGTGCATGACCCGATAGACCTGTTCCCTTTTGCGTTCGCGTTTGTGTTTGCTGGATCGAA
106◀ H  Q  G  R  I  F  T  V  Y  Q  A  I  Q  V  L  S  F  A  L  A  F  V  F  S  R  A  Q

5041 GCAGTGGGCTTACATGGCGATAGCTAGACTGGGCGGTTTTATGGCCAGCAAGCGAACCGGAATTGCCAGCTGGGCGCCC
     CGTCACCCGAATGTACCGCTATCGATCTGACCCGCCAAAATACCGGTCGTTCGCTTGGCCTTAACGGTCGACCCCGCGGG
 79◀ L  P  S  V  H  R  Y  S  S  Q  A  T  K  H  G  A  L  S  G  S  N  G  A  P  A  G

5121 TCTGGTAAGGTTGGGAAGCCCTGCAAAGTAAACTGGATGGCTTTCTTGCCGCCAAGGATCTGATGGCGCAGGGGATCAAG
     AGACCATTCCAACCCTTCGGGACGTTTCATTTGACCTACCGAAAGAACGGCGGTTCCTAGACTACCGCGTCCCCTAGTTC
 52◀ E  P  L  T  P  F  G  Q  L  T  F  Q  I  A  K  K  G  G  L  I  Q  H  R  L  P  D  L

TrfA
5201 ATCGACGGATCGATCCGGGGAATTCCGGGGCAATCCCGCAAGGAGGGTGAATGAATCGGACGTTTGACCGGAAGGCATAC
     TAGCTGCCTAGCTAGGCCCCTTAAGGCCCCGTTAGGGCGTTCCTCCCACTTACTTAGCCTGCAAACTGGCCTTCCGTATG
                                                  1▶ M  N  R  T  F  D  R  K  A  Y
 26◀ D  V  S  R  D  P  S  N  R  P  L  G  A  L  L  T  F  S  D  S  T  Q  G  S  P  M

5281 AGGCAAGAACTGATCGACGCGGGGTTTTCCGCCGAGGATGCCGAAACCATCGCAAGCCGCACCGTCATGCGTGCGCCCCG
     TCCGTTCTTGACTAGCTGCGCCCCAAAAGGCGGCTCCTACGGCTTTGGTAGCGTTCGGCGTGGCAGTACGCACGCGGGGC
 11▶ R  Q  E  L  I  D  A  G  F  S  A  E  D  A  E  T  I  A  S  R  T  V  M  R  A  P  R

5361 CGAAACCTTCCAGTCCGTCGGCTCGATGGTCCAGCAAGCTACGGCCAAGATCGAGCGCGACAGCGTGCAACTGGCTCCCC
     GCTTTGGAAGGTCAGGCAGCCGAGCTACCAGGTCGTTCGATGCCGGTTCTAGCTCGCGCTGTCGCACGTTGACCGAGGGG
 37▶ E  T  F  Q  S  V  G  S  M  V  Q  Q  A  T  A  K  I  E  R  D  S  V  Q  L  A  P

5441 CTGCCCTGCCCGCGCCATCGGCCGCCGTGGAGCGTTCGCGTCGTCTCGAACAGGAGGCGGCAGGTTTGGCGAAGTCGATG
     GACGGGACGGGCGCGGTAGCCGGCGGCACCTCGCAAGCGCAGCAGAGCTTGTCCTCCGCCGTCCAAACCGCTTCAGCTAC
 64▶ P  A  L  P  A  P  S  A  A  V  E  R  S  R  R  L  E  Q  E  A  A  G  L  A  K  S  M

5521 ACCATCGACACGCGAGGAACTATGACGACCAAGAAGCGAAAAACCGCCGGCGAGGACCTGGCAAAACAGGTCAGCGAGGC
     TGGTAGCTGTGCGCTCCTTGATACTGCTGGTTCTTCGCTTTTTGGCGGCCGCTCCTGGACCGTTTTGTCCAGTCGCTCCG
 91▶ T  I  D  T  R  G  T  M  T  T  K  K  R  K  T  A  G  E  D  L  A  K  Q  V  S  E  A

5601 CAAGCAGGCCGCGTTGCTGAAACACACGAAGCAGCAGATCAAGGAAATGCAGCTTTCCTTGTTCGATATTGCGCCGTGGC
     GTTCGTCCGGCGCAACGACTTTGTGTGCTTCGTCGTCTAGTTCCTTTACGTCGAAAGGAACAAGCTATAACGCGGCACCG
117▶ K  Q  A  A  L  L  K  H  T  K  Q  Q  I  K  E  M  Q  L  S  L  F  D  I  A  P  W

5681 CGGACACGATGCGAGCGATGCCAAACGACACGGCCCGCTCTGCCCTGTTCACCACGCGCAACAAGAAAATCCCGCGCGAG
     GCCTGTGCTACGCTCGCTACGGTTTGCTGTGCCGGGCGAGACGGGACAAGTGGTGCGCGTTGTTCTTTTAGGGCGCGCTC
144▶ P  D  T  M  R  A  M  P  N  D  T  A  R  S  A  L  F  T  T  R  N  K  K  I  P  R  E

5761 GCGCTGCAAAACAAGGTCATTTTCCACGTCAACAAGGACGTGAAGATCACCTACACCGGCGTCGAGCTGCGGGCCGACGA
     CGCGACGTTTTGTTCCAGTAAAAGGTGCAGTTGTTCCTGCACTTCTAGTGGATGTGGCCGCAGCTCGACGCCCGGCTGCT
171▶ A  L  Q  N  K  V  I  F  H  V  N  K  D  V  K  I  T  Y  T  G  V  E  L  R  A  D  D

5841 TGACGAACTGGTGTGGCAGCAGGTGTTGGAGTACGCGAAGCGCACCCCTATCGGCGAGCCGATCACCTTCACGTTCTACG
     ACTGCTTGACCACACCGTCGTCCACAACCTCATGCGCTTCGCGTGGGGATAGCCGCTCGGCTAGTGGAAGTGCAAGATGC
197▶ D  E  L  V  W  Q  Q  V  L  E  Y  A  K  R  T  P  I  G  E  P  I  T  F  T  F  Y

5921 AGCTTTGCCAGGACCTGGGCTGGTCGATCAATGGCCGGTATTACACGAAGGCCGAGGAATGCCTGTCGCGCCTACAGGCG
     TCGAAACGGTCCTGGACCCGACCAGCTAGTTACCGGCCATAATGTGCTTCCGGCTCCTTACGGACAGCGCGGATGTCCGC
224▶ E  L  C  Q  D  L  G  W  S  I  N  G  R  Y  Y  T  K  A  E  E  C  L  S  R  L  Q  A
```

MODIFICATION OF THE STANDARD PROPHAGE

*attL int xis* $t_{L3}$ *exo bet gam kil cIII* $t_{L2}$ $t_{L1}$ *N* $p_L/o_L$ *rex cI*$^{857}$ $p_R/o_R$ (Δ*cro-bioA*)

$t_{L2}$ $t_{L1}$   transcription terminators that prevent Red expression unless N anti-termination function is active

*attL int xis* $t_{L3}$ *exo bet gam* $p_L/o_L$ *rex*<>*cat/amp cI*$^{857}$ $p_R/o_R$

*kil-N*

1. *N-kil* deletion eliminates transcription terminators making Red expression N independent
2. *rex* replaced by a selectable drug marker

GENERATION OF A PLASMID-CONTAINING PROPHAGE RECOMBINATION SYSTEM

CREATION OF A VECTOR REPLICON FOR GAP REPAIR

PCR amplification of *ori* of plasmid using hybrid primers with homology to the prophage ORIGIN REPLACEMENT
$ori_{pBR322}$ replacement by other $ori$ regions

FIG. 17A

35734 The rexB rexA genes of lambda

```
35734 AGTTGTATCTATTTTTCAATAAATACAATTGGTTATGTGTTTGGGGCGATCGTGAGGCAAAGAAACCCGGCGCTGAGGCCGGTTATTCTTGTTCTTG
       TCAACATAGATAAATAAAAGTTATTTATGTTAACCAATACAAAACCCCCGCTAGCACTCCGTTTCTTTTGGGCGACT· GGCCAATAAGAACAAGAGAC
                                                                                1441 E  Q  E  R

35840 GTCAATTATATAGTTGGAAAACAAGGATGCATATATGAATGAACGATGCAGAGGCAATGCCGATGGCGATAGTGGGTATCATGTAGCGCCTTATGCTGGAAGAA
       CAGTTAATATATCAACCTTTGTTCCTACGTATATACTTACTTGCTACGTCTCCGTTACGGCTACCGCTATCACCCATAGTACATCGGCGGAATACGACCTTCTT
  1394 T  L  N  Y  L  Q  F  V  L  I  C  I  H  I  F  S  A  S  I  G  I  A  I  T  P  I  M  Y  G  S  I  S  S  L  L

35946 GCAATAACCCGCAGAAAACAAAGCTCCAAGCTCAACAAAACTAAGGCATAGACAATAACTAAGGATGCTATATACCATGTCTATCTTGGCCAGTCGGCG
       CGTTATTGGGCGTCTTTTGTTTCGAGGTTCGAGTTGTTTGATTCCGTATCGTATTGTTATTGCTACAGTATATGGTACAGAGATGAACCGGTCAGCCGC
  1044 L  L  G  C  F  F  L  A  G  L  E  V  F  S  L  A  Y  V  I  V  V  S  T  M  Y  G  Y  E  R  I  K  A  L  R  R

36052 CGTTCTGCTTCCGATTAGAAACGTCAAGCAGCAATCAGGATTGCAATCATGGTTCCTGCATATGATGACAATGTCGCCCAAGACACATCTCTATGAGCTGAAAAA
       GCAAGACGAAGGCTAATCTTTTGCAGTTCGTCCGTTAGTCGTTAGTTCCTAACGTTATGCATTTGCATTCCTTAATAGATACATTTGTTACAGGACAAGGGTATTAAT
   691 T  R  S  G  I  L  F  T  L  A  A  I  L  I  A  I  M  T  G  A  Y  S  S  L  T  A  G  L  G  D  R  H  A  S  F

36158 GAAACACCAGGAATGTAGTGCGGAAAAGGAGATAGCAAATGCTACGATAAGCGTAAGGAATTATTACTAGTAAACACCAGG· ·TGATTCTGTTCCGAGCTAATATTA
       CTTTGTGGTCCTTACATCACCGCCTTTTCCTCTATCGTTTACGATGCTATTCGCATTCCTAATAATGATACATTTGTGTCC· ·ACTAAGACAAGGGCTATTAT
   334 S  V  G  P  I  Y  H  R  F  L  L  Y  C  I  S  V  I  V  Y  P  I  I  V  I  Y  V  G  P  F  I  R  N  R  M

36264 CTCCTGATAATTAATCCTTAACTTGCCCACCTGCCTTTAAACATTCCAGTATGCTATATCACTTTTCATTCTTGCTAGCAATATGCTCGTATATCGTAGCAATCTGAGCTATCTCAGC
       GAGGACTATTAATTAGGAATTGAACGGGTGGACGGAAATTTGTAAGGTCATATCGATATAGTGAAAAGTAAGACGATCGTTATACGGTAGAAGTCGATAGAGTCG

36370 ATTGGTGACCTTGTTCAGAGGCGCTGAGAGATGGCCTTTTTCTGATAGATAATGTTCTGTTAAAATATCTCGGCCTCATCTTTGCCGCAGGCTAATGTCTGAA
       TAACCACTGGAACAAGTCTCCGCGACTCTCTACCGAATCGGAAAAAGACTATCTATTACAGACAATTTTATAGAGGCCGGAGTAGAAACGGGCGTCCGATTACAGATT
   248 N  T  V  K  N  L  P  A  S  L  H  G  K  E  S  L  Y  H  E  T  L  I  D  G  A  E  D  K  A  R  L  S  I  D  S

36476 AATTGAGGTGACGGGTTAAAAAATAATATCCTTGGCAACCTTTAAATTTGGCTTAAATTTTAAACCGAATTACTCAGTTTTCGAGGGAAGTT
       TTAACTCCACTGCCGCAATTTTATTATAGGAACCGTTGGAAATTTAAAGACCGAATTTAAAAATTTTTAAGGCTTAATGAGTCAAAAGCTCCCCTTCAA
   212 F  Q  P  S  P  N  F  I  I  D  K  A  V  K  K  I  D  R  K  F  K  P  K  I  V  I  D  L  S  D  F  L  E  G  E  I

36582 TATCTGTTGCCCTAAGACTTTAATATATGCCAATACAGGTACTTGGCTTCTACCTTCACCGTTGTTCGGCGGATGAATGCATATGCATAACATGTCTTT
       ATAGACAACGGGATTCTGAAATTATATACGGTTATGTCCATCGAACCGAAGATGGCAACAAGCCGGCACTTACGTATGCATAACGTATTGTAGCAGAAA
   177 D  T  A  G  L  V  K  L  I  D  G  F  V  P  L  K  A  E  V  K  V  T  T  R  G  I  F  H  M  H  M  V  D  D  K

36688 GGTGGTCCCCTCATCAGTGCTCTATCTGAACGGCCTCTCCACTGCTTAATGACATTCCTTTCCGATTAAAAAATCTGTCAGATCGGATGTGGTCGGCCCGAAA
       CCACCAGGGAGTAGTCACGAGATAGACATTGCCGGAGACTTGCGGAGGTGACGAATTACTGTAAGGAAAGGCTAATTTTTAGACAGTGAGCTACAGCCAGCCGGGCTTT
   142 T  T  G  R  M  L  P  E  I  Q  V  R  E  G  S  S  L  S  M  G  K  G  I  L  F  D  T  L  D  S  T  T  P  G  F
```

```
                                                                                         HindIII
36794 ACAGTTCTGGCAAACCAATGTGTCGCCTTCAACAACAAAAAGATGGAATCCCAATGATTCGTCATCGCGAGGCTGTTCTTAATATCTTCAACTGAAGCTT
      TGTCAAGACCGTTTGGTTACCACAGCGAAGTTGTTGTTTTTCTACCCTTAGGTTACTAAGCAGTAGACGCTCCGACAAGAATTATAGAAGTTGACTTGAA
                                                                 ↓
1064 V  T  R  A  F  G  I  T  D  G  E  V  F  L  F  S  P  F  G  L  S  E  D  D  A  L  S  N  K  I  D  E  V  S  A  K 36900 TAGCCGATTTATCTTCTGAACCAGACTCTTGGTCATTTGTTTGGTAAGAGAAAAGTTTTTCCATCGATTTTATGAATATACAAATAATTGGAGCCAACTGCAG
      ATCTCGCTAAATAGAAGACTTGGTCTGAGAACAGACCAGTAAACAAACCATTTCTCTTTTCAAAAGGTAGCTAAATACTTATATGTTTATTAACCTCGGTTGGACGTC 714   S  R  N  I  K  Q  V  L  S  K  D  N  T  K  T  F  L  F  T  K  G  D  I  K  H  I  Y  L  Y  N  S  G  V  Q  L 37006 GTGATGATTATCAGCAGCAGAGAATTAAGGAAAACAGACAGGTTTATTGAGCGCTTATCTTTCCCTTTATTTTTGCTGCGGTAGTCGCATAAAAACCATTCTTC
      CACTACTAATAGTCGTCGTCTCTTAATTCCTTTTGTCTGTCCAAATAACTCGCGAATAGAAAGGAATAAAACGACGCCATAGCTATTTTTGGTAAGAAG 364   H  H  N  D  A  L  L  S  N  L  F  V  S  L  N  I  S  R  K  D  K  G  K  N  K  S  R  Y  T  A  Y  F  G  N  K

37112 ATAATTCAATCCATTTACTAT
      TATTAAGTTAGGTAAATGATA

FIG. 18A bp 35374    The rexB and rexA are replaced by TetR and TetA

```
                                                                                        rexB  TAA
AGTTGTATCTATTTATTTTCAATAAATACAATTGGTTGTGTTTGGGGCGATCGTGAGGCAAAGAAAAACCCGGCTGAGGC...GTTAACTCGACATCTTGGTTACC
TCAACATAGATAAATAAAAAGTTATTTATGTTAACAATACAAAACCCCGCACTCCGTTCTTTGGGCCGACTCCGG..CAATTGAGCTGTAGAACCAATGG GTGAAGTTACCATCACGGAAAAGGTTATGCTGCTTTTAAGACCACTTCACATTTAAGTGTTTTTCTAATCCGATATGATCAATTCAAGGCCGAATAAGAAGGCTGGC
CACTTCAATGGTAGTGCCTTTTCCAATACGACGAAAATTCTGGGTGAAGTGTAAATTCAACAAAAGATTAGGCGTATACTAGTTAAGTTCCGGCTTATTCTTCCGACCG
          ◀ S  G  S  E  C  K  L  Q  K  E  L  G  C  I  I  L  E  L  G  F  L  F  A  P TCTGCACCTTGGTGATCAAATAATTCGTCGTAATAATGCGGCATACTATCAGTAGTAGGTGTTTCCCTTCTTCTTTAGCGACTTGATGCTCTTGATCTTCCA
AGACGTGGAACCACTAGTTATTAAGCTATCGAACAGCATTATTACCGTATGATAGTCATCCACAAAGGGAAGAGAAATCGCTGACTACGAGAACTAGAAGGT
 ◀ E  A  G  Q  H  D  F  L  E  I  A  Q  R  L  L  P  P  M  S  D  T  T  P  T  E  R  E  E  K  A  V  Q  H  E  Q  D  E  L ATACGCAACCTAAAGTAAAAATGCCCCACAGCGTCGCTAAATGTACTTTTGCTCCATCGGATGACTACTTAGTAAAGACATCTAAAACTTTTAGCGTTATTACGTAAAAAATCTTGCCAGTTTCCCT
TATGCGTTGGATTCATTTTACGGCGTGTCGCAGCGATTTACATGAATCACCGATATATATCGGTAGCCTACTGATGAATCATTTTCGATT..CTAAAGCTCAAGTATGAC
 ◀ V  C  G  L  T  F  F  H  G  V  A  S  L  A  Y  L  A  N  E  L  S  F  G  Q  Q  C  L  F  A  L  Q  N  E  L  T  E  Y  Q TTTTTCTGTAGGCCGTGTACCTAAATGTACTTTTGCTCCATCGCGATGACTACTTAGTAAAGACATCTAAAACTTTTAGCGTTATTACGTAAAAAATCTTGCCAGTTTCCCT
AAAAAGACATCCGGACACATGGATTTACATGAAAACGAGGATAGCCTACTGATGAATCATTTCTGTAGATTCATTTTTGAAATCGCATTTTAGAACGGTCAAAGGGGA
 ◀ K  E  T  P  R  T  G  L  H  V  K  A  G  D  R  H  S  L  L  A  C  R  F  S  K  A  N  N  R  L  F  D  Q  W  S  E  G TCTAAAGGGCAAAAGTGAGTATGTGCCTATCTAACATCTCAATGGCGTCGAAGCGTCTAAGCGATTCCGAGCAAAGCCCGCTTATTTTTACATGCCAATACAATGTAGGCTCTACACCTA
AGATTTCCGTTTCACTCACTAGATTGTAGAGTTACCGATTCGCAGCTTCGGCGAATAAAAATGTACGGTTATGTTACATCCGACGAGATGTGGAT
 ◀ E  L  P  C  F  H  T  H  H  R  D  L  M  E  I  A  L  A  D  L  L  A  R  K  N  K  V  H  W  Y  L  T  P  Q  E  V  G  L TetR
GCTTCTGGGCCAGTTGTTAAACCTTGTTAAACAATTCGATTCCGACCTCATTAAGCAGCTCTAATGCGCTGTTAATCACTTTACTTTATCTAATCGAGACATCATTAATTCCTA
CGAAGACCCGCTCAAATGCCCAACATGGTAAGCTGAGATTCGTCGAGATTACGCGACAATTAGTAGAAATGAAATTAGATCGTGAGTAATTAAGGAT
 ◀ K  Q  A  L  K  R  T  T  L  G  E  I  G  V  E  N  L  L  E  L  A  S  N  I  V  K  S  K  D  L  R  S  M  M ATTTTGTTGACACTGTTATCATTGATAGAGTTATTTTACCACTCCTATCAGTGATAGATAGAAAAGTGAAATGAATAGTTCGACAAAGATCGCATTGGTAATTAGTTACTCG
TAAAACAACTGTGAGATGTAGATAACTATCATAAAAATGGTGAGGAGATACTCATCCTTTCACTTATTAATCAAGCTGTTTCTAGCGATTGTAACCATTAATGCAATGAGC
                                       ▶ M  N  S  S  T  K  I  A  L  V  I  T  L  L ATGCCATGGGATTGGCCTTATCATGCCAGTCTTGCCAACGTTATTACGTGAATTTATTGCTTCGGAAGATATCGCTAACCACTTTGGCGTATTGCTTCACTTATGCGTT
TACGGTACCCCTAACCGGAATAGTACGGTTGCAGATAGTCAGAACGGTTGCAATAATGCACTTAATAACGAAGCCTTGTAAACCGCATAACGACCGCATAACGCCAA
 ▶ D  A  M  G  I  L  I  M  P  V  L  P  T  L  L  R  E  F  I  A  S  E  D  I  A  N  H  F  G  V  L  L  A  L  Y  A  L AATGCAGGTTATCTTTGCTCCTTTGGCTTGGAAAATGTCTGACAGATTTGGTCGGCGCCAGTGCTGTTGTTGTCATTAATAATAGGCGCA..GGCTGGATTACTTATTGCTGCT
TTACGTCCAATAGAAACGAGGAAACGAACCGAACCCTTTTACAGACTGGCTAAACGAGGACAGTAACACTAATATTCCGCGTAGCGACCTAATGAATAACGACCGA
 ▶ M  Q  V  I  F  A  P  W  L  G  K  M  S  D  R  F  G  R  R  P  V  L  L  S  L  I  G  A  S  L  D  Y  L  L  L  A
```

FIG. 18B

```
       This is the S gene in lambda with its coordinates           S
39886  TAATCGACCTTATTCCTAATTAAATAGAGCAAATCCCCTTATTGGGGTAAGACATGAAGATGCCAGAAAAACATGA
       ATTAGCTGGAATAAGGATTAATTTATCTCGTTTAGGGGAATAACCCCATTCTGTACTTCTACGGTCTTTTTGTACT
                                                            1▶MetLysMetProGluLysHisAs 39963  CCTGTTGGCCGCCATTCTCGCGGCAAAGGAACAAGGCATCGGGGCAATCCTTGCGTTTGCAATGGCGTACCTTCGCG
       GGACAACCGGCGGTAAGAGCGCCGTTTCCTTGTTCCGTAGCCCCGTTAGGAACGCAAACGTTACCGCATGGAAGCGC
     8▶pLeuLeuAlaAlaIleLeuAlaAlaLysGluGlnGlyIleGlyAlaIleLeuAlaPheAlaMetAlaTyrLeuArgG 40040  GCAGATATAATGGCGGTGCGTTTACAAAAACAGTAATCGACGCAACGATGTGCGCCATTATCGCCTAGTTCATTCGT
       CGTCTATATTACCGCCACGCAAATGTTTTTGTCATTAGCTGCGTTGCTACACGCGGTAATAGCGGATCAAGTAAGCA
    34▶lyArgTyrAsnGlyGlyAlaPheThrLysThrValIleAspAlaThrMetCysAlaIleIleAla

40117  GACCTTCTCGACTTCGC
       CTGGAAGAGCTGAAGCG
```

```
   1 ATGAATCTGAAAGAGAAAACGCGCGCCTGTTTGCTGAAATTTTCGGCTACCCTGCTACCCACACGATTCAGGCGCCAG
     TACTTAGACTTTCTCTTTTGCGCGCGGACAAACGACTTTAAAAGCCGATGGGACGATGGGTGTGCTAAGTCCGCGGTC
   1▶ M  N  L  K  E  K  T  R  A  L  F  A  E  I  F  G  Y  P  A  T  H  T  I  Q  A  P

80 GCCGCGTCAATCTGATCGGCGAGCACACTGATTACAATGATGGTTTTGTTCTGCCCTGCGCTATCGATTACCAGACCG
     CGGCGCAGTTAGACTAGCCGCTCGTGTGACTAATGTTACTACCAAAACAAGACGGGACGCGATAGCTAATGGTCTGGCA
  27▶ G  R  V  N  L  I  G  E  H  T  D  Y  N  D  G  F  V  L  P  C  A  I  D  Y  Q  T  V

159 AATTAGCTGTGCGCCGCGCGACGATCGTACCGTACGGGTGATTGCCGCCGATTACGACAATCAGGTGGACGAATTTTCA
     TTAATCGACACGCGGCGCGCTGCTAGCATGGCATGCCCACTAACGGCGGCTAATGCTGTTAGTCCACCTGCTTAAAAGT
  53▶ I  S  C  A  P  R  D  D  R  T  V  R  V  I  A  A  D  Y  D  N  Q  V  D  E  F  S

238 CTGGATGCGCCGATCGTGACCCACGATAGCCAGCAGTGGTCTAACTATGTGCGCGGCGTAGTGAAACACCTGCAGCAG
     GACCTACGCGGCTAGCACTGGGTGCTATCGGTCGTCACCAGATTGATACACGCGCCGCATCACTTTGTGGACGTCGTCG
  80▶ L  D  A  P  I  V  T  H  D  S  Q  Q  W  S  N  Y  V  R  G  V  V  K  H  L  Q  Q

317 GTAACAACGCGTTTGGCGGCGTGGATATGGTCATCAGCGGCAATGTGCCGCAGGGCGCCGGGTTAAGCTCCTCCGCCTC
     CATTGTTGCGCAAACCGCCGCACCTATACCAGTAGTCGCCGTTACACGGCGTCCCGCGGCCCAATTCGAGGAGGCGGAG
 106▶ R  N  N  A  F  G  G  V  D  M  V  I  S  G  N  V  P  Q  G  A  G  L  S  S  S  A  S

GTGTTCA
 396 GCTGGAAGTGGCGGTGGGCACCGTCTTCCAGCAGCTTTATCACCTGCCGCTGGACGGCGCGCAAATTGCGCTCAACGGA
     CGACCTTCACCGCCACCCGTGGCAGAAGGTCGTCGAAATAGTGGACGGCGACCTGCCGCGCGTTTAACGCGAGTTGCCT
 132▶ L  E  V  A  V  G  T  V  F  Q  Q  L  Y  H  L  P  L  D  G  A  Q  I  A  L  N  G

475 CAAGAGGCCGAGAACCAGTTTGTCGGCTGTAACTGCGGCATTATGGATCAGCTCATCTCTGCGCTCGGCAAAAAAGATC
     GTTCTCCGGCTCTTGGTCAAACAGCCGACATTGACGCCGTAATACCTAGTCGAGTAGAGACGCGAGCCGTTTTTTCTAG
 159▶ Q  E  A  E  N  Q  F  V  G  C  N  C  G  I  M  D  Q  L  I  S  A  L  G  K  K  D

554 ATGCGCTGCTGATTGATTGCCGTACGCTCGGCGCCAAAGCGGTTTCATGCCGAAAGGTGTCGCCGTGGTGATCATCAA
     TACGCGACGACTAACTAACGGCATGCGAGCCGCGGTTTCGCCAAAGGTACGGCTTTCCACAGCGGCACCACTAGTAGTT
 185▶ H  A  L  L  I  D  C  R  T  L  G  A  K  A  V  S  M  P  K  G  V  A  V  V  I  I  N

633 CAGTAACTTTAAGCGCACGCTGGTGGGCAGCGAGTATAATACCCGCCGTGAACAGTGCGAAACCGGCGCCCGTTTCTTC
     GTCATTGAAATTCGCGTGCGACCACCCGTCGCTCATATTATGGGCGGCACTTGTCACGCTTTGGCCGCGGGCAAAGAAG
 211▶ S  N  F  K  R  T  L  V  G  S  E  Y  N  T  R  R  E  Q  C  E  T  G  A  R  F  F

712 CAGCAGCCGGCCCTGCGCGATGTCAGCCTTGAGGCGTTCAATGCCGTTGCCAGCGAACTGGACCCGGTAGTCGCAAAAC
     GTCGTCGGCCGGGACGCGCTACAGTCGGAACTCCGCAAGTTACGGCAACGGTCGCTTGACCTGGGCCATCAGCGTTTTG
 238▶ Q  Q  P  A  L  R  D  V  S  L  E  A  F  N  A  V  A  S  E  L  D  P  V  V  A  K

791 GCGTTCGCCATGTATTGAGCGAAAATGCGCGCACCGTTGAAGCGGCAAGCGCGCTGGAGAAAGGTGATTTGCAACGTAT
     CGCAAGCGGTACATAACTCGCTTTTACGCGCGTGGCAACTTCGCCGTTCGCGCGACCTCTTTCCACTAAACGTTGCATA
 264▶ R  V  R  H  V  L  S  E  N  A  R  T  V  E  A  A  S  A  L  E  K  G  D  L  Q  R  M

870 GGGCCAACTGATGGCGGAGTCCCATGCCTCAATGCGCGATGATTTCGAAATTACCGTCCCGCAGATAGACACGCTGGTA
     CCCGGTTGACTACCGCCTCAGGGTACGGAGTTACGCGCTACTAAAGCTTTAATGGCAGGGCGTCTATCTGTGCGACCAT
 290▶ G  Q  L  M  A  E  S  H  A  S  M  R  D  D  F  E  I  T  V  P  Q  I  D  T  L  V

949 GACATCGTCAAAGCGACCATCGGCGATCGAGGCGGCGTGCGCATGACCGGCGGCGGCTTTGGCGGGTGTGTTGTCGCAC
     CTGTAGCAGTTTCGCTGGTAGCCGCTAGCTCCGCCGCACGCGTACTGGCCGCCGCCGAAACCGCCCACACAACAGCGTG
 317▶ D  I  V  K  A  T  I  G  D  R  G  G  V  R  M  T  G  G  G  F  G  G  C  V  V  A

1028 TGATCCCGGAAGATCTGGTTCCCGCTGTTCGGCAGGCCGTTGCGCAACAGTACGAAGCGAAAACCGGAATCAAAGAAAC
     ACTAGGGCCTTCTAGACCAAGGGCGACAAGCCGTCCGGCAACGCGTTGTCATGCTTCGCTTTTGGCCTTAGTTTCTTTG
 343▶ L  I  P  E  D  L  V  P  A  V  R  Q  A  V  A  Q  Q  Y  E  A  K  T  G  I  K  E  T

1107 CTTTTATGTATGCAAACCGTCACAAGGAGCAGGACAGTGC
     GAAAATACATACGTTTGGCAGTGTTCCTCGTCCTGTCACG
 369▶ F  Y  V  C  K  P  S  Q  G  A  G  Q  C
```

FIG. 21

PLASMIDS AND PHAGES FOR HOMOLOGOUS RECOMBINATION AND METHODS OF USE

PRIORITY CLAIM

This is a divisional of U.S. patent application Ser. No. 13/928,237, filed on Jun. 26, 2013, which is a continuation of U.S. patent application Ser. No. 12/688,764, filed on Jan. 15, 2010, which issued as U.S. Pat. No. 8,541,229, and is a divisional of U.S. patent application Ser. No. 11/134,795, filed on May 20, 2005, which issued as U.S. Pat. No. 7,674,621, and which claims the benefit of U.S. Provisional Application No. 60/655,729, filed Feb. 22, 2005, U.S. Provisional Application No. 60/653,259, filed Feb. 14, 2005, and U.S. Provisional Application No. 60/573,504, filed May 21, 2004. All of the prior applications are incorporated by reference herein in their entirety.

FIELD

This application relates to recombinant DNA technology, specifically to plasmids and phages of use for introducing homologous recombination functions into host cells.

BACKGROUND

Concerted use of restriction endonucleases and DNA ligases allows in vitro recombination of DNA sequences. The recombinant DNA generated by restriction and ligation may be amplified in an appropriate microorganism such as *E. coli*, and used for diverse purposes including gene therapy. However, the restriction-ligation approach has two practical limitations: first, DNA molecules can be precisely combined only if convenient restriction sites are available; second, because useful restriction sites often repeat in a long stretch of DNA, the size of DNA fragments that can be manipulated are limited, usually to less than about 20 kilobases.

Homologous recombination, generally defined as an exchange of homologous segments anywhere along a length of two DNA molecules, provides an alternative method for engineering DNA. In generating recombinant DNA with homologous recombination, a microorganism such as *E. coli*, or a eukaryotic cell such as a yeast or vertebrate cell, is transformed with an exogenous strand of DNA. The center of the exogenous DNA contains the desired transgene, whereas each flank contains a segment of homology with the cell's DNA. The exogenous DNA is introduced into the cell with standard techniques such as electroporation or calcium phosphate-mediated transfection, and recombines into the cell's DNA, for example with the assistance of recombination-promoting proteins in the cell.

In generating recombinant DNA by homologous recombination, it is often advantageous to work with short linear segments of DNA. For example, a mutation may be introduced into a linear segment of DNA using polymerase chain reaction (PCR) techniques. Under proper circumstances, the mutation may then be introduced into cellular DNA by homologous recombination. Such short linear DNA segments can transform yeast, but subsequent manipulation of recombinant DNA in yeast is laborious. It is generally easier to work in bacteria, but linear DNA fragments do not readily transform bacteria (due in part to degradation by bacterial exonucleases). Accordingly, recombinants are rare, require special poorly-growing strains (such as RecBCD− strains) and generally require thousands of base pairs of homology.

Recently, a method for homologous recombination, termed "recombineering" has made it possible to clone nucleic acids in specific strains of *E. coli* using homologous recombination. However, the number of strains of *E. coli* that can be used in this method are limited. Thus, methods of introducing recombineering functions into other strains of *E. coli* are needed. In addition, methods of introducing these functions into other bacteria, including other gram negative bacteria, are also needed.

SUMMARY

Recombineering utilizes the recombination functions encoded by lambdoid bacteriophages to efficiently catalyze homologous recombination in vivo between DNA sequences with homologies as short as 35 bases. Recombineering provides methods to clone and modify genes on plasmids, on BACs, on the chromosome of enteric bacteria, and on bacteriophage λ, without the necessity of restriction enzymes or DNA ligase. Recombineering also allows rapid and precise in vivo manipulation of DNA.

Disclosed herein are plasmids that can be used to confer recombineering functions to a variety of cells, including strains of *E. coli, Salmonella, Pseudomonas, Cyanobacteria*, and *Spirochaetes*, amongst others. These mobilizable plasmids can be manipulated in vitro and can be used to transform bacterial cells, such as gram negative bacteria. These plasmids include an origin of replication specific for the bacterial cell(s) of interest, a de-repressible promoter, and a nucleic acid encoding a single-stranded binding protein such as Beta. In additional embodiments, the plasmids include a nucleic acid encoding Exo and/or Gam. In one example, the plasmid includes an origin of replication and a lambda genome having DNA encoding functional Beta and optionally Exo, and Gam, or functional fragments or variants thereof, operably linked to a de-repressible promoter (such as, but not limited to, the λ $P_L$ promoter). In one example, the plasmids include an origin of replication, a nucleic acid encoding a selectable marker, a nucleic acid encoding a promoter operably linked to nucleic acid sequence encoding a repressor that specifically binds a de-repressible promoter, and the de-repressible promoter operably linked to a nucleic acid encoding Beta and a terminator 3' of the nucleic acid encoding a single-stranded binding protein. Bacterial host cells transformed with the vector are capable of performing homologous recombination.

Lambda phages that can be used to introduce recombineering functions into host cells are also disclosed herein. These phages include amber mutations in an essential gene(s) and include a selectable marker. In this manner, the phage will enter the lytic cycle in a host cell that includes a suppressor of the amber mutation and cause host cell death. However, the phage will be able to lysogenize in cells that do not include the suppressor mutation(s). In one example, the phage includes a repressor that binds a $P_L$ promoter, a promoter operably linked to a nucleic acid encoding a heterologous nucleic acid sequence, $P_L$, and a nucleic acid encoding Beta operably linked to $P_L$, a nucleic acid encoding P, a nucleic acid encoding O, and a nucleic acid encoding Cro. At least two of the nucleic acids (genes) encoding P, the nucleic acid encoding O, and the nucleic acid encoding Cro include an amber codon. Thus, at least two of P, O, and Cro proteins are not produced when the lambda phage is introduced into a suppressor minus host cell, but are produced in host cells that include appropriate tRNA suppressors. In this manner lytic phage in high yields can be produced in host cells that include the appropriate tRNA suppressors.

The foregoing and other features and advantages will become more apparent from the following detailed description of several embodiments, which proceeds with reference to the accompanying figures.

BRIEF DESCRIPTION OF THE FIGURES

FIG. 2 is a schematic diagram of the genetic map of lambda phage, showing the position of the major genes in a wild-type lambda nucleic acid.

FIGS. 4A-F are the nucleic acid sequence (SEQ ID NO: 2) of pSIM4 (see FIG. 3), which encodes cI (SEQ ID NO: 10), Gam (SEQ ID NO: 11), Bet (SEQ ID NO: 12) and Exo (SEQ ID NO: 13) and Bla (Amp$^R$) (SEQ ID NO: 15). The amino acid sequence for each of the proteins is shown below the DNA sequence of pSIM4 (SEQ ID NO: 2) identified with its letters. Since the genes are transcribed from the sequence shown in the figure from right to left the proteins are shown in this orientation, and the number of the amino acid is shown at the left edge. Each protein starts with M (for methionine) and above that M in the DNA sequence is the name of the gene (protein) Gam, Beta or Exo (SEQ ID NOs: 11-13). In the sequence shown in the panels of this figure, the coding sequence of DNA is the bottom strand. Thus, the start codon is "GTA" on the bottom but is read right to left as "ATG." Exo starts M T P D I I (the first amino acids of SEQ ID NO: 13), Beta starts M S T A L (the first amino acids of SEQ ID NO: 12), Gam starts M N A Y Y (the first amino acids of SEQ ID NO: 11). The nucleic acid encoding the phage genes from pSIM4, pSIM6 and pSIM8 is set forth as SEQ ID NO: 9.

FIGS. 6A-G is the nucleotide sequence of pSIM5 (SEQ ID NO: 3). The phage genes from pSIM5 are set forth in the nucleotide sequence of SEQ ID NO: 8 (the amino acid sequences of Beta, Gam and Exo are set forth as SEQ ID NOs: 11-13). The sequence of the CAT drug cassette is shown in SEQ ID NO: 14, and the amino acid sequence of Repts is shown in SEQ ID NO: 16. The amino acid sequence of cI857 is shown in SEQ ID NO: 10, and the amino acid sequence of the Orf of pSIM5 is set forth as SEQ ID NO: 17.

FIGS. 8A-F are the nucleic acid sequence (SEQ ID NO: 4) of pSIM6-pSC101 rex< >amp (see FIG. 7) and the polypeptides encoded by this plasmid (SEQ ID NOs: 10-13, 15, 16 and 17). The phage genes of pSIM6 are shown in the nucleotide sequence set forth as SEQ ID NO: 9.

FIGS. 10A-G are the nucleic acid sequence (SEQ ID NO: 6) of plasmid pSIM8-pBBR1 rex< >amp and the polypeptides encoded by this plasmid (SEQ ID NOs: 10-13, 15, 18). The phage genes of pSIM8 are shown in the nucleotide sequence set forth as SEQ ID NO: 9.

FIGS. 12A-E are the nucleotide sequence of pSIM2 (SEQ ID NO: 1) and the encoded polypeptides (SEQ ID NOs: 10-14). The phage genes of pSIM2 are set forth as SEQ ID NO: 8.

FIG. 14A-G are the nucleotide sequence of pSIM7 (SEQ ID NO: 5); the nucleotide sequence of the phage genes are set forth as SEQ ID NO: 8. Polypeptides encoded by the plasmid are set forth as SEQ ID NOs: 10-13, 14, and 18.

FIGS. 15A-G are the nucleotide sequence of pSIM9 (SEQ ID NO:7). The amino acid sequences of the encoded polypeptides (SEQ ID NOs: 10-14, 14, 18 and 19) are also shown.

FIG. 16A is a schematic diagram of a lambda prophage without the N-kil region and wherein a selectable marker is inserted into the prophage rex genes.

FIGS. 17A-B are the lambda nucleic acid sequence (SEQ ID NO: 24) showing the rex genes. The sequence numbers are the same as in the lambda genomic sequence. The protein sequence of RexA (SEQ ID NO: 25 and RexB (SEQ ID NO: 26) is shown. Note that the amino acid sequence of RexA and RexB each begin with a methioine (M). In the figure the sequences are read from the initiating methionine (at the N-terminus) from right to left.

FIGS. 18A-B are the nucleic acid sequence of the rexAB< >tetRA wherein the tet genes (SEQ ID NO: 29) replace the rexAB genes (SEQ ID NO: 25, SEQ ID NO: 26). The flanking sequence of lambda is used to illustrate the exact sequence replacement. The sequence numbers at the top left are the same as in the lambda genomic sequence. The amino acid sequences of tetA (SEQ ID NO: 28) and tetR (SEQ ID NO: 27) are shown.

FIG. 19 is the lambda nucleic acid sequence of the S gene (SEQ ID NO: 30) encoding the S protein (SEQ ID NO: 31). The sequence numbers are the same as in the lambda genomic sequence.

FIGS. 20A-B are the sequence of S< >tetRA wherein the S gene is replaced by the tetRA genes. The sequence numbers at the top left are the same as in the lambda genomic sequence. The amino acid sequences of tetA (SEQ ID NO: 13) and tetR (SEQ ID NO: 14) are shown.

FIG. 21 is the nucleic acid sequence (SEQ ID NO: 21) encoding the *S. typhimurium* galK protein (galK−, SEQ ID NO: 20).

SEQUENCE LISTING

Figures 1A, 1B:
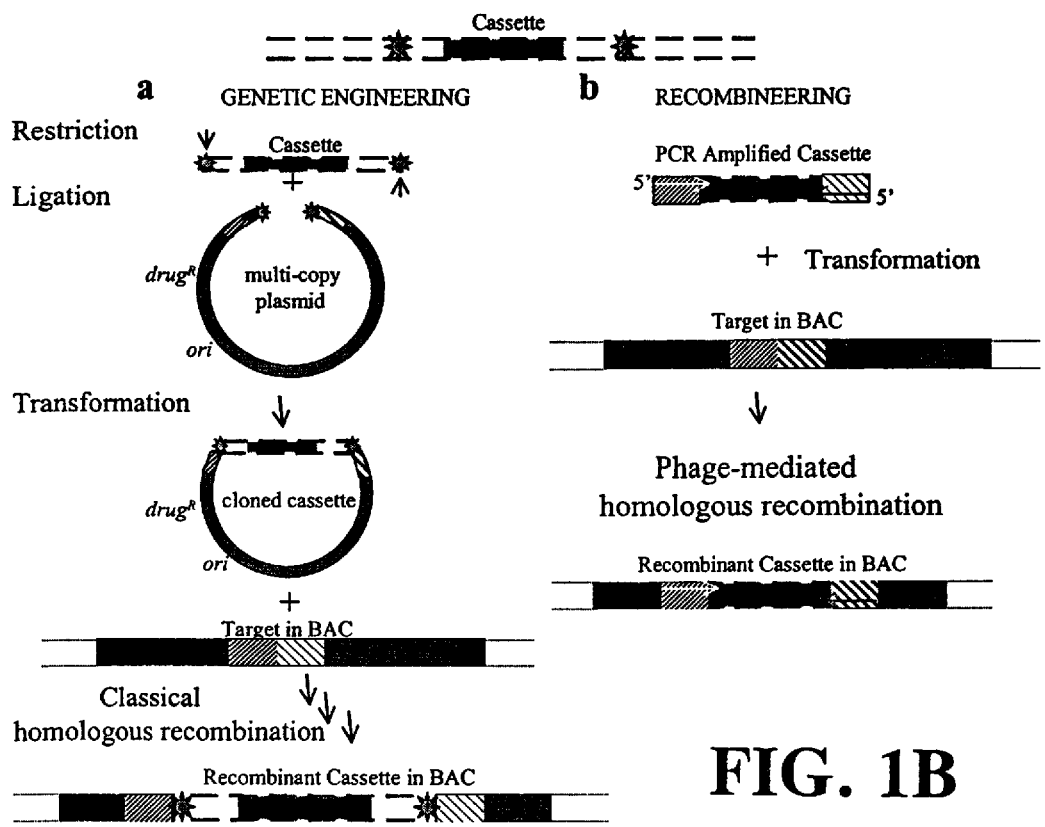
FIG. 1A is a schematic diagram showing classical recombinant technology.
FIG. 1B is a schematic diagram showing "recombineering" using homologous recombination, as disclosed herein.
Figure 3:
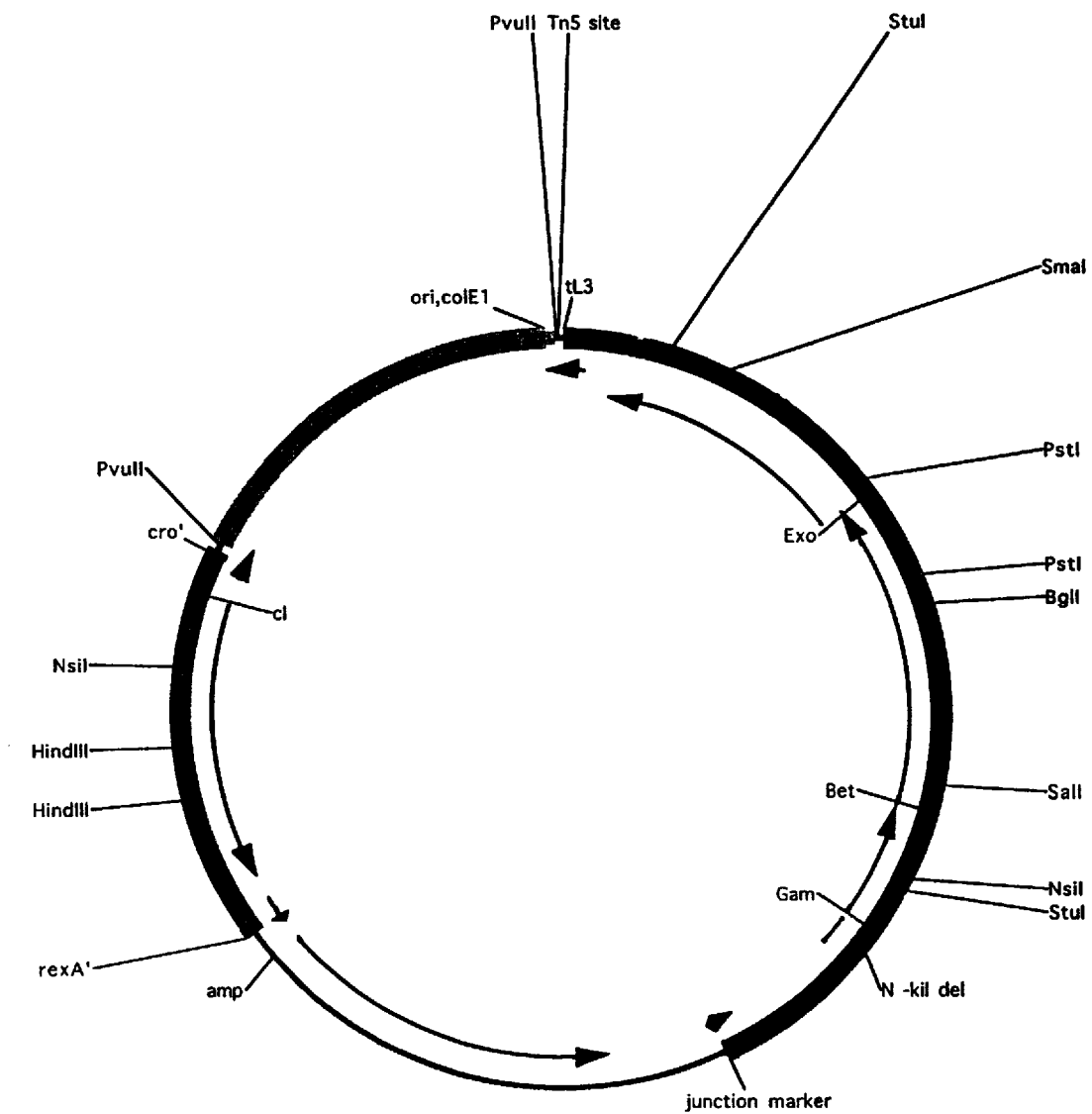
FIG. 3 is a schematic diagram of the plasmid pSIM4 pUC rex< >amp.

The nucleic and amino acid sequences listed in the accompanying sequence listing are shown using standard letter abbreviations for nucleotide bases, and three letter code for amino acids, as defined in 37 C.F.R. 1.822. If only one strand of each nucleic acid sequence is shown, the complementary strand is understood as included by any reference to the displayed strand, if appropriate in context.

The Sequence Listing is submitted as an ASCII text file [4239-68523-06_Sequence_Listing.txt, Sep. 9, 2014, 105 KB], which is incorporated by reference herein.

In the accompanying sequence listing:
SEQ ID NO: 1 is the nucleic acid sequence of pSIM2.
SEQ ID NO: 2 is the nucleic acid sequence of pSIM4.
SEQ ID NO: 3 is the nucleic acid sequence of pSIM5.
SEQ ID NO: 4 is the nucleic acid sequence of pSIM6.
SEQ ID NO: 5 is the nucleic acid sequence of pSIM7.

SEQ ID NO: 6 is the nucleic acid sequence of pSIM8.

SEQ ID NO: 7 is the nucleic acid sequence of pSIM9.

SEQ ID NO: 8 is the nucleic acid sequence of the phage genes of pSIM2, pSIM5, pSIM7 and pSIM9 plasmids.

SEQ ID NO: 9 is the nucleic acid sequence of the phage genes of pSIM4, pSIM6 and pSIM8 plasmids.

SEQ ID NO: 10 is the amino acid sequence of cI857.

SEQ ID NO: 11 is the amino acid sequence of Gam.

SEQ ID NO: 12 is the amino acid sequence of Beta.

SEQ ID NO: 13 is the amino acid sequence of Exo.

SEQ ID NO: 14 is the amino acid sequence of the CAT drug cassette, used in pSIM2, pSIM5, pSIM7 and pSIM9.

SEQ ID NO: 15 is the amino acid sequence of the Amp drug cassette, used in pSIM4, pSIM6 and pSIM8.

SEQ ID NO: 16 is the amino acid sequence of Repts of pSIM5 and pSIM6.

SEQ ID NO: 17 is the amino acid sequence of the Orf of pSIM5 and pSIM6.

SEQ ID NO: 18 is the amino acid sequence of Rep of pSIM7 and pSIM8.

SEQ ID NO: 19 is the amino acid sequence of the replication gene TrfAts from pSIM9.

SEQ ID NO: 20 is the amino acid sequence of galK.

SEQ ID NO: 21 is the nucleic acid sequence encoding galK.

SEQ ID NO: 22 is the nucleic acid sequence of an oligonucleotide.

SEQ ID NO: 23 is the nucleic acid sequence of an oligonucleotide.

SEQ ID NO: 24 is the nucleic acid sequence encoding RexAB.

SEQ ID NO: 25 is the amino acid sequence of RexA.

SEQ ID NO: 26 is the amino acid sequence of RexB.

SEQ ID NO: 27 is the amino acid sequence of tetR.

SEQ ID NO: 28 is the amino acid sequence of tetA.

SEQ ID NO: 29 is the nucleic acid sequence encoding tetRA.

SEQ ID NO: 30 is the nucleic acid sequence encoding S.

SEQ ID NO: 31 is the amino acid sequence of S.

SEQ ID NO: 32 is the nucleic acid sequence of an oligonucleotide.

SEQ ID NO: 33 is the nucleic acid sequence of an oligonucleotide.

SEQ ID NO: 34 is the nucleic acid sequence of an oligonucleotide.

SEQ ID NO: 35 is the nucleic acid sequence of an oligonucleotide.

DETAILED DESCRIPTION

I. Abbreviations

Amp: ampicillin
BAC: bacterial artificial chromosome
Bp: base pairs
Cat: chloramphenicol acetyl-transferase
Ini: initiation
λ: lambda
Ori: origin of replication II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Antibiotic resistance cassette: A nucleic acid sequence encoding a selectable marker which confers resistance to that antibiotic in a host cell in which the nucleic acid is translated. Examples of antibiotic resistance cassettes include, but are not limited to: kanamycin, ampicillin, tetracycline, chloramphenicol, neomycin, hygromycin and zeocin.

Attachment site (att): A specific site for recombination that occurs on either a phage or a chromosome. An attachment site on lambda is termed "attP," while an attachment site of a bacterial chromosome is "attB." Integrase mediated recombination of an attP site with an attB site leads to integration of the λ prophage in the bacterial chromosome.

Bacterial artificial chromosome (BAC): Bacterial artificial chromosomes (BACs) have been constructed to allow the cloning of large DNA fragments in *E. coli*, as described in O'Conner et al., *Science* 244:1307-12, 1989; Shizuya et al., *Proc. Natl. Acad. Sci. U.S.A.* 89:8794-7, 1992; Hosoda et al., *Nucleic Acids Res.* 18:3863-9, 1990; and Ausubel et al., eds., *Current Protocols In Molecular Biology*, John Wiley & Sons (c) 1998 (hereinafter Ausubel et al., herein incorporated in its entirety). This system is capable of stably propagating mammalian DNA over 300 kb. In one embodiment, a BAC carries the F replication and partitioning systems that ensure low copy number and faithful segregation of plasmid DNA to daughter cells. Large genomic fragments can be cloned into F-type plasmids, making them of use in constructing genomic libraries.

Beta: The 28 kDa lambda Beta ssDNA binding polypeptide (and nucleic acid encoding lambda beta) involved in double-strand break repair homologous recombination. DNA encoding Beta (bet) and polypeptide chains having lambda Beta activity are also referred to herein as bet. See Examples 1 and 14 and references therein for further information. The lambda Beta protein binds to single-stranded DNA and promotes renaturation of complementary single-strand regions of DNA (see also Karakousis et al., *J. Mol. Biol.* 276:721-733, 1998; Li et al., *J. Mol. Biol.* 276:721-733, 1998; Passy et al., *PNAS* 96:4279-4284, 1999).

Functional fragments and variants of Beta include those variants that maintain their ability to bind to ssDNA and mediate the recombination function of lambda Beta as described herein, and in the publications referenced herein. It is recognized that the gene encoding Beta may be considerably mutated without materially altering the ssDNA binding function or homologous recombination function of lambda Beta. First, the genetic code is well-known to be degenerate, and thus different codons encode the same amino acids. Second, even where an amino acid mutation is introduced, the mutation may be conservative and have no material impact on the essential functions of lambda Beta. See Stryer, *Biochemistry* 3rd Ed., (c) 1988. Third, part of the lambda Beta polypeptide chain may be deleted without impairing or eliminating its ssDNA binding protein function, or its recombination function. Fourth, insertions or additions may be made in the lambda Beta polypeptide chain—for example, adding epitope tags—without impairing or eliminating its essential functions (see Ausubel et al., 1997, supra).

Biolistics: Insertion of DNA into cells using DNA-coated micro-projectiles. Also known as particle bombardment or microparticle bombardment. The approach is further described and defined in U.S. Pat. No. 4,945,050, which is herein incorporated by reference.

cDNA (complementary DNA): A piece of DNA lacking internal, non-coding segments (introns) and regulatory sequences that determine transcription. cDNA may be synthesized in the laboratory by reverse transcription from messenger RNA extracted from cells.

Cro: A very small protein, the wild-type form of which includes 66 amino acids. The protein includes a single domain which contains a DNA-binding helix-turn-helix. The Cro protein binds the operator sites ($O_L$ and $O_R$) of lambda. It interferes with the binding of cI, which is a repressor that also binds to the operator sites of lambda. Transcription of the Cro and cI is regulated by the cI protein. Specifically, in the absence of cI proteins, the Cro gene can be transcribed, while in the presence of cI proteins, only the cI gene is transcribed. At high concentrations of cI, transcriptions of both genes are repressed. Temperature sensitive mutations of cI have been described, such as cI857. In these temperature sensitive forms, the function of cI is inhibited at high temperatures (such as when the temperature is increased from 37° C. to 42° C.). The sequence and functions of Cro and cI are well known, and are described, for example, in Ptashne et al., *A Genetic Switch, Third Edition, Phage Lambda Revisited*, Cold Spring Harbor Press, Cold Spring Harbor, N.Y., 2004, which is incorporated herein by reference. The structure and sequence of lambda, including Cro and cI can also be found on the internet.

De-repressible promoter: When a repressor is bound to a de-repressible promoter, transcription is substantially decreased as compared to transcription from the de-repressible promoter in the absence of the repressor. By regulating the binding of the repressor, such as by changing the environment, the repressor is released from the de-repressible promoter and transcription increases.

One specific, non-limiting example of a de-repressible promoter is the $P_L$ promoter, which is regulated by the repressor cI. $P_L$ is not activated by an activator, and thus is not an inducible promoter. An "activatable promoter" is a promoter wherein binding of an activator to the promoter increases transcription from the promoter. The arabinose promoter, pBAD is not a simple de-repressible promoter; arabinose inactivates the repressor AraC and converts it to an activator. Thus, pBAD is an activatable promoter.

In one embodiment, the de-repressible promoter is a temperature sensitive de-repressible promoter. A temperature sensitive de-repressible promoter is a promoter that is de-repressed only at a specified temperature, or range of temperatures. In one embodiment, by increasing the temperature, the repressor is released from the promoter, or can no longer bind to the promoter with a high affinity, and transcription is increased from the promoter. One specific, non-limiting example is the induction of $P_L$ promoter activity by increasing the temperature of the cell using cI87. Increased temperature inactivates the temperature-sensitive repressor cI, allowing genes that are operably linked to the $P_L$ promoter to be expressed at increased levels. One of skill in the art can readily identify a de-repressible promoter.

In one embodiment, a de-repressible promoter is auto-regulated. One specific, non-limiting example of an auto-regulated de-repressible promoter is $P_L$. If only one copy of a gene encoding cI is present, yet many copies of the $P_L$ promoter are present, expression of cI is upregulated such that transcription is blocked from any of the $P_L$ promoters.

Double-strand break repair recombination: A type of homologous recombination exemplified by the lambda recombination proteins Exo, Beta and Gam, and shared by numerous other recombinase systems. A double-strand break is the initiation point for concerted action of recombination proteins. Typically, an exonuclease degrades processively from the 5' ends of these break sites, and ssDNA binding polypeptide binds to the remaining 3' single-strand tail, protecting and preparing the recessed DNA for homologous strand invasion (Szostak et al., *Cell* 33:25-35, 1983; Little, *J. Biol. Chem.* 242:679-686, 1967; Carter et al., *J. Biol. Chem.* 246:2502-2512, 1971; Lindahl et al., *Science* 286:1897-1905, 1999). Examples of ssDNA binding polypeptides which bind to either ssDNA and/or dsDNA with 3' overhangs and promote double-strand break repair recombination include lambda Beta, RecT of *E. coli*, Erf of phage p22, and Rad52 in various eukaryotic cells including yeast and mammalian cells.

Electrocompetent: Cells capable of macromolecular uptake upon treatment with electroporation.

Electroporation: A method of inducing or allowing a cell to take up macromolecules by applying electric fields to reversibly permeabilize the cell walls. Various methods and apparatuses used are further defined and described in: U.S. Pat. No. 4,695,547; U.S. Pat. No. 4,764,473; U.S. Pat. No. 4,946,793; U.S. Pat. No. 4,906,576; U.S. Pat. No. 4,923,814; and U.S. Pat. No. 4,849,089, all of which are herein incorporated by reference.

Eukaryotic cell: A cell having an organized nucleus bounded by a nuclear membrane. These include lower organisms such as yeasts, slime molds, and the like, as well as cells from multicellular organisms such as invertebrates, vertebrates and mammals. They include a variety of tissue types, such as, but not limited to, endothelial cell, smooth muscle cell, epithelial cell, hepatocyte, cells of neural crest origin, tumor cell, hematopoietic cell, immunologic cell, T cell, B cell, monocyte, macrophage, dendritic cell, fibroblast, keratinocyte, neuronal cell, glial cell, adipocyte, myoblast, myocyte, chondroblast, chondrocyte, osteoblast, osteocyte, osteoclast, secretory cell, endocrine cell, oocyte, and spermatocyte. These cell types are described in standard histology texts, such as McCormack, *Introduction to Histology*, (c) 1984 by J.P. Lippincott Co.; Wheater et al., eds., *Functional Histology*, 2nd Ed., (c) 1987 by Churchill Livingstone; Fawcett et al., eds., Bloom and Fawcett: *A Textbook of Histology*, (c) 1984 by William and Wilkins, all of which are incorporated by reference in their entirety. In one specific, non-limiting example, a eukaryotic cell is a stem cell, such as an embryonic stem cell.

Exo: The exonuclease of lambda (and the nucleic acid encoding the exonuclease protein) involved in double-strand break repair homologous recombination. See Example 1 and references therein for further description.

Exogenous: The term "exogenous" as used herein with reference to nucleic acid and a particular cell refers to any nucleic acid that does not originate from that particular cell as found in nature. Thus, a non-naturally-occurring nucleic acid is considered to be exogenous to a cell once introduced into the cell. Nucleic acid that is naturally occurring also can be exogenous to a particular cell. For example, an entire chromosome isolated from a cell of subject X is an exogenous nucleic acid with respect to a cell of subject Y once that chromosome is introduced into Y's cell.

Extrachromosomal: Not incorporated into the chromosome or chromosomes of a cell. In the context of nucleic acids, extrachromosomal indicates a DNA oligonucleotide that is not covalently incorporated into the chromosome or chromosomes of a cell. Intrachromosomal refers to material such as an oligonucleotide that is incorporated into the chromosome or chromosomes of a cell, such as a DNA oligonucleotide covalently incorporated into the chromosomal DNA of a cell.

Flanking: In the sequence "A-B-A", nucleic acid sequence "A" flanks nucleic acid sequence "B." In one specific, non-limiting example, nucleic acid sequence "A" is located immediately adjacent to nucleic acid "B." In another specific, non-limiting example, an linker sequence of not more than 500 nucleotides is between each copy of "A" and "B," such as a linker sequences of about 200, about 100, about 50, or about 10 nucleotides in length. Nucleotide sequences "A" and "B" can be of any length. "Adjacent" refers to a first nucleic acid sequence next to a second amino acid sequence. Thus, in the sequence A-B-C, A is 5' to B and adjacent to B. However, A is 5' to C but is not adjacent to C. B is 3' of A and 5' of C; B is adjacent to both A and C and is flanked by A and C.

Gam: A lambda protein (and nucleic acid encoding Gam) involved in double-strand break repair homologous recombination. It is believed to inhibit cellular nuclease activity such as that encoded by the recBCD and sbcC system of $E.$ $coli$. See Examples 1, 7 and 14 and references therein for further description. Gam function, when expressed in the cell, is extremely toxic to the cell, and prevents growth. For this reason tight controls over its expression are always required. As described herein, $P_L$ and cI 857 are able to regulate Gam expression.

Functional fragments and variants of Exo and Gam: As discussed for Beta (see "Functional Fragments And Variants Of Beta"), it is recognized that genes encoding Exo or Gam may be considerably mutated without materially altering their function, because of genetic code degeneracy, conservative amino acid substitutions, non-critical deletions or insertions, etc. Unless the context makes otherwise clear, the term lambda Exo, Exo or lambda exonuclease are all intended to include the native lambda exonuclease, and all fragments and variants of lambda exonuclease.

Gene: A nucleic acid encoding a protein product. In a specific non-limiting example, a gene includes at least one expression control sequence, such as a promoter, enhancer or a repressor. In another specific, non-limiting example, a gene includes at least one intron and at least one exon.

Homology arm: Nucleotides at or near 5' or 3' end of a polynucleotide which are identical or similar in sequence to the target nucleic acid in a cell, and capable of mediating homologous recombination with the target nucleic acid. Homology arms are also referred to as homologous arms. In one embodiment, a homology arm includes at least 20 bases of a sequence homologous to a nucleic acid of interest. In another embodiment, the homology arm includes at least 30 base pairs of a sequence homologous to a nucleic acid of interest. In yet another embodiment, a homology arm includes at least 40 base pairs of a sequence homologous to a nucleic acid of interest. In a further embodiment, a homology arm includes from about 50 to about 100 base pairs of a sequence homologous to a nucleic acid of interest.

Homologous recombination: An exchange of homologous polynucleotide segments anywhere along a length of two nucleic acid molecules. In one embodiment, two homologous sequences are 100% identical. In another embodiment, two homologous sequences are sufficiently identical such that they can undergo homologous recombination. Specific, non-limiting examples of homologous sequences are nucleic acid sequences that are at least 95% identical, such as about 99% identical, about 98% identical, about 97% identical, or about 96% identical.

Host cell: A cell that is used in lab techniques such as DNA cloning to receive exogenous nucleic acid molecules. In one embodiment a host cell is used to maintain or allow the reproduction of a vector, or to facilitate the manipulation of nucleic acid molecules in vitro. A host cell can be a prokaryotic or a eukaryotic cell. In one embodiment, a host cell is a gram negative bacterial cell. In another embodiment, a host cell is a gram positive host cell.

HVJ-mediated gene transfer: A method of macromolecular transfer into cells using inactivated hemagglutinating virus of Japan and liposomes, as described in Morishita et al., $J.$ $Clin.$ $Invest.$ 91:2580-2585, 1993; Morishita et al., $J.$ $Clin.$ $Invest.$ 94:978-984, 1994; which are herein incorporated by reference.

Inducible promoter: A promoter whose activity can be increased by the binding of an inducer to the promoter. Examples of inducible promoters abound in nature, and a broad range of environmental or hormonal changes may activate or repress them. One specific example of an inducible promoter is pBAD.

Initiation site or replication: The site on a nucleic acid sequence wherein of DNA replication occurs. For example, a bacterial origin of replication is the site on the bacterial DNA wherein DNA replication starts. For example, an initiation site can be a ColE1 initiation site (Tomizawa et al., $PNAS$ 74:1865-69, 1077) or an $E.$ $coli$ or $B.$ $subtilis$ oriC (see Seitz et al., $EMBO$ $Reports$ 2:1003-1006, 2001).

Intron: An intragenic nucleic acid sequence in eukaryotes that is not expressed in a mature RNA molecule. Introns of the present disclosure include full-length intron sequences, or a portion thereof, such as a part of a full-length intron sequence.

Isolated: An "isolated" biological component (such as a nucleic acid or protein) has been substantially separated or purified away from other biological components in the cell of the organism in which the component naturally occurs, i.e., other chromosomal and extra-chromosomal DNA and RNA, and proteins. Thus, nucleic acids and proteins that have been "isolated" include nucleic acids and proteins purified by standard purification methods. The term also embraces nucleic acids and proteins prepared by recombinant expression in a host cell as well as chemically synthesized nucleic acids.

Knockout: Inactivation of a gene such that a functional protein product cannot be produced. A conditional knockout is a gene that is inactivated under specific conditions, such as a gene that is inactivated in a tissue-specific or a temporal-specific pattern. A conditional knockout vector is a vector including a gene that can be inactivated under specific conditions. A conditional knockout transgenic animal is a transgenic animal including a gene that can be inactivated in a tissue-specific or a temporal-specific manner.

Linear plasmid vector: A DNA sequence (1) containing a bacterial plasmid origin of replication, (2) having a free 5' and 3' end, and (3) capable of circularizing and replicating as a bacterial plasmid by joining its free 5' and 3' ends. Examples of linear plasmid vectors include the linearized pBluescript vector and linearized pBR322 vectors described herein.

Linker region: DNA which connects flanking regions of a plasmid. The linker region can include multi-cloning sites which contain recognition sites for specific restriction endonucleases and transcriptional terminator-sequence. Linker regions can be ligated to the ends of DNA fragments prepared by cleavage with some other enzyme. A linker region can also have unique restriction endonuclease sites at the location of the start and stop codon to ligate the 5' flanking region, as well as the 3' flanking region to the nucleic acid of the linker. In particular, the linker region provides recognition sites, i.e., the "multicloning sites," for inserting the nucleic acid cassette which contains a specific nucleic sequence to be expressed. These recognition sites may be a restriction endonuclease site in the linker, such as BamHI, EcoRI, HindIII, ClaI, NotI, XmaI, BglII, PacI, XhoI, NheI, SfiI, which are only examples and not meant to be limiting. The multicloning site permits easy insertion of expression nucleic acid elements such as promoters, nucleic acids encoding selectable markers or therapeutic genes, etc. For example, the multicloning site in pBluescript KS+ provides 17-23 unique restriction sites useful in inserting expression elements or previously constructed nucleic acid cassettes.

Lipofection: The process of macromolecular transfer into cells using liposomes. See U.S. Pat. No. 5,651,981, which is herein incorporated by reference.

Mini-lambda: A derivative of lambda (λ) wherein most of the viral lytic genes, including those required for replication and lysis, are deleted. A mini-lambda maintains the Red functions (Beta, Exo, and Gam) for homologous recombination and maintains the integration/excision functions (for example, att, integrase (int) and excisionase (xis)) to insert and excise its DNA from the chromosome.

Nucleic acid: A deoxyribonucleotide or ribonucleotide polymer in either single- or double-stranded form, including known analogs of natural nucleotides unless otherwise indicated.

Oligonucleotide (oligo): A single-stranded nucleic acid ranging in length from 2 to about 500 bases, for example, polynucleotides that contain at least 20 or 40 nucleotides (nt). Oligonucleotides are often synthetic but can also be produced from naturally occurring polynucleotides.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Operator site ($O_R$ and $O_L$): A nucleic acid sequence found in lambda, repressor binding at these sites reduces transcription of N and Cro from $P_L$ and $P_R$, respectively. The right complete operator region ($O_R$) can be subdivided into three operators, $O_R1$, $O_R2$, and $O_R3$. Similarly, the left complete operator can also be subdivided into three operators. The repressor, cI, binds to both $O_R1$ and $O_R2$, and binding to $O_R2$ stimulates the transcription of the cI mRNA. The repressor, cI, binds to the three operator regions in the order of: cI binds most tightly to $O_R1$, next to $O_R2$, and lastly to $O_R3$. The binding of Cro and cI to this region differs in terms of the order of interaction; Cro binds most tightly to $O_R3$, next to $O_R2$, and lastly to $O_R1$. Similarly, Cro and cI bind to $O_L1$, $O_L2$, and $O_L3$ with different affinities.

Origin of replication (ori): A nucleotide sequence at which DNA synthesis for the purpose of replicating the nucleic acid sequence begins. This is generally termed an "ori" site. Circular bacterial chromosomes generally have a single on site, whereas there are many on sites on each eukaryotic chromosome. This term includes replicons, which as used herein refers to a genetic element that behaves as an autonomous unit during DNA replication. In bacteria, the chromosome functions as a single replicon, whereas eukaryotic chromosomes contain hundreds of replicons in series.

The on site of plasmids can allow replication in one or more bacterial species, such as a gram negative or a gram positive species. For example, an on can allow replication in one or more of *E. Coli, Yersinia,* or *Salmonella.* Specific, non-limiting examples of an on are a ColE1 origin and its derivatives, a pSC101 origin and its derivatives, a pBBR1 origin and its derivatives, and a RK2 origin and its derivatives. In one specific example, a ColE1 origin of replication is described in Tomizawa et al., *Proc. Natl. Acad. Sci.* (*PNAS*) 74:1865-69, 1977 (such as −420 to −613 base pairs (upstream) of the initiation site of ColE1 replication).

A "conditional origin of replication" refers to an origin of replication that requires the presence of a functional transacting factor (e.g., a replication factor) in a prokaryotic host cell. Conditional origins of replication encompass temperature-sensitive replicons such as rep pSC101.

Operator sequence: A specific nucleic acid sequence capable of interacting with a specific repressor, thereby controlling the function of genes in adjacent cistrons and regulator genes. In general, a regulator gene is a gene whose primary function is to control the rate of synthesis of the products of other distant genes. The regulator gene controls the synthesis of a protein repressor, which inhibits the action of an operator gene and thus turns off the operon it controls. The repressor usually is present in small amounts. It may possess two sites, one of which can attach to the operator and one of which can bind an effector molecule. In one embodiment, once a repressor is bound to an effector molecule, the repressor changes shape and cannot attach to the operator. In another embodiment (such as for λ cI857) heat itself can inactivate or denature the intact repressor so that it does not attach to the operator. An operon is a unit of nucleic acid sequence consisting of one or more cistrons that function coordinately under the control of an operator sequence.

Thus, the repressor is a protein, synthesized by a regulator gene, that binds to an operator locus and blocks transcription of that operon. The repressor causes repression of transcription. When de-repressed, transcription and/or translation are increased.

Phage-based recombination systems: Bacteria such as *E. coli* encode their own homologous recombination systems, which are used in repair of DNA damage and to maintain a functional chromosome. The viruses or phages that inhabit bacteria often carry their own recombination functions. Phage λ carries the Red recombination system. These phage systems can work with the bacterial recombination functions or independently of them. It should be noted that a prophage is the latent state of a phage in a lysogenic bacterium. "Induction" is the process that converts a prophage into a phage.

$P_L$ promoter: The major leftward promoter of bacteriophage lambda. Once the lambda DNA is incorporated into the bacterial chromosome, transcription from this promoter is substantially repressed by the cI repressor. Upon inactivation of the cI repressor, for example by heat shock of a temperature sensitive mutant, transcription from the $P_L$ promoter is de-repressed, leading to expression of lambda genes. See Sambrook et al., "Bacteriophage Lambda Vectors," Chapter 2 in *Molecular Cloning: a Laboratory Manual,* 2nd Ed., (c) 1989 (hereinafter Sambrook et al.); Stryer, "Control of Gene Expression in Procaryotes," Chapter 32 in *Biochemistry* 3rd Ed., pp. 799-823, (c) 1988 (hereinafter Stryer); and Court and Oppenheim, pp. 251-277 in Hendrix et al. eds., *Lambda II,* Cold Spring Harbor Lab Press, (c) 1983 (hereinafter Court and Oppenheim).

$P_R$ promoter: The major rightward promoter of bacteriophage lambda. Once the lambda DNA is incorporated into the bacterial chromosome, transcription from this promoter is substantially repressed by the cI repressor. Upon inactivation of the cI repressor, for example by heat shock of a temperature sensitive mutant, transcription from the $P_R$ promoter is de-repressed, leading to expression of lambda genes. See Sambrook et al., "Bacteriophage Lambda Vectors," Chapter 2 in *Molecular Cloning: a Laboratory Manual,* 2nd Ed., (c) 1989

(hereinafter Sambrook et al.); Stryer, "Control of Gene Expression in Procaryotes," Chapter 32 in *Biochemistry* 3rd Ed., pp. 799-823, (c) 1988.

Plasmid: A plasmid is a construction of genetic material designed to direct transformation of a targeted cell. Plasmids include a construction of extrachromosomal genetic material, usually of a circular duplex of DNA which can replicate independently of chromosomal DNA. A plasmid generally contains multiple genetic elements positional and sequentially oriented with other necessary genetic elements such that the nucleic acid in a nucleic acid cassette can be transcribed and when necessary translated in the transfected cells. Plasmids include nucleic acids that are DNA derived from a plasmid vector, cosmids, or phagemids wherein one or more fragments of nucleic acid may be inserted or cloned which encode for particular genes of interest. The plasmid can have a linear or circular configuration.

Plasmids generally contain one or more unique restriction sites. In addition, a plasmid can confer some well-defined phenotype on the host organism which is either selectable or readily detected. Thus, the plasmid can include an expression cassette, wherein a polypeptide is encoded. Expression includes the efficient transcription of an inserted gene, nucleic acid sequence, or nucleic acid cassette with the plasmid. Expression products can be proteins, polypeptides or RNA.

In one embodiment, when a circular plasmid is transferred into a bacterial cell, it can be an autonomously replicating, extra-chromosomal DNA molecule, distinct from the normal bacterial genome and nonessential for bacterial cell survival under nonselective conditions. The term "persistent expression" as used herein refers to introduction of genes into the cell together with genetic elements which enable episomal (extra-chromosomal) replication and/or maintenance of the genetic material in the cell. This can lead to apparently stable transformation of the cell without the integration of the novel genetic material into the chromosome of the host cell.

A plasmid can also introduce genetic material into chromosomes of the targeted cell where it integrates and becomes a permanent component of the genetic material in that cell. Gene expression after stable introduction can permanently alter the characteristics of the cell and its progeny arising by replication leading to stable transformation.

Polynucleotide: A double-stranded or single-stranded nucleic acid sequence of any length. Therefore, a polynucleotide includes molecules which are 15, 50, 100, 200 nucleotides long (oligonucleotides) and also nucleotides as long as a full length cDNA.

Probes and primers: A nucleic acid probe comprises an isolated nucleic acid attached to a detectable label or reporter molecule. Typical labels include radioactive isotopes, ligands, chemiluminescent agents and enzymes. Methods for labeling and guidance in the choice of labels appropriate for various purposes are discussed, e.g., in Sambrook et al. (1989) and Ausubel et al. (1997).

Primers are short nucleic acids, preferably DNA oligonucleotides about fifteen nucleotides or more in length. Primers may be annealed to a complementary target DNA strand by nucleic acid hybridization to form a hybrid between the primer and the target DNA strand. The 3' hydroxyl end of the primer may be then extended along the target DNA strand through the use of a DNA polymerase enzyme. Primer pairs (one on either side of the target nucleic acid sequence) can be used for amplification of a nucleic acid sequence, e.g., by the polymerase chain reaction (PCR) or other nucleic-acid amplification methods known in the art.

Methods for preparing and using probes and primers are described, for example, in Sambrook et al. (1989), Ausubel et al. (1987). PCR primer pairs can be derived from a known sequence, for example, by using computer programs intended for that purpose such as Primer (Version 0.5,© 1991, Whitehead Institute for Biomedical Research, Cambridge, Mass.). Under appropriate conditions, the specificity of a particular probe or primer increases with its length. Thus, in order to obtain greater specificity, probes and primers may be selected that comprise 20, 25, 30, 35, 40, 50 or more consecutive nucleotides of related cDNA or gene sequence.

Prokaryote: Cell or organism lacking a membrane-bound, structurally discrete nucleus and other subcellular compartments.

Prokaryotic transcription termination sequence: A nucleic acid sequence which is recognized by the RNA polymerase of a prokaryotic host cell and results in the termination of transcription. There are two types of terminators, one requires the Rho protein in combination with RNA polymerase at certain Rho-dependent sequences while the other is intrinsic and depends on sequence alone to stop polymerase. Prokaryotic intrinsic termination sequences commonly include a GC-rich region that has a twofold symmetry followed by an AT-rich sequence (Stryer, supra). A commonly used prokaryotic termination sequence is the rRNA operon termination sequence. A variety of termination sequences are known to the art and may be employed in nucleic acid constructs including the $T_{INT}$, $T_{L1}$, $T_{L2}$, $T_{L3}$, $T_{R1}$, $T_{R2}$, $T_{6S}$ termination signals derived from the bacteriophage lambda, and termination signals derived from bacterial genes such as the trp gene of *E. coli* (see Stryer, supra).

Promoter: An array of nucleic acid control sequences which direct transcription of a nucleic acid. A promoter includes necessary nucleic acid sequences near the start site of transcription, such as in the case of a polymerase II type promoter, a TATA element. Enhancer and repressor elements can be located adjacent or distal to the promoter, and can be located as much as several thousand base pairs from the start site of transcription. Examples of promoters include, but are not limited to, the λ $P_L$ and $P_R$ promoters, the SV40 promoter, the CMV promoter, the β-actin promoter, and tissue-specific promoters. A hybrid promoter is a promoter that directs transcription of a nucleic acid in both eukaryotic and prokaryotic cells. One specific, non-limiting example of a hybrid promoter is a PGK-EM7 promoter. Another specific, non-limiting example of a hybrid promoter is PGK-Tnf.

Recombinant nucleic acid molecule: A nucleic acid molecule which is comprised of segments of DNA joined together by means of molecular biological techniques, or that is produced from such a molecule, such as following replication of a plasmid. Strands of a DNA molecule are said to have 5' ends and 3' ends because mononucleotides are reacted to make oligonucleotides in a manner such that the 5' phosphate of one mononucleotide pentose ring is attached to the 3' oxygen of its neighbor in one direction via a phosphodiester linkage. In a duplex DNA molecule, each strand has a 5' and a 3' end. An end of an oligonucleotide referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements relative to a reference nucleic acid sequence of a fixed element in DNA that has a polarized direction in a single strand. This terminology reflects the fact that transcription proceeds by making RNA in a 5' to 3' fashion along one of the DNA strands (such as an unmethylated strand of DNA). The promoter and enhancer elements which direct transcription of a linked gene are generally located 5' relative to a strand transcribed into RNA, or upstream of the coding region. However, enhancer elements can exert their effect even when located 3' of the promoter element and the coding region. Transcription termination and polyadenylation signals are located 3' or downstream of the coding region.

Regulatory element: A genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. Regulatory elements include "promoter" and "enhancer" elements. Promoters and enhancers consist of short arrays of DNA sequences that interact specifically with cellular proteins involved in transcription (Maniatis et al., *Science* 236:1237, 1987). Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types. A regulatory element can be "endogenous" or "heterologous." An "endogenous" regulatory element is one which is naturally linked with a given gene in the genome. A "heterologous" regulatory element is one which is placed in juxtaposition to a gene by means of genetic manipulation; the regulatory element is not naturally found adjacent to a reference nucleic acid sequence, such as in a wild-type organism.

Restriction endonucleases and restriction enzymes: Bacterial enzymes, each of which cut double-stranded DNA at or near a specific nucleotide sequence. A "restriction site" is a deoxyribonucleic acid sequence at which one or more specific restriction endonucleases cleave the molecule.

Selectable marker: A nucleic acid (or a protein encoded by the nucleic acid) which can be used to identify a cell, such as a host cell, of interest. Selectable markers include but are not limited to: (1) nucleic acid segments that encode products which provide resistance against otherwise toxic compounds (e.g., antibiotics); (2) nucleic acid segments that encode products which are otherwise lacking in the recipient cell (e.g., tRNA genes, auxotrophic markers); (3) nucleic acids that encode products which suppress the activity of a gene product; (4) nucleic acids that encode products which can be readily identified (such as phenotypic markers such as β-galactosidase, green fluorescent protein (GFP), and cell surface proteins); (5) nucleic acids that bind products which are otherwise detrimental to cell survival and/or function; (6) nucleic acids that otherwise inhibit the activity of any of the nucleic acids described in Nos. 1-5 above (e.g., antisense oligonucleotides); (7) nucleic acids that bind products that modify a substrate (e.g. restriction endonucleases); (8) nucleic acids that can be used to isolate a desired molecule (e.g. specific protein binding sites); (9) a specific nucleotide sequence which can be otherwise non-functional (e.g., for PCR amplification of subpopulations of molecules); and/or (10) DNA segments, which when absent, directly or indirectly confer sensitivity to particular compounds.

In one example, the nucleic acid encodes an enzymatic activity that confers the ability to grow in medium lacking what would otherwise be an essential nutrient (e.g., the TRP1 gene in yeast cells). In another example, a selectable marker can confer resistance (or sensitivity) to an antibiotic or drug upon the cell in which the selectable marker is expressed. In a further example, the selectable marker can also be used to confer a particular phenotype upon a host cell.

When a host cell must express a selectable marker to grow in selective medium, the marker is said to be a positive selectable marker (e.g., antibiotic resistance genes which confer the ability to grow in the presence of the appropriate antibiotic). Selectable markers can also be used to select against host cells containing a particular gene (e.g., the sacB gene which, if expressed, kills the bacterial host cells grown in medium containing 5% sucrose); selectable markers used in this manner are referred to as negative selectable markers or counter-selectable markers.

Sequence identity: The relatedness between two nucleic acid sequences, or two amino acid sequences is expressed in terms of the similarity between the sequences, otherwise referred to as sequence identity or homology. Sequence identity is frequently measured in terms of percentage identity (or similarity or homology); the higher the percentage, the more similar/homologous are the two sequences.

Methods of alignment of sequences for comparison are well-known in the art. Various programs and alignment algorithms are described in: Smith and Waterman, *Adv. Appl. Math.* 2:482, 1981; Needleman and Wunsch, *J. Mol. Bio.* 48:443, 1970; Pearson and Lipman, *Methods in Molec. Biology* 24:307-331, 1988; Higgins and Sharp, *Gene* 73:237-244, 1988; Higgins and Sharp, *CABIOS* 5:151-153, 1989; Corpet et al., *Nucleic Acids Research* 16:10881-90, 1988; Huang et al., *Computer Applications in BioSciences* 8:155-65, 1992; and Pearson et al., *Methods in Molecular Biology* 24:307-31, 1994. Altschul et al. (*Nature Genet.*, 6:119-29, 1994) presents a detailed consideration of sequence alignment methods and homology calculations.

The NCBI Basic Local Alignment Search Tool (BLAST) (Altschul et al., *J. Mol. Biol.* 215:403-410, 1990) is available from several sources, including the National Center for Biological Information (NBCI, Bethesda, Md.) and on the internet, for use in connection with the sequence analysis programs blastp, blastn, blastx, tblastn and tblastx. It can be accessed at the NCBI website, together with a description of how to determine sequence relatedness using this program.

Homologs of lambda Beta, Exo and Gam, and ssDNA binding proteins (such as the Herpes simplex virus single-stranded binding protein) typically possess at least some (for example, at least 60%) sequence identity counted over limited or full-length alignment with the amino acid sequence of the protein being evaluated (that is, lambda Beta, Exo or Gam, or other ssDNA binding protein). Homologs of other proteins, such as P22 Erf, RecT, and Rad52, or the Herpes virus single ICP8 stranded binding protein and UL12 exonuclease can also be identified. Homologs of a protein can be identified, for example, using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, at least 75%, at least 80%, at least 90%, at least 95%, at least 98%, or at least 99% sequence identity. When less than the entire sequence is being compared for sequence relatedness, homologs will typically possess at least 75% sequence identity over short windows of 10-20 amino acids, and may possess sequence identities of at least 85% or at least 90% or 95% depending on their similarity to the reference sequence. Methods for determining sequence identity over such short windows are described at the NCBI website One of skill in the art will appreciate that these sequence identity ranges are provided for guidance only; it is entirely possible that strongly significant homologs or other variants could be obtained that fall outside of the ranges provided.

Single-stranded DNA (ssDNA) and double-stranded DNA (dsDNA): ssDNA is DNA in a single polynucleotide chain; the DNA bases are not involved in Watson-Crick base pairing with another polynucleotide chain. dsDNA involves two or more complementary polynucleotide chains, in which the two polynucleotide chains are at least partially Watson-Crick base-paired to each other. Note that a segment of DNA may be partially ssDNA and partially dsDNA, for example if there are gaps in one polynucleotide chain of a segment of dsDNA, or there are 5' or 3' overhangs. ssDNA and dsDNA may contain nucleotide analogs, non-naturally occurring or synthetic nucleotides, biotin, or epitope or fluorescent tags. ssDNA or dsDNA may be labeled; typical labels include radioactive isotopes, ligands, chemiluminescent agents and enzymes.

Suppressor of nonsense mutations: Nonsense mutations are examples of conditional mutations—in a strain lacking a nonsense suppressor (suppressor minus or sup°), the mutation causes premature termination of protein synthesis, but in a strain with an appropriate nonsense suppressor (sup), functional protein can be made. If a phage vector contains nonsense mutations in a gene essential for lysis, it will only be able to reproduce in a bacterial host with an appropriate nonsense suppressor.

One type of a nonsense mutation is an amber mutation. An amber suppressor inserts an amino acid at only an amber (UAG) codon. A supB or supC suppressor inserts an amino acid at UAA and UAG codons. Another type of nonsense mutation is an ochre mutation. In one example, if a phage mutant with an amber mutation at position #50 of an essential gene infects a sup° host, no functional protein will be made and the phage will not reproduce. If the phage infects a supD host (which includes a tRNA that recognizes the amber codon and inserts a serine), a serine will be inserted at position #50 of the protein; if the phage infects a supE host, a glutamine will be inserted at position #50 of the protein; if the phage infects a supF host, a tyrosine will be inserted at position #50 of the protein; and so on. If the amino acid inserted at this position results in a misfolded, truncated, or otherwise nonfunctional protein, the phage will not reproduce on the suppressor containing host. However, if the amino acid inserted at this site yields a functional protein, the phage will reproduce. A number of suppressors are known:

| name | original anticodon | suppressor anticodon | codon suppressed | amino-acid inserted |
|---|---|---|---|---|
| supB | UUG | UUA | UAA, UAG | Gln |
| supC | GUA | UUA | UAA, UAG | Tyr |
| supD | CGA | CUA | UAG | Ser |
| supE | CUG | CUA | UAG | Gln |
| supF | GUA | CUA | UAG | Tyr |
| supG | UUU | UUA | UAA, UAG | Lys |
| supM | | | UAA, UAG | Tyr |
| supN | | | UAA, UAG | Lys |
| supO | | | UAA, UAG | Tyr |
| supP | | | UAG | Leu |
| supU | CCA | UCA | UGA | Trp |

Transcriptional terminator element: A nucleotide sequence that functions to stop transcription of an RNA polymerase without additional factors is an intrinsic terminator. This intrinsic sequence can be located within the linker region, or after a nucleic acid encoding Bet, Gam or Exo, but can be located at other sites in the plasmid. These sequences ensure transcription of the nucleic acid sequence does not read through into other functional regions of the plasmid. The term "transcription" or "transcribe" refers to the process by which RNA molecules are formed upon DNA templates by complementary base pairing. This process is mediated by RNA polymerase. In one embodiment, the terminators are derived from E. coli rrnB operon. Additional terminators include the λ terminators in the $P_L$ and $P_R$ operon, such as $T_{L3}$, $T_{L4}$ and $T_{L2}$.

Transformation, Transduction and Transfection: The introduction of foreign DNA into prokaryotic or eukaryotic cells. Transformation of prokaryotic cells may be accomplished by a variety of means known to the art including the treatment of host cells with $CaCl_2$ to make competent cells, electroporation, etc. Transfection of eukaryotic cells can be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection and biolistics.

Upstream: Refers to nucleic acid sequences that precede the codons that are transcribed into an RNA of interest, or to a nucleic acid sequences 5' of a nucleic acid of interest. Similarly, "downstream" refers to nucleic acid sequences that follow codons that are transcribed into a RNA of interest, or to nucleic acid sequences 3' of a nucleic acid of interest.

Vector: Nucleic acid molecules that transfer DNA segment(s) from one cell to another. A "vector" is a type of "nucleic acid construct." The term "nucleic acid construct" includes circular nucleic acid constructs such as plasmid constructs, cosmid vectors, etc. as well as linear nucleic acid constructs (e.g., λ phage constructs, PCR products). The nucleic acid construct may include expression signals such as a promoter and/or an enhancer (in such a case, it is referred to as an expression vector). An "expression vector" is a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter and can also include an operator. Eukaryotic cells are known to utilize promoters, enhancers, and termination and polyadenylation signals.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods and examples are illustrative only and not intended to be limiting.

DETAILED DESCRIPTION OF SPECIFIC EMBODIMENTS

There exists a need in the art for methods of precisely and efficiently altering predetermined endogenous genetic sequences by homologous recombination in vivo, in a variety of gram negative bacterial cells. Plasmids, phages and methods are disclosed herein for cloning DNA molecules in gram negative bacterial cells using homologous recombination mediated by lambda recombinases.

Recombineering

FIG. 1A depicts a classical genetic engineering protocol to modify a target on a BAC clone with a cassette and compares the classical technology with the recombineering technology disclosed herein that uses special phage recombination functions. In general, there are many steps required for classical engineering, and the final product cannot be engineered as precisely as by the new recombineering technology. An advance in the recombineering methodology is the use of phage recombination functions that generate recombination products using homologies of 50 bases (or less). Note that the target homologies in FIG. 1A and FIG. 1B are represented by the striped boxes. In the method outlined in FIG. 1A, those boxes must be at least 500 base pairs long, whereas in the method outlined in FIG. 1B, they can be about 40 to about 50 base pairs long. In several examples, the homologies are about 30 to 100 bases long, or from about 40 to about 100 bases in length.

One method of recombineering involves transforming a gram negative bacterial cell of interest (such as, but not limited to, an *E. coli* cell) with a plasmid including an origin of replication, and a lambda genome having DNA encoding functional Beta and optionally Exo, and Gam, or functional fragments or variants thereof, operably linked to the a de-repressible promoter (such as, but not limited to, the $P_L$ promoter). De-repression of the de-repressible promoter (for example, the induction of transcription from the $P_L$ promoter by inactivation of cI) induces expression of Exo, Bet and Gam. In some embodiments de-repression may be selectively activated for this purpose. Another method of recombineering involves the introduction of a phage or a phage including the $P_L$ promoter operably linked to a nucleic acid encoding Beta, and optionally Exo and Gam, or functional fragments or variants thereof.

In recombineering, a polynucleotide which is homologous to a target DNA sequence (capable of undergoing homologous recombination with the target DNA sequence) is introduced into the cell. Cells in which homologous recombination has occurred are either selected or found by direct screening of cells. In particular embodiments, the nucleic acid introduced into the cell may be single-stranded DNA, double-stranded DNA, or DNA with 5' overhangs. These methods are disclosed, for example, in PCT Publication No. WO 02/14495 A2 and in U.S. Patent Publication No. US-2003-0224521-A1 (both of which incorporated by reference herein in their entirety).

Briefly, the recombineering methodology utilizes recombination functions (such as phage recombination functions) under control of a de-repressible promoter to generate recombination products using homologies of at least 20 base pairs. Thus, in one embodiment, recombineering uses a cell including Beta under the control of a de-repressible promoter. In a specific, non-limiting example, expression of Beta alone (without Exo and Gam) is under the control of the de-repressible promoter (e.g. the nucleic acid encoding Beta is operably linked to the de-repressible promoter). In another embodiment, expression of Beta, in addition to Gam and/or Exo, is under the control of the de-repressible promoter. In further embodiments, the gene encoding ICP8, RecT, P22 Erf, or Rad52 is operably linked to a de-repressible promoter. In yet another embodiment, DNA bound to a Beta protein is introduced into a host cell.

In recombineering, phage recombination functions can be used to introduce recombination into a target nucleic acid sequence in a host cell. The host cell can be prokaryotic. In specific non-limiting examples, the host cell is any gram negative bacterial cell, including, but not limited to, *E. coli* or *S. typhimurium*. The target can be on the chromosome, or can be on an extra-chromosomal element. In several specific, non-limiting examples, the target nucleic acid can be included in a plasmid, a bacterial artificial chromosome (BAC), a yeast artificial chromosome, a cosmid or a vector, including but not limited to a viral vector. In one specific non-limiting example, recombination is induced in a BAC strain or a BAC DNA is introduced into strain carrying recombination functions.

The length of the homologous sequence can be varied. In several embodiments, the homology is at least 20, at least 25, at least 30, at least 40, at least 50, at least 75 or at least 100 nucleotides in length. However, larger regions of homology can also be utilized. Thus, in one embodiment, between about 20 and about 1,000 nucleotides of homologous sequence is utilized, between about 30 and about 1,000 nucleotides of homologous sequence is utilized. In one specific, non-limiting example, the ssDNA is about 20, about 25, about 30, about 40, about 50, about 75 or about 100 nucleotides in length. In one embodiment, the homologous nucleic acid is a single-stranded nucleic acid. In another embodiment, the homologous nucleic acid is a double-stranded nucleic acid. Double-stranded nucleic acids include molecules that are completely double-stranded, as well as nucleic acid molecules that have a 5' or a 3' overhang.

A single-stranded nucleic acid or double-stranded nucleic acid including sufficient homology to the target sequence is introduced into the host cell. "Sufficient homology" is any region of sufficient identity to the target sequence such that recombination can occur. In several embodiments, sufficient homology includes a sequence of at least 20 nucleotides in length, wherein at most five, at most three, at most two, at most one nucleotide, or no nucleotides differ from the target nucleic acid sequence. In additional embodiments, sufficient homology includes a sequence of at least 25 nucleotides in length, wherein at most five, at most three, at most two, at most one nucleotide, or no nucleotides differ from the target nucleic acid sequence. Similarly, sufficient homology can readily be determined for a nucleic acid of at least 30, at least 40, at least 50, or at least 100 nucleotides in length.

If the single-stranded nucleic acid or double-stranded nucleic acid differs from the target nucleic acid, these differences can be clustered (i.e. at one area in the target nucleic acid) or can be scattered in the sequences (for example two nucleotide differences from the target sequence, wherein each difference is located at different areas in the sequence). In another embodiment, sufficient homology includes about a 100%, 99%, 98%, or 97% sequence identity between the homologous nucleic acid (e.g., the single-stranded or the double-stranded nucleic acid) and the target nucleic acid sequence. In another specific, non-limiting example, sufficient homology includes at least 90% sequence identity between the single-stranded or double-stranded nucleic acid and the target nucleic acid, such as nucleic acid sequences that are at least 91%, at least 92%, at least 93%, at least 94%, at least 95%, at least 96%, at least 97%, at least 98%, or at least 99% identical. It should be noted that a homologous nucleic acid sequence can differ from a target nucleic acid by substitutions, deletions and/or additions of nucleotides. In another embodiment, the single-stranded nucleic acid (or double-stranded nucleic acid) is labeled, such as with a biotinylated nucleotide, a methylated nucleotide, or a DNA adduct.

The homologous nucleic acid (e.g., the single-stranded nucleic acid or double-stranded nucleic acid) can be introduced into the host cell by any means known to one of skill in the art. In one embodiment, the host cell is deficient in mismatch repair, such as a cell that can repair mismatched nucleotides at a reduced frequency as compared to a wild-type cell (such as at least 50%, 60%, 70%, 80%, 90%, 95%, 98%, or 99% reduction in mismatch repair). In one specific, non-limiting example, mismatch repair is reduced at least 90% as compared to a wild-type cell. A host cell deficient for mismatch repair can include a mutation in a nucleic acid sequence encoding a protein involved in mismatch repair, such that the protein has reduced function (or its function is eliminated). In several embodiments, the function of one or more mismatch repair proteins is decreased at least 80%, such as at least 90%, 95%, 96%, 97%, 98%, 99%, or is completely absent in the host cell deficient for mismatch repair as compared to a wild-type cell. In this context, a wild-type cell is a cell of the same species that does not include a mutation in the gene encoding the protein involved in mismatch repair.

In one embodiment, mismatch repair can be constitutively reduced in the host cell. Thus, if the cell is a prokaryotic cell, a cell that is deficient for mismatch repair can have a mutation in one or more nucleic acids encoding mutS, mutH, mutL, uvrD, or dam. The mutS, mutH, mutL, uvrD, or dam protein produced from the mutated gene has a substantially reduced (or no) function in mismatch repair. Thus, a corresponding wild-type cell does not have a mutation in the nucleic acid encoding MutS, MutH, MutL, uvrD, or dam, respectively. A cell deficient for mismatch repair can also have more than one mutation or the nucleic acid encoding MutS, MutH, MutL, uvrD, or dam, or can have mutations in more than one of these genes. The mutation can be an insertion, deletion, or a point mutation. Thus, in several specific, non-limiting examples, a prokaryotic cell deficient for mismatch repair has a mutation in a nucleic acid encoding MutS (mutS–, or ΔmutS), MutH (mutH– or ΔmutH), MutL (mutL– or ΔmutL), UvrD (uvrD– or ΔuvrD), or Dam (dam– or Δdam), or a combination (e.g. mutS-mutH– (ΔmutSΔmutH), mutS-mutL– (ΔmutSΔmutL), mutH-mutL– (ΔmutHΔmutL), mutH-uvrD– (ΔmutHΔuvrD), etc.).

The homologous nucleic acid (e.g. the single-stranded nucleic acid or double-stranded nucleic acid) is introduced into the host cell, the de-repressible promoter is de-repressed, and recombinants are generated in vivo. Thus, in one specific, non-limiting example, if the de-repressible promoter is $P_L$, and the repressor is cI857, the host cell is treated with heat to induce the expression of Beta (see Copeland et al., *Nature Reviews* 2:769, 2001, and Ellis et al., *Proc. Natl. Acad. Sci.* 98:6742-6746, 2001, which are herein incorporated by reference), and optionally Exo and Gam. Generally, the homologous nucleic acid, whether it is a single-stranded nucleic acid or a double-stranded nucleic acid, differs from the target nucleic acid by at least one nucleotide, but is sufficiently homologous to undergo recombination with the target sequence (see above).

Recombinants can be detected by any means known to one of skill in the art. If recombination has occurred in a nucleic acid encoding a marker, such as a nucleic acid encoding a polypeptide involved in antibiotic resistance, detection can be performed by drug selection. However, detection can also be performed by direct screening (e.g. colony hybridization or sequencing). Detection can also be performed by detecting a label on the nucleic acid (e.g. when DNA includes a DNA adduct or a marker such as biotin).

As has been described (see PCT Publication No. WO 02/14495 A2, herein incorporated by reference), a single base change has been substituted in the galK gene and a 3.3 kbp insertion removed from the galK gene using single-stranded oligos. Single-stranded oligos have also been used to precisely remove five different Tn10 insertions at different places on the *E. coli* chromosome. Whereas Exo, Beta, and Gam facilitate recombination of PCR amplified dsDNA cassettes with flanking homologies, only Beta is required for ssDNA recombination.

Plasmids Conferring Recombineering Functions to Bacterial Host Cells

Disclosed herein are plasmids that can be used to confer recombineering functions to cells, such as prokaryotic cells. These plasmids can be used to confer recombineering functions to a variety of strains of *E. coli*. In addition, disclosed herein are plasmids that can be used to confer recombineering functions to other bacteria, including *Salmonella, Pseudomonas, Cyanobacteria*, and *Spirochaetes*, amongst others. These mobilizable plasmids can be manipulated in vitro and can be used to transform gram negative bacteria. These plasmids include an origin of replication specific for the bacterial cell(s) of interest, a de-repressible promoter, and a nucleic acid encoding a single-stranded binding protein such as Beta. In additional embodiments, the plasmids include a nucleic acid encoding Exo and/or Gam. In one example, the plasmid includes an origin of replication and a lambda genome having DNA encoding functional Beta and optionally Exo and Gam, or functional fragments or variants thereof, operably linked to the de-repressible promoter (such as, but not limited to, the $P_L$ promoter). In one embodiment, the plasmid is circular, but it can be linearized for some uses. The plasmid can optionally include a selectable marker, such as a drug-resistant cassette (for example, encoding chloramphenicol resistance or ampicillin resistance).

For ease in review, the discussion below refers to the Red recombineering system, which utilizes the single-stranded binding protein Beta, and optionally Gam and Exo. However, one of skill in the art can construct and use the plasmid systems with other single-stranded binding proteins, such as *E. coli* RecT, Erf of bacteriophage P22, Rad52 of yeast, or ICT8 of Herpes simplex virus.

Generally, the plasmid includes an on site that allows replication in bacterial host cells, such as gram negative bacterial cells and/or gram positive bacterial cells. The gram negative bacterial cells can be *E. coli* bacterial cells. However, the on site can be selected to allow replication in other bacterial gram negative cells. These gram negative cells include, but are not limited to, Enterobacteriaceae (such as *Escherichia, Shigella, Salmonella, Yersinia pseudotuberculosis*). Thus, nucleic acids encoding recombineering proteins can also be transferred to *Pseudomonas, Acetobacter, Alcaligenes, Bacteroides Amoebobacter, Chromatium, Lamprobacter, Lamprocystis, Thiocapsa, Thiocystis, Thiodictyon, Thiopedia* and *Thiospirillum, Legionella, Neisseria, Nitrobacter, Nitrospina, Nitrococcus, Nitrosipra, Pseudomonas, Xanthomonas, Zoogloea* and *Fraturia, Rhizobium, Bradyrhizobium, Azorhizobium, Sinorhizobium Rochalimaea, Ehrlichia, Cowdria, Rickettsia Neorickettsia Spirochaetaceae, Vibrio, Aeromonas, Plesiomonas* and *Photobacterium* host cells.

Figure 4F:
Figure 5:
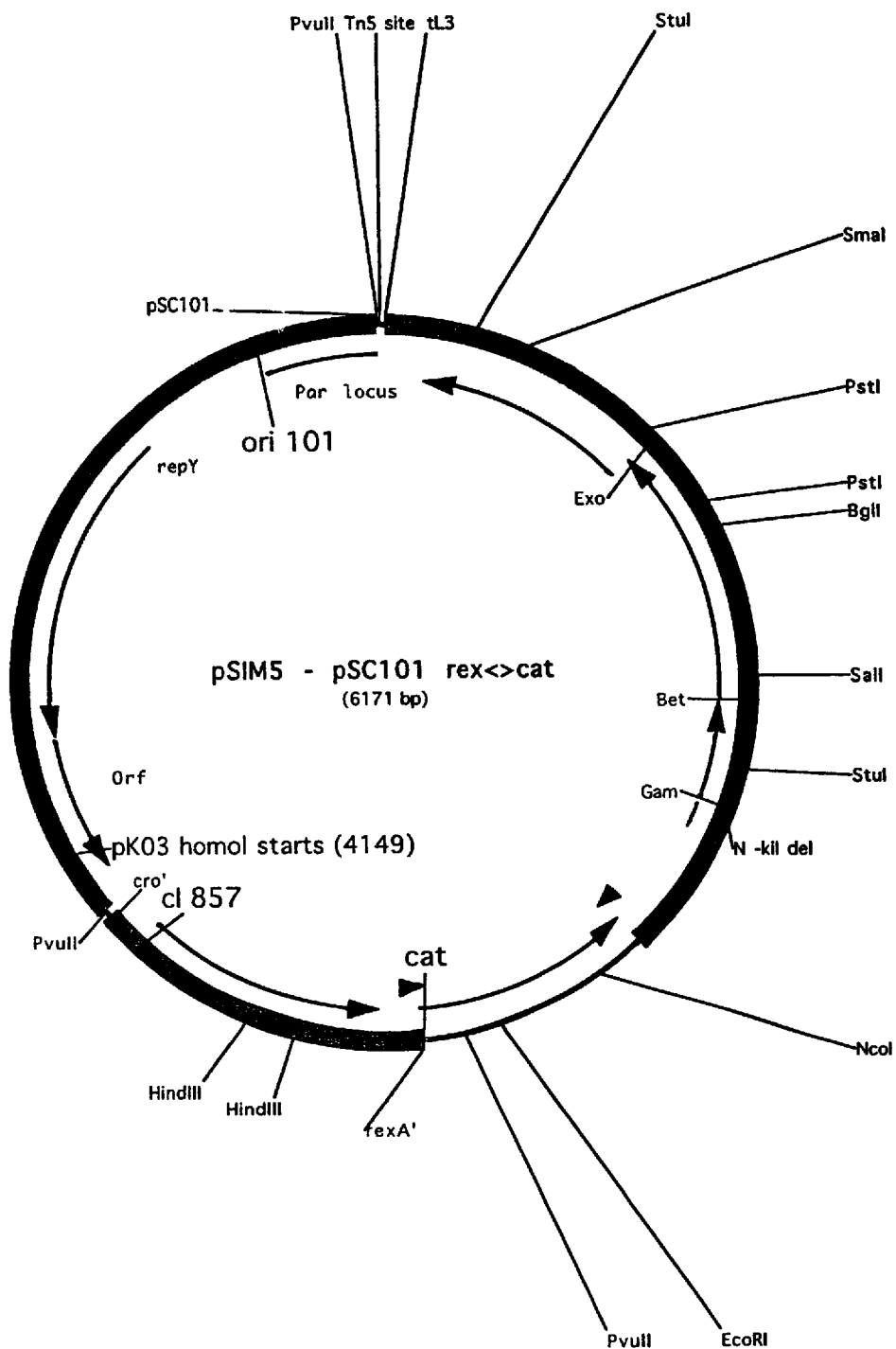
FIG. 5 is a schematic diagram of the plasmid pSIM 5-pSC101 rex< >cat.
Figure 7:
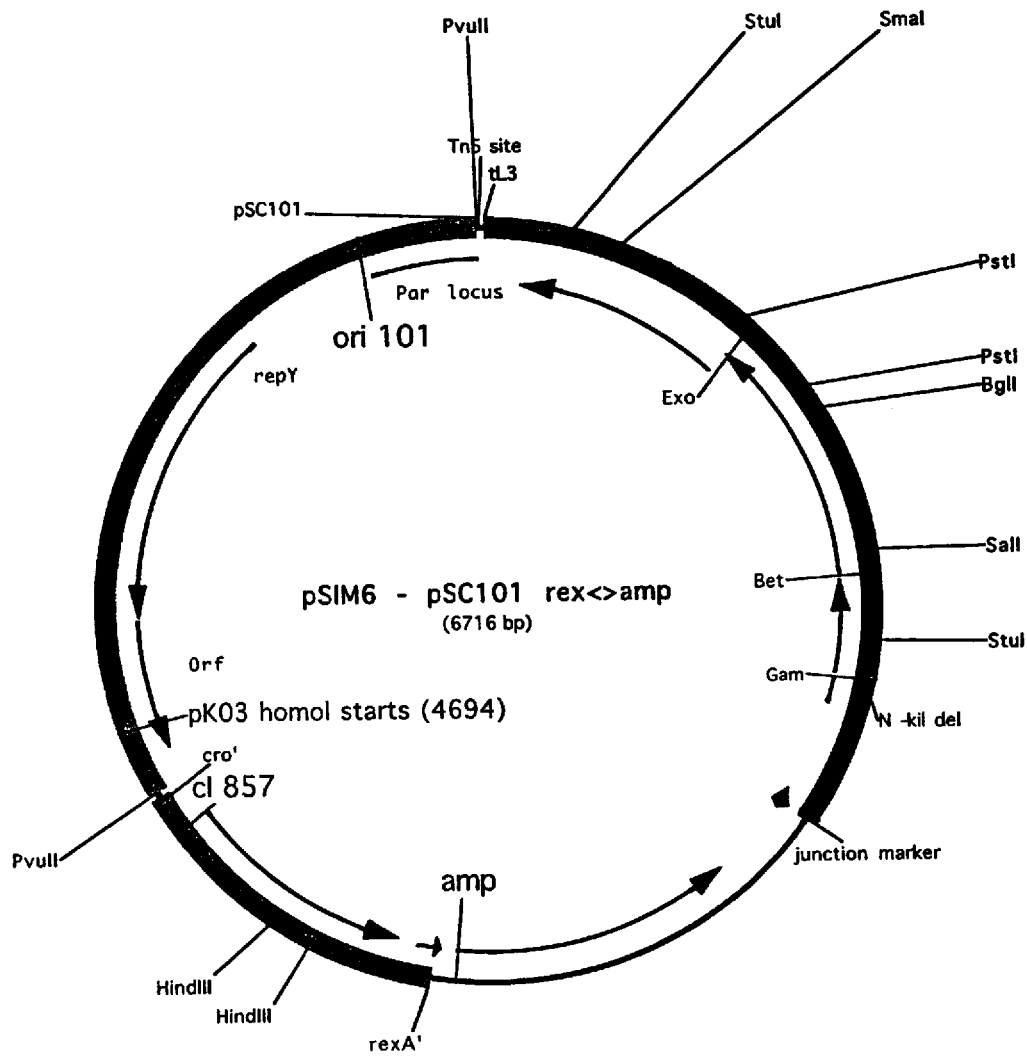
FIG. 7 is a schematic diagram of plasmid pSIM6-pSC101 rex< >amp (SEQ ID NO: 4).
Figure 9:
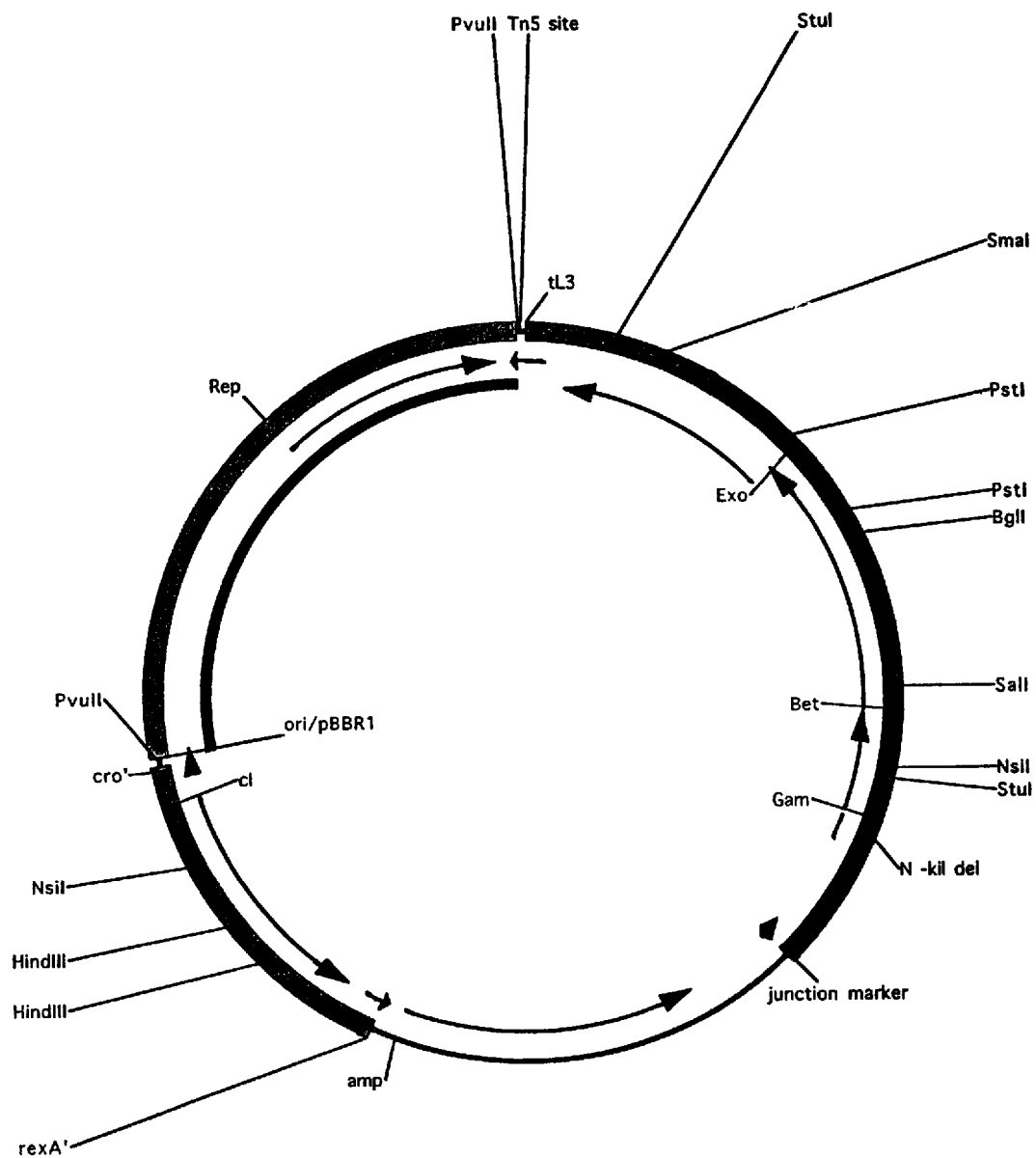
FIG. 9 is a schematic diagram of plasmid pSIM8-pBBR1 rex< >amp (SEQ ID NO: 6).
Figure 11:
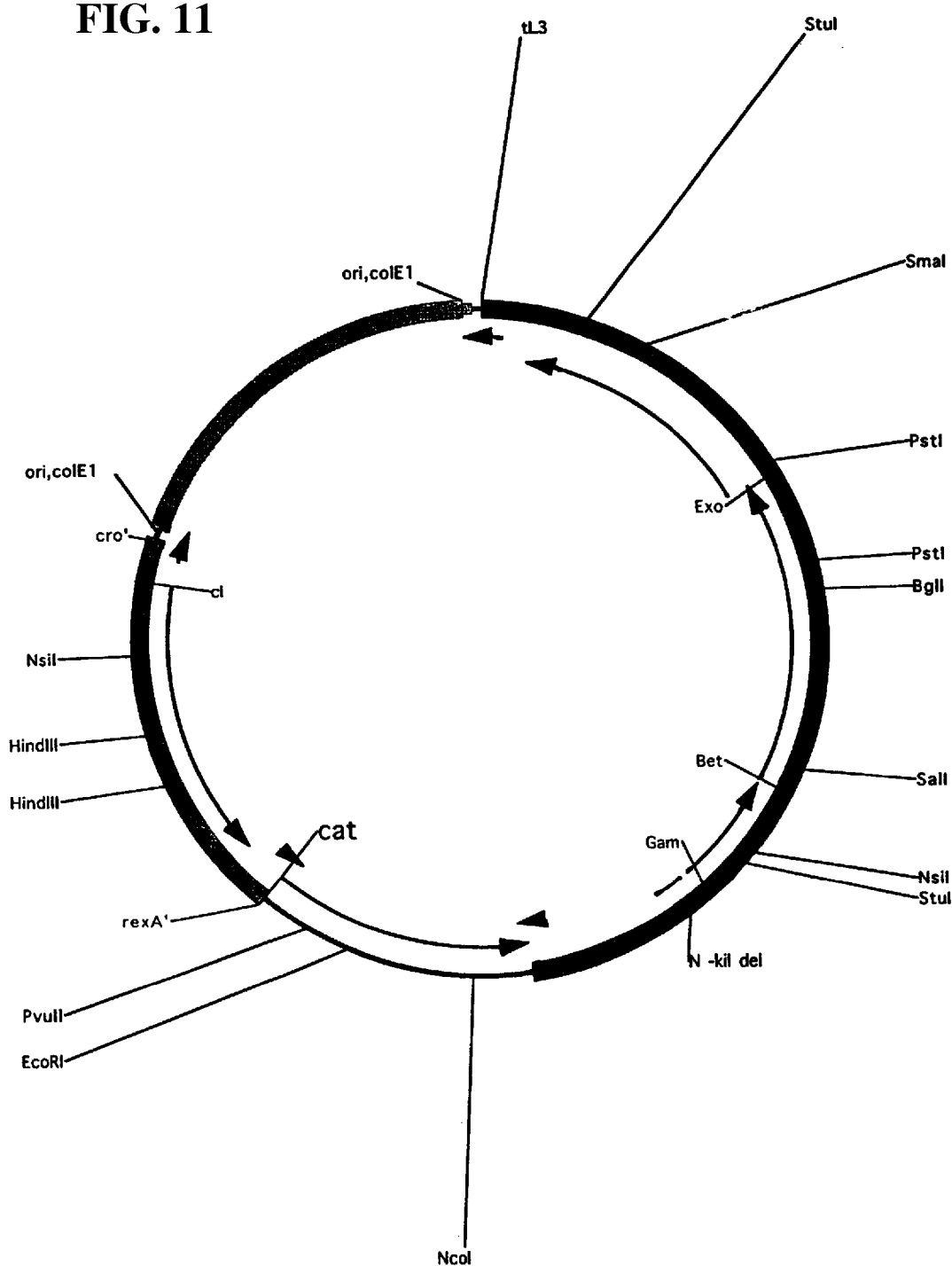
FIG. 11 is a schematic diagram of plasmid pSIM2 with rex< >cat.
Figure 13:
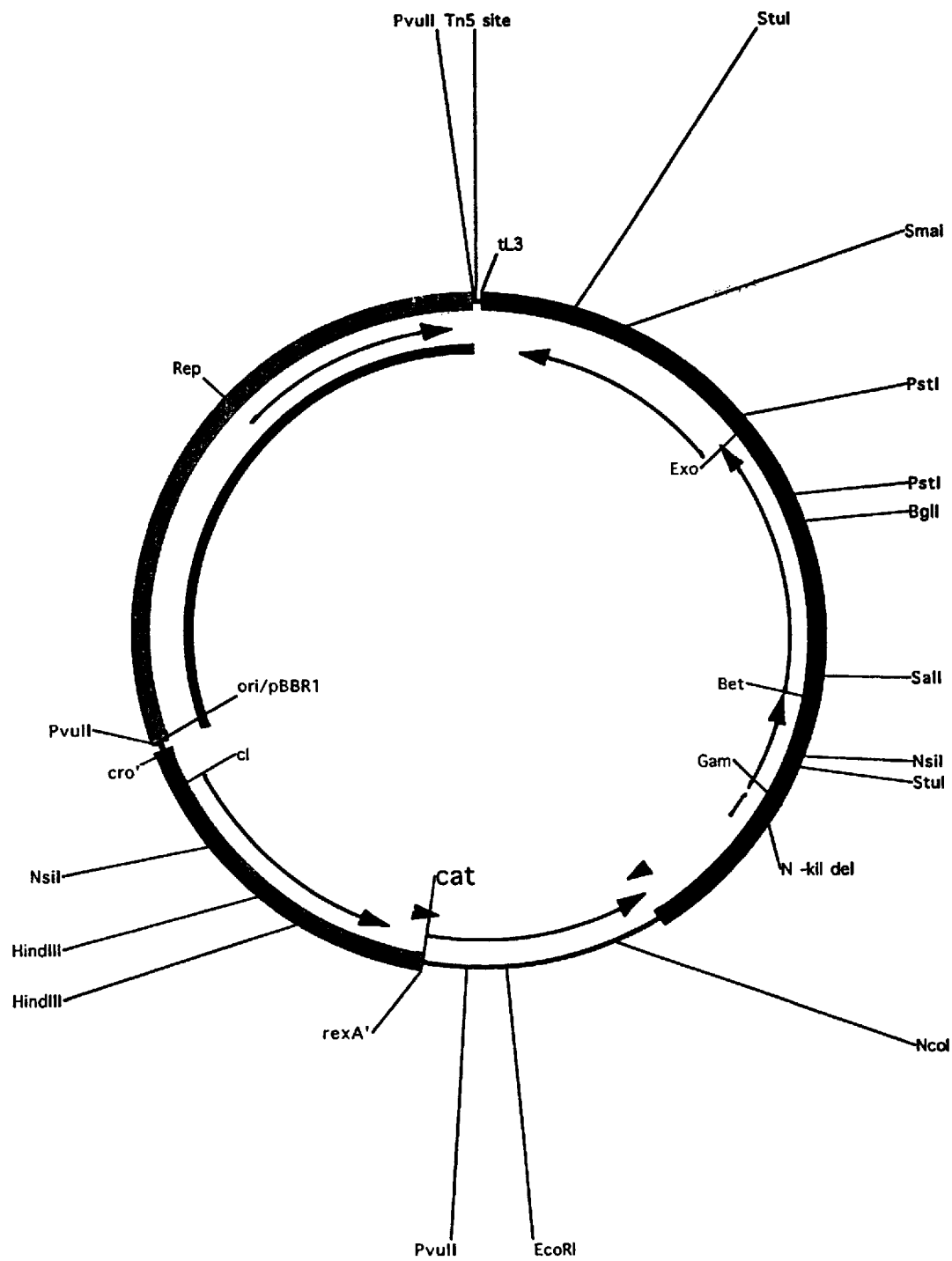
FIG. 13 is a schematic diagram of plasmid pSIM7 with rex< >cat (SEQ ID NO: 5).
Figure 15G:

The origin of replication can be from any plasmid of interest, and thus can function in gram negative and/or gram positive cells, and/or eurkaryotes. In one embodiment, the origin of replication (such as the on from plasmid pMB1) functions in a broad host range of gram negative bacterial cells, such as pBBR1, pRK2 or IncQ. However, in other embodiments, the origin of replication can confer the ability to replicate in a more limited number of bacterial cells. A conditional origin of replication can also be utilized. Conditional origins of replication are also known to one of skill in the art. Generally, conditional origins of replication are tight down-regulated in the selected host cells in the absence of a compatible inducing agent, and are strongly induced in the presence of the inducing agent. The conditional on, when provided in combination with the compatible inducing agent, should have sufficient activity to amplify the vector within the host cells. One exemplary conditional on is oriV, GENBANK™ No. L 13843, although the conditional on could be any on that functions in the host cell and is normally inactive until exposed to the replication-inducing agent. Additional conditional origins of replication of use are found on plasmids commonly used, such as pBBR1 and pSC101. Suitable origins of replication are from the plasmids pSC101, pBBR, pBR322, pUC5, pUC8, pBBR1, RK2, P1, F, amongst others. In addition to the on, the plasmid can include additional plasmid sequences, such as Orf or rep γ that can activate replication. Exemplary nucleic acid sequences of Orf and rep γ are shown in FIGS. 4, 9 and 10. In one embodiment a plasmid can replicate at 32° C. but not at 37° C.

The plasmids include a de-repressible promoter operably linked to a nucleic acid encoding a single-stranded binding protein such as Beta. Optionally, the de-repressible promoter also is operably linked to a nucleic acid encoding Gam and/or Exo. In one specific, non-limiting example, the de-repressible promoter is $P_L$. The plasmid can also include one or more of $P_R$, $O_L$, and $O_R$. In one example, the plasmid includes, $P_L O_L$, and $P_R O_R$, in the same sequence and orientation as found in phage lambda (λ).

A terminator can be included, such that transcription is terminated following transcription of bet. If nucleic acids encoding Exo and Gam are included in the plasmid, the terminator can be included 3' of these nucleic acid sequences. Terminators are well known in the art, and include, but are not limited to, $T_{L3}$ of phage λ. Other terminators of use include the $T_{INT}$, $T_{L1}$, $T_{L2}$, $T_{R1}$, $T_{R2}$, $T_{6S}$, $T_{OOP}$ termination signals derived from the bacteriophage lambda, and termination signals derived from bacterial genes such as the TrpT for the trp gene of *E. coli*. These terminators prevent the plasmid origin from being transcribed by the $P_L$ promoter. Thus, in one example, $P_L$ is operably linked to nucleic acid sequences encoding Gam, Bet, and Exo, and a terminator, such as TL3, is included 3' of Gam.

Generally, the plasmid encodes a repressor such as cI that binds $P_L$. In one embodiment, the repressor is temperature sensitive, such as cI857. In some particular examples, the disclosed plasmids include an inducible promoter upstream of the cI857 gene. The cI gene can also include an ind1 mutation to prevent spontaneous induction at low temperatures.

Optionally, the plasmid can also include a nucleic acid encoding a selectable marker. For example, a nucleic acid can be included that encodes an enzymatic activity that confers the ability to grow in medium lacking what would otherwise be an essential nutrient (e.g., the TRP1 gene in yeast cells), or that confers resistance (or sensitivity) to an antibiotic or drug upon the cell in which the selectable marker is expressed. Exemplary markers confer resistance to ampicillin (amp), neomycin (neo), or chloramphenicol (cat). A negative selective marker can also be utilized, such as a nucleic acid encoding the sacB gene (which, if expressed, kills the bacterial host cells grown in medium containing 5% sucrose). In yet another example, a marker is utilized, such as a nucleic acid sequence that encodes an antigenic epitope; cells that express the antigenic epitope can be screened and identified by the binding of an antibody.

In one embodiment, the plasmid includes the following components in 5' to 3' order: a nucleic acid sequence for an origin of replication; a nucleic acid encoding a promoter operably linked to nucleic acid sequence a repressor that specifically binds an operator for a de-repressible promoter, such as the $P_R$ promoter; a nucleic acid sequence encoding a selectable marker; a de-repressible promoter that is repressed by the repressor, such as $P_L$ promoter of lambda phage, operably linked to a nucleic acid encoding lambda Beta and a terminator. Transformation of a bacterial cell with the plasmid allows homologous recombination to occur in the bacterial cell. In another embodiment, the plasmid also includes a nucleic acid encoding an exonuclease operably linked to the de-repressible promoter. For example, the plasmid can include lambda Exo operably linked to the $P_L$ promoter. The plasmid can also include a nucleic acid encoding Gam operably linked to the de-repressible promoter, such as $P_L$ promoter. It should be noted that the plasmid can include RecE and RecT operably linked to a de-repressible promoter. The plasmid can further include other regulatory elements, such as $P_R$ and $O_R$ 5' of the nucleic acid encoding the selectable marker. Thus, in an additional embodiment, the plasmid comprises $O_L$ 3' of the $P_L$ promoter.

In one embodiment, the plasmid includes an origin of replication, a nucleic acid encoding a promoter operably linked to a repressor, such as cI, a nucleic acid encoding a plasmid operably linked to the promoter, or to a second promoter, and a nucleic acid encoding Beta operably linked to the first or the second promoter, or to a third promoter. A nucleic acid encoding Exo and/or Gam can be linked to the first, second or third promoter. The plasmid does not encode a functional N protein. Exemplary plasmids are pSIM2, pSIM4, pSIM6, pSIM5, pSIM7, pSIM8 and pSIM9. Schematic diagrams of these plasmids, their nucleic acid sequence, and the amino acid sequence of the encoded proteins are shown in FIGS. 4, 7, 8, 9, 10, 11, 12, 13, 14 and 15.

In another embodiment, the plasmid includes an origin of replication and a lambda genome, wherein the lambda genome comprises, in 5' to 3' order (1) a repressor that binds the $P_R$ promoter; (2) $O_R$; (3) a promoter operably linked to a nucleic acid encoding a heterologous nucleic acid sequence; (4) $P_L$; (5) $O_L$; (6) a nucleic acid encoding Beta. In one example, the plasmid includes an origin of replication and a lambda genome. As noted above, the origin of replication can be any origin of replication that allows replication of the plasmid in the cell of interest.

The plasmid can also include a nucleic acid encoding a selectable marker. The lambda nucleic acid sequence can include a heterologous nucleic acid that encodes a selectable marker. Selectable markers of use are known to one of skill in the art, and are briefly described above. In one embodiment, the selectable marker is included within the rexA of lambda. In another embodiment, the selectable marker is included along with rexA and rexB in the lambda nucleic acid sequence. The lambda can include the phage immunity region and both the $O_L$ and $O_R$ operators and the main leftward operon under control of the $P_L$ promoter, but does not include the major rightward operon encoding the DNA replication genes, the lysis genes and the phage structural genes. Operationally, this means that following prophage induction, the prophage chromosome cannot excise and the cells will not lyse, nor will phage particles be produced.

In yet another embodiment, the lambda nucleic acid includes an N-kil deletion. In one specific, non-limiting example, the lambda genome does not encode a functional N (anti-terminator) protein. In another specific example, the lambda genome includes an N-kil deletion (see FIG. 1) such that the lambda does not encode a functional N protein, and such that the transcription terminators included in this region between $P_L$ and gam are removed. The N-kil deletion leaves intact the Gam gene whose AUG begins at position 33112 on the lambda DNA sequence and deletes a longer form of the gam gene that has been previous described (Court and Oppenheim, pp. 251-277 in Hendrix et al. eds., *Lambda II*, Cold Spring Harbor Lab Press, (c) 1983, which is incorporated herein by reference). Deletion of the kil gene removes a function that kills bacterial cells, such as *E. coli*, when expressed.

Thus, the lambda genome can include, in 5' to 3' order, a repressor that binds the $P_R$ promoter at $O_R$ and a promoter operably linked to a nucleic acid encoding a heterologous nucleic acid sequence, $P_L$, $O_L$, a nucleic acid encoding Bet. The lambda genome can include an N-kil deletion to remove the genes N through kil. Optionally, additional sequences are included, such as rep γ or Orf nucleic acid sequences. Nucleic acid sequences encoding Exo and/or Gam can also be included.

A defective λ can be utilized that encodes Red with an intact cI repression system with various plasmid origins (FIG. 16). In this prophage, most of the nonessential region of the $P_L$ operon has been removed, including the toxic kil gene, transcription terminators, and the anti-termination gene N (FIG. 16A). Other genes are also deleted, such as sieB, ral, ssb and cIII. The rex genes downstream of the cI repressor gene have been replaced by drug cassettes allowing selection for either chloramphenicol (cat) or ampicillin (amp). The $P_L$ promoter on these constructs is still regulated by the temperature sensitive cI857 repressor, with $O_L$ and $O_R$ operators present to ensure the tightest control (Dodd et al., *Genes Dev.* 15(22):3013-22, 2001; Dodd et al., *Genes Dev.* 18(3):344-54, 2004). In this system, raising the temperature and inactivating the repressor directly induces the Red functions without the intermediate step of N anti-termination.

A method is disclosed herein for producing plasmids including an origin of replication and a lambda phage of interest. Thus, using the plasmid sequences disclosed herein, and the technique of recombineering, many plasmids can be generated including different origins of replication. For example, primers can be generated that have homology to an origin of replication in a plasmid (for example, one of the plasmids schematically diagrammed in FIGS. 3, 5, 7, 9, 11 and 13), and that have homology to a lambda nucleic acid sequence. In one example, the origin of replication is contained in a pBR322 origin segment, and the plasmid also has homology at its 5' end to a lambda nucleic acid sequence.

Thus, each one of the primers in a primer pair includes nucleic acid sequences that prime DNA synthesis (using amplification techniques, such as PCR) of the origin of replication, and also include nucleic acid sequences that can pair with (as they are sufficiently homologous to) a lambda nucleic acid. In one embodiment, the set of primers is used to amplify the origin of replication of interest. Thus, a nucleic acid sequence is amplified that includes the origin of replication, and is flanked by nucleic acid sequences homologous to lambda at each end (homology arms). This nucleic acid, including one homology arm to lambda, an origin of replication, and a second homology arm to lambda is then introduced into a gram negative bacterial cell which contains a lambda prophage inserted into the chromosomal DNA. The lysogenic lambda DNA present on the bacterial chromosome was pre-induced to produce Beta, Exo and Gam. Optionally, the lysogenic lambda phage includes a heterologous nucleic acid sequence encoding a selectable marker. Once the Red functions of lambda are induced (by de-repressing the $P_L$ promoter), and the linear plasmid replicon segment has been introduced (such as by electroporation), recombination occurs between the linear nucleic acid vector and the lambda prophage. Thus, a plasmid is generated by gap repair recombination that includes both the origin of replication and the lambda nucleic acid sequence between the two flanking homologies incorporated on the linear origin DNA. Following outgrowth, circular gap-repaired plasmids with the origin of replication (such as the pBR322 origin of replication) can be isolated using selection for the marker (such as a drug resistance marker) on the prophage and standard molecular biological techniques, such as a "mini-prep" (see Sambrook et al., *Molecular Cloning: a Laboratory Manual,* 2nd Ed., (c) 1989).

It should be noted that other plasmid origins like that of pSC101 can be amplified in the same way as that described above for pBR322 with the same flanking lambda DNA homology using primers. In one example, the lambda DNA is the prophage recombined on the pBR322 origin by gap repair on the plasmid and it is not present on the chromosome. The linear pSC101 with lambda arms is electroporated into cells with the PBR322 plasmid carrying lambda Red functions (pSIM2 or pSIM4) which have been pre-induced to express Red functions. Recombination occurs between the lambda homology on the linear pSC101 and the lambda DNA on the pBR322 derivative plasmid. Recombinants are generated that replace the pBR322 origin with the pSC101 origin. The recombination mixture is grown overnight and in one embodiment, the plasmid mixture is isolated and introduced into cells that only allow replication of a specific origin of replication of interest. For example, the cells can be polA-defective cells, which do not allow the replication of pBR322, but allow replication from alternative origins of replication. In another example, the lambda phage includes a heterologous nucleic acid encoding a selectable marker. Bacterial cells are transformed with plasmids, and the selection system is utilized to isolate plasmids including an origin of replication and the selectable marker.

A method is disclosed herein for producing plasmids including an origin of replication and a lambda phage of interest. Thus, using the plasmid sequences disclosed herein, and the technique of recombineering, many plasmids can be generated including different origins of replication. For example, primers can be generated that have homology to an origin of replication in a plasmid (for example, one of the plasmids schematically diagrammed in FIGS. 3, 5, 7, 9, 11 and 13), and that have homology to a lambda nucleic acid sequence. For example, one primer can include a sufficient number of consecutive nucleic acids from the 5' region of an origin of replication, such as at least 5, at least 10, at least 15, at least 20 at least 30, at least 50, or at least 100 nucleotides, such that the primer can hybridize to the origin of replication. The 5' end of this primer also includes a sufficient number of consecutive nucleic acids from lambda sequences, such as at least 5, at least 10, at least 15, at least 20, at least 30, at least 50, or at least 100 nucleotides, such that the primer can also hybridize to lambda. A second primer can include a sufficient number of consecutive nucleic acids from the distal region of an origin of replication, such as at least 5, at least 10, at least 15, at least 20, at least 30, at least 50, or at least 100 nucleotides, such that the primer can hybridize to the origin of replication. The primer also includes a sufficient number of consecutive nucleic acids from lambda sequences at it's 5' end, such as at least about 5, at least about 10, at least about 15, at least about 20, at least about 30, at least about 50, or at least about 100 nucleotides, such that the 3' primer can hybridize also to lambda. It should be noted that about 15 to about 100 nucleotides of a nucleotide sequence homologous to lambda, such as about 30 to about 100 nucleotides, such as about 50 to about 100 nucleotides, can be used in each of the first and second primers. In one specific example, at least 30 consecutive nucleotides from lambda sequences are utilized, such as 30 to 100 consecutive nucleotides from lambda.

These primers are then used in an amplification reaction, such that the origin of replication is amplified and the product includes a nucleotide sequence homologous to lambda at each end of the amplified product. Homologous recombination (such as "recombineering") is then used to transfer the new origin of replication such that a plasmid is generated that includes a plasmid origin of replication and lambda nucleic acid sequences joined together.

In one example, the origin of replication of interest is a pBR322 origin segment; and the plasmid is constructed that includes the pBR322 origin and lambda. Thus, each one of the primers in a primer pair (a first primer and a second primer that can be used to amplify a sequence of interest) includes nucleic acid sequences that prime DNA synthesis (using amplification techniques, such as PCR) of the pBR322 origin of replication, and also include nucleic acid sequences that are homologous to a lambda nucleic acid. The pair of primers is used to amplify the origin of replication of interest, such as the pBR322 origin. Thus, a nucleic acid sequence is amplified that includes the desired origin of replication, and is flanked by nucleic acid sequences homologous to lambda at each end (homology arms). This nucleic acid, including one homology arm to lambda, an origin of replication, and a second homology arm to lambda is then introduced into a gram negative bacterial cell which contains a lambda prophage inserted into the chromosomal DNA (note that the lambda DNA can also be included on a plasmid, see below). The lysogenic lambda DNA present on the bacterial chromosome is pre-induced to produce Beta, Exo and Gam, by de-repressing the de-repressible promoter. Optionally, the lysogenic lambda phage includes a heterologous nucleic acid sequence encoding a selectable marker. Once the Red functions of lambda are induced (by de-repressing the $P_L$ promoter), and the linear plasmid replicon segment has been introduced (such as by electroporation or transformation), recombination occurs between the linear nucleic acid and the lambda phage. Thus, a plasmid is generated by gap repair recombination that includes both the origin of replication and the lambda nucleic acid sequence between the two flanking homologies incorporated on the linear origin DNA. Following outgrowth, plasmids with the origin of replication (such as the pBR322 origin of replication) can be isolated using selection for the marker on the prophage and standard molecular biological techniques, such as a "mini-prep" (see Sambrook et al., *Molecular Cloning: a Laboratory Manual,* 2nd Ed., (c) 1989).

It should be noted that other plasmid origins can be amplified in the same way as that described above for the origin of pBR322 with the same flanking lambda DNA homology using primers. For example, the origin of replication can be one that functions in a broad host range of gram negative bacterial cells, such as the origin of replication found on pBBR1, pRK2 or IncQ. However, in other embodiments, the origin of replication can confer the ability to replicate in a more limited number of bacterial cells, such as the origin of replication found in pMB1. A conditional origin of replication can also be utilized. Conditional origins of replication are also known to one of skill in the art, and are described above.

In one example, the origin from plasmid pSC101 is the origin of replication. To create a plasmid including this origin of replication, lambda DNA is utilized that is the prophage recombined on a different origin, such as a pBR322 origin, by gap-repair (such that the lambda DNA is included on a plasmid and is not present on the chromosome). The linear pSC101 with lambda arms is electroporated into cells with a plasmid carrying lambda Red functions, which have been induced. Recombination occurs between the lambda homology on the linear pSC101 and the lambda DNA on the pBR322 derivative. Recombinants are generated that replace the pBR322 origin with the pSC101 origin. The recombination mixture is grown overnight and in one embodiment, the mixture of plasmids is isolated and introduced into cells that only allow replication of a specific origin of replication of interest. For example, the cells can be polA− cells, which do not allow the replication of pBR322, but allow replication from alternative origins of replication.

Growth in a specific cell type is not the only selection system that can be used to isolate plasmids including an origin of replication and lambda. In another example, the lambda phage also includes a heterologous nucleic acid encoding a selectable marker. This selectable marker can then be utilized to select the plasmids of interest.

Infective Phage Conferring Recombineering Functions to Bacterial Host Cells

Use of a phage with its endogenous regulatory elements can be used to achieve controlled, coordinate expression of the required genes (see Court et al., *Ann. Rev. Genet.* 36:361-88, 2002, herein incorporated by reference). The genome of lambda encodes about 50 genes, all of which have been sequenced (see GENBANK™ Accession No. J02459, incorporated herein by reference, restriction map available at the Fermenta website, and Daniels et al., Appendix II, Complete Annotated Lambda Sequence, Hendrix et al. (eds.), *Lambda II*, Cold Spring Harbor Press, Cold Spring Harbor, N.Y., pp. 519-676, 1983, herein incorporated by reference in their entirety). The amino acid sequence of each gene product is also known (GENBANK™ Accession No. J02459 and Daniels et al., supra, both incorporated by reference in their entirety). It should be noted that a phage in the lysogenic phase, which is integrated into the chromosome of a bacterial cell is termed a "prophage." Both prophages and phages are encompassed by the present disclosure.

Disclosed herein is an infectious lambda phage that includes a repressor that binds a $P_L$ promoter, a promoter operably linked to a nucleic acid encoding a heterologous nucleic acid sequence, $P_L$, and a nucleic acid encoding Beta operably linked to $P_L$, a nucleic acid encoding P, a nucleic acid encoding O, and a nucleic acid encoding cro. At least two of the nucleic acids encoding P, encoding O, and encoding Cro include an amber codon such that at least two of P, O and Cro proteins are not produced when the lambda phage is introduced into a suppressor minus host cell. In such suppressor minus cells a lysogenic prophage can form after infection. The full length O and P gene products allow the phage origin to replicate from the phage origin. A diagram of the genetic map of bacteriophage λ is shown in FIG. 2.

In several embodiments, the phage does not include a bacterial or plasmid origin of replication, such as a ColE1 origin of replication, and/or does not include a bacterial initiation site of replication. For example, the phage does not include the initiation site (Mi) of ColE1replication (see for example, Tomizawa et al., *PNAS* 74:1865-1869, 1977). Generally, for the purposes of this disclosure, unless otherwise stated, a "λ phage" or a "λ prophage" does not include a bacterial or plasmid origin of replication or a bacterial initiation site. Naturally occurring non-recombinant phages, including λ phage, do not include a bacterial origin of replication.

In one embodiment, the prophage contains the phage immunity region and the main leftward operon under control of the $P_L$ promoter, but is missing the major rightward operon encoding the DNA replication genes, the lysis cassette, and the structural genes. Operationally, this means that following prophage induction, the cells will not lyse, nor will phage particles be produced. In one example, this phage does not include any origin of replication.

In lambda, the exo, bet and gam genes are clustered in the $P_L$ operon and are expressed after induction of the prophage. The cI repressor directly controls the $P_L$ promoter. A temperature sensitive repressor mutation, cI857, can be used so that cells transferred to 42° C. are rapidly induced as the repressor is inactivated. This mutant repressor rapidly regains activity upon transfer of the cells to lower temperatures, so that recombination functions are expressed transiently from $P_L$, then shut off completely. Following removal of the repressor by heat induction, the expression of the exo, bet, and gam genes from $P_L$ is initially prevented by transcriptional terminators. Ultimately, λ N function, encoded by the first gene in the pL operon, which is expressed following de-repression, modifies RNA polymerase to prevent transcription termination (Court and Oppenheim, *Lambda II*, pp. 251-277, Cold Spring Harbor Press, Cold Spring Harbor, N.Y., 1983, incorporated herein by reference), thereby coordinately activating all the genes in the pL operon and allowing expression of the recombination functions.

Generally, the phages disclosed herein include Beta operably linked to the $P_L$ promoter. The phages can also include a nucleic acid encoding Gam and Exo operably linked to the $P_L$ promoter. However, in some examples, the phages do not encode Exo or Gam. The phage can optionally include repy, Orf, or both, such as for plasmid replication. In one example, the phage encodes its own origin but the replication proteins O and P are disabled by amber mutations preventing replication.

It is desirable to be able to produce a phage that encodes the recombineering functions (for example, bet alone or bet in combination with exo and/or gam) and can infect a cell of interest to transfer the recombineering functions. The recombination functions Exo and Beta of λ have homologs throughout the virus kingdom. These homologs even include the Herpes virus proteins UL12 and ICP8. Thus, the phage can encode these proteins instead of Exo and Beta. The cell can be a prokaryotic or a eukaryotic cell. The phage can be λ phage, but is not necessarily λ phage. Thus, a bacterial virus or a eurkaryotic virus can be utilized. In several examples, bacteriophage 434, 21 or phi-80 are utilized.

In order to promote homologous recombination once the phage has infected the cell of interest, the phage must not enter the lytic cycle in this cell. Thus, it is desirable to produce a phage (or virus) that (1) transfers recombineering functions to a cell of interest but does not rapidly kill the cell, and (2) in another cell of interest the prophage can be induced to enter the lytic cycle to produce large quantities of phage, which in turn can be used to infect additional cells of interest.

In one embodiment, a phage (or prophage) is utilized that includes at least two amber (stop) mutations. These mutations change a codon normally encoding an amino acid to a UAG (stop) codon. The amber mutations produce truncated proteins in many wild-type *E. coli* (such as W3110, DH10B, MG1655, amongst others). The truncated proteins do not retain the function of the full length protein. However, full-length proteins can be produced in *E. coli* that carry amber suppressor tRNAs (such as LE392); in the presence of amber suppressor tRNAs, full-length functional protein are produced. These are called sup.

The phage (or prophage) includes one amber (UAG stop) mutation in the P or O gene, although amber mutations can be included in both the P and the O genes. For example, a P amber 80 (also called P sus80 or P80) mutation can be included in the P gene (see Campbell, *Virology* 14:22-32, 1961). In this example, P protein is only produced in a supE carrying *E. coli* strain. However, any amber mutation can be used in the O and/or the P genes. In one embodiment, the mutation in the P or O gene is suppressed in either a supE or a supF strain.

The phage (or prophage) can also include an amber (UAG stop) mutation in cro. For example, the tyrosine at position 26 in the cro gene can be mutated to an amber (UAG stop) codon. In this example, the amber mutation is suppressed in a supF strain such that Cro is produced. Optionally, the phage can also include a temperature sensitive mutation, cI857 in the λ cI repressor gene. Thus, the cI gene, a temperature sensitive cI protein, and the cro gene, an amber mutation, encodes a truncated defective Cro protein.

In one embodiment, the phage (or prophage) includes an amber mutation in the P, O or both P and O genes that is suppressed in either a supE or a supF strain. The phage further includes an amber mutation in the Cro gene that is suppressed in either a supE or a supF strain. However, the amber mutations differ; one mutation is included that is suppressed in a supE strain and one mutation is included that is suppressed in a supF strain. For example, the phage can include a mutation in the P gene that is suppressed by supE and a mutation in cro that is suppressed by supF. The phage can include a mutation in the P gene that is suppressed by supF and a mutation in cro that is suppressed by supE. The phage can include a mutation in the P and the O gene that is suppressed by supF and also includes a mutation in cro that is suppressed by supE. Similarly, the phage can include a mutation in the O gene that is suppressed by supF and a mutation in cro that is suppressed by supE, or a mutation in the O gene that is suppressed by supE and a mutation in cro that is suppressed by supF. In this manner, both supE and supF are required to induce lysis. Thus, if the phage infects a cell that is supE and supF, the phage will enter the lytic cycle and phage particles will be produced. When these phage particles infect a cell of interest that does not contain any suppressors, like most "wild-type" strains, the phage does not reproduce and the cell survives. The phage can become a lysogen in a cell without a suppressor and repress its $P_L$ and $P_R$ operons. Thus, the recombineering functions will be transferred to the cell of interest, and homologous recombination can occur inside the cell upon de-repression of the $P_L$ promoter at 42° C.

The phage can also include a nucleic acid encoding a selectable marker. Any selectable marker can be utilized, such as a nucleic acid encoding drug resistance, a nucleic acid encoding an enzyme, or a nucleic acid encoding a detectable label. In one example, the nucleic acid encodes a protein that confers resistance to an antibiotic. Suitable selectable markers encode tetracycline resistance or ampicillin resistance. However, the heterologous nucleic acid can be a nucleic acid that encodes an enzyme, such as beta-galactosidase, galactokinase or tryptophan synthetase. These markers allow ease of selection of lysogens carrying the prophage.

Generally, the nucleic acid encoding a selectable marker is inserted into a phage gene encoding a protein that is not essential for the production of phage particles. For example, the nucleic acid encoding the selectable marker can be introduced to replace the λ rexA and/or λ rexB genes, or both. The nucleic acid encoding a selectable marker can also be introduced in the S gene of phage λ.

Thus, upon introduction of the phage into a host cell including amber suppressors, phage particles can be produced. However, upon introduction of the phage into a suppressor minus strain, the phage will integrate into a chromosome of the host cell and exist as a defective prophage.

Thus, a lambda phage (or prophage) is disclosed herein that includes, consists essentially of, or consists of, a temperature sensitive cI repressor that binds a $P_L$ promoter, a promoter operably linked to a nucleic acid encoding a heterologous nucleic acid sequence, $P_L$ promoter, and a nucleic acid encoding Beta operably linked to $P_L$, a nucleic acid encoding P, a nucleic acid encoding O, and a nucleic acid encoding Cro, wherein at least two of the nucleic acid encoding P, the nucleic acid encoding O, and the nucleic acid encoding Cro comprise an amber codon such that at least two of P, O, and Cro proteins are not produced when the lambda phage is introduced into a suppressor minus host cell. The phage (or prophage) can include cI857; the phage (or prophage) does include an origin of replication. In several examples, a defective prophage is also missing the major rightward operon encoding the DNA replication genes, the lysis cassette, and the structural genes. In an additional example, the phage (or prophage) includes an amber mutation in P and an amber mutation in O, and a tet cassette for tetracycline resistance in the S gene.

Thus, a homologous recombination system can be introduced into cells of interest by phage infection. A viable λ plaque-forming phage that contains multiple conditional mutations is used to infect a bacterial cell of interest. The phage can optionally include a selectable marker, such as a nucleic acid encoding drug resistance. In specific cell types, the phage will integrate into the nucleic acid of the host cells and will exist as a prophage. The selectable marker can be used to select cells of interest that include the phage as a prophage, in order to obtain host cells that express the recombineering functions.

In one example, this phage can be used to introduce recombineering functions into a culture of E. coli containing mixed, complete eukaryotic genomic libraries by infecting the complete library population with this phage. The introduction of phages into bacterial cells, such as gram negative cells, is well known in the art (see Ptashne et al., supra). Thus, lysogens of the entire population (bacterial cells now carrying the integrated phage) can be selected using a selectable marker. For example, host cells can be selected that are tetracycline resistant due to a cassette carried by the infecting phage. In the library strain, the defective prophage construct conveys the recombination functions and conveys the selectable marker.

Any phage (including but not limited to λ phage) can be engineered to provide homologous recombination functions (such as Beta, Gam and/or Exo) to a host cell. It is known that derivatives of λ phage infect only a few species of bacteria (such as those related to E. coli K12). By appropriate engineering of other phages based on the disclosure presented herein, recombineering functions can be introduced into many species. For example, phages can be engineered for use in Bacillus subtilis or other bacterial cells.

The phages or plasmids disclosed herein can be used to introduce recombineering functions into any host cell of interest. This system can be used in all types of bacterial cells, including gram negative and gram positive bacterial cells. In this manner, a nucleic acid sequence of interest can be introduced into a target nucleic acid. Methods are described for example, in published U.S. Patent Publication No. US-2003-0224521-A1, which is incorporated by reference herein.

The disclosure is illustrated by the following non-limiting Examples.

EXAMPLES

A new in vivo genetic engineering technology, recombineering, developed recently allows rapid and precise in vivo manipulation of DNA and shows great promise for use in functional genomic analysis. It does not rely on restriction sites for cloning, instead uses short regions of homology and bacteriophage lambda encoded Red proteins (Exo, Bet and Gam) capable of catalyzing recombination between these homologies to link novel combinations of genes and other genetic elements (see FIG. 1). To be able to use recombineering in different prokaryotic systems, the Red system must be transferred to these organisms. A minimal Red expression cassette on plasmid vectors has been generated and is disclosed herein. These plasmids provide easy mobility in different bacterial backgrounds in addition to tight and coordinated gene regulation.

Example 1

Generation of Plasmid Constructs

Plasmid with phage genes were cloned and generated by a gap repair mechanism which entails the retrieval of Red genes along with the λ regulatory elements from a defective lambdoid prophage into linear PCR amplified origin of replication sequences of the plasmids. This method eliminates standard cloning technology for the phage DNA and importantly the cloned segment is not replicated in vitro by PCR. Thus, the chances of extraneous changes occurring in the sequence are reduced.

A prophage lambda derivative was created from the recombineering strain DY330 in which the N through kil genes were deleted using an oligonucleotide of sequence 5' to 3' as follows:

```
                                          (SEQ ID NO: 32
ACGAAACGAAGCATTGGCCGTAAGTGCGATTCCGGATTACTAATC
GCCCGGCATTTCGCGGGCGATATTTTCACAGC;
``` the deletion junction is illustrated, wherein base 33132 (no underlining, last A in regular text) is next to base 35445 of phage λ, first base of underlined sequence)), and deleting lambda published nucleotide sequence from 33131 to 35444 respectively, by recombineering technology. Strain DY330 is temperature sensitive for growth at 42° C. before of kil gene expression from this prophage. The deletion removes kil, allowing the DY330 derivative to grow at 42° C. Next the rexAB coding region was replaced by recombineering with either the CmR cassette cat or the AmpR cassette amp to create plasmids (termed pSIM plasmids, see FIG. 16A), selecting for the respective drug resistance marker.

Figure 16B:
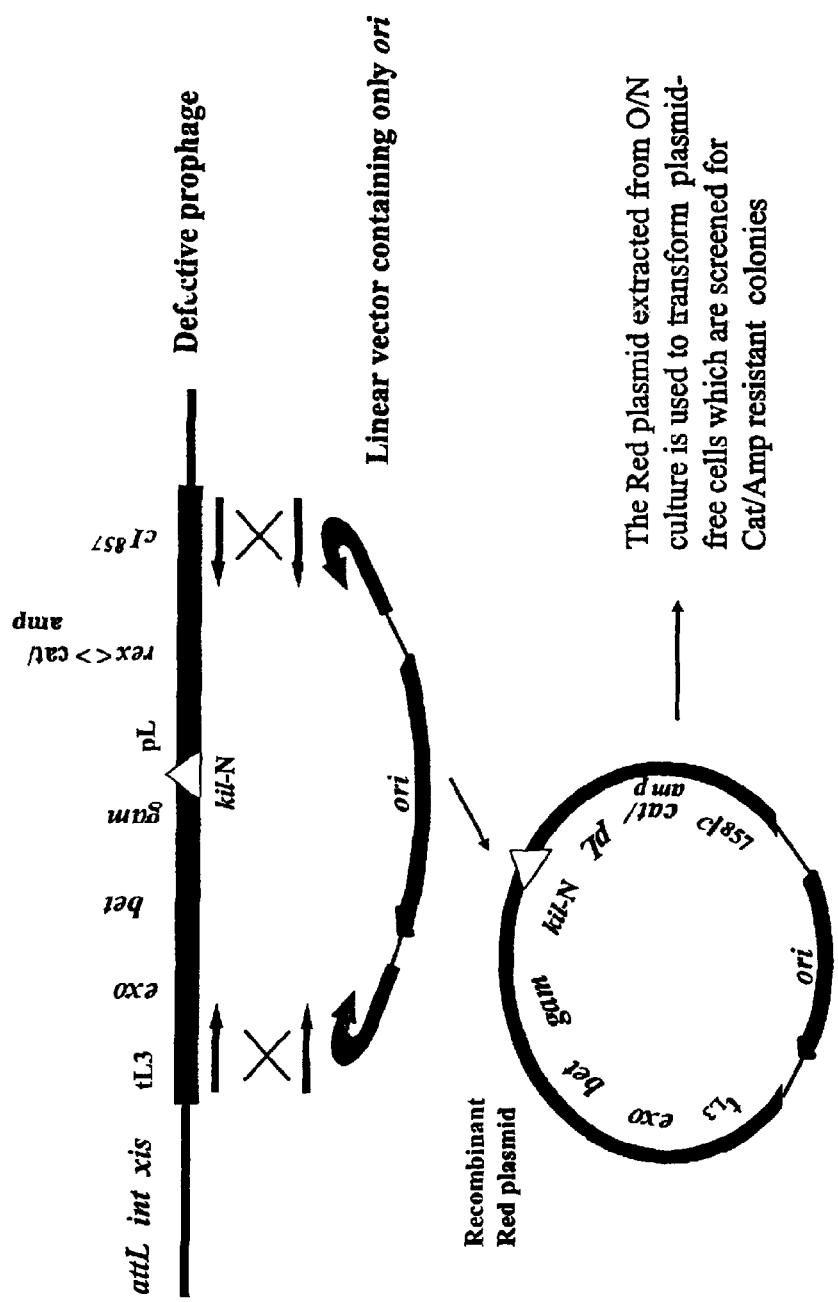
FIG. 16B is a schematic diagram of the generation of a plasmid using the prophage shown in FIG. 16A by the method of recombineering (retrieval by gap repair of a linear vector containing terminal homologies to the target).
Figure 16C:
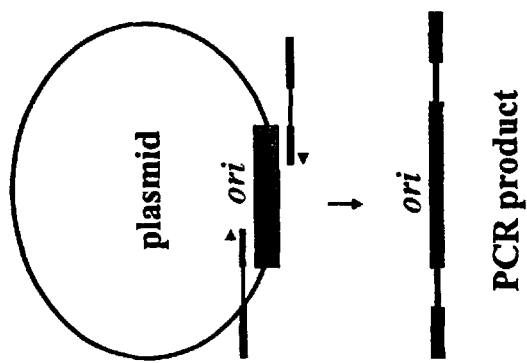
FIGS. 16C-16D are schematic diagrams of the creation of a PCR product including a pBR322-type origin of replication (FIG. 16C) and the replacement of an origin on a plasmid with another origin of interest (FIG. 16D).

The genes of this new prophage from pR through exo tL3 were retrieved into the plasmid on of pBR322 by recombineering (for example, see FIG. 16B). The pBR322 plasmid origin was PCR amplified using primers with 5' homologies to the pR and tL3 regions of lambda (FIG. 16C). The prophage strain was induced for Red functions and electroporated with the PCR on product. The electroporated cells were diluted into 10 ml of LB and incubated overnight at 32° C. (see FIGS. 3 and 13). The plasmid recombinant pSIM2 (or pSIM4) was found by transforming strain W3110 and selecting $Cm^R$ or $Amp^R$, respectively.

Figure 16D:
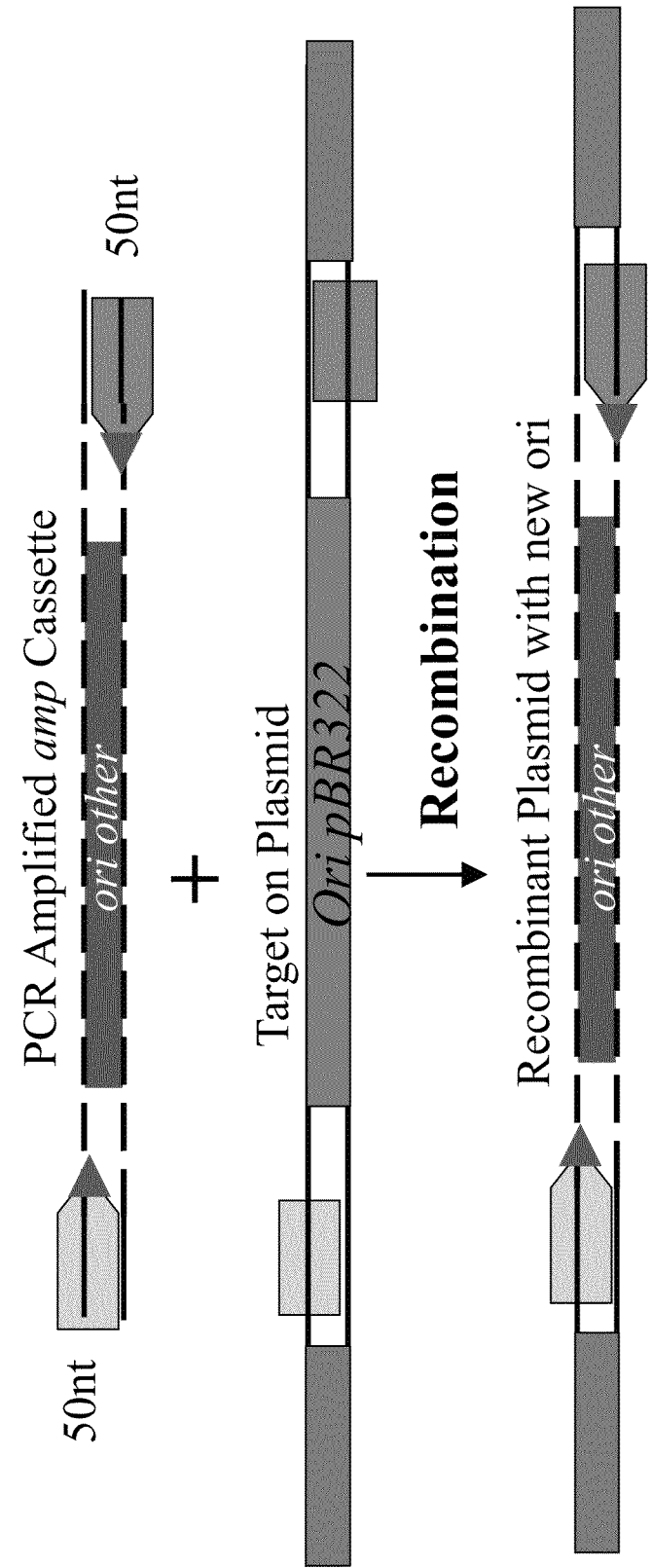

The ori segment (from pBR322) was replaced for pSIM2 or pSIM4 with the origins from the other plasmids such as pSC101, pBBR1 and RK2 using homology arms flanking the on regions made by polymerase chain reaction (see FIG. 16D). Red functions were induced from the pSIM2 or pSIM4 containing strains and the homology flanked origin PCR fragments were electroporated and the culture diluted into 10 ml of LB for overnight growth at 32° C. Mini-preps were made and the plasmid recombinants for $Cm^R$ or $Amp^R$ were selected on a W3110 polA mutant strain which does not allow pBR322 origin containing plasmids to replicate. Thus, the pSC101, pBBR1 and RK2 recombinants containing the defective prophage were selected as recombinant plasmids. Methods used for producing these plasmids are disclosed in (Constantino and Court, PNAS 100:15748-15753, 2003; Court et al., Ann. Rev. Genet. 36:361-388, 2002; Yu et al., PNAS 97:5978-5983, 2000; Lee et al., Genomics 73:56-65, 2001; Thomason et al., "Recombineering-Genetic Engineering in Bacteria Using Homologous Recombination," in *Current Protocols in Molecular Biology* (Ausbel et al., eds.), John Wiley & Sons, Unit 1.16, 2003, all of which are incorporated herein by reference).

In the plasmid construct most of the non-essential genes in the $P_L$ operon have been removed, including the transcription terminators and the anti-termination gene N. The rex genes of the phage have been replaced by a drug marker for selection. The $P_L$ promoter is regulated by the temperature sensitive cI857 repressor and the $O_L$ and $O_R$ operators are present to ensure tight repressor control. Raising the temperature from 32° C. to 42° C. inactivates the repressor and induces the Red functions from $P_L$ without requiring the intermediate step of N anti-termination. The vector carrying the minimal Red system has the on sequences derived either from pUC or temperature sensitive mutant of pSC101 or the broad host range plasmid pBBR1 or RK2.

Using the plasmid constructs in *E. coli* for recombineering, recombination frequencies of $\geq 10^4/10^8$ viable cells have been achieved with PCR products containing drug resistance cassettes, while with single-strand oligos recombination frequencies of $\geq 10^7/10^8$ viable cells were observed. The pSC101 based Red system has been successfully applied in *Salmonella* to achieve efficient recombination, as shown herein.

Example 2

Exemplary Plasmids

One plasmid/prophage system was generated that has a temperature sensitive pSC101 replication origin (pSIM5 is $Cm^R$; pSIM6 is $Amp^R$). This plasmid catalyzes Red recombination as efficiently as does the defective prophage in *E. coli*; the level of unwanted induced background recombination is also as low as that of the single copy prophage (see Table 1). A comparison of the chromosomal defective system and the plasmid defective prophage systems described here and the pBAD plasmid expression system of Datsenko and Wanner (*Proc. Natl. Acad. Sci. USA.* 97:6640-5, 2001) is presented in Table 1.

The same minimal prophage has also been combined with a temperature sensitive RK2 (pSIM9, $Cm^R$) origin of replication to make another broad host range, low copy number vector. Low copy number reduces undesirable background recombination: a colE1-based plasmid (pUC) origin lacking copy number control and carrying the same minimal prophage gives an unacceptably high number of recombinants (about 1.000-fold greater than the single copy prophage) in the absence of heat induction (see Table 1), and places a metabolic load on the host, as evidenced by slow growth of cultures carrying these high copy number plasmids (pSIM1 and pSIM2). A broad host range plasmid carrying the pBBR1 origin, pSIM7/8 has an intermediate copy number (Table 1). It should be noted that the broad host range plasmids can be further modified by addition of mobilization functions that would enable mating between more distantly related species.

Example 3

Recombineering Using galK< >Amp PCR Product for Either *E. coli* or Typhimurium galK Sequence 1. Linear Drug Cassettes and Single-Strand Oligonucleotides Used for Recombineering:

The ampicillin resistant (ApR) cassette amp used to replace the galK gene of *E. coli* and *Salmonella typhimurium* was amplified from pBluescript SK (+) (Stratagene) with primers SD3, SD4 and SD5, SD6, respectively (Table 1). The primers contain two parts: a 5' end homologous to the flanking regions of galK of *E. coli* or *Salmonella* and a 3' end that primes the cassette for replication (indicated in italics, Table 1).

The ssDNA oligo used for recombineering was supplied by Invitrogen as salt free but otherwise unpurified. The sequence of the 70-mer Oligo 144 which corrects the TAG stop codon of *E. coli* galK gene to a TAC tyrosine codon is:

```
                                          (SEQ ID NO: 33)
5'AAGTCGCGGTCGGAACCGTATTGCAGCAGCTTTACCATCTGCCGCT
GGACGGCGCACAAATCGCGCTTAA-3'.
```

2. Preparation of Cells for Recombineering:

The strains carrying the minimal defective prophage SIMD3/SIMD4 were grown and induced for Red functions for 15 minutes as in Yu et al., supra, 2000 Briefly, overnight cultures of SIMD3/SIMD4 grown at 32° C. from isolated colonies were diluted 70-fold in LB medium and grown at 32° C. with shaking to an $OD_{600}$=0.4-0.6. Induction was performed on a 15 ml culture in a baffled conical flask by placing the flask in a water bath maintained at 42° C. for 15 minutes under shaking conditions (200 revolutions per minute) Immediately after the 15-minute induction, the flask was swirled in ice water slurry to cool for 10 minutes. An uninduced control culture was also placed into the ice slurry. The cooled 15 ml culture was centrifuged for 7 minutes at 6,700×g at 4° C. The cell pellet was suspended in 1 ml of ice-cold sterile water followed by addition of another 30 ml of ice-cold water before centrifuging again at 6,700×g for 7 minutes. The supernatant was carefully discarded and the pellet was suspended in 1 ml of ice-cold sterile water and transferred to a 1.5-ml eppendorf tube, and was spun for 1 minute at 4° C. at maximum speed in a microfuge. The cell pellet was resuspended in 200 μl of ice-cold sterile water and 50 μl of these cells and 100 ng of PCR product or single-strand oligo were used for each electroporation. After electroporation 1 ml LB was immediately added to the electroporation mix and the cells were grown at 30° C. either overnight (during making of the Red expression vector) or for 2 hours for recombineering using both double-stranded DNA or ss oligo before being diluted for plating.

3. Screening of Recombinants

Cells were diluted in 1XM9 salt buffer before plating for drug resistance selection. Generally the LA plates containing 30≡g/ml of ampicillin or 10 μg/ml of chloramphenicol were used for plating and recombinants were selected at 32° C. The Gal⁻ phenotype was also tested by streaking colonies on Mac Conkey galactose indicator agar that gave white or colorless colonies in contrast to the Red colonies of Gal⁺ cells. Gal⁺ recombinant colonies were selected on M63 minimal galactose plates with biotin and viable cells were counted on LB agar.

4. Results

The results are shown below in Table 2.

TABLE 2

Recombineering with RED Plasmids Using galK < > amp PCR Product for either *E. coli* or *Salmonella typhimurium* galK Sequence

| Source of RED | Plasmid Origin | Amp$^R$ recombinants per $10^8$ viable cells *E. coli* | Amp$^R$ recombinants per $10^8$ viable cells *S. typhimurium* |
|---|---|---|---|
| pSIM2 | pBR322 | $1.5 \times 10^4$ | Not Done |
| pSIM5 | pSC101ts | $2.8 \times 10^4$ | $9.0 \times 10^3$ |
| pSIM7 | PBBR1 | $2.3 \times 10^4$ | $9.6 \times 10^3$ |
| pSIM9 | RK2ts | $4.5 \times 10^4$ | $1.3 \times 10^3$ |

The functionality of the Red system has already been demonstrated in *Salmonella* and recombineering can be used in *Salmonella* species (see the above examples). Thus, Red or RecET-like systems will be operative in other gram-negative bacteria closely related to *E. coli*, such as *Pseudomonas* and *Streptomyces* species, or *Vibrio* and *Shigella*. It should be noted that dsDNA viruses other than λ encode Red-like SynExo two component recombinases (see Vellani and Myers, *J. Bacteriol.* 185:2465-74, 2003; Reuven et al., *J. Virol.* 77:7425-33, 2003, Mikhailov et al., *J. Virol.* 77:2436-44, 2003); such recombinases are likely to catalyze efficient and accurate recombination in their particular host, and could be substituted for lambda Red functions. Currently, there are three well-studied families of exonucleases (λ Exo, RecE and ABC2-modified RecBCD) and five families of synaptases (Beta, RecT, ERF, ICP8 and LEF-3), identified by BLAST searches, ultrastructural analysis and enzymology. Thus, there is a superfamily of Beta single-strand annealing proteins with members widespread throughout the prokaryotic world. Indeed, members of the Red Beta family have been in many bacteria, including *Borrelia, Listeria* and *Streptococcus*. The *Bacillus* phage SPP1 Chu/gp35 SynExo recombinase (Vellani and Myers, supra, 2003) could also be used for recombineering in *Bacillus* bacterial cells. Phage functions that co-evolved with the host bacteria are optimized to maintain allele-specific interactions with host proteins likely to facilitate high efficiency and high fidelity recombination. Without being bound by theory, for optimal recombineering, it is believed that the nuclease and synaptase pairs should be evolutionary partners.

The λ Gam protein specifically inhibits the *E. coli* RecBCD and SbcCD nucleases, and BLAST analysis suggests that it is less widely distributed than the Red and RecET functions, as it is present in only some pathogenic strains of *E. coli*, *Shigella*, and *Salmonella* prophages. While RecBCD-like ExoV enzymes are found in many gram-negative bacterial species, the gram-positive bacteria often contain a two-subunit form of this enzyme (AddAB or RexAB). Given the widespread distribution of ExoV activity in bacteria, there may be functional analogs of ExoV in other phages. If analogs to ExoV and the SbcCD nucleases are not present in the organism of interest, λ Gam is likely to be ineffective, and other non-RecBCD-like nucleases may degrade introduced linear DNA even in the presence of Gam. Some phages have proteins that protect linear DNA from degradation, and some of these could, like λ Gam, protect dsDNA while still allowing its participation in recombination reactions. It should be noted that not all phage-encoded nuclease inhibitors will be useful in this context, since some (i.e. Mu Gam and T4 gp2) act by apparently binding DNA ends, protecting them from degradation, but also making them unavailable to participate in recombination.

Example 4

Generation of a Phage

The sequences of the rexAB genes and the S gene of lambda are shown in FIGS. 17 and 19; the tetracycline cassette is inserted to replace these genes in lambda (see FIGS. 18 and 20).

The first phage used was lambda cI857 ind1 rexAB< >tetRA Cro Tyr26 TAG Pam80=Gln60 TAG. A second phage is created that is identical to the first except that rexAB will be intact and the S gene will be replaced with tetRA [S< >tetRA] (see FIG. 18).

Lambda cI857, used for the generation of the multiply mutant phages (a phage with more than one mutation in its genome), had the cI857 allele change and the ind1 allele, which is indicated in the cI gene annotation of that sequence (see Ptashne, M., "A Genetic Switch," Third Edition, *phage Lambda Revised*, Cold Spring Harbor Lab, New York, ISBN No. 0-8769-716, 2004). The prophage in strains DY329, DY330, DY331, DY378 include the cI857 allele but are ind+ (these strains do not carry the ind1 mutation), while the prophage in strain DY380 carries both the cI857 and ind1 mutant alleles.

The multiply mutant lambda phage was further changed by adding two additional point mutations, both of which were amber mutations. The amber mutations were introduced into the phage so that the phage will be defective for killing with a 15 minute induction at 42° C. (because of the P amber 80 mutation, see below) and will be constitutive for pL expression (because of the Cro amber mutation, see below) as a prophage in a particular *E. coli* strain. The amber mutations cause defective proteins in *E. coli* including W3110, DH10B, MG1655 and others. In this manner, a pair of amber mutations was inserted that are suppressed by two different suppressor tRNAs for functional expression of both gene products.

Both of these suppressor tRNA mutations are present in LE392 strain. In this host (or similar hosts with both suppressors) this phage made plaques and could be propagated lytically to make high titer lysates (>1 billion phage/ml). These lysates could be used to infect and lysogenize the DH10B like strains, which have no suppressor tRNA (and are called sup zero or sup minus). In these sup zero strains, the phages are defective (and have an effect similar to the defective prophages in DY329 and DY380). However, it should be noted that a substantial difference exists between the presently generated phage and the prophages DY329 and DY380: high titer phage lysates can be made using the phages containing the amber mutants by infecting sup+ hosts like LE392.

The amber mutation in Cro changes a tyrosine codon at position 26 in the cro gene to a UAG amber codon. This amber mutation is suppressed only by the supF tyr tRNA (see Oppenheim et al., *Virology* 319:185-189, 2004, incorporated by reference herein, which describes methods of use in generating amber mutants in lambda). The amber mutation in P is the P sus80 mutation (see Campbell, *Virology* 14:22-32, 1961, which is incorporated by reference herein). This mutation is also called P80 or P amber80. This mutation was added to the cI857 ind1 cro amber phage using the Oppenheim method of mutagenesis (see Oppenheim et al., op. cit., incorporated by reference). These mutations were detected by being able to form plaques on LE392 but not a supF only strain (because the P amber is not suppressed by supF; it needs supE to allow P protein to be made). This phage does not grow on a supE only strain like C600 because of the cro amber mutation.

It should be noted that other combinations of different ambers could be used in cro or P. Alternatively, an amber mutation in O could be produced, instead of P, as a prophage that includes an amber mutation in O is also replication defective. Thus, a prophage including an amber mutation in O and an amber mutation in cro could also be lytic in the LE392 strain, but not in a sup minus strain of bacteria.

Once the amber mutations were introduced into the phage, the tetR gene was PCR amplified with flanking homologies to the rexAB genes. FIG. 17 shows the sequence of the rexAB genes. Using recombineering, these tet genes were crossed into the amber mutant phage in the rex region as shown in FIG. 18. In addition, another phage was recombined with tetRA replacing the S gene (see FIG. 19) of the amber phage. Thus, a similar cross (as with rex) was done by recombineering using S flanking homologies to insert tetRA in place of S gene in the phage carrying the amber mutants (see FIG. 20). When rexAB is replaced the phage still made plaques on LE392 but not on DH10B. However, Tet resistant lysogens can be formed in DH10B (or other strains on which plaques do not form). The phage enters the lysogenic cycle and integrates its DNA in the bacterial chromosome at attB. When S is replaced by tetRA then the phage becomes defective for plaque formation in all strains because S is needed to make a plaque. However, S is not needed to produce phage in bacterial cells. Thus, the recombineering cross to create the S< >tetRA mutant was itself used to infect LE392 and TetR lysogens were selected in the suppressor strain.

These lambda cI857 ind1 Cro amber Pamber S< >tetRA lysogens of LE392 can be induced by growing a culture in LB broth until OD 600 of 0.4 at 32° C. and then shifting to 42° C. for 15 minutes and back to 39° C. for 2 hours with shaking in a water bath. During these two hours, phage production progressed in LE392 and the cells did not lyse (because the S gene is needed for lysis). After two hours the cells were concentrated by centrifugation and suspended in a small volume of buffer (Tris 0.01M, Mg++ 0.01M) and treated with chlorophorm, which caused lysis and release of large numbers of phage (>10 billion/ml). This pure preparation of phage can be used to infect DH10B or other suppressor defective *E. coli* selecting for TetR lysogens at 32° C.

This strategy allows (with either the rex or S phage) the selection of TetR lysogens in various hosts, including recA defective hosts or other recombination defective strains. This strategy also allows large cultures of non-lysogenic strains. For example, a BAC library of human genomic clones or another such library can be infected and converted to TetR, being lysogenic for these defective lambda phages. These defective prophages can be used to induce recombineering in any cell of interest. Temperate phages other than phage λ can be changed to ind-like as shown by Friedman et al. Such ind− phages can then be converted to carry a temperature sensitive repressor like cI857 (see Tyler and Friedmen, *J. Bacteriol.* 186:7670-9, 2004).

Mutations can be created in phage, including bacteriophage λ, using recombineering. Briefly, *E. coli* harboring a defective λ prophage is infected with the phage to be engineered. The partial prophage carries the $P_L$ operon under control of the cI857 temperature sensitive repressor. The lysogen is induced to express the Red functions (Beta, Gam and/or Exo), the induced cells are made competent for electroporation, and the PCR produce of oligonucleotide is introduced by a standard method of introducing nucleic acids into bacterial cells, such as electroporation. Following electroporation, a phage lysate is made from the electroporation mix.

Thus, as disclosed herein, mutations can be created in phage, including bacteriophage λ, using recombineering. Briefly, *E. coli* harboring a defective λ prophage is infected with the phage to be engineered. The partial prophage carries the $P_L$ operon under control of the cI857 temperature sensitive repressor. The lysogen is induced to express the Red functions (Beta, Gam and/or Exo), the induced cells are made competent for electroporation, and the PCR product of oligonucleotide is introduced by a standard method of introducing nucleic acids into bacterial cells, such as electroporation. Following electroporation, a phage lysate is made from the electroporation mix. (see Oppenheim et al., *Virology* 319: 185-189, 2004, which is herein incorporated by reference in its entirety).

Example 5

Generation of Phages

Phages were generated that include suppressible mutations by introducing UAG termination codons in the essential λ genes O, P, Q, (Oppenheim et al., *Virology* 319:185-189, 2004, which is herein incorporated by reference in its entirety) S, and E. The target phage λ cI168 acquired these amber mutations at a frequency of 1-3% in a cross with 70-nucleotide long single-stranded oligos with the UAG codon at the center of the oligonucleotide. Amber mutants were easily identified as cloudy plaques with a double-layer bacterial lawn (see Campbell, Genetic Structure. In: Hershey (ed), *The Bacteriophage Lambda*, Cold Spring Harbor Laboratory Press, Cold Spring Harbor, N.Y., pp 13-44, 1971; Oppenheim et al., supra). The lower layer contains the restrictive host W3110 and the top layer contains the infected supF suppressor host LE392 cells and form cloudy plaques (because W3110 cells in the lower layer grow to confluence and remain unlysed by the amber mutant phage).

Previous studies of λ Cro function were based primarily on the use of one missense mutant, cro27. The phage cI857 cro27 forms clear plaques at 37° C. but cannot form plaques at either 32° C. or 42° C. (Eisen, H., and Ptashne, M., "Regulation of repressor synthesis," A. D., p. 239-245, 1971). The Cro protein contains three tyrosine residues, and each tyrosine codon (70-base oligo used) was independently replaced with UAG. Screening plaques at 42° C. in a double layer, approximately 2% of total plaques were cloudy. On LE392, the resultant mutants grow at 32° C., 37° C. and 42° C., but on W3110 they form plaques only at 37° C. An 80-nucleotide oligonucleotide was used to generate a 326-bp deletion of the cII gene in λ c+. This ss-oligo provides 40 bases of homology at each end of the segment to be deleted. λ c+ normally forms turbid plaques.

Clear plaque recombinants were found at a frequency of 2%. Sequencing showed that the resulting clear mutant phage carried a deletion exactly corresponding to the original design. This deletion fuses the cII translation initiation condon to the downstream O gene, creating a phage with O at the normal cII location. It should be noted that, using recombineering, deletions as large as 5 kb have been generated with oligonucleotides on the E. coli chromosome with good efficiency.

The phage λ rexA and rexB genes were replaced precisely with a bla gene conferring ampicillin resistance. The bla gene was first amplified by PCR using primers with 5' homology to the flanking regions of the rexAB genes; the PCR product was then targeted to the 2, chromosome with recombineering. A phage lysate was grown from the electroporation mix and used to form lysogens. AmpR lysogens were selected and the replacement of the rexAB genes by the bla gene in such lysogens was confirmed by PCR analysis (Yu et al., supra, 2000) and by the ability of the recombinant lysogens to plate T4rII mutant phage (Benzer, Proc. Natl. Acad. Sci. U.S.A. 41:344-354, 1955). Using appropriate PCR primers and the gene SOEing technique (Horton et al., Biotechniques 8 (5): 528-535, 1990), a linear DNA product was created containing an intact copy of the wild-type λ P gene adjoining a precise deletion of the entire ren gene but with homology beyond ren in the ninR region of the phage. The construct was targeted to an infecting Pam80 phage; P$^+$ recombinants were selected and screened for the ren deletion. P$^+$ recombinants were obtained at a frequency of 2%; 20% of these had the deletion.

1. Analysis of Mutations Arising from the Use of Oligonucleotides in Recombineering.

It has been demonstrated that recombineering provides an efficient way to manipulate the bacteriophage genome. However, it was found that sometimes oligonucleotide recombination has associated unwanted mutations. To understand the origin and nature of these unwanted mutants, a protocol was designed to score for both true recombinants and unwanted changes. Phage λ cI857 carries a temperature-sensitive mutation in repressor; thus, the phage forms clear plaques at 37° C. and turbid plaques at 30° C. (Sussman and Jacob, C. R. Acad. Sci. (Paris) 254:1517-1519, 1962). Two complementary oligonucleotides were designed that were 82 residues long, with wild-type repressor gene sequence that could generate wild-type λ recombinants in a cross with λ cI857 (FIG. 1). These oligos cover about 1/10 of the cI coding region and are centered on the cI857 allele. The recombinant lysate was diluted and plated on W3110 at either 37° C. or 32° C. At 37° C., λ c$^+$ recombinants form turbid plaques. At 32° C., both parent and recombinant should form turbid plaques. When plaques from the recombineering cross were grown at 37° C., most were clear, however, 4-13% were turbid as expected of wild-type recombinants (Table 1). When the recombinant lysate was plated at 32° C., most plaques were turbid as expected, however, a significant proportion, 0.5-2%, was clear. This number is 10-40 times higher than the spontaneous frequency of clear plaques (approximately 0.05%) found in lysates prepared the same way but without the addition of oligonucleotide or with the addition of an oligonucleotide lacking homology.

To understand the source of the unwanted clear mutations, clear and turbid recombinants were purified and sequenced their cI gene. Fourteen turbid λ cI$^+$ recombinants isolated at 37° C. had all been corrected for the cI857 mutation without additional mutations. However, all clear plaques identified at 32° C. contained other mutations of cI. These mutations were about equally produced by the two oligonucleotides. Twenty-four or twenty-five of those sequenced had mutations in the region covered by the ss-oligo. Among these 24 mutants, 22 had also converted the cI857 allele to wild-type. One of these 22 mutants was a GC to TA transversion, the rest were deletions of one or more bases of the cI sequence. The one change outside of the oligo region was a GC to TA transversion that retained the cI857 allele and possibly arose spontaneously.

To demonstrate that these mutations were not specific to cI857 or to the oligo sequence, the experiment was repeated using wild-type λ cI$^+$ and complementary ss-oligos from a different region of the cI gene in a cross. These oligonucleotides carried a single silent AT to GC change. As before, clear plaques were found in the lysate following recombineering. The DNA from 16 clear plaques was sequenced. Fifteen carried the silent mutation indicating that they had undergone recombineering. Nine had a single base pair deletion, three had longer deletions, one mutant had an added AT base pair, one showed a CG to TA transition, and one had a GC to AT base substitution mutation located outside the region covered by the ss-oligo. The one mutant lacking the signature change had a CG to TA transition outside the region covered by the ss-oligo and may have been a spontaneous clear mutant.

| Exp. # | Host | Oligo | λ c$^+$ % | λ cI$^-$ % |
| --- | --- | --- | --- | --- |
| 1 | DY433 | W | 6 | 2 |
| 2 | HME31 | W | 6 | 1.5 |
| 3 | HME31 | C | 13 | 2 |
| 4 | HME31 recA | W | 4 | 0.5 |
| 5 | HME31 | — | <0.05 | <0.05 |
| 5 | HME31 | #100 | <0.05 | <0.05 |
| 6 | HME31 | C* | 3.2 | 0.1 |

The results presented above suggest that most of the mutations were introduced during synthesis of the single stranded oligonucleotides (ss-oligos). Based on the results and chemistry of synthesis, one would expect that at each position of the oligonucleotide there would be an equal chance of not incorporating the added base (Hecker and Rill, Biotechniques 24(2):256-260 1998; Temsamani et al., Nucleic Acids Research 23(11):1841-1844 1995). Examination of the sequence changes among the frameshifts show that they cluster toward the center of the ss-oligo. The terminal regions lack mutations, suggesting that complete base pairing at the termini may be important for efficient annealing to the phage DNA.

To reduce the frequency of frameshift mutations, the ss-oligos were further purified. Purification by HPLC did not reduce the mutation frequency (data not shown) probably because HPLC does not efficiently separate oligos of this length, whereas PAGE-purified oligonucleotides yielded efficient recombineering with fewer frameshifts (see above table). This result supports the notion that base deletions originating during chemical synthesis of the oligonucleotides are responsible for generating mutations. Single base frameshift deletions occur rarely as spontaneous mutations (Schaaper and Dunn, Genetics 129(2):317-326, 1991). In the above examples, deletion mutations formed usually also carried the designed change present on the ss-oligo, suggesting that the frameshifts were conferred by the synthetic ss-oligo. Thus, the experimental approach described herein provides a simple and sensitive assay for oligonucleotide quality. Recombineering with unpurified synthetic oligonucleotides could also be used to provide an efficient way to introduce random single base deletions at specific sites in genes or regulatory regions. The results do not suggest that the act of recombineering causes random mutagenesis.

When recombineering with the bacterial chromosome, one of two complementary ss-oligos gives more recombinants (Ellis et al., supra, 2001; Zhang et al., *Nature Genetics* 20:123-128, 2003). This strand bias depends upon the direction of replication through the recombining region with the lagging strand being the more recombinogenic. In the phage crosses, both complementary oligos were equally efficient in promoting recombination at λ cI. Without being bound by theory, this can be due to the rolling circle mode of phage DNA replication, which can roll in either direction (Takahashi, *Mol. Gen. Genet.* 142(2):137-153, 1975). Thus, replication forms pass through cI in both directions and neither strand is exclusively leading or lagging.

In the cross with λ cI857, mottled plaques were observed at 37° C., which suggested that the λ DNA was packaged with a heteroduplex allele in cI (Huisman and Fox, *Genetics* 112(3): 409-420, 1986). Six independent mottled plaques were purified; they gave rise to a mixture of turbid and clear plaques. Sequence analysis showed that in all cases the turbid plaques had incorporated the wild-type allele, whereas the clear plaques retained the original cI857 mutation, indicating that the oligonucleotide paired with the phage chromosome and was incorporated without mismatch correction. These heterozygous phages are generated in recA mutant crosses, which suggests that the ss-oligo is annealed by Beta protein to single-strand gaps at the replication fork (Court et al., *Annu. Rev. Genet.* 36:361-388, 2003; Stahl et al., *Genetics* 147(3): 961-977, 1997).

2. Materials and Methods a. Creating Mutations with Recombineering.

The strains used for recombineering carry a defective λ prophage containing the $p_L$ operon under control of the temperature-sensitive repressor cI857. The genotype of one commonly used strain, DY330, is W3110 ΔlacU169 gal490 pglΔ8 λcI857 Δ(cro-bioA). The strain of choice is grown in a shaking water bath at 32° C. in LB with 0.4% maltose to mid-exponential phase, $A_{600}$ 0.4-0.6 (30 ml is adequate for several recombineering reactions). The culture is harvested by centrifugation and resuspended in 1 ml TM (10 mM Tris base, 10 mM $MgSO_4$, pH 7.4). The phage to be engineered is added at a multiplicity of infection of 1-3 phages/cell (assume a cell density of approximately 1×10⁸/ml before concentration) and allowed to adsorb at room temperature for 15 minutes (this step would need modification for other phages, i.e., adsorption on ice). Meanwhile, two flasks with 5-ml broth are pre-warmed to 32 and 42° C. in separate shaking water baths. The infected culture is divided and half-inoculated into each flask; the cultures are incubated an additional 15 minutes. The 42° C. heat pulse induces prophage functions; the 32° C. uninduced culture is a control. After induction, the flasks are well chilled in an ice water bath and the cells transferred to chilled 35-ml centrifuge tubes and harvested by centrifugation at approximately 6500×g for 7 minutes. The cells are washed once with 30-ml ice-cold sterile water; the pellet is quickly resuspended in 1-ml ice-cold sterile water and pelleted briefly (30 seconds) in a refrigerated microfuge. The pellet is resuspended in 200-μl cold sterile water and 50-100 μl aliquots are used for electroporation with 100-150 ng PCR product or 10-100 ng oligonucleotide. A BioRad *E. coli* Gene Pulser was used set at 1.8 mV and 0.1-cm cuvettes. Electroporated cells are diluted into 5 ml 39° C. LB medium and incubated to allow completion of the lytic cycle. The resulting phage lysate is diluted and tittered on appropriate bacterial to obtain single plaques (for more details, see Thompson et al., *Current Protocols in Mol. Bio.* 1.16.1-1.16.16, 2003).

b. Oligonucleotides.

The oligonucleotides were purchased from Invitrogen without additional purification. The purified oligonucleotide was subjected to electrophoresis in a 15% PAGE-Urea gel, excised from the gel without direct UV irradiation and eluted using the Elutrap electro-separation system (Schleicher and Schuell). The size-purified oligonucleotide was then precipitated with isopropanol, washed with ethanol, dried and stored at −20° C.

Example 6

Use of Single-Strand Oligo Recombineering in *Salmonella*

Wild-type galK⁺ *Salmonella* does not grow on minimal medium with glycerol as carbon source when 2-deoxygalactose is also present. This is due to the galactokinase function of galK⁺, which converts 2-deoxygalactose to a toxic compound for the cell causing death. Forms of *Salmonella* that are galK− can grow on glycerol with 2-deoxygalactose. The oligonucleotide sequence of the *Salmonella typhimurium* galK gene is shown with the changes incorporated to make it Gal- (SEQ ID NO: 21). The *S. typhimurium* gal .GTGTTCA oligo has the sequence set forth below that is 70 bases in length:

(SEQ ID NO: 34)
AAGTGGCGGTGGGCACCGTCTTCCAGCAGCTTTA<u>GTGTTCA</u>CCGCTGG
ACGGCGCGCAAATTGCGCTCAA

This oligonucleotide was used to mutate the galK gene to Gal−. The sequence shown as SEQ ID NO: 34 has the 7 bases underlined changed from the wild-type sequence.

The *Salmonella typhimurium* (St)144 oligonucleotide has the sequence set forth below:

(SEQ ID NO: 35)
AAGTGGCGGTGGGCACCGTCTTCCAGCAGCTTTA<u>CCACCTG</u>CCGCTGG
ACGGCGCGCAAATTGCGCTCAA

The St 144 oligonucleotide was used to correct the mutation, and make the cells Gal+. It should be noticed that this oligo creates the wild-type galK sequence with the exception of the TAT tyrosine codon, which became TAC tryrosine in the Gal⁺ recombinant.

These oligonucleotides were introduced into *S. typhimurium* cells transformed with plasmid pSIM5. Red functions were induced by a 15 minute temperature shift to 42° C. Recombinants with the *S. typhimurium*. galK.GTGTTCA oligo become galK− and survive on 2-deoxygalactose, but cannot use galactose as the only carbon source. GalK⁺ recombinants produced using the 144 oligonucleotide grow on galactose as sole carbon source and were selected in minimal galactose agar. These Gal⁺ strains were produced using recombineering with the St 144 oligo.

The new galK+ strain produced by recombineering differed from wild-type at the one base of the TAT codon position 144 where the recombinant is TAC. The frequency of going from galK+ to galK−, or from galK− to galK+ (in the two recombineering crosses with oligos *S. typhimurium* galK.GTGTTCA and *S. typhimurium* (St)144) was 5% in each case. These results demonstrate that the plasmids disclosed herein can be used to introduce recombineering functions into *S. typhimurium*.

It will be apparent that the precise details of the methods or compositions described may be varied or modified without departing from the spirit of the described invention. We claim all such modifications and variations that fall within the scope and spirit of the claims below.

SEQUENCE LISTING

<160> NUMBER OF SEQ ID NOS: 35

<210> SEQ ID NO 1
<211> LENGTH: 4907
<212> TYPE: DNA
<213> ORGANISM: artificial sequence
<220> FEATURE:
<223> OTHER INFORMATION: plasmid

<400> SEQUENCE: 1

| | | | | |
|---|---|---|---|---|
| cagctgtctc | ttatacacat | ctccgctgtg | ctttcagtgg | atttcggata acagaaaggc | 60 |
| cgggaaatac | ccagcctcgc | tttgtaacgg | agtagacgaa | agtgattgcg cctacccgga | 120 |
| tattatcgtg | aggatgcgtc | atcgccattg | ctccccaaat | acaaaaccaa tttcagccag | 180 |
| tgcctcgtcc | atttttcga | tgaactccgg | cacgatctcg | tcaaaactcg ccatgtactt | 240 |
| ttcatcccgc | tcaatcacga | cataatgcag | gccttcacgc | ttcatacgcg ggtcatagtt | 300 |
| ggcaaagtac | caggcatttt | ttcgcgtcac | ccacatgctg | tactgcacct gggccatgta | 360 |
| agctgacttt | atggcctcga | aaccaccgag | ccggaacttc | atgaaatccc gggaggtaaa | 420 |
| cgggcatttc | agttcaaggc | cgttgccgtc | actgcataaa | ccatcgggag agcaggcggt | 480 |
| acgcatactt | tcgtcgcgat | agatgatcgg | ggattcagta | acattcacgc cggaagtgaa | 540 |
| ctcaaacagg | gttctggcgt | cgttctcgta | ctgttttccc | caggccagtg ctttagcgtt | 600 |
| aacttccgga | gccacaccgg | tgcaaacctc | agcaagcagg | gtgtggaagt aggacatttt | 660 |
| catgtcaggc | cacttctttc | cggagcgggg | ttttgctatc | acgttgtgaa cttctgaagc | 720 |
| ggtgatgacg | ccgagccgta | atttgtgcca | cgcatcatcc | ccctgttcga cagctctcac | 780 |
| atcgatcccg | gtacgctgca | ggataatgtc | cggtgtcatg | ctgccacctt ctgctctgcg | 840 |
| gctttctgtt | tcaggaatcc | aagagctttt | actgcttcgg | cctgtgtcag ttctgacgat | 900 |
| gcacgaatgt | cgcggcgaaa | tatctgggaa | cagagcggca | ataagtcgtc atcccatgtt | 960 |
| ttatccaggg | cgatcagcag | agtgttaatc | tcctgcatgg | tttcatcgtt aaccggagtg | 1020 |
| atgtcgcgtt | ccggctgacg | ttctgcagtg | tatgcagtat | tttcgacaat gcgctcggct | 1080 |
| tcatccttgt | catagatacc | agcaaatccg | aaggccagac | gggcacactg aatcatggct | 1140 |
| ttatgacgta | acatccgttt | gggatgcgac | tgccacggcc | ccgtgatttc tctgccttcg | 1200 |
| cgagttttga | atggttcgcg | gcggcattca | tccatccatt | cggtaacgca gatcggatga | 1260 |
| ttacggtcct | tgcggtaaat | ccggcatgta | caggattcat | tgtcctgctc aaagtccatg | 1320 |
| ccatcaaact | gctggttttc | attgatgatg | cgggaccagc | catcaacgcc caccaccgga | 1380 |
| acgatgccat | tctgcttatc | aggaaaggcg | taaatttctt | tcgtccacgg attaaggccg | 1440 |
| tactggttgg | caacgatcag | taatgcgatg | aactgcgcat | cgctggcatc acctttaaat | 1500 |
| gccgtctggc | gaagagtggt | gatcagttcc | tgtgggtcga | cagaatccat gccgacacgt | 1560 |
| tcagccagct | tcccagccag | cgttgcgagt | gcagtactca | ttcgttttat acctctgaat | 1620 |
| caatatcaac | ctggtggtga | gcaatggttt | caaccatgta | ccggatgtgt tctgccatgc | 1680 |
| gctcctgaaa | ctcaacatcg | tcatcaaacg | cacgggtaat | ggattttttg ctggcccgt | 1740 |
| ggcgttgcaa | atgatcgatg | catagcgatt | caaacaggtg | ctggggcagg ccttttttcca | 1800 |
| tgtcgtctgc | cagttctgcc | tctttctctt | cacgggcgag | ctgctggtag tgacgcgccc | 1860 |
| agctctgagc | ctcaagacga | tcctgaatgt | aataagcgtt | catggctgaa ctcctgaaat | 1920 |
| agctgtgaaa | atatcgcccg | cgaaatgccg | ggctgattag | taatccggaa tcgcacttac | 1980 |
| ggccaatgct | tcgtttcgta | tcacacaccc | caaagccttc | tgctttgaat gctgcccttc | 2040 |

```
ttcagggctt aattttttaag agcgtcacct tcatggtggt cagtgcgtcc tgctgatgtg    2100
ctcagtatca ccgccagtgg tatttatgtc aacaccgcca gagataattt atcaccgcag    2160
atggttatct gtatgttttt tatatgaatt tattttttgc agggggcat tgtttggtag      2220 gtgagagatc tgaattgcta tgtttagtga gttgtatcta tttattttc aataaataca      2280 attggttatg tgttttgggg gcgatcgtga ggcaaagaaa acccggcgct gaggccgggt     2340
tacgccccgc cctgccactc atcgcagtac tgttgtaatt cattaagcat tctgccgaca     2400
tggaagccat cacagacggc atgatgaacc tgaatcgcca gcggcatcag caccttgtcg     2460
ccttgcgtat aatatttgcc catggtgaaa acggggcga agaagttgtc catattggcc      2520
acgtttaaat caaaactggt gaaactcacc cagggattgg ctgagacgaa aaacatattc     2580
tcaataaacc cttagggaa ataggccagg ttttcaccgt aacacgccac atcttgcgaa      2640
tatatgtgta gaaactgccg gaaatcgtcg tggtattcac tccagagcga tgaaaacgtt    2700
tcagtttgct catggaaaac ggtgtaacaa gggtgaacac tatcccatat caccagctca    2760
ccgtctttca ttgccatacg gaattccgga tgagcattca tcaggcgggc aagaatgtga    2820
ataaaggccg gataaaactt gtgcttattt ttctttacgg tctttaaaaa ggccgtaata    2880
tccagctgaa cggtctggtt ataggtacat tgagcaactg actgaaatgc ctcaaaatgt    2940
tctttacgat gccattggga tatatcaacg gtggtatatc cagtgatttt tttctccata    3000
attcaatcca tttactatgt tatgttctga ggggagtgaa aattcccta attcgatgaa      3060 gattcttgct caattgttat cagctatgcg ccgaccagaa caccttgccg atcagccaaa   3120
cgtctcttca ggccactgac tagcgataac tttccccaca acggaacaac tctcattgca    3180
tgggatcatt gggtactgtg ggtttagtgg ttgtaaaaac acctgaccgc tatccctgat    3240
cagtttcttg aaggtaaact catcacccc aagtctggct atgcagaaat cacctggctc     3300
aacagcctgc tcagggtcaa cgagaattaa cattccgtca ggaaagcttg gcttggagcc    3360
tgttggtgcg gtcatggaat taccttcaac ctcaagccag aatgcagaat cactggcttt    3420
tttggttgtg cttacccatc tctccgcatc acctttggta aaggttctaa gcttaggtga    3480
gaacatccct gcctgaacat gagaaaaaac agggtactca tactcacttc taagtgacgg    3540
ctgcatacta accgcttcat acatctcgta gatttctctg gcgattgaag gctaaattc     3600 ttcaacgcta actttgagaa ttttttgtaag caatgcggcg ttataagcat ttaatgcatt   3660
gatgccatta aataaagcac caacgcctga ctgccccatc cccatcttgt ctgcgacaga    3720
ttcctgggat aagccaagtt cattttttctt tttttcataa attgctttaa ggcgacgtgc   3780
gtcctcaagc tgctcttgtg ttaatggttt cttttttgtg ctcatacgtt aaatctatca    3840
ccgcaaggga taaatatcta acaccgtgcg tgttgactat tttacctctg gcggtgataa    3900
tggttgcatg tactaaggag gttgtatgga acaacgagat gtgtataaga gacagctggc    3960
gctcttccgc ttcctcgctc actgactcgc tgcgctcggt cgttcggctg cggcgagcgg    4020
tatcagctca ctcaaaggcg gtaatacggt tatccacaga atcaggggat aacgcaggaa    4080
agaacatgtg agcaaaaggc cagcaaaagg ccaggaaccg taaaaaggcc gcgttgctgg    4140
cgttttccca taggctccgc ccccctgacg agcatcacaa aaatcgacgc tcaagtcaga    4200
ggtggcgaaa cccgacagga ctataaagat accaggcgtt tcccctggaa gctccctcg    4260 tgcgctctcc tgttccgacc ctgccgctta ccggatacct gtccgccttt ctcccttcgg    4320
gaagcgtggc gctttctcat agctcacgct gtaggtatct cagttcggtg taggtcgttc    4380
```

```
gctccaagct gggctgtgtg cacgaacccc ccgttcagcc cgaccgctgc gccttatccg    4440
gtaactatcg tcttgagtcc aacccggtaa gacacgactt atcgccactg gcagcagcca    4500
ctggtaacag gattagcaga gcgaggtatg taggcggtgc tacagagttc ttgaagtggt    4560
ggcctaacta cggctacact agaaggacag tatttggtat ctgcgctctg ctgaagccag    4620
ttaccttcgg aaaaagagtt ggtagctctt gatccggcaa acaaaccacc gctggtagcg    4680
gtggtttttt tgtttgcaag cagcagatta cgcgcagaaa aaaaggatct caagaagatc    4740
ctttgatctt ttctacgggg tctgacgctc agtggaacga aaactcacgt taagggattt    4800
tggtcatgag attatcaaaa aggatcttca cctagatcct tttaaattaa aaatgaagtt    4860
ttaaatcaat ctaaagtata tatgagtaaa cttggtctga cagttac                 4907

<210> SEQ ID NO 2
<211> LENGTH: 5452
<212> TYPE: DNA
<213> ORGANISM: artificial sequence
<220> FEATURE:
<223> OTHER INFORMATION: plasmid

<400> SEQUENCE: 2
cgtgaggatg cgtcatcgcc attgctcccc aaatacaaaa ccaatttcag ccagtgcctc      60
gtccattttt tcgatgaact ccggcacgat ctcgtcaaaa ctcgccatgt acttttcatc     120
ccgctcaatc acgacataat gcaggccttc acgcttcata cgcgggtcat agttggcaaa     180
gtaccaggca ttttttcgcg tcacccacat gctgtactgc acctgggcca tgtaagctga     240
ctttatggcc tcgaaaccac cgagccgaa cttcatgaaa tcccgggagg taaacgggca     300
tttcagttca aggccgttgc cgtcactgca taaaccatcg ggagagcagg cggtacgcat     360
actttcgtcg cgatagatga tcggggattc agtaacattc acgccggaag tgaactcaaa     420
cagggttctg gcgtcgttct cgtactgttt tccccaggcc agtgctttag cgttaacttc     480
cggagccaca ccggtgcaaa cctcagcaag cagggtgtgg aagtaggaca ttttcatgtc     540
aggccacttc tttccggagc ggggttttgc tatcacgttg tgaacttctg aagcggtgat     600
gacgccgagc cgtaatttgt gccacgcatc atcccctgt tcgacagctc tcacatcgat     660
cccggtacgc tgcaggataa tgtccggtgt catgctgcca ccttctgctc tgcggctttc     720
tgtttcagga atccaagagc ttttactgct tcggcctgtg tcagttctga cgatgcacga     780
atgtcgcggc gaaatatctg ggaacagagc ggcaataagt cgtcatccca tgttttatcc     840
agggcgatca gcagagtgtt aatctcctgc atggtttcat cgttaaccgg agtgatgtcg     900
cgttccggct gacgttctgc agtgtatgca gtattttcga caatgcgctc ggcttcatcc     960
ttgtcataga taccagcaaa tccgaaggcc agacgggcac actgaatcat ggctttatga    1020
cgtaacatcc gtttgggatg cgactgccac ggccccgtga tttctctgcc ttcgcgagtt    1080
ttgaatggtt cgcggcggca ttcatccatc cattcggtaa cgcagatcgg atgattacgg    1140
tccttgcggt aaatccggca tgtacaggat tcattgtcct gctcaaagtc catgccatca    1200
aactgctggt tttcattgat gatgcgggac cagccatcaa cgcccaccac cggaacgatg    1260 ccattcgct tatcaggaaa ggcgtaaatt tctttcgtcc acggattaag gccgtactgg    1320
ttggcaacga tcagtaatgc gatgaactgc gcatcgctgg catcacctt aaatgccgtc    1380 tggcgaagag tggtgatcag ttcctgtggg tcgacagaat ccatgccgac acgttcagcc    1440
agcttcccag ccagcgttgc gagtgcagta ctcattcgtt ttatacctct gaatcaatat    1500
caacctggtg gtgagcaatg gtttcaacca tgtaccggat gtgttctgcc atgcgctcct    1560
```

```
gaaactcaac atcgtcatca aacgcacggg taatggattt tttgctggcc ccgtggcgtt   1620
gcaaatgatc gatgcatagc gattcaaaca ggtgctgggg caggccttt tccatgtcgt    1680 ctgccagttc tgcctctttc tcttcacggg cgagctgctg gtagtgacgc gcccagctct   1740
gagcctcaag acgatcctga atgtaataag cgttcatggc tgaactcctg aaatagctgt   1800
gaaaatatcg cccgcgaaat gccgggctga ttagtaatcc ggaatcgcac ttacggccaa   1860
tgcttcgttt cgtatcacac accccaaagc cttctgcttt gaatgctgcc cttcttcagg   1920
gcttaatttt taagagcgtc accttcatgg tggtcagtgc gtcctgctga tgtgctcagt   1980
atcaccgcca gtggtatttta tgtcaacacc gccagagata atttatcacc gcagatggtt   2040
atctgtatgt ttttatatg aatttatttt ttgcagggg gcattgtttg gtaggtgaga     2100
gatctgaatt gctatgttta gtgagttgta tctatttatt tttcaataaa tacaattggt   2160
tatgtgtttt gggggcgatc gtgaggcaaa gaaacccgg cgctgaggcc gggttaagag    2220
ttggtagctc ttgatccggc aaacaaacca ccgctggtag cggtggtttt tttgtttgca   2280
agcagcagat tacgcgcaga aaaaaggat ctcaagaaga tcctttgatc ttttctacgg    2340
ggtctgacgc tcagtggaac gaaaactcac gttaagggat tttggtcatg agattatcaa   2400
aaaggatctt cacctagatc cttttaaatt aaaaatgaag ttttaaatca atctaaagta   2460
tatatgagta aacttggtct gacagttacc aatgcttaat cagtgaggca cctatctcag   2520
cgatctgtct atttcgttca tccatagttg cctgactccc cgtcgtgtag ataactacga   2580
tacgggaggg cttaccatct ggccccagtg ctgcaatgat accgcgagac ccacgctcac   2640
cggctccaga tttatcagca ataaaccagc cagccggaag ggccgagcgc agaagtggtc   2700
ctgcaacttt atccgcctcc atccagtcta ttaattgttg ccgggaagct agagtaagta   2760
gttcgccagt taatagtttg cgcaacgttg ttgccattgc tgcaggcatc gtggtgtcac   2820
gctcgtcgtt tggtatggct tcattcagct ccggttccca acgatcaagg cgagttacat   2880 gatccccat gttgtgcaaa aaagcggtta gctccttcgg tcctccgatc gttgtcagaa    2940
gtaagttggc cgcagtgtta tcactcatgg ttatggcagc actgcataat tctcttactg   3000
tcatgccatc cgtaagatgc ttttctgtga ctggtgagta ctcaaccaag tcattctgag   3060
aatagtgtat gcggcgaccg agttgctctt gcccggcgtc aacacgggat aataccgcgc   3120
cacatagcag aactttaaaa gtgctcatca ttggaaaacg ttcttcgggg cgaaaactct   3180
caaggatctt accgctgttg agatccagtt cgatgtaacc cactcgtgca cccaactgat   3240
cttcagcatc ttttactttc accagcgttt ctgggtgagc aaaaacagga aggcaaaatg   3300
ccgcaaaaaa gggaataagg gcgacacgga aatgttgaat actcatactc ttcctttttc   3360
aatattattg aagcatttat cagggttatt gtctcatgag cggatacata tttgaatgaa   3420
ttcaatccat ttactatgtt atgttctgag gggagtgaaa attcccctaa ttcgatgaag   3480
attcttgctc aattgttatc agctatgcgc cgaccagaac ccttgccga tcagccaaac    3540 gtctcttcag gccactgact agcgataact ttccccacaa cggaacaact ctcattgcat   3600
gggatcattg gtactgtgg gtttagtggt tgtaaaaaca cctgaccgct atccctgatc    3660
agtttcttga aggtaaactc atcaccccca agtctgctaa tgcagaaatc acctggctca   3720
acagcctgct cagggtcaac gagaattaac attccgtcag gaaagcttgg cttggagcct   3780
gttggtgcgg tcatggaatt accttcaacc tcaagccaga atgcagaatc actggctttt   3840
ttggttgtgc ttacccatct ctccgcatca cctttggtaa aggttctaag cttaggtgag   3900
```

```
aacatccctg cctgaacatg agaaaaaaca gggtactcat actcacttct aagtgacggc    3960
tgcatactaa ccgcttcata catctcgtag atttctctgg cgattgaagg gctaaattct    4020
tcaacgctaa ctttgagaat ttttgtaagc aatgcggcgt tataagcatt taatgcattg    4080
atgccattaa ataaagcacc aacgcctgac tgccccatcc ccatcttgtc tgcgacagat    4140
tcctgggata agccaagttc attttctttt ttttcataaa ttgctttaag gcgacgtgcg    4200
tcctcaagct gctcttgtgt taatggtttc tttttttgtgc tcatacgtta aatctatcac    4260
cgcaagggat aaatatctaa caccgtgcgt gttgactatt ttacctctgg cggtgataat    4320
ggttgcatgt actaaggagg ttgtatggaa caacgagatg tgtataagag acagctggcg    4380
ctcttccgct tcctcgctca ctgactcgct gcgctcggtc gttcggctgc ggcgagcggt    4440
atcagctcac tcaaaggcgg taatacggtt atccacagaa tcaggggata acgcaggaaa    4500
gaacatgtga gcaaaaggcc agcaaaaggc caggaaccgt aaaaaggccg cgttgctggc    4560
gtttttccat aggctccgcc ccctgacga gcatcacaaa aatcgacgct caagtcagag    4620
gtggcgaaac ccgacaggac tataaagata ccaggcgttt ccccctggaa gctccctcgt    4680
gcgctctcct gttccgaccc tgccgcttac cggatacctg tccgcctttc tcccttcggg    4740
aagcgtggcg ctttctcata gctcacgctg taggtatctc agttcggtgt aggtcgttcg    4800
ctccaagctg ggctgtgtgc acgaaccccc cgttcagccc gaccgctgcg ccttatccgg    4860
taactatcgt cttgagtcca acccggtaag acacgactta tcgccactgg cagcagccac    4920
tggtaacagg attagcagag cgaggtatgt aggcggtgct acagagttct tgaagtggtg    4980
gcctaactac ggctacacta aaggacagt atttggtatc tgcgctctgc tgaagccagt    5040
taccttcgga aaaagagttg gtagctcttg atccggcaaa caaaccaccg ctggtagcgg    5100 tggtttttt gtttgcaagc agcagattac gcgcagaaaa aaaggatctc aagaagatcc    5160
tttgatcttt tctacggggt ctgacgctca gtggaacgaa aactcacgtt aagggatttt    5220
ggtcatgaga ttatcaaaaa ggatcttcac ctagatcctt ttaaattaaa aatgaagttt    5280
taaatcaatc taaagtatat atgagtaaac ttggtctgac agttaccagc tgtctcttat    5340
acacatctcc gctgtgcttt cagtggattt cggataacag aaaggccggg aaataccccag    5400 cctcgctttg taacggagta gacgaaagtg attgcgccta cccggatatt at    5452
```

<210> SEQ ID NO 3
<211> LENGTH: 6171
<212> TYPE: DNA
<213> ORGANISM: artificial sequence
<220> FEATURE:
<223> OTHER INFORMATION: plasmid

<400> SEQUENCE: 3

```
cagctgtctc ttatacacat ctccgctgtg ctttcagtgg atttcggata acagaaaggc      60
cgggaaatac ccagcctcgc tttgtaacgg agtagacgaa agtgattgcg cctacccgga    120
tattatcgtg aggatgcgtc atcgccattg ctccccaaat acaaaaccaa tttcagccag    180
tgcctcgtcc atttttttcga tgaactccgg cacgatctcg tcaaaactcg ccatgtactt    240
ttcatcccgc tcaatcacga cataatgcag gccttcacgc ttcatacgcg ggtcatagtt    300
ggcaaagtac caggcatttt ttcgcgtcac ccacatgctg tactgcacct gggccatgta    360
agctgacttt atggcctcga aaccaccgag ccggaacttc atgaaatccc gggaggtaaa    420
cgggcatttc agttcaaggc cgttgccgtc actgcataaa ccatcgggag agcaggcggt    480
acgcatactt tcgtcgcgat agatgatcgg ggattcagta acattcacgc cggaagtgaa    540
```

```
ctcaaacagg gttctggcgt cgttctcgta ctgttttccc caggccagtg ctttagcgtt    600
aacttccgga gccacaccgg tgcaaacctc agcaagcagg gtgtggaagt aggacatttt    660
catgtcaggc cacttctttc cggagcgggg ttttgctatc acgttgtgaa cttctgaagc    720
ggtgatgacg ccgagccgta atttgtgcca cgcatcatcc ccctgttcga cagctctcac    780
atcgatcccg gtacgctgca ggataatgtc cggtgtcatg ctgccacctt ctgctctgcg    840
gctttctgtt tcaggaatcc aagagctttt actgcttcgg cctgtgtcag ttctgacgat    900
gcacgaatgt cgcggcgaaa tatctgggaa cagagcggca ataagtcgtc atcccatgtt    960
ttatccaggg cgatcagcag agtgttaatc tcctgcatgg tttcatcgtt aaccggagtg   1020
atgtcgcgtt ccggctgacg ttctgcagtg tatgcagtat tttcgacaat gcgctcggct   1080
tcatccttgt catagatacc agcaaatccg aaggccagac gggcacactg aatcatggct   1140
ttatgacgta acatccgttt gggatgcgac tgccacggcc ccgtgatttc tctgccttcg   1200
cgagttttga atggttcgcg gcggcattca tccatccatt cggtaacgca gatcggatga   1260
ttacggtcct tgcggtaaat ccggcatgta caggattcat tgtcctgctc aaagtccatg   1320
ccatcaaact gctggttttc attgatgatg cgggaccagc catcaacgcc caccaccgga   1380
acgatgccat tctgcttatc aggaaaggcg taaatttctt tcgtccacgg attaaggccg   1440
tactggttgg caacgatcag taatgcgatg aactgcgcat cgctggcatc acctttaaat   1500
gccgtctggc gaagagtggt gatcagttcc tgtgggtcga cagaatccat gccgacacgt   1560
tcagccagct tcccagccag cgttgcgagt gcagtactca ttcgttttat acctctgaat   1620
caatatcaac ctggtggtga gcaatggttt caaccatgta ccggatgtgt tctgccatgc   1680
gctcctgaaa ctcaacatcg tcatcaaacg cacgggtaat ggattttttg ctggccccgt   1740
ggcgttgcaa atgatcgatg catagcgatt caaacaggtg ctggggcagg ccttttttcca  1800 tgtcgtctgc cagttctgcc tctttctctt cacgggcgag ctgctggtag tgacgcgccc   1860
agctctgagc ctcaagacga tcctgaatgt aataagcgtt catggctgaa ctcctgaaat   1920
agctgtgaaa atatcgcccg cgaaatgccg ggctgattag taatccggaa tcgcacttac   1980
ggccaatgct tcgtttcgta tcacacaccc caaagccttc tgctttgaat gctgcccttc   2040
ttcagggctt aattttttaag agcgtcacct tcatggtggt cagtgcgtcc tgctgatgtg   2100
ctcagtatca ccgccagtgg tatttatgtc aacaccgcca gagataattt atcaccgcag   2160
atggttatct gtatgttttt tatatgaatt tattttttgc aggggggcat tgtttggtag   2220
gtgagagatc tgaattgcta tgtttagtga gttgtatcta tttatttttc aataaataca   2280
attggttatg tgtttggggg gcgatcgtga ggcaaagaaa acccggcgct gaggccgggt   2340
tacgccccgc cctgccactc atcgcagtac tgttgtaatt cattaagcat tctgccgaca   2400
tggaagccat cacagacggc atgatgaacc tgaatcgcca gcggcatcag cccttgtcg    2460 ccttgcgtat aatatttgcc catggtgaaa acggggcga agaagttgtc catattggcc    2520
acgtttaaat caaaactggt gaaactcacc cagggattgg ctgagacgaa aaacatattc    2580
tcaataaacc ctttagggaa ataggccagg ttttcaccgt aacacgccac atcttgcgaa    2640
tatatgtgta gaaactgccg gaaatcgtcg tggtattcac tccagagcga tgaaaacgtt    2700
tcagtttgct catggaaaac ggtgtaacaa gggtgaacac tatcccatat caccagctca    2760
ccgtctttca ttgccatacg gaattccgga tgagcattca tcaggcgggc aagaatgtga    2820
ataaaggccg gataaaactt gtgcttattt ttctttacgg tctttaaaaa ggccgtaata    2880
```

```
tccagctgaa cggtctggtt ataggtacat tgagcaactg actgaaatgc ctcaaaatgt    2940
tctttacgat gccattggga tatatcaacg gtggtatatc cagtgatttt tttctccata    3000
attcaatcca tttactatgt tatgttctga ggggagtgaa aattccccta attcgatgaa    3060
gattcttgct caattgttat cagctatgcg ccgaccagaa caccttgccg atcagccaaa    3120
cgtctcttca ggccactgac tagcgataac tttccccaca acggaacaac tctcattgca    3180
tgggatcatt gggtactgtg ggtttagtgg ttgtaaaaac acctgaccgc tatccctgat    3240
cagtttcttg aaggtaaact catcaccccc aagtctggct atgcagaaat cacctggctc    3300
aacagcctgc tcagggtcaa cgagaattaa cattccgtca ggaaagcttg cttggagcc    3360 tgttggtgcg gtcatggaat taccttcaac ctcaagccag aatgcagaat cactggcttt    3420
tttggttgtg cttacccatc tctccgcatc acctttggta aaggttctaa gcttaggtga    3480
gaacatccct gcctgaacat gagaaaaaac agggtactca tactcacttc taagtgacgg    3540
ctgcatacta accgcttcat acatctcgta gatttctctg gcgattgaag ggctaaattc    3600
ttcaacgcta actttgagaa ttttgtaag caatgcggcg ttataagcat ttaatgcatt    3660
gatgccatta aataaagcac caacgcctga ctgccccatc ccatcttgt ctgcgacaga    3720 ttcctgggat aagccaagtt catttttctt ttttcataa attgctttaa ggcgacgtgc    3780
gtcctcaagc tgctcttgtg ttaatggttt cttttttgtg ctcatacgtt aaatctatca    3840
ccgcaaggga taaatatcta acaccgtgcg tgttgactat tttacctctg gcggtgataa    3900
tggttgcatg tactaaggag gttgtatgga caacgagat gtgtataaga dacagctgac    3960
gggttttgct gcccgcaaac gggctgttct ggtgttgcta gtttgttatc agaatcgcag    4020
atccggcttc aggtttgccg gctgaaagcg ctatttcttc cagaattgcc atgatttttt    4080
ccccacggga ggcgtcactg gctcccgtgt tgtcggcagc tttgattcga taagcagcat    4140
cgcctgtttc aggctgtcta tgtgtgactg ttgagctgta acaagttgtc tcaggtgttc    4200
aatttcatgt tctagttgct ttgttttact ggtttcacct gttctattag gtgttacatg    4260
ctgttcatct gttacattgt cgatctgttc atggtgaaca gctttgaatg caccaaaaac    4320
tcgtaaaagc tctgatgtat ctatcttttt tacaccgttt tcatctgtgc atatggacag    4380
ttttcccttt gatatgtaac ggtgaacagt tgttctactt ttgtttgtta gtcttgatgc    4440
ttcactgata gatacaagag ccataagaac ctcagatcct tccgtattta gccagtatgt    4500
tctctagtgt ggttcgttgt ttttgcgtga gccatgagaa cgaaccattg agatcatact    4560
tactttgcat gtcactcaaa aattttgcct caaaactggt gagctgaatt tttgcagtta    4620
aagcatcgtg tagtgttttt cttagtccgt tatgtaggta ggaatctgat gtaatggttg    4680
ttggtatttt gtcaccattc attttatct ggttgttctc aagttcggtt acgagatcca    4740
tttgtctatc tagttcaact tggaaaatca acgtatcagt cgggcggcct cgcttatcaa    4800
ccaccaattt catattgctg taagtgttta atctttact tattggtttc aaaacccatt    4860
ggttaagcct tttaaactca tggtagttat tttcaagcat taacatgaac ttaaattcat    4920
caaggctaat ctctatattt gccttgtgag ttttcttttg tgttagttct tttaataacc    4980
actcataaat cctcatagag tatttgtttt caaaagactt aacatgttcc agattatatt    5040
ttatgaattt ttttaactgg aaaagataag gcaatatctc ttcactaaaa actaattcta    5100 attttttcgct tgagaacttg gcatagtttg tccactggaa aatctcaaag cctttaacca    5160
aaggattcct gatttccaca gttctcgtca tcagctctct ggttgcttta gctaatacac    5220
cataagcatt ttccctactg atgttcatca tctgagcgta ttggttataa gtgaacgata    5280
```

```
ccgtccgttc tttccttgta gggttttcaa tcgtggggtt gagtagtgcc acacagcata    5340
aaattagctt ggtttcatgc tccgttaagt catagcgact aatcgctagt tcatttgctt    5400
tgaaaacaac taattcagac atacatctca attggtctag gtgattttaa tcactatacc    5460
aattgagatg ggctagtcaa tgataattac tagtcctttt cctttgagtt gtgggtatct    5520
gtaaattctg ctagaccttt gctggaaaac ttgtaaattc tgctagaccc tctgtaaatt    5580
ccgctagacc tttgtgtgtt ttttttgttt atattcaagt ggttataatt tatagaataa    5640
agaaagaata aaaaagata aaagaatag atcccagccc tgtgtataac tcactacttt     5700
agtcagttcc gcagtattac aaaaggatgt cgcaaacgct gtttgctcct ctacaaaaca    5760
gaccttaaaa ccctaaaggc ttaagtagca ccctcgcaag ctcgggcaaa tcgctgaata    5820
ttccttttgt ctccgaccat caggcacctg agtcgctgtc tttttcgtga cattcagttc    5880
gctgcgctca cggctctggc agtgaatggg ggtaaatggc actacaggcg ccttttatgg    5940
attcatgcaa ggaaactacc cataatacaa gaaaagcccg tcacgggctt tcagggcgt     6000 tttatggcgg gtctgctatg tggtgctatc tgactttttg ctgttcagca gttcctgccc    6060
tctgattttc cagtctgacc acttcggatt atcccgtgac aggtcattca gactggctaa    6120
tgcacccagt aaggcagcgg tatcatcaac aggcttaccc gtcttactgt c             6171
```

<210> SEQ ID NO 4
<211> LENGTH: 6716
<212> TYPE: DNA
<213> ORGANISM: artificial sequence
<220> FEATURE:
<223> OTHER INFORMATION: plasmid

<400> SEQUENCE: 4

```
cagctgtctc ttatacacat ctccgctgtg ctttcagtgg atttcggata acagaaaggc      60
cgggaaatac ccagcctcgc tttgtaacgg agtagacgaa agtgattgcg cctacccgga    120
tattatcgtg aggatgcgtc atcgccattg ctccccaaat acaaaaccaa tttcagccag    180
tgcctcgtcc atttttcga tgaactccgg cacgatctcg tcaaaactcg ccatgtactt     240 tcatcccgc tcaatcacga cataatgcag gccttcacgc ttcatacgcg ggtcatagtt     300
ggcaaagtac caggcatttt tcgcgtcac ccacatgctg tactgcacct gggccatgta     360
agctgacttt atggcctcga aaccaccgag ccggaacttc atgaaatccc gggaggtaaa    420
cgggcatttc agttcaaggc cgttgccgtc actgcataaa ccatcgggag agcaggcggt    480
acgcatactt tcgtcgcgat agatgatcgg ggattcagta acattcacgc cggaagtgaa    540
ctcaaacagg gttctggcgt cgttctcgta ctgttttccc caggccagtg ctttagcgtt    600
aacttccgga gccacaccgg tgcaaacctc agcaagcagg gtgtggaagt aggacatttt    660
catgtcaggc cacttctttc cggagcgggg ttttgctatc acgttgtgaa cttctgaagc    720
ggtgatgacg ccgagccgta atttgtgcca cgcatcatcc cctgttcga cagctctcac    780 atcgatcccg gtacgctgca ggataatgtc cggtgtcatg ctgccacctt ctgctctgcg    840
gctttctgtt tcaggaatcc aagagctttt actgcttcgg cctgtgtcag ttctgacgat    900
gcacgaatgt cgcggcgaaa tatctgggaa cagagcggca ataagtcgtc atcccatgtt    960
ttatccaggg cgatcagcag agtgttaatc tcctgcatgg tttcatcgtt aaccggagtg   1020
atgtcgcgtt ccgctgacg ttctgcagtg tatgcagtat tttcgacaat gcgctcggct    1080
tcatccttgt catagatacc agcaaatccg aaggccagac gggcacactg aatcatggct    1140
```

```
ttatgacgta acatccgttt gggatgcgac tgccacggcc ccgtgatttc tctgccttcg    1200
cgagttttga atggttcgcg gcggcattca tccatccatt cggtaacgca gatcggatga    1260
ttacggtcct tgcggtaaat ccggcatgta caggattcat tgtcctgctc aaagtccatg    1320
ccatcaaact gctggttttc attgatgatg cgggaccagc catcaacgcc caccaccgga    1380
acgatgccat tctgcttatc aggaaaggcg taaatttctt tcgtccacgg attaaggccg    1440
tactggttgg caacgatcag taatgcgatg aactgcgcat cgctggcatc acctttaaat    1500
gccgtctggc gaagagtggt gatcagttcc tgtgggtcga cagaatccat gccgacacgt    1560
tcagccagct tcccagccag cgttgcgagt gcagtactca ttcgttttat acctctgaat    1620
caatatcaac ctggtggtga gcaatggttt caaccatgta ccggatgtgt tctgccatgc    1680
gctcctgaaa ctcaacatcg tcatcaaacg cacgggtaat ggattttttg ctggccccgt    1740
ggcgttgcaa atgatcgatg catagcgatt caaacaggtg ctggggcagg ccttttttcca   1800 tgtcgtctgc cagttctgcc tctttctctt cacgggcgag ctgctggtag tgacgcgccc    1860
agctctgagc ctcaagacga tcctgaatgt aataagcgtt catggctgaa ctcctgaaat    1920
agctgtgaaa atatcgcccg cgaaatgccg ggctgattag taatccggaa tcgcacttac    1980
ggccaatgct tcgtttcgta tcacacaccc caaagccttc tgctttgaat gctgcccttc    2040
ttcagggctt aattttaag agcgtcacct tcatggtggt cagtgcgtcc tgctgatgtg     2100
ctcagtatca ccgccagtgg tatttatgtc aacaccgcca gagataattt atcaccgcag    2160
atggttatct gtatgttttt tatatgaatt tatttttgc aggggggcat tgtttggtag     2220
gtgagagatc tgaattgcta tgtttagtga gttgtatcta tttatttttc aataaataca    2280
attggttatg tgttttgggg gcgatcgtga ggcaaagaaa acccggcgct gaggccgggt    2340
taagagttgg tagctcttga tccggcaaac aaaccaccgc tggtagcggt ggttttttg     2400 tttgcaagca gcagattacg cgcagaaaaa aaggatctca agaagatcct ttgatctttt    2460
ctacggggtc tgacgctcag tggaacgaaa actcacgtta agggattttg gtcatgagat    2520
tatcaaaaag gatcttcacc tagatccttt taaattaaaa atgaagtttt aaatcaatct    2580
aaagtatata tgagtaaact tggtctgaca gttaccaatg cttaatcagt gaggcaccta    2640
tctcagcgat ctgtctattt cgttcatcca tagttgcctg actccccgtc gtgtagataa    2700
ctacgatacg ggagggctta ccatctggcc ccagtgctgc aatgataccg cgagacccac    2760
gctcaccggc tccagattta tcagcaataa accagccagc cggaagggcc gagcgcagaa    2820
gtggtcctgc aactttatcc gcctccatcc agtctattaa ttgttgccgg gaagctagag    2880
taagtagttc gccagttaat agtttgcgca acgttgttgc cattgctgca ggcatcgtgg    2940
tgtcacgctc gtcgtttggt atggcttcat tcagctccgg ttcccaacga tcaaggcgag    3000
ttacatgatc ccccatgttg tgcaaaaaag cggttagctc cttcggtcct ccgatcgttg    3060
tcagaagtaa gttggccgca gtgttatcac tcatggttat ggcagcactg cataattctc    3120
ttactgtcat gccatccgta agatgctttt ctgtgactgg tgagtactca accaagtcat    3180
tctgagaata gtgtatgcgg cgaccgagtt gctcttgccc ggcgtcaaca cgggataata    3240
ccgcgccaca tagcagaact ttaaaagtgc tcatcattgg aaaacgttct cggggcgaa    3300 aactctcaag gatcttaccg ctgttgagat ccagttcgat gtaacccact cgtgcaccca    3360
actgatcttc agcatctttt actttcacca gcgtttctgg gtgagcaaaa acaggaaggc    3420
aaaatgccgc aaaaaaggga ataagggcga cacggaaatg ttgaatactc atactcttcc    3480
tttttcaata ttattgaagc atttatcagg gttattgtct catgagcgga tacatatttg    3540
```

```
aatgaattca atccatttac tatgttatgt tctgagggga gtgaaaattc ccctaattcg    3600
atgaagattc ttgctcaatt gttatcagct atgcgccgac cagaacacct tgccgatcag    3660
ccaaacgtct cttcaggcca ctgactagcg ataactttcc ccacaacgga acaactctca    3720
ttgcatggga tcattgggta ctgtgggttt agtggttgta aaaacacctg accgctatcc    3780
ctgatcagtt tcttgaaggt aaactcatca cccccaagtc tggctatgca gaaatcacct    3840
ggctcaacag cctgctcagg gtcaacgaga attaacattc cgtcaggaaa gcttggcttg    3900
gagcctgttg gtgcggtcat ggaattacct tcaacctcaa gccagaatgc agaatcactg    3960
gcttttttgg ttgtgcttac ccatctctcc gcatcacctt tggtaaaggt tctaagctta    4020
ggtgagaaca tccctgcctg aacatgagaa aaaacagggt actcatactc acttctaagt    4080
gacggctgca tactaaccgc ttcatacatc tcgtagattt ctctggcgat tgaagggcta    4140
aattcttcaa cgctaacttt gagaattttt gtaagcaatg cggcgttata agcatttaat    4200
gcattgatgc cattaaataa agcaccaacg cctgactgcc ccatccccat cttgtctgcg    4260
acagattcct gggataagcc aagttcattt ttcttttttt cataaattgc tttaaggcga    4320
cgtgcgtcct caagctgctc ttgtgttaat ggtttctttt ttgtgctcat acgttaaatc    4380
tatcaccgca agggatatat atctaacacc gtgcgtgttg actattttac ctctggcggt    4440
gataatggtt gcatgtacta aggaggttgt atggaacaac gagatgtgta taagagacag    4500
ctgacgggtt ttgctgcccg caaacgggct gttctggtgt tgctagtttg ttatcagaat    4560
cgcagatccg gcttcaggtt tgccggctga aagcgctatt tcttccagaa ttgccatgat    4620
tttttcccca cgggaggcgt cactggctcc cgtgttgtcg gcagctttga ttcgataagc    4680
agcatcgcct gtttcaggct gtctatgtgt gactgttgag ctgtaacaag ttgtctcagg    4740
tgttcaattt catgttctag ttgctttgtt ttactggttt cacctgttct attaggtgtt    4800
acatgctgtt catctgttac attgtcgatc tgttcatggt gaacagcttt gaatgcacca    4860
aaaactcgta aaagctctga tgtatctatc ttttttacac cgttttcatc tgtgcatatg    4920
gacagttttc cctttgatat gtaacggtga acagttgttc tacttttgtt tgttagtctt    4980
gatgcttcac tgatagatac aagagccata agaacctcag atccttccgt atttagccag    5040
tatgttctct agtgtggttc gttgtttttg cgtgagccat gagaacgaac cattgagatc    5100
atacttactt tgcatgtcac tcaaaaattt tgcctcaaaa ctggtgagct gaatttttgc    5160
agttaaagca tcgtgtagtg ttttttcttag tccgttatgt aggtaggaat ctgatgtaat    5220
ggttgttggt atttttgtcac cattcatttt tatctggttg ttctcaagtt cggttacgag    5280
atccatttgt ctatctagtt caacttggaa aatcaacgta tcagtcgggc ggcctcgctt    5340
atcaaccacc aatttcatat tgctgtaagt gtttaaatct ttacttattg gtttcaaaac    5400
ccattggtta agcctttaa actcatggta gttattttca agcattaaca tgaacttaaa    5460
ttcatcaagg ctaatctcta tatttgcctt gtgagttttc ttttgtgtta gttcttttaa    5520
taaccactca taaatcctca tagagtattt gttttcaaaa gacttaacat gttccagatt    5580
atattttatg aatttttta actgaaaaag ataaggcaat atctcttcac taaaaactaa    5640
ttctaatttt tcgcttgaga acttggcata gttttgtccac tggaaaatct caaagccttt    5700
aaccaaagga ttcctgattt ccacagttct cgtcatcagc tctctggttg ctttagctaa    5760
tacaccataa gcatttttccc tactgatgtt catcatctga gcgtattggt tataagtgaa    5820
cgataccgtc cgttctttcc ttgtagggtt ttcaatcgtg gggttgagta gtgccacaca    5880
```

| | |
|---|---|
| gcataaaatt agcttggttt catgctccgt taagtcatag cgactaatcg ctagttcatt | 5940 |
| tgctttgaaa acaactaatt cagacataca tctcaattgg tctaggtgat tttaatcact | 6000 |
| ataccaattg agatgggcta gtcaatgata attactagtc cttttccttt gagttgtggg | 6060 |
| tatctgtaaa ttctgctaga cctttgctgg aaaacttgta aattctgcta gaccctctgt | 6120 |
| aaattccgct agacctttgt gtgttttttt tgtttatatt caagtggtta taatttatag | 6180 |
| aataaagaaa gaataaaaaa agataaaaag aatagatccc agccctgtgt ataactcact | 6240 |
| actttagtca gttccgcagt attacaaaag gatgtcgcaa acgctgtttg ctcctctaca | 6300 |
| aaacagacct taaaccccta aaggcttaag tagcaccctc gcaagctcgg gcaaatcgct | 6360 |
| gaatattcct tttgtctccg accatcaggc acctgagtcg ctgtcttttt cgtgacattc | 6420 |
| agttcgctgc gctcacggct ctggcagtga atggggtaa atggcactac aggcgccttt | 6480 |
| tatggattca tgcaaggaaa ctacccataa tacaagaaaa gcccgtcacg ggcttctcag | 6540 |
| ggcgttttat ggcgggtctg ctatgtggtg ctatctgact ttttgctgtt cagcagttcc | 6600 |
| tgccctctga ttttccagtc tgaccacttc ggattatccc gtgacaggtc attcagactg | 6660 |
| gctaatgcac ccagtaaggc agcggtatca tcaacaggct tacccgtctt actgtc | 6716 |

<210> SEQ ID NO 5
<211> LENGTH: 5676
<212> TYPE: DNA
<213> ORGANISM: artificial sequence
<220> FEATURE:
<223> OTHER INFORMATION: plasmid

<400> SEQUENCE: 5

| | |
|---|---|
| cagctgtctc ttatacacat ctccgctgtg ctttcagtgg atttcggata acagaaaggc | 60 |
| cgggaaatac ccagcctcgc tttgtaacgg agtagacgaa agtgattgcg cctacccgga | 120 |
| tattatcgtg aggatgcgtc atcgccattg ctccccaaat acaaaaccaa tttcagccag | 180 |
| tgcctcgtcc atttttcga tgaactccgg cacgatctcg tcaaaactcg ccatgtactt | 240 |
| ttcatcccgc tcaatcacga cataatgcag gccttcacgc ttcatacgcg ggtcatagtt | 300 |
| ggcaaagtac caggcatttt ttcgcgtcac ccacatgctg tactgcacct gggccatgta | 360 |
| agctgacttt atggcctcga aaccaccgag ccggaacttc atgaaatccc gggaggtaaa | 420 |
| cgggcatttc agttcaaggc cgttgccgtc actgcataaa ccatcgggag agcaggcggt | 480 |
| acgcatactt tcgtcgcgat agatgatcgg ggattcagta acattcacgc cggaagtgaa | 540 |
| ctcaaacagg ttctggcgt cgttctcgta ctgttttccc caggccagtg ctttagcgtt | 600 |
| aacttccgga gccacaccgg tgcaaacctc agcaagcagg gtgtggaagt aggacatttt | 660 |
| catgtcaggc cacttctttc cggagcgggg ttttgctatc acgttgtgaa cttctgaagc | 720 |
| ggtgatgacg ccgagccgta atttgtgcca cgcatcatcc cctgttcga cagctctcac | 780 |
| atcgatcccg gtacgctgca ggataatgtc cggtgtcatg ctgccacctt ctgctctgcg | 840 |
| gctttctgtt tcaggaatcc aagagctttt actgcttcgg cctgtgtcag ttctgacgat | 900 |
| gcacgaatgt cgcggcgaaa tatctgggaa cagagcggca ataagtcgtc atcccatgtt | 960 |
| ttatccaggg cgatcagcag agtgttaatc tcctgcatgg tttcatcgtt aaccggagtg | 1020 |
| atgtcgcgtt ccggctgacg ttctgcagtg tatgcagtat tttcgacaat cgctcggct | 1080 |
| tcatccttgt catagatacc agcaaatccg aaggccagac gggcacactg aatcatggct | 1140 |
| ttatgacgta acatccgttt gggatgcgac tgccacggcc ccgtgatttc tctgccttcg | 1200 |
| cgagttttga atggttcgcg gcggcattca tccatccatt cggtaacgca gatcggatga | 1260 |

```
ttacggtcct tgcggtaaat ccggcatgta caggattcat tgtcctgctc aaagtccatg    1320
ccatcaaact gctggttttc attgatgatg cgggaccagc catcaacgcc caccaccgga    1380
acgatgccat tctgcttatc aggaaaggcg taaatttctt tcgtccacgg attaaggccg    1440
tactggttgg caacgatcag taatgcgatg aactgcgcat cgctggcatc acctttaaat    1500
gccgtctggc gaagagtggt gatcagttcc tgtgggtcga cagaatccat gccgacacgt    1560
tcagccagct tcccagccag cgttgcgagt gcagtactca ttcgttttat acctctgaat    1620
caatatcaac ctggtggtga gcaatggttt caaccatgta ccggatgtgt tctgccatgc    1680
gctcctgaaa ctcaacatcg tcatcaaacg cacgggtaat ggattttttg ctggccccgt    1740
ggcgttgcaa atgatcgatg catagcgatt caaacaggtg ctggggcagg ccttttccca    1800
tgtcgtctgc cagttctgcc tctttctctt cacgggcgag ctgctggtag tgacgcgccc    1860
agctctgagc ctcaagacga tcctgaatgt aataagcgtt catggctgaa ctcctgaaat    1920
agctgtgaaa atatcgcccg cgaaatgccg ggctgattag taatccggaa tcgcacttac    1980
ggccaatgct tcgtttcgta tcacacaccc caaagccttc tgctttgaat gctgcccttc    2040
ttcagggctt aattttaag agcgtcacct tcatggtggt cagtgcgtcc tgctgatgtg    2100
ctcagtatca ccgccagtgg tatttatgtc aacaccgcca gagataattt atcaccgcag    2160
atggttatct gtatgttttt tatatgaatt tattttttgc aggggggcat tgttggtag    2220 gtgagagatc tgaattgcta tgtttagtga gttgtatcta tttatttttc aataaataca    2280
attggttatg tgttttgggg gcgatcgtga ggcaaagaaa accggcgct gaggccgggt    2340 tacgccccgc cctgccactc atcgcagtac tgttgtaatt cattaagcat tctgccgaca    2400
tggaagccat cacagacggc atgatgaacc tgaatcgcca gcggcatcag cccttgtcg    2460 ccttgcgtat aatatttgcc catggtgaaa acggggcga agaagttgtc catattggcc    2520
acgtttaaat caaaactggt gaaactcacc cagggattgg ctgagacgaa aaacatattc    2580
tcaataaacc ctttagggaa ataggccagg ttttcaccgt aacacgccac atcttgcgaa    2640
tatatgtgta gaaactgccg gaaatcgtcg tggtattcac tccagagcga tgaaaacgtt    2700
tcagtttgct catggaaaac ggtgtaacaa gggtgaacac tatcccatat caccagctca    2760
ccgtctttca ttgccatacg gaattccgga tgagcattca tcaggcgggc aagaatgtga    2820
ataaaggccg gataaaactt gtgcttattt ttctttacgg tctttaaaaa ggccgtaata    2880
tccagctgaa cggtctggtt ataggtacat tgagcaactg actgaaatgc ctcaaaatgt    2940
tctttacgat gccattggga tatatcaacg gtggtatatc cagtgatttt tttctccata    3000
attcaatcca tttactatgt tatgttctga ggggagtgaa aattccccta attcgatgaa    3060
gattcttgct caattgttat cagctatgcg ccgaccagaa caccttgccg atcagccaaa    3120
cgtctcttca ggccactgac tagcgataac tttccccaca acggaacaac tctcattgca    3180
tgggatcatt gggtactgtg ggtttagtgg ttgtaaaaac acctgaccgc tatccctgat    3240
cagtttcttg aaggtaaact catcaccccc aagtctggct atgcagaaat cacctggctc    3300
aacagcctgc tcagggtcaa cgagaattaa cattccgtca ggaaagcttg cttggagcc    3360 tgttggtgcg gtcatggaat taccttcaac ctcaagccag aatgcagaat cactggcttt    3420
tttggttgtg cttacccatc tctccgcatc acctttggta aaggttctaa gcttaggtga    3480
gaacatccct gcctgaacat gagaaaaaac agggtactca tactcacttc taagtgacgg    3540
ctgcatacta accgcttcat acatctcgta gatttctctg gcgattgaag gctaaattc    3600
```

```
ttcaacgcta actttgagaa ttttttgtaag caatgcggcg ttataagcat ttaatgcatt      3660
gatgccatta aataaagcac caacgcctga ctgccccatc cccatcttgt ctgcgacaga      3720
ttcctgggat aagccaagtt catttttctt tttttcataa attgctttaa ggcgacgtgc      3780
gtcctcaagc tgctcttgtg ttaatggttt ctttttttgtg ctcatacgtt aaatctatca      3840
ccgcaaggga taaatatcta acaccgtgcg tgttgactat tttacctctg gcggtgataa      3900
tggttgcatg tactaaggag gttgtatgga acaacgagat gtgtataaga gacagctggc      3960
ctgcccctcc cttttggtgt ccaaccggct cgacggggc agcgcaaggc ggtgcctccg       4020
gcgggccact caatgcttga gtatactcac tagactttgc ttcgcaaagt cgtgaccgcc      4080 tacgcggct gcggcgccct acgggcttgc tctccgggct tcgccctgcg cggtcgctgc       4140
gctcccttgc cagcccgtgg atatgtggac gatggccgcg agcggccacc ggctggctcg      4200
cttcgctcgg cccgtggaca accctgctgg acaagctgat ggacaggctg cgcctgccca     4260
cgagcttgac cacagggatt gcccaccggc tacccagcct tcgaccacat acccaccggc      4320
tccaactgcg cggcctgcgg ccttgcccca tcaattttttt taattttctc tggggaaaag    4380
cctccggcct gcggcctgcg cgcttcgctt gccggttgga caccaagtgg aaggcgggtc     4440
aaggctcgcg cagcgaccgc gcagcggctt ggccttgacg cgcctggaac gacccaagcc     4500
tatgcgagtg ggggcagtcg aaggcgaagc ccgcccgcct gccccccgag cctcacggcg    4560
gcgagtgcgg gggttccaag ggggcagcgc caccttgggc aaggccgaag gccgcgcagt    4620
cgatcaacaa gccccggagg ggccactttt tgccggaggg ggagccgcgc cgaaggcgtg    4680 ggggaaccc gcaggggtgc ccttctttgg gcaccaaaga actagatata gggcgaaatg     4740
cgaaagactt aaaaatcaac aacttaaaaa agggggtac gcaacagctc attgcggcac      4800
cccccgcaat agctcattgc gtaggttaaa gaaaatctgt aattgactgc cacttttacg    4860
caacgcataa ttgttgtcgc gctgccgaaa agttgcagct gattgcgcat ggtgccgcaa   4920
ccgtgcggca ccctaccgca tggagataag catggccacg cagtccagag aaatcggcat    4980
tcaagccaag aacaagcccg gtcactgggt gcaaacggaa cgcaaagcgc atgaggcgtg    5040
ggccgggctt attgcgagga aacccacggc ggcaatgctg ctgcatcacc tcgtggcgca    5100
gatgggccac cagaacgccg tggtggtcag ccagaagaca cttttccaagc tcatcggacg    5160 ttctttgcgg acggtccaat acgcagtcaa ggacttggtg gccgagcgct ggatctccgt     5220
cgtgaagctc aacggccccg gcaccgtgtc ggcctacgtg gtcaatgacc gcgtggcgtg    5280
gggccagccc cgcgaccagt tgcgcctgtc ggtgttcagt gccgccgtgg tggttgatca    5340
cgacgaccag gacgaatcgc tgttggggca tggcgacctg cgccgcatcc cgaccctgta    5400
tccgggcgag cagcaactac cgaccggccc cggcgaggag ccgcccagcc agcccggcat    5460
tccgggcatg gaaccagacc tgccagcctt gaccgaaacg gaggaatggg aacggcgcgg    5520
gcagcagcgc ctgccgatgc ccgatgagcc gtgttttctg gacgatggcg agccgttgga   5580
gccgccgaca cgggtcacgc tgccgcgccg gtagcacttg ggttgcgcag caacccgtaa    5640
gtgcgctgtt ccagactatc ggctgtagcc gcctcg                              5676
```

<210> SEQ ID NO 6
<211> LENGTH: 6221
<212> TYPE: DNA
<213> ORGANISM: artificial sequence
<220> FEATURE:
<223> OTHER INFORMATION: plasmid

<400> SEQUENCE: 6

```
cagctgtctc ttatacacat ctccgctgtg ctttcagtgg atttcggata acagaaaggc      60
cgggaaatac ccagcctcgc tttgtaacgg agtagacgaa agtgattgcg cctacccgga     120
tattatcgtg aggatgcgtc atcgccattg ctccccaaat acaaaaccaa tttcagccag     180
tgcctcgtcc attttttcga tgaactccgg cacgatctcg tcaaaactcg ccatgtactt     240
ttcatcccgc tcaatcacga cataatgcag gccttcacgc ttcatacgcg ggtcatagtt     300
ggcaaagtac caggcatttt ttcgcgtcac ccacatgctg tactgcacct gggccatgta     360
agctgacttt atggcctcga aaccaccgag ccggaacttc atgaaatccc gggaggtaaa     420
cgggcatttc agttcaaggc cgttgccgtc actgcataaa ccatcgggag agcaggcggt     480
acgcatactt tcgtcgcgat agatgatcgg ggattcagta acattcacgc cggaagtgaa     540
ctcaaacagg gttctggcgt cgttctcgta ctgttttccc caggccagtg ctttagcgtt     600
aacttccgga gccacaccgg tgcaaacctc agcaagcagg gtgtggaagt aggacatttt     660
catgtcaggc cacttctttc cggagcgggg ttttgctatc acgttgtgaa cttctgaagc     720
ggtgatgacg ccgagccgta atttgtgcca cgcatcatcc ccctgttcga cagctctcac     780
atcgatcccg gtacgctgca ggataatgtc cggtgtcatg ctgccacctt ctgctctgcg     840
gctttctgtt tcaggaatcc aagagctttt actgcttcgg cctgtgtcag ttctgacgat     900
gcacgaatgt cgcggcgaaa tatctgggaa cagagcggca ataagtcgtc atcccatgtt     960
ttatccaggg cgatcagcag agtgttaatc tcctgcatgg tttcatcgtt aaccggagtg    1020
atgtcgcgtt ccggctgacg ttctgcagtg tatgcagtat tttcgacaat gcgctcggct    1080
tcatccttgt catagatacc agcaaatccg aaggccagac gggcacactg aatcatggct    1140
ttatgacgta acatccgttt gggatgcgac tgccacggcc ccgtgatttc tctgccttcg    1200
cgagttttga atggttcgcg gcggcattca tccatccatt cggtaacgca gatcggatga    1260
ttacggtcct tgcggtaaat ccggcatgta caggattcat tgtcctgctc aaagtccatg    1320
ccatcaaact gctggttttc attgatgatg cgggaccagc catcaacgcc caccaccgga    1380
acgatgccat tctgcttatc aggaaaggcg taaatttctt tcgtccacgg attaaggccg    1440
tactggttgg caacgatcag taatgcgatg aactgcgcat cgctggcatc accttttaaat    1500
gccgtctggc gaagagtggt gatcagttcc tgtgggtcga cagaatccat gccgacacgt    1560
tcagccagct tcccagccag cgttgcgagt gcagtactca ttcgttttat acctctgaat    1620
caatatcaac ctggtggtga gcaatggttt caaccatgta ccggatgtgt tctgccatgc    1680
gctcctgaaa ctcaacatcg tcatcaaacg cacgggtaat ggatttttg ctggccccgt    1740
ggcgttgcaa atgatcgatg catagcgatt caaacaggtg ctggggcagg ccttttttcca    1800
tgtcgtctgc cagttctgcc tctttctctt cacgggcgag ctgctggtag tgacgcgccc    1860
agctctgagc ctcaagacga tcctgaatgt aataagcgtt catggctgaa ctcctgaaat    1920
agctgtgaaa atatcgcccg cgaaatgccg ggctgattag taatccggaa tcgcacttac    1980
ggccaatgct tcgtttcgta tcacacaccc caaagccttc tgctttgaat gctgcccttc    2040
ttcagggctt aatttttaag agcgtcacct tcatggtggt cagtgcgtcc tgctgatgtg    2100
ctcagtatca ccgccagtgg tatttatgtc aacaccgcca gagataattt atcaccgcag    2160
atggttatct gtatgttttt tatatgaatt tattttttgc agggggggcat tgtttggtag    2220
gtgagagatc tgaattgcta tgtttagtga gttgtatcta tttatttttc aataaataca    2280
attggttatg tgtttggggg gcgatcgtga ggcaaagaaa acccggcgct gaggccgggt    2340
```

```
taagagttgg tagctcttga tccggcaaac aaaccaccgc tggtagcggt ggttttttg    2400
tttgcaagca gcagattacg cgcagaaaaa aaggatctca agaagatcct ttgatctttt    2460
ctacggggtc tgacgctcag tggaacgaaa actcacgtta agggattttg gtcatgagat    2520
tatcaaaaag gatcttcacc tagatccttt taaattaaaa atgaagtttt aaatcaatct    2580
aaagtatata tgagtaaact tggtctgaca gttaccaatg cttaatcagt gaggcaccta    2640
tctcagcgat ctgtctattt cgttcatcca tagttgcctg actccccgtc gtgtagataa    2700
ctacgatacg ggagggctta ccatctggcc ccagtgctgc aatgataccg cgagacccac    2760
gctcaccggc tccagattta tcagcaataa accagccagc cggaagggcc gagcgcagaa    2820
gtggtcctgc aactttatcc gcctccatcc agtctattaa ttgttgccgg gaagctagag    2880
taagtagttc gccagttaat agtttgcgca acgttgttgc cattgctgca ggcatcgtgg    2940
tgtcacgctc gtcgtttggt atggcttcat tcagctccgg ttcccaacga tcaaggcgag    3000
ttacatgatc ccccatgttg tgcaaaaaag cggttagctc cttcggtcct ccgatcgttg    3060
tcagaagtaa gttggccgca gtgttatcac tcatggttat ggcagcactg cataattctc    3120
ttactgtcat gccatccgta agatgctttt ctgtgactgg tgagtactca accaagtcat    3180
tctgagaata gtgtatgcgg cgaccgagtt gctcttgccc ggcgtcaaca cgggataata    3240
ccgcgccaca tagcagaact ttaaaagtgc tcatcattgg aaaacgttct cggggcgaa    3300
aactctcaag gatcttaccg ctgttgagat ccagttcgat gtaacccact cgtgcaccca    3360
actgatcttc agcatctttt actttcacca gcgtttctgg gtgagcaaaa acaggaaggc    3420
aaaatgccgc aaaaaaggga ataagggcga cacggaaatg ttgaatactc atactcttcc    3480
tttttcaata ttattgaagc atttatcagg gttattgtct catgagcgga tacatatttg    3540
aatgaattca atccatttac tatgttatgt tctgagggga gtgaaaattc ccctaattcg    3600
atgaagattc ttgctcaatt gttatcagct atgcgccgac cagaacacct tgccgatcag    3660
ccaaacgtct cttcaggcca ctgactacgc ataactttcc ccacaacgga acaactctca    3720
ttgcatggga tcattgggta ctgtgggttt agtggttgta aaaacacctg accgctatcc    3780
ctgatcagtt tcttgaaggt aaactcatca cccccaagtc tggctatgca gaaatcacct    3840
ggctcaacag cctgctcagg gtcaacgaga attaacattc cgtcaggaaa gcttggcttg    3900
gagcctgttg gtgcggtcat ggaattacct tcaacctcaa gccagaatgc agaatcactg    3960
gctttttttgg ttgtgcttac ccatctctcc gcatcacctt tggtaaaggt tctaagctta    4020
ggtgagaaca tccctgcctg aacatgagaa aaaacagggt actcatactc acttctaagt    4080
gacggctgca tactaaccgc ttcatacatc tcgtagattt ctctggcgat tgaagggcta    4140
aattcttcaa cgctaacttt gagaatttt gtaagcaatg cggcgttata agcatttaat    4200
gcattgatgc cattaaataa agcaccaacg cctgactgcc ccatccccat cttgtctgcg    4260
acagattcct gggataagcc aagttcattt ttcttttttt cataaattgc tttaaggcga    4320
cgtgcgtcct caagctgctc ttgtgttaat ggtttctttt ttgtgctcat acgttaaatc    4380
tatcaccgca aggataaat atctaacacc gtgcgtgttg actattttac ctctggcggt    4440
gataatggtt gcatgtacta aggaggttgt atggaacaac gagatgtgta taagagacag    4500
ctggcctgcc cctccctttt ggtgtccaac cggctcgacg ggggcagcgc aaggcggtgc    4560
ctccggcggg ccactcaatg cttgagtata ctcactagac tttgcttcgc aaagtcgtga    4620
ccgcctacgg cggctgcggc gccctacggg cttgctctcc gggcttcgcc ctgcgcggtc    4680
gctgcgctcc cttgccagcc cgtggatatg tggacgatgg ccgcgagcgg ccaccggctg    4740
```

```
gctcgcttcg ctcggcccgt ggacaaccct gctggacaag ctgatggaca ggctgcgcct    4800
gcccacgagc ttgaccacag ggattgccca ccggctaccc agccttcgac cacatacccca   4860 ccggctccaa ctgcgcggcc tgcggccttg ccccatcaat ttttttaatt ttctctgggg    4920
aaaagcctcc ggcctgcggc ctgcgcgctt cgcttgccgg ttggacacca agtggaaggc    4980
gggtcaaggc tcgcgcagcg accgcgcagc ggcttggcct tgacgcgcct ggaacgaccc    5040
aagcctatgc gagtggggc agtcgaaggc gaagcccgcc cgcctgcccc ccgagcctca     5100
cggcggcgag tgcgggggtt ccaaggggc agcgccacct tgggcaaggc cgaaggccgc     5160
gcagtcgatc aacaagcccc ggaggggcca cttttttgccg gagggggagc cgcgccgaag   5220
gcgtggggga accccgcagg ggtgcccttc tttgggcacc aaagaactag atatagggcg    5280
aaatgcgaaa gacttaaaaa tcaacaactt aaaaaggggg ggtacgcaac agctcattgc    5340 ggcaccccc gcaatagctc attgcgtagg ttaaagaaaa tctgtaattg actgccactt     5400
ttacgcaacg cataattgtt gtcgcgctgc cgaaaagttg cagctgattg cgcatggtgc    5460
cgcaaccgtg cggcaccccta ccgcatggag ataagcatgg ccacgcagtc cagagaaatc   5520
ggcattcaag ccaagaacaa gcccggtcac tgggtgcaaa cggaacgcaa agcgcatgag    5580
gcgtgggccg ggcttattgc gaggaaaccc acggcggcaa tgctgctgca tcacctcgtg    5640
gcgcagatgg gccaccagaa cgccgtggtg gtcagccaga agacactttc caagctcatc    5700
ggacgttctt tgcggacggt ccaatacgca gtcaaggact tggtggccga gcgctggatc    5760
tccgtcgtga agctcaacgg ccccggcacc gtgtcggcct acgtggtcaa tgaccgcgtg    5820
gcgtgggccc agccccgcga ccagttgcgc ctgtcggtgt tcagtgccgc cgtggtggtt    5880
gatcacgacg accaggacga atcgctgttg gggcatggcg acctgcgccg catcccgacc    5940
ctgtatccgg gcgagcagca actaccgacc ggccccggcg aggagccgcc cagccagccc    6000
ggcattccgg gcatggaacc agacctgcca gccttgaccg aaacggagga atgggaacgg    6060
cgcgggcagc agcgcctgcc gatgcccgat gagccgtgtt ttctggacga tggcgagccg    6120
ttggagccgc cgacacgggt cacgctgccg cgccggtagc acttgggttg cgcagcaacc    6180
cgtaagtgcg ctgttccaga ctatcggctg tagccgcctc g                       6221
```

<210> SEQ ID NO 7
<211> LENGTH: 6435
<212> TYPE: DNA
<213> ORGANISM: artificial sequence
<220> FEATURE:
<223> OTHER INFORMATION: plasmid

<400> SEQUENCE: 7

```
cagctgtctc ttatacacat ctccgctgtg ctttcagtgg atttcggata acagaaaggc      60
cgggaaatac ccagcctcgc tttgtaacgg agtagacgaa agtgattgcg cctacccgga    120
tattatcgtg aggatgcgtc atcgccattg ctccccaaat acaaaaccaa tttcagccag    180
tgcctcgtcc attttttcga tgaactccgg cacgatctcg tcaaaactcg ccatgtactt    240
ttcatcccgc tcaatcacga cataatgcag gccttcacgc ttcatacgcg ggtcatagtt    300
ggcaaagtac caggcatttt ttcgcgtcac ccacatgctg tactgcacct gggccatgta    360
agctgacttt atggcctcga aaccaccgag ccggaacttc atgaaatccc gggaggtaaa    420
cgggcatttc agttcaaggc cgttgccgtc actgcataaa ccatcgggag agcaggcggt    480
acgcatactt tcgtcgcgat agatgatcgg ggattcagta acattcacgc cggaagtgaa    540
```

```
ctcaaacagg gttctggcgt cgttctcgta ctgttttccc caggccagtg ctttagcgtt    600
aacttccgga gccacaccgg tgcaaacctc agcaagcagg gtgtggaagt aggacatttt    660
catgtcaggc cacttctttc cggagcgggg ttttgctatc acgttgtgaa cttctgaagc    720
ggtgatgacg ccgagccgta atttgtgcca cgcatcatcc ccctgttcga cagctctcac    780
atcgatcccg gtacgctgca ggataatgtc cggtgtcatg ctgccacctt ctgctctgcg    840
gctttctgtt tcaggaatcc aagagctttt actgcttcgg cctgtgtcag ttctgacgat    900
gcacgaatgt cgcggcgaaa tatctgggaa cagagcggca ataagtcgtc atcccatgtt    960
ttatccaggg cgatcagcag agtgttaatc tcctgcatgg tttcatcgtt aaccggagtg   1020
atgtcgcgtt ccggctgacg ttctgcagtg tatgcagtat tttcgacaat gcgctcggct   1080
tcatccttgt catagatacc agcaaatccg aaggccagac gggcacactg aatcatggct   1140
ttatgacgta acatccgttt gggatgcgac tgccacggcc ccgtgatttc tctgccttcg   1200
cgagttttga atggttcgcg gcggcattca tccatccatt cggtaacgca gatcggatga   1260
ttacggtcct tgcggtaaat ccggcatgta caggattcat tgtcctgctc aaagtccatg   1320
ccatcaaact gctggttttc attgatgatg cgggaccagc catcaacgcc caccaccgga   1380
acgatgccat tctgcttatc aggaaaggcg taaatttctt tcgtccacgg attaaggccg   1440
tactggttgg caacgatcag taatgcgatg aactgcgcat cgctggcatc acctttaaat   1500
gccgtctggc gaagagtggt gatcagttcc tgtgggtcga cagaatccat gccgacacgt   1560
tcagccagct tcccagccag cgttgcgagt gcagtactca ttcgttttat acctctgaat   1620
caatatcaac ctggtggtga gcaatggttt caaccatgta ccggatgtgt tctgccatgc   1680
gctcctgaaa ctcaacatcg tcatcaaacg cacgggtaat ggatttttg ctggccccgt   1740 ggcgttgcaa atgatcgatg catagcgatt caaacaggtg ctggggcagg cctttttcca   1800
tgtcgtctgc cagttctgcc tctttctctt cacgggcgag ctgctggtag tgacgcgccc   1860
agctctgagc ctcaagacga tcctgaatgt aataagcgtt catggctgaa ctcctgaaat   1920
agctgtgaaa atatcgcccg cgaaatgccg ggctgattag taatccggaa tcgcacttac   1980
ggccaatgct tcgtttcgta tcacacaccc caaagccttc tgctttgaat gctgcccttc   2040
ttcagggctt aattttaag agcgtcacct tcatggtggt cagtgcgtcc tgctgatgtg   2100
ctcagtatca ccgccagtgg tatttatgtc aacaccgcca gagataattt atcaccgcag   2160
atggttatct gtatgttttt tatatgaatt tatttttgc aggggggcat tgtttggtag   2220
gtgagagatc tgaattgcta tgtttagtga gttgtatcta tttatttttc aataaataca   2280
attggttatg tgttttgggg gcgatcgtga ggcaaagaaa acccggcgct gaggccgggt   2340
tacgccccgc cctgccactc atcgcagtac tgttgtaatt cattaagcat tctgccgaca   2400
tggaagccat cacagacggc atgatgaacc tgaatcgcca gcggcatcag caccttgtcg   2460
ccttgcgtat aatatttgcc catggtgaaa cggggggcga agaagttgtc catattggcc   2520
acgtttaaat caaaactggt gaaactcacc cagggattgg ctgagacgaa aaacatattc   2580
tcaataaacc ctttagggaa ataggccagg ttttcaccgt aacacgccac atcttgcgaa   2640
tatatgtgta gaaactgccg gaaatcgtcg tggtattcac tccagagcga tgaaaacgtt   2700
tcagtttgct catggaaaac ggtgtaacaa gggtgaacac tatcccatat caccagctca   2760
ccgtctttca ttgccatacg gaattccgga tgagcattca tcaggcgggc aagaatgtga   2820
ataaaggccg gataaaactt gtgcttattt ttctttacgg tctttaaaaa ggccgtaata   2880
tccagctgaa cggtctggtt ataggtacat tgagcaactg actgaaatgc ctcaaaatgt   2940
```

```
tctttacgat gccattggga tatatcaacg gtggtatatc cagtgatttt tttctccata    3000
attcaatcca tttactatgt tatgttctga ggggagtgaa aattcccta attcgatgaa     3060 gattcttgct caattgttat cagctatgcg ccgaccagaa caccttgccg atcagccaaa   3120
cgtctcttca ggccactgac tagcgataac tttccccaca acggaacaac tctcattgca   3180
tgggatcatt gggtactgtg ggtttagtgg ttgtaaaaac acctgaccgc tatccctgat   3240
cagtttcttg aagtaaaact catcaccccc aagtctggct atgcagaaat cacctggctc   3300
aacagcctgc tcagggtcaa cgagaattaa cattccgtca ggaaagcttg gcttggagcc   3360
tgttggtgcg gtcatggaat taccttcaac ctcaagccag aatgcagaat cactggcttt   3420
tttggttgtg cttacccatc tctccgcatc acctttggta aaggttctaa gcttaggtga   3480
gaacatccct gcctgaacat gagaaaaaac agggtactca tactcacttc taagtgacgg   3540
ctgcatacta accgcttcat acatctcgta gatttctctg gcgattgaag gctaaattc    3600 ttcaacgcta actttgagaa ttttgtaag caatgcggcg ttataagcat ttaatgcatt    3660
gatgccatta aataaagcac caacgcctga ctgccccatc ccatcttgt ctgcgacaga    3720 ttcctgggat aagccaagtt catttttctt tttttcataa attgctttaa ggcgacgtgc   3780
gtcctcaagc tgctcttgtg ttaatggttt cttttttgtg ctcatacgtt aaatctatca   3840
ccgcaaggga taaatatcta acaccgtgcg tgttgactat tttacctctg gcggtgataa   3900
tggttgcatg tactaaggag gttgtatgga acaacgagat gtgtataaga gacagctgaa   3960
acgccgtcga agccgtgtgc gagacaccgc ggccgccggc gttgtggata ccacgcggaa   4020
aacttggccc tcactgacag atgaggggcg gacgttgaca cttgaggggc cgactcaccc   4080
ggcgcggcgt tgacagatga ggggcaggct cgatttcggc cggcgacgtg gagctggcca   4140
gcctcgcaaa tcggcgaaaa cgcctgattt tacgcgagtt tcccagacat gatgtggaca   4200
agcctgggga taagtgccct gcggtattga cacttgaggg gcgcgactac tgacagatga   4260
ggggcgcgat ccttgacact tgaggggcag agtgatgaca gatgaggggc gcacctattg   4320
acatttgagg ggctgtccac aggcagaaaa tccagcattt gcaagggttt ccgcccgttt   4380
ttcggccacc gctaacctgt cttttaacct gcttttaaac caatatttat aaaccttgtt   4440
tttaaccagg gctgcgccct ggcgcgtgac cgcgcacgcc gaaggggggt gccccccctt   4500
ctcgaaccct cccggctaac gcgggcctcc catcccccg gctgcgccct tcggccgcga    4560
acggcctcac cccaaaaatg gcagcgctgg cagtccttgc cattgccggg atcggggcag   4620
taacgggatg ggcgatcagc ccgagcgcga cgcccggaag cattgacgtg ccgcaggtgc   4680
tggcatcgac attcagcgac caggtgccgg gcagtgaggg cggcggcctg ggtggcggcc   4740
tgcccttcac ttcggccgtc ggggcattca cggacttcat ggcggggcgg gcaatttta    4800 ccttgggcat tcttggcata gtggtcgcgg gtgccgtgct cgtgttcggg ggtgaattaa   4860
ttccccggat cgatccgtca gcttcacgct gccgcaagca ctcagggcgc aagggctgct   4920
aaaggaagcg gaacacgtag aaagccagtc cgcagaaacg gtgctgaccc cggatgaatg   4980
tcacgtactg ggctatctgg acaagggaaa acgcaagcgc aaacacaaac gacctagctt   5040
gcagtgggct tacatggcga tagctagact gggcggtttt atggccagca agcgaaccgg   5100
aattgccagc tggggcgccc tctggtaagg ttgggaagcc ctgcaaagta aactggatgg   5160 cttcttgcc gccaaggatc tgatggcgca ggggatcaag atcgacggat cgatccgggg   5220
aattccgggg caatcccgca aggagggtga atgaatcgga cgtttgaccg gaaggcatac   5280
```

| | |
|---|---|
| aggcaagaac tgatcgacgc ggggttttcc gccgaggatg ccgaaaccat cgcaagccgc | 5340 |
| accgtcatgc gtgcgcccg cgaaaccttc cagtccgtcg gctcgatggt ccagcaagct | 5400 |
| acggccaaga tcgagcgcga cagcgtgcaa ctggctcccc ctgccctgcc cgcgccatcg | 5460 |
| gccgccgtgg agcgttcgcg tcgtctcgaa caggaggcgg caggtttggc gaagtcgatg | 5520 |
| accatcgaca cgcgaggaac tatgacgacc aagaagcgaa aaccgccgg cgaggacctg | 5580 |
| gcaaaacagg tcagcgaggc caagcaggcc gcgttgctga acacacgaa gcagcagatc | 5640 |
| aaggaaatgc agcttttcctt gttcgatatt gcgccgtggc cggacacgat gcgagcgatg | 5700 |
| ccaaacgaca cggcccgctc tgccctgttc accacgcgca acaagaaaat cccgcgcgag | 5760 |
| gcgctgcaaa acaaggtcat tttccacgtc aacaaggacg tgaagatcac ctacaccggc | 5820 |
| gtcgagctgc gggccgacga tgacgaactg gtgtggcagc aggtgttgga gtacgcgaag | 5880 |
| cgcaccccta tcggcgagcc gatcaccttc acgttctacg agctttgcca ggacctgggc | 5940 |
| tggtcgatca atggccggta ttacacgaag gccgaggaat gcctgtcgcg cctacaggcg | 6000 |
| acggcgatgg gcttcacgtc cgaccgcgtt gggcacctgg aatcggtgtc gctgctgcac | 6060 |
| cgcttccgcg tcctggaccg tggcaagaaa acgtcccgtt gccaggtcct gatgcacgag | 6120 |
| gaaatcgtcg tgcagtttgc tggcgaccac tacacgaaat tcatatggga gaagtaccgc | 6180 |
| aagctgtcgc cgacggcccg acggatgttc gactatttca gctcgcaccg ggagccgtac | 6240 |
| ccgctcaagc tggaaacctt ccgcctcatg tgcggatcgg attccacccg cgtgaagaag | 6300 |
| tggcgcgagc aggtcggcga agcctgcgaa gagttgcgag gcagcggcct ggtggaacac | 6360 |
| gcctgggtca atgatgacct ggtgcattgc aaacgctagg gccttgtggg gtcagttccg | 6420 |
| gctgggggtt cagca | 6435 |

<210> SEQ ID NO 8
<211> LENGTH: 3914
<212> TYPE: DNA
<213> ORGANISM: artificial sequence
<220> FEATURE:
<223> OTHER INFORMATION: phage genes

<400> SEQUENCE: 8

| | |
|---|---|
| ccgctgtgct ttcagtggat ttcggataac agaaaggccg ggaaatacccc agcctcgctt | 60 |
| tgtaacggag tagacgaaag tgattgcgcc tacccggata ttatcgtgag gatgcgtcat | 120 |
| cgccattgct ccccaaatac aaaaccaatt tcagccagtg cctcgtccat tttttcgatg | 180 |
| aactccggca cgatctcgtc aaaactcgcc atgtactttt catcccgctc aatcacgaca | 240 |
| taatgcaggc cttcacgctt catacgcggg tcatagttgg caaagtacca ggcatttttt | 300 |
| cgcgtcaccc acatgctgta ctgcacctgg gccatgtaag ctgactttat ggcctcgaaa | 360 |
| ccaccgagcc ggaacttcat gaaatcccgg gaggtaaacg ggcatttcag ttcaaggccg | 420 |
| ttgccgtcac tgcataaacc atcgggagag caggcggtac gcatactttc gtcgcgatag | 480 |
| atgatcgggg attcagtaac attcacgccg gaagtgaact caaacagggt tctggcgtcg | 540 |
| ttctcgtact gttttcccca ggccagtgct ttagcgttaa cttccggagc cacaccggtg | 600 |
| caaacctcag caagcagggt gtggaagtag acattttca tgtcaggcca cttctttccg | 660 |
| gagcggggtt ttgctatcac gttgtgaact tctgaagcgg tgatgacgcc gagccgtaat | 720 |
| ttgtgccacg catcatcccc ctgttcgaca gctctcacat cgatcccggt acgctgcagg | 780 |
| ataatgtccg gtgtcatgct gccacctcct gctctgcgca tttctgtttc aggaatccaa | 840 |
| gagcttttac tgcttcggcc tgtgtcagtt ctgacgatgc acgaatgtcg cggcgaaata | 900 |

```
tctgggaaca gagcggcaat aagtcgtcat cccatgtttt atccagggcg atcagcagag    960
tgttaatctc ctgcatggtt tcatcgttaa ccggagtgat gtcgcgttcc ggctgacgtt   1020
ctgcagtgta tgcagtattt tcgacaatgc gctcggcttc atccttgtca tagataccag   1080
caaatccgaa ggccagacgg gcacactgaa tcatggcttt atgacgtaac atccgtttgg   1140
gatgcgactg ccacggcccc gtgatttctc tgccttcgcg agttttgaat ggttcgcggc   1200
ggcattcatc catccattcg gtaacgcaga tcggatgatt acggtccttg cggtaaatcc   1260
ggcatgtaca ggattcattg tcctgctcaa agtccatgcc atcaaactgc tggttttcat   1320
tgatgatgcg ggaccagcca tcaacgccca ccaccggaac gatgccattc tgcttatcag   1380
gaaaggcgta aatttctttc gtccacggat taaggccgta ctggttggca acgatcagta   1440
atgcgatgaa ctgcgcatcg ctggcatcac ctttaaatgc cgtctggcga agagtggtga   1500
tcagttcctg tgggtcgaca gaatccatgc cgacacgttc agccagcttc ccagccagcg   1560
ttgcgagtgc agtactcatt cgttttatac ctctgaatca atatcaacct ggtggtgagc   1620
aatggtttca accatgtacc ggatgtgttc tgccatgcgc tcctgaaact caacatcgtc   1680
atcaaacgca cgggtaatgg attttttgct ggccccgtgg cgttgcaaat gatcgatgca   1740
tagcgattca aacaggtgct ggggcaggcc ttttccatg tcgtctgcca gttctgcctc   1800
tttctcttca cgggcgagct gctggtagtg acgcgcccag ctctgagcct caagacgatc   1860
ctgaatgtaa taagcgttca tggctgaact cctgaaatag ctgtgaaaat atcgcccgcg   1920
aaatgccggg ctgattagta atccggaatc gcacttacgg ccaatgcttc gtttcgtatc   1980
acacacccca aagccttctg ctttgaatgc tgcccttctt cagggcttaa ttttaagag    2040
cgtcaccttc atggtggtca gtgcgtcctg ctgatgtgct cagtatcacc gccagtggta   2100
tttatgtcaa caccgccaga gataatttat caccgcagat ggttatctgt atgttttta    2160
tatgaattta tttttttgcag ggggcattg tttggtaggt gagagatctg aattgctatg   2220
tttagtgagt tgtatctatt tattttcaa taaatacaat tggttatgtg ttttggggc    2280
gatcgtgagg caaagaaaac ccggcgctga ggccgggtta cgcccgccc tgccactcat    2340
cgcagtactg ttgtaattca ttaagcattc tgccgacatg gaagccatca cagacggcat   2400
gatgaacctg aatcgccagc ggcatcagca ccttgtcgcc ttgcgtataa tatttgccca   2460
tggtgaaaac gggggcgaag aagttgtcca tattggccac gtttaaatca aaactggtga   2520
aactcaccca gggattggct gagacgaaaa acatattctc aataaaccct ttagggaaat   2580
aggccaggtt ttcaccgtaa cacgccacat cttgcgaata tatgtgtaga aactgccgga   2640
aatcgtcgtg gtattcactc cagagcgatg aaaacgtttc agtttgctca tggaaaacgg   2700
tgtaacaagg gtgaacacta tcccatatca ccagctcacc gtctttcatt gccatacgga   2760
attccggatg agcattcatc aggcgggcaa gaatgtgaat aaaggccgga taaaacttgt   2820
gcttattttt cttacggtc tttaaaaagg ccgtaatatc cagctgaacg gtctggttat    2880
aggtacattg agcaactgac tgaaatgcct caaaatgttc tttacgatgc cattgggata   2940
tatcaacggt ggtatatcca gtgattttt tctccataat tcaatccatt tactatgtta    3000
tgttctgagg ggagtgaaaa ttcccctaat tcgatgaaga ttcttgctca attgttatca   3060
gctatgcgcc gaccagaaca ccttgccgat cagccaaacg tctcttcagg ccactgacta   3120
gcgataactt tccccacaac ggaacaactc tcattgcatg ggatcattgg gtactgtggg   3180
tttagtggtt gtaaaaacac ctgaccgcta tccctgatca gtttcttgaa ggtaaactca   3240
```

| | |
|---|---|
| tcaccccaa gtctggctat gcagaaatca cctggctcaa cagcctgctc agggtcaacg | 3300 |
| agaattaaca ttccgtcagg aaagcttggc ttggagcctg ttggtgcggt catggaatta | 3360 |
| ccttcaacct caagccagaa tgcagaatca ctggctttt tggttgtgct tacccatctc | 3420 |
| tccgcatcac ctttggtaaa ggttctaagc ttaggtgaga acatccctgc ctgaacatga | 3480 |
| gaaaaacag ggtactcata ctcacttcta agtgacggct gcatactaac cgcttcatac | 3540 |
| atctcgtaga tttctctggc gattgaaggg ctaaattctt caacgctaac tttgagaatt | 3600 |
| tttgtaagca atgcggcgtt ataagcattt aatgcattga tgccattaaa taaagcacca | 3660 |
| acgcctgact gccccatccc catcttgtct gcgacagatt cctgggataa gccaagttca | 3720 |
| ttttctttt tttcataaat tgctttaagg cgacgtgcgt cctcaagctg ctcttgtgtt | 3780 |
| aatggtttct tttttgtgct catacgttaa atctatcacc gcaagggata aatatctaac | 3840 |
| accgtgcgtg ttgactattt tacctctggc ggtgataatg gttgcatgta ctaaggaggt | 3900 |
| tgtatggaac aacg | 3914 |

<210> SEQ ID NO 9
<211> LENGTH: 4459
<212> TYPE: DNA
<213> ORGANISM: artificial sequence
<220> FEATURE:
<223> OTHER INFORMATION: phages genes

<400> SEQUENCE: 9

| | |
|---|---|
| ccgctgtgct ttcagtggat ttcggataac agaaaggccg ggaaataccc agcctcgctt | 60 |
| tgtaacggag tagacgaaag tgattgcgcc tacccggata ttatcgtgag gatgcgtcat | 120 |
| cgccattgct ccccaaatac aaaaccaatt tcagccagtg cctcgtccat tttttcgatg | 180 |
| aactccggca cgatctcgtc aaaactcgcc atgtactttt catcccgctc aatcacgaca | 240 |
| taatgcaggc cttcacgctt catacgcggg tcatagttgg caaagtacca ggcatttttt | 300 |
| cgcgtcaccc acatgctgta ctgcacctgg gccatgtaag ctgactttat ggcctcgaaa | 360 |
| ccaccgagcc ggaacttcat gaaatcccgg gaggtaaacg ggcatttcag ttcaaggccg | 420 |
| ttgccgtcac tgcataaacc atcgggagag caggcggtac gcatactttc gtcgcgatag | 480 |
| atgatcgggg attcagtaac attcacgccg gaagtgaact caaacagggt tctggcgtcg | 540 |
| ttctcgtact gttttcccca ggccagtgct ttagcgttaa cttccggagc cacaccggtg | 600 |
| caaacctcag caagcagggt gtggaagtag gacatttca tgtcaggcca cttctttccg | 660 |
| gagcggggtt ttgctatcac gttgtgaact tctgaagcgg tgatgacgcc gagccgtaat | 720 |
| ttgtgccacg catcatcccc ctgttcgaca gctctcacat cgatcccggt acgctgcagg | 780 |
| ataatgtccg gtgtcatgct gccaccttct gctctgcggc tttctgtttc aggaatccaa | 840 |
| gagcttttac tgcttcggcc tgtgtcagtt ctgacgatgc acgaatgtcg cggcgaaata | 900 |
| tctgggaaca gagcggcaat aagtcgtcat cccatgtttt atccagggcg atcagcagag | 960 |
| tgttaatctc ctgcatggtt tcatcgttaa ccggagtgat gtcgcgttcc ggctgacgtt | 1020 |
| ctgcagtgta tgcagtattt tcgacaatgc gctcggcttc atccttgtca tagataccag | 1080 |
| caaatccgaa ggccagacgg gcacactgaa tcatggcttt atgacgtaac atccgtttgg | 1140 |
| gatgcgactg ccacggcccc gtgatttctc tgccttcgcg agttttgaat ggttcgcggc | 1200 |
| ggcattcatc catccattcg gtaacgcaga tcggatgatt acggtccttg cggtaaatcc | 1260 |
| ggcatgtaca ggattcattg tcctgctcaa agtccatgcc atcaaactgc tggttttcat | 1320 |
| tgatgatgcg ggaccagcca tcaacgccca ccaccggaac gatgccattc tgcttatcag | 1380 |

```
gaaaggcgta aatttctttc gtccacggat taaggccgta ctggttggca acgatcagta    1440
atgcgatgaa ctgcgcatcg ctggcatcac ctttaaatgc cgtctggcga agagtggtga    1500
tcagttcctg tgggtcgaca gaatccatgc cgacacgttc agccagcttc ccagccagcg    1560
ttgcgagtgc agtactcatt cgttttatac ctctgaatca atatcaacct ggtggtgagc    1620
aatggtttca accatgtacc ggatgtgttc tgccatgcgc tcctgaaact caacatcgtc    1680
atcaaacgca cgggtaatgg attttttgct ggccccgtgg cgttgcaaat gatcgatgca    1740
tagcgattca aacaggtgct ggggcaggcc ttttccatg tcgtctgcca gttctgcctc    1800
tttctcttca cgggcgagct gctggtagtg acgcgcccag ctctgagcct caagacgatc    1860
ctgaatgtaa taagcgttca tggctgaact cctgaaatag ctgtgaaaat atcgcccgcg    1920
aaatgccggg ctgattagta atccggaatc gcacttacgg ccaatgcttc gtttcgtatc    1980
acacacccca aagccttctg ctttgaatgc tgcccttctt cagggcttaa ttttaagag    2040 cgtcaccttc atggtggtca gtgcgtcctg ctgatgtgct cagtatcacc gccagtggta    2100
tttatgtcaa caccgccaga gataatttat caccgcagat ggttatctgt atgttttta    2160 tatgaattta ttttttgcag gggggcattg tttggtaggt gagagatctg aattgctatg    2220
tttagtgagt tgtatctatt tattttcaa taaatacaat tggttatgtg ttttgggggc    2280
gatcgtgagg caaagaaaac ccggcgctga ggccgggtta agagttggta gctcttgatc    2340
cggcaaacaa accaccgctg gtagcggtgg ttttttttgtt tgcaagcagc agattacgcg    2400
cagaaaaaaa ggatctcaag aagatccttt gatcttttct acggggtctg acgctcagtg    2460
gaacgaaaac tcacgttaag ggattttggt catgagatta tcaaaagga tcttcaccta    2520 gatccttta aattaaaaat gaagttttaa atcaatctaa agtatatatg agtaaacttg    2580
gtctgacagt taccaatgct taatcagtga ggcacctatc tcagcgatct gtctatttcg    2640
ttcatccata gttgcctgac tccccgtcgt gtagataact acgatacggg agggcttacc    2700
atctggcccc agtgctgcaa tgataccgcg agacccacgc tcaccggctc cagatttatc    2760
agcaataaac cagccagccg gaagggccga gcgcagaagt ggtcctgcaa ctttatccgc    2820
ctccatccag tctattaatt gttgccggga agctagagta agtagttcgc cagttaatag    2880
tttgcgcaac gttgttgcca ttgctgcagg catcgtggtg tcacgctcgt cgtttggtat    2940
ggcttcattc agctccggtt cccaacgatc aaggcgagtt acatgatccc ccatgttgtg    3000
caaaaaagcg gttagctcct tcggtcctcc gatcgttgtc agaagtaagt tggccgcagt    3060
gttatcactc atggttatgg cagcactgca taattctctt actgtcatgc catccgtaag    3120
atgcttttct gtgactggtg agtactcaac caagtcattc tgagaatagt gtatgcggcg    3180
accgagttgc tcttgcccgg cgtcaacacg ggataatacc gcgccacata gcagaacttt    3240
aaaagtgctc atcattggaa aacgttcttc ggggcgaaaa ctctcaagga tcttaccgct    3300
gttgagatcc agttcgatgt aacccactcg tgcacccaac tgatcttcag catcttttac    3360
tttcaccagc gtttctgggt gagcaaaaac aggaaggcaa aatgccgcaa aaaagggaat    3420
aagggcgaca cggaaatgtt gaatactcat actcttcctt tttcaatatt attgaagcat    3480
ttatcagggt tattgtctca tgagcggata catatttgaa tgaattcaat ccatttacta    3540
tgttatgttc tgagggagt gaaaattccc ctaattcgat gaagattctt gctcaattgt    3600
tatcagctat gcgccgacca gaacaccttg ccgatcagcc aaacgtctct tcaggccact    3660
gactagcgat aactttcccc acaacggaac aactctcatt gcatgggatc attgggtact    3720
```

```
gtgggtttag tggttgtaaa acacctgac cgctatccct gatcagtttc ttgaaggtaa    3780
actcatcacc cccaagtctg ctatgcaga atcacctgg ctcaacagcc tgctcagggt    3840
caacgagaat taacattccg tcaggaaagc ttggcttgga gcctgttggt gcggtcatgg    3900 aattccttc aacctcaagc cagaatgcag atcactggc ttttttggtt gtgcttaccc    3960
atctctccgc atcacctttg gtaaaggttc taagcttagg tgagaacatc cctgcctgaa    4020
catgagaaaa aacagggtac tcatactcac ttctaagtga cggctgcata ctaaccgctt    4080
catacatctc gtagatttct ctggcgattg aagggctaaa ttcttcaacg ctaactttga    4140
gaatttttgt aagcaatgcg gcgttataag catttaatgc attgatgcca ttaaataaag    4200
caccaacgcc tgactgcccc atccccatct tgtctgcgac agattcctgg gataagccaa    4260
gttcattttt cttttttttca taaattgctt taaggcgacg tgcgtcctca agctgctctt    4320
gtgttaatgg tttctttttt gtgctcatac gttaaatcta tcaccgcaag ggataaatat    4380
ctaacaccgt gcgtgttgac tattttacct ctggcggtga taatggttgc atgtactaag    4440
gaggttgtat ggaacaacg                                                4459
```

<210> SEQ ID NO 10
<211> LENGTH: 237
<212> TYPE: PRT
<213> ORGANISM: Bacteriophage lambda

<400> SEQUENCE: 10

```
Met Ser Thr Lys Lys Pro Leu Thr Gln Glu Gln Leu Glu Asp Ala
1               5                   10                  15

Arg Arg Leu Lys Ala Ile Tyr Glu Lys Lys Asn Glu Leu Gly Leu
                20                  25                  30

Ser Gln Glu Ser Val Ala Asp Lys Met Gly Met Gly Gln Ser Gly Val
            35                  40                  45

Gly Ala Leu Phe Asn Gly Ile Asn Ala Leu Asn Ala Tyr Asn Ala Ala
        50                  55                  60

Leu Leu Thr Lys Ile Leu Lys Val Ser Val Glu Glu Phe Ser Pro Ser
65                  70                  75                  80

Ile Ala Arg Glu Ile Tyr Glu Met Tyr Glu Ala Val Ser Met Gln Pro
                85                  90                  95

Ser Leu Arg Ser Glu Tyr Glu Tyr Pro Val Phe Ser His Val Gln Ala
            100                 105                 110

Gly Met Phe Ser Pro Lys Leu Arg Thr Phe Thr Lys Gly Asp Ala Glu
        115                 120                 125

Arg Trp Val Ser Thr Thr Lys Lys Ala Ser Asp Ser Ala Phe Trp Leu
    130                 135                 140

Glu Val Glu Gly Asn Ser Met Thr Ala Pro Thr Gly Ser Lys Pro Ser
145                 150                 155                 160

Phe Pro Asp Gly Met Leu Ile Leu Val Asp Pro Glu Gln Ala Val Glu
                165                 170                 175

Pro Gly Asp Phe Cys Ile Ala Arg Leu Gly Gly Asp Glu Phe Thr Phe
            180                 185                 190

Lys Lys Leu Ile Arg Asp Ser Gly Gln Val Phe Leu Gln Pro Leu Asn
        195                 200                 205

Pro Gln Tyr Pro Met Ile Pro Cys Asn Glu Ser Cys Ser Val Val Gly
    210                 215                 220

Lys Val Ile Ala Ser Gln Trp Pro Glu Glu Thr Phe Gly
225                 230                 235
```

<210> SEQ ID NO 11
<211> LENGTH: 98
<212> TYPE: PRT
<213> ORGANISM: Bacteriophage lambda

<400> SEQUENCE: 11

Met Asn Ala Tyr Tyr Ile Gln Asp Arg Leu Glu Ala Gln Ser Trp Ala
1               5                   10                  15

Arg His Tyr Gln Gln Leu Ala Arg Glu Glu Lys Glu Ala Glu Leu Ala
            20                  25                  30

Asp Asp Met Glu Lys Gly Leu Pro Gln His Leu Phe Glu Ser Leu Cys
        35                  40                  45

Ile Asp His Leu Gln Arg His Gly Ala Ser Lys Lys Ser Ile Thr Arg
    50                  55                  60

Ala Phe Asp Asp Val Glu Phe Gln Glu Arg Met Ala Glu His Ile
65                  70                  75                  80

Arg Tyr Met Val Glu Thr Ile Ala His His Gln Val Asp Ile Asp Ser
                85                  90                  95

Glu Val

<210> SEQ ID NO 12
<211> LENGTH: 261
<212> TYPE: PRT
<213> ORGANISM: Bacteriophage lambda

<400> SEQUENCE: 12

Met Ser Thr Ala Leu Ala Thr Leu Ala Gly Lys Leu Ala Glu Arg Val
1               5                   10                  15

Gly Met Asp Ser Val Asp Pro Gln Glu Leu Ile Thr Thr Leu Arg Gln
            20                  25                  30

Thr Ala Phe Lys Gly Asp Ala Ser Asp Ala Gln Phe Ile Ala Leu Leu
        35                  40                  45

Ile Val Ala Asn Gln Tyr Gly Leu Asn Pro Trp Thr Lys Glu Ile Tyr
    50                  55                  60

Ala Phe Pro Asp Lys Gln Asn Gly Ile Val Pro Val Val Gly Val Asp
65                  70                  75                  80

Gly Trp Ser Arg Ile Ile Asn Glu Asn Gln Gln Phe Asp Gly Met Asp
                85                  90                  95

Phe Glu Gln Asp Asn Glu Ser Cys Thr Cys Arg Ile Tyr Arg Lys Asp
            100                 105                 110

Arg Asn His Pro Ile Cys Val Thr Glu Trp Met Asp Glu Cys Arg Arg
        115                 120                 125

Glu Pro Phe Lys Thr Arg Glu Gly Arg Glu Ile Thr Gly Pro Trp Gln
    130                 135                 140

Ser His Pro Lys Arg Met Leu Arg His Lys Ala Met Ile Gln Cys Ala
145                 150                 155                 160

Arg Leu Ala Phe Gly Phe Ala Gly Ile Tyr Asp Lys Asp Glu Ala Glu
                165                 170                 175

Arg Ile Val Glu Asn Thr Ala Tyr Thr Ala Glu Arg Gln Pro Glu Arg
            180                 185                 190

Asp Ile Thr Pro Val Asn Asp Glu Thr Met Gln Glu Ile Asn Thr Leu
        195                 200                 205

Leu Ile Ala Leu Asp Lys Thr Trp Asp Asp Leu Leu Pro Leu Cys
    210                 215                 220

Ser Gln Ile Phe Arg Arg Asp Ile Arg Ala Ser Ser Glu Leu Thr Gln

```
                    225                 230                 235                 240
Ala Glu Ala Val Lys Ala Leu Gly Phe Leu Lys Gln Lys Ala Ala Glu
                245                 250                 255

Gln Lys Val Ala Ala
            260

<210> SEQ ID NO 13
<211> LENGTH: 226
<212> TYPE: PRT
<213> ORGANISM: Bacteriophage lambda

<400> SEQUENCE: 13

Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
            20                  25                  30

Thr Ala Ser Glu Val His Asn Val Ile Ala Lys Pro Arg Ser Gly Lys
        35                  40                  45

Lys Trp Pro Asp Met Lys Met Ser Tyr Phe His Thr Leu Leu Ala Glu
    50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225

<210> SEQ ID NO 14
<211> LENGTH: 219
<212> TYPE: PRT
<213> ORGANISM: artificial sequence
<220> FEATURE:
<223> OTHER INFORMATION: drug cassette

<400> SEQUENCE: 14

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45
```

```
Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
 65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
        130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
                180                 185                 190

His Ala Val Cys Asp Gly Phe His Val Gly Arg Met Leu Asn Glu Leu
            195                 200                 205

Gln Gln Tyr Cys Asp Glu Trp Gln Gly Gly Ala
        210                 215

<210> SEQ ID NO 15
<211> LENGTH: 286
<212> TYPE: PRT
<213> ORGANISM: artificial sequence
<220> FEATURE:
<223> OTHER INFORMATION: drug cassette

<400> SEQUENCE: 15

Met Ser Ile Gln His Phe Arg Val Ala Leu Ile Pro Phe Phe Ala Ala
 1               5                  10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
        50                  55                  60

Pro Met Met Ser Thr Phe Lys Val Leu Leu Cys Gly Ala Val Leu Ser
 65                  70                  75                  80

Arg Val Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
        130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Ala Ala Met Ala Thr Thr Leu Arg Lys Leu Leu
                180                 185                 190
```

```
Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
                260                 265                 270

Arg Gln Ile Ala Glu Ile Gly Ala Ser Leu Ile Lys His Trp
            275                 280                 285
```

<210> SEQ ID NO 16
<211> LENGTH: 301
<212> TYPE: PRT
<213> ORGANISM: Artificial sequence
<220> FEATURE:
<223> OTHER INFORMATION: repts, pSIM5, 6

<400> SEQUENCE: 16

```
Met Ser Glu Leu Val Phe Lys Ala Asn Glu Leu Ala Ile Ser Arg
1               5                   10                  15

Tyr Asp Leu Thr Glu His Glu Thr Lys Leu Ile Leu Cys Cys Val Ala
            20                  25                  30

Leu Leu Asn Pro Thr Ile Glu Asn Pro Thr Arg Lys Glu Arg Thr Val
            35                  40                  45

Ser Phe Thr Tyr Asn Gln Tyr Ala Gln Met Met Asn Ile Ser Arg Glu
    50                  55                  60

Asn Ala Tyr Gly Val Leu Ala Lys Ala Thr Arg Glu Leu Met Thr Arg
65                  70                  75                  80

Thr Val Glu Ile Arg Asn Pro Leu Val Lys Gly Phe Glu Ile Phe Gln
                85                  90                  95

Trp Thr Asn Tyr Ala Lys Phe Ser Ser Glu Lys Leu Glu Leu Val Phe
            100                 105                 110

Ser Glu Glu Ile Leu Pro Tyr Leu Phe Gln Leu Lys Lys Phe Ile Lys
            115                 120                 125

Tyr Asn Leu Glu His Val Lys Ser Phe Glu Asn Lys Tyr Ser Met Arg
    130                 135                 140

Ile Tyr Glu Trp Leu Leu Lys Glu Leu Thr Gln Lys Lys Thr His Lys
145                 150                 155                 160

Ala Asn Ile Glu Ile Ser Leu Asp Glu Phe Lys Phe Met Leu Met Leu
                165                 170                 175

Glu Asn Asn Tyr His Glu Phe Lys Arg Leu Asn Gln Trp Val Leu Lys
            180                 185                 190

Pro Ile Ser Lys Asp Leu Asn Thr Tyr Ser Asn Met Lys Leu Val Val
            195                 200                 205

Asp Lys Arg Gly Arg Pro Thr Asp Thr Leu Ile Phe Gln Val Glu Leu
    210                 215                 220

Asp Arg Gln Met Asp Leu Val Thr Glu Leu Glu Asn Asn Gln Ile Lys
225                 230                 235                 240

Met Asn Gly Asp Lys Ile Pro Thr Thr Ile Thr Ser Asp Ser Tyr Leu
                245                 250                 255

His Asn Gly Leu Arg Lys Thr Leu His Asp Ala Leu Thr Ala Lys Ile
            260                 265                 270
```

```
Gln Leu Thr Ser Phe Glu Ala Lys Phe Leu Ser Asp Met Gln Ser Lys
        275                 280                 285

Tyr Asp Leu Asn Gly Ser Phe Ser Trp Leu Thr Gln Lys
        290                 295                 300
```

<210> SEQ ID NO 17
<211> LENGTH: 137
<212> TYPE: PRT
<213> ORGANISM: Artificial sequence
<220> FEATURE:
<223> OTHER INFORMATION: Orf of pSIM5, 6

<400> SEQUENCE: 17

```
Met Ala Leu Val Ser Ile Ser Glu Ala Ser Arg Leu Thr Asn Lys Ser
1               5                   10                  15

Arg Thr Thr Val His Arg Tyr Ile Ser Lys Gly Lys Leu Ser Ile Cys
            20                  25                  30

Thr Asp Glu Asn Gly Val Lys Lys Ile Asp Thr Ser Glu Leu Leu Arg
        35                  40                  45

Val Phe Gly Ala Phe Lys Ala Val His His Glu Gln Ile Asp Asn Val
    50                  55                  60

Thr Asp Glu Gln His Val Thr Pro Asn Arg Thr Gly Glu Thr Ser Lys
65                  70                  75                  80

Thr Lys Gln Leu Glu His Glu Ile Glu His Leu Arg Gln Leu Val Thr
                85                  90                  95

Ala Gln Gln Ser His Ile Asp Ser Leu Lys Gln Ala Met Leu Leu Ile
            100                 105                 110

Glu Ser Lys Leu Pro Thr Thr Arg Glu Pro Val Thr Pro Pro Val Gly
        115                 120                 125

Lys Lys Ser Trp Gln Phe Trp Lys Lys
    130                 135
```

<210> SEQ ID NO 18
<211> LENGTH: 220
<212> TYPE: PRT
<213> ORGANISM: Artificial sequence
<220> FEATURE:
<223> OTHER INFORMATION: Rep protein of pSIM7, 8

<400> SEQUENCE: 18

```
Met Ala Thr Gln Ser Arg Glu Ile Gly Ile Gln Ala Lys Asn Lys Pro
1               5                   10                  15

Gly His Trp Val Gln Thr Glu Arg Lys Ala His Glu Ala Trp Ala Gly
            20                  25                  30

Leu Ile Ala Arg Lys Pro Thr Ala Ala Met Leu Leu His His Leu Val
        35                  40                  45

Ala Gln Met Gly His Gln Asn Ala Val Val Val Ser Gln Lys Thr Leu
    50                  55                  60

Ser Lys Leu Ile Gly Arg Ser Leu Arg Thr Val Gln Tyr Ala Val Lys
65                  70                  75                  80

Asp Leu Val Ala Glu Arg Trp Ile Ser Val Val Lys Leu Asn Gly Pro
                85                  90                  95

Gly Thr Val Ser Ala Tyr Val Val Asn Asp Arg Val Ala Trp Gly Gln
            100                 105                 110

Pro Arg Asp Gln Leu Arg Leu Ser Val Phe Ser Ala Ala Val Val Val
        115                 120                 125

Asp His Asp Asp Gln Asp Glu Ser Leu Leu Gly His Gly Asp Leu Arg
```

```
                130             135             140
Arg Ile Pro Thr Leu Tyr Pro Gly Glu Gln Gln Leu Pro Thr Gly Pro
145                 150                 155                 160

Gly Glu Glu Pro Pro Ser Gln Pro Gly Ile Pro Gly Met Glu Pro Asp
                165                 170                 175

Leu Pro Ala Leu Thr Glu Thr Glu Glu Trp Glu Arg Arg Gly Gln Gln
            180                 185                 190

Arg Leu Pro Met Pro Asp Glu Pro Cys Phe Leu Asp Asp Gly Glu Pro
            195                 200                 205

Leu Glu Pro Pro Thr Arg Val Thr Leu Pro Arg Arg
    210                 215                 220

<210> SEQ ID NO 19
<211> LENGTH: 382
<212> TYPE: PRT
<213> ORGANISM: Artificial sequence
<220> FEATURE:
<223> OTHER INFORMATION: replication gene, pSIM9

<400> SEQUENCE: 19

Met Asn Arg Thr Phe Asp Arg Lys Ala Tyr Arg Gln Glu Leu Ile Asp
1               5                   10                  15

Ala Gly Phe Ser Ala Glu Asp Ala Glu Thr Ile Ala Ser Arg Thr Val
                20                  25                  30

Met Arg Ala Pro Arg Glu Thr Phe Gln Ser Val Gly Ser Met Val Gln
            35                  40                  45

Gln Ala Thr Ala Lys Ile Glu Arg Asp Ser Val Gln Leu Ala Pro Pro
50                  55                  60

Ala Leu Pro Ala Pro Ser Ala Ala Val Glu Arg Ser Arg Arg Leu Glu
65                  70                  75                  80

Gln Glu Ala Ala Gly Leu Ala Lys Ser Met Thr Ile Asp Thr Arg Gly
                85                  90                  95

Thr Met Thr Thr Lys Lys Arg Lys Thr Ala Gly Glu Asp Leu Ala Lys
            100                 105                 110

Gln Val Ser Glu Ala Lys Gln Ala Ala Leu Leu Lys His Thr Lys Gln
        115                 120                 125

Gln Ile Lys Glu Met Gln Leu Ser Leu Phe Asp Ile Ala Pro Trp Pro
    130                 135                 140

Asp Thr Met Arg Ala Met Pro Asn Asp Thr Ala Arg Ser Ala Leu Phe
145                 150                 155                 160

Thr Thr Arg Asn Lys Lys Ile Pro Arg Glu Ala Leu Gln Asn Lys Val
                165                 170                 175

Ile Phe His Val Asn Lys Asp Val Lys Ile Thr Tyr Thr Gly Val Glu
            180                 185                 190

Leu Arg Ala Asp Asp Asp Glu Leu Val Trp Gln Gln Val Leu Glu Tyr
        195                 200                 205

Ala Lys Arg Thr Pro Ile Gly Glu Pro Ile Thr Phe Thr Phe Tyr Glu
    210                 215                 220

Leu Cys Gln Asp Leu Gly Trp Ser Ile Asn Gly Arg Tyr Tyr Thr Lys
225                 230                 235                 240

Ala Glu Glu Cys Leu Ser Arg Leu Gln Ala Thr Ala Met Gly Phe Thr
                245                 250                 255

Ser Asp Arg Val Gly His Leu Glu Ser Val Ser Leu Leu His Arg Phe
            260                 265                 270

Arg Val Leu Asp Arg Gly Lys Lys Thr Ser Arg Cys Gln Val Leu Met
```

```
                275                 280                 285
    His Glu Glu Ile Val Val Gln Phe Ala Gly Asp His Tyr Thr Lys Phe
        290                 295                 300
    Ile Trp Glu Lys Tyr Arg Lys Leu Ser Pro Thr Ala Arg Arg Met Phe
    305                 310                 315                 320
    Asp Tyr Phe Ser Ser His Arg Glu Pro Tyr Pro Leu Lys Leu Glu Thr
                    325                 330                 335
    Phe Arg Leu Met Cys Gly Ser Asp Ser Thr Arg Val Lys Lys Trp Arg
                340                 345                 350
    Glu Gln Val Gly Glu Ala Cys Glu Glu Leu Arg Gly Ser Gly Leu Val
                    355                 360                 365
    Glu His Ala Trp Val Asn Asp Leu Val His Cys Lys Arg
        370                 375                 380

<210> SEQ ID NO 20
<211> LENGTH: 382
<212> TYPE: PRT
<213> ORGANISM: Salmonella typhimurium

<400> SEQUENCE: 20

Met Asn Leu Lys Glu Lys Thr Arg Ala Leu Phe Ala Glu Ile Phe Gly
1               5                   10                  15
Tyr Pro Ala Thr His Thr Ile Gln Ala Pro Gly Arg Val Asn Leu Ile
            20                  25                  30
Gly Glu His Thr Asp Tyr Asn Asp Gly Phe Val Leu Pro Cys Ala Ile
        35                  40                  45
Asp Tyr Gln Thr Val Ile Ser Cys Ala Pro Arg Asp Asp Arg Thr Val
    50                  55                  60
Arg Val Ile Ala Ala Asp Tyr Asp Asn Gln Val Asp Glu Phe Ser Leu
65                  70                  75                  80
Asp Ala Pro Ile Val Thr His Asp Ser Gln Gln Trp Ser Asn Tyr Val
                85                  90                  95
Arg Gly Val Val Lys His Leu Gln Gln Arg Asn Asn Ala Phe Gly Gly
            100                 105                 110
Val Asp Met Val Ile Ser Gly Asn Val Pro Gln Gly Ala Gly Leu Ser
        115                 120                 125
Ser Ser Ala Ser Leu Glu Val Ala Val Gly Thr Val Phe Gln Gln Leu
    130                 135                 140
Tyr His Leu Pro Leu Asp Gly Ala Gln Ile Ala Leu Asn Gly Gln Glu
145                 150                 155                 160
Ala Glu Asn Gln Phe Val Gly Cys Asn Cys Gly Ile Met Asp Gln Leu
                165                 170                 175
Ile Ser Ala Leu Gly Lys Lys Asp His Ala Leu Leu Ile Asp Cys Arg
            180                 185                 190
Thr Leu Gly Ala Lys Ala Val Ser Met Pro Lys Gly Val Ala Val Val
        195                 200                 205
Ile Ile Asn Ser Asn Phe Lys Arg Thr Leu Val Gly Ser Glu Tyr Asn
    210                 215                 220
Thr Arg Arg Glu Gln Cys Glu Thr Gly Ala Arg Phe Phe Gln Gln Pro
225                 230                 235                 240
Ala Leu Arg Asp Val Ser Leu Glu Ala Phe Asn Ala Val Ala Ser Glu
                245                 250                 255
Leu Asp Pro Val Val Ala Lys Arg Val Arg His Val Leu Ser Glu Asn
            260                 265                 270
```

```
Ala Arg Thr Val Glu Ala Ala Ser Ala Leu Glu Lys Gly Asp Leu Gln
        275                 280                 285

Arg Met Gly Gln Leu Met Ala Glu Ser His Ala Ser Met Arg Asp Asp
    290                 295                 300

Phe Glu Ile Thr Val Pro Gln Ile Asp Thr Leu Val Asp Ile Val Lys
305                 310                 315                 320

Ala Thr Ile Gly Asp Arg Gly Val Arg Met Thr Gly Gly Gly Gly Phe
                325                 330                 335

Gly Gly Cys Val Val Ala Leu Ile Pro Glu Asp Leu Val Pro Ala Val
                340                 345                 350

Arg Gln Ala Val Ala Gln Gln Tyr Glu Ala Lys Thr Gly Ile Lys Glu
            355                 360                 365

Thr Phe Tyr Val Cys Lys Pro Ser Gln Gly Ala Gly Gln Cys
    370                 375                 380

<210> SEQ ID NO 21
<211> LENGTH: 1149
<212> TYPE: DNA
<213> ORGANISM: Salmonella typhimurium

<400> SEQUENCE: 21
atgaatctga aagagaaaac gcgcgcgctg tttgctgaaa ttttcggcta ccctgctacc      60
cacacgattc aggcgccagg ccgcgtcaat ctgatcggcg agcacactga ttacaatgat     120
ggttttgttc tgccctgcgc tatcgattac agaccgtaa ttagctgtgc gccgcgcgac      180
gatcgtaccg tacgggtgat tgccgccgat tacgacaatc aggtggacga attttcactg     240
gatgcgccga tcgtgaccca cgatagccag cagtggtcta actatgtgcg cggcgtagtg     300
aaacacctgc agcagcgtaa caacgcgttt ggcggcgtgg atatggtcat cagcggcaat     360
gtgccgcagg gcgccgggtt aagctcctcc gcctcgctgg aagtggcggt gggcaccgtc     420
ttccagcagc tttatcacct gccgctggac ggcgcgcaaa ttgcgctcaa cggacaagag     480
gccgagaacc agtttgtcgg ctgtaactgc ggcattatgg atcagctcat ctctgcgctc     540
ggcaaaaaag atcatgcgct gctgattgat tgccgtacgc tcggcgccaa agcggtttcc     600
atgccgaaag gtgtcgccgt ggtgatcatc aacagtaact ttaagcgcac gctggtgggc     660
agcgagtata taccgccg tgaacagtgc gaaaccggcg cccgtttctt ccagcagccg      720
gccctgcgcg atgtcagcct tgaggcgttc aatgccgttg ccagcgaact ggacccggta     780
gtcgcaaaac gcgttcgcca tgtattgagc gaaaatgcgc gcaccgttga gcggcaagc      840 gcgctggaga aggtgatttt gcaacgtatg gccaactga tggcggagtc ccatgcctca     900
atgcgcgatg atttcgaaat taccgtcccg cagatagaca cgctggtaga catcgtcaaa     960
gcgaccatcg gcgatcgagg cggcgtgcgc atgaccggcg gcggctttgg cgggtgtgtt    1020
gtcgcactga tcccggaaga tctggttccc gctgttcggc aggccgttgc gcaacagtac    1080
gaagcgaaaa ccggaatcaa agaaaccttt tatgtatgca accgtcaca aggagcagga    1140 cagtgctaa                                                            1149

<210> SEQ ID NO 22
<211> LENGTH: 70
<212> TYPE: DNA
<213> ORGANISM: artificial sequence
<220> FEATURE:
<223> OTHER INFORMATION: oligonucleotide

<400> SEQUENCE: 22
```

```
aagtggcggt gggcaccgtc ttccagcagc tttagtgttc accgctggac ggcgcgcaaa    60
ttgcgctcaa                                                           70

<210> SEQ ID NO 23
<211> LENGTH: 70
<212> TYPE: DNA
<213> ORGANISM: artificial sequence
<220> FEATURE:
<223> OTHER INFORMATION: oligonucleotide

<400> SEQUENCE: 23
aagtggcggt gggcaccgtc ttccagcagc tttaccacct gccgctggac ggcgcgcaaa    60
ttgcgctcaa                                                           70

<210> SEQ ID NO 24
<211> LENGTH: 1403
<212> TYPE: DNA
<213> ORGANISM: Bacteriophage lambda

<400> SEQUENCE: 24
agtgagttgt atctatttat ttttcaataa atacaattgg ttatgtgttt tgggggcgat    60
cgtgaggcaa agaaaacccg cgctgaggc cgggttattc ttgttctctg gtcaaattat   120
atagttggaa acaaggatg catatatgaa tgaacgatgc agaggcaatg ccgatggcga   180
tagtgggtat catgtagccg cttatgctgg aaagaagcaa taccccgcag aaaaacaaag   240
ctccaagctc aacaaaacta agggcataga caataactac cgatgtcata tacccatact   300
ctctaatctt ggccagtcgg cgcgttctgc ttccgattag aaacgtcaag gcagcaatca   360
ggattgcaat catggttcct gcatatgatg acaatgtcgc cccaagacca tctctatgag   420
ctgaaaaaga aacaccagga atgtagtggc ggaaaaggag atagcaaatg cttacgataa   480
cgtaaggaat tattactatg taaacaccag gcatgattct gttccgcata attactcctg   540
ataattaatc cttaactttg cccacctgcc ttttaaaaca ttccagtata tcactttttca   600 ttcttgcgta gcaatatgcc atctcttcag ctatctcagc attggtgacc ttgttcagag   660
gcgctgagag atggcctttt tctgatagat aatgttctgt taaatatct ccggcctcat   720 cttttgcccg caggctaatg tctgaaaatt gaggtgacgg gttaaaaata atatccttgg   780 caacctttttt tatatccctt ttaaattttg gcttaatgac tatatccaat gagtcaaaaa   840 gctcccctttc aatatctgtt gcccctaaga cctttaatat atcgccaaat acaggtagct   900
tggcttctac cttcaccgtt gttcggccga tgaaatgcat atgcataaca tcgtctttgg   960
tggttcccct catcagtggc tctatctgaa cgcgctctcc actgcttaat gacattcctt  1020
tcccgattaa aaatctgtc agatcggatg tggtcggccc gaaaacagtt ctggcaaaac  1080
caatggtgtc gccttcaaca aacaaaaaag atgggaatcc caatgattcg tcatctgcga  1140
ggctgttctt aatatcttca actgaagctt tagagcgatt tatcttctga accagactct  1200
tgtcatttgt tttggtaaag agaaaagttt ttccatcgat tttatgaata tacaaataat  1260
tggagccaac ctgcaggtga tgattatcag ccagcagaga attaaggaaa acagacaggt  1320
ttattgagcg cttatctttc cctttatttt tgctgcggta agtcgcataa aaaccattct  1380
tcataattca atccatttac tat                                         1403

<210> SEQ ID NO 25
<211> LENGTH: 279
<212> TYPE: PRT
<213> ORGANISM: Bacteriophage lambda
```

<400> SEQUENCE: 25

| Met<br>1 | Lys | Asn | Gly | Phe<br>5 | Tyr | Ala | Thr | Tyr | Arg<br>10 | Ser | Lys | Asn | Lys | Gly<br>15 | Lys |
|---|---|---|---|---|---|---|---|---|---|---|---|---|---|---|---|

Asp Lys Arg Ser Ile Asn Leu Ser Val Phe Leu Asn Ser Leu Leu Ala
              20               25             30

Asp Asn His His Leu Gln Val Gly Ser Asn Tyr Leu Tyr Ile His Lys
        35               40              45

Ile Asp Gly Lys Thr Phe Leu Phe Thr Lys Thr Asn Asp Lys Ser Leu
50               55              60

Val Gln Lys Ile Asn Arg Ser Lys Ala Ser Val Glu Asp Ile Lys Asn
65            70            75             80

Ser Leu Ala Asp Asp Glu Ser Leu Gly Phe Pro Ser Phe Leu Phe Val
        85             90             95

Glu Gly Asp Thr Ile Gly Phe Ala Arg Thr Val Phe Gly Pro Thr Thr
         100          105           110

Ser Asp Leu Thr Asp Phe Leu Ile Gly Lys Gly Met Ser Leu Ser Ser
        115           120           125

Gly Glu Arg Val Gln Ile Glu Pro Leu Met Arg Gly Thr Thr Lys Asp
130             135            140

Asp Val Met His Met His Phe Ile Gly Arg Thr Thr Val Lys Val Glu
145            150           155         160

Ala Lys Leu Pro Val Phe Gly Asp Ile Leu Lys Val Leu Gly Ala Thr
           165          170          175

Asp Ile Glu Gly Glu Leu Phe Ser Leu Asp Ile Val Ile Lys Pro
        180          185          190

Lys Phe Lys Arg Asp Ile Lys Lys Val Ala Lys Asp Ile Ile Phe Asn
         195         200          205

Pro Ser Pro Gln Phe Ser Asp Ile Ser Leu Arg Ala Lys Asp Glu Ala
210            215           220

Gly Asp Ile Leu Thr Glu His Tyr Leu Ser Glu Lys Gly His Leu Ser
225            230          235         240

Ala Pro Leu Asn Lys Val Thr Asn Ala Glu Ile Ala Glu Glu Met Ala
         245          250          255

Tyr Cys Tyr Ala Arg Met Lys Ser Asp Ile Leu Glu Cys Phe Lys Arg
        260         265          270

Gln Val Gly Lys Val Lys Asp
        275

<210> SEQ ID NO 26
<211> LENGTH: 144
<212> TYPE: PRT
<213> ORGANISM: Bacteriophage lambda

<400> SEQUENCE: 26

Met Arg Asn Arg Ile Met Pro Gly Val Tyr Ile Val Ile Pro Tyr
1             5              10            15

Val Ile Val Ser Ile Cys Tyr Leu Leu Phe Arg His Tyr Ile Pro Gly
             20             25             30

Val Ser Phe Ser Ala His Arg Asp Gly Leu Gly Ala Thr Leu Ser Ser
        35             40             45

Tyr Ala Gly Thr Met Ile Ala Ile Leu Ile Ala Ala Leu Thr Phe Leu
50               55              60

Ile Gly Ser Arg Thr Arg Arg Leu Ala Lys Ile Arg Glu Tyr Gly Tyr
65            70            75             80

```
Met Thr Ser Val Val Ile Val Tyr Ala Leu Ser Phe Val Glu Leu Gly
                85                  90                  95

Ala Leu Phe Phe Cys Gly Leu Leu Leu Ser Ser Ile Ser Gly Tyr
            100                 105                 110

Met Ile Pro Thr Ile Ala Ile Gly Ile Ala Ser Ala Ser Phe Ile His
            115                 120                 125

Ile Cys Ile Leu Val Phe Gln Leu Tyr Asn Leu Thr Arg Glu Gln Glu
    130                 135                 140

<210> SEQ ID NO 27
<211> LENGTH: 205
<212> TYPE: PRT
<213> ORGANISM: Salmonella typhimurium

<400> SEQUENCE: 27

Arg Leu Asp Lys Ser Lys Val Ile Asn Ser Ala Leu Glu Leu Leu Asn
1               5                   10                  15

Glu Val Gly Ile Glu Gly Leu Thr Thr Arg Lys Leu Ala Gln Lys Leu
            20                  25                  30

Gly Val Glu Gln Pro Thr Leu Tyr Trp His Val Lys Asn Lys Arg Ala
        35                  40                  45

Leu Leu Asp Ala Leu Ala Ile Glu Met Leu Asp Arg His His Thr His
    50                  55                  60

Phe Cys Pro Leu Glu Gly Glu Ser Trp Gln Asp Phe Leu Arg Asn Asn
65                  70                  75                  80

Ala Lys Ser Phe Arg Cys Ala Leu Leu Ser His Arg Asp Gly Ala Lys
                85                  90                  95

Val His Leu Gly Thr Arg Pro Thr Glu Lys Gln Tyr Glu Thr Leu Glu
            100                 105                 110

Asn Gln Leu Ala Phe Leu Cys Gln Gln Gly Phe Ser Leu Glu Asn Ala
        115                 120                 125

Leu Tyr Ala Leu Ser Ala Val Gly His Phe Thr Leu Gly Cys Val Leu
    130                 135                 140

Glu Asp Gln Glu His Gln Val Ala Lys Glu Glu Arg Glu Thr Pro Thr
145                 150                 155                 160

Thr Asp Ser Met Pro Pro Leu Leu Arg Gln Ala Ile Glu Leu Phe Asp
                165                 170                 175

His Gln Gly Ala Glu Pro Ala Phe Leu Phe Gly Leu Glu Leu Ile Ile
            180                 185                 190

Cys Gly Leu Glu Lys Gln Leu Lys Cys Glu Ser Gly Ser
        195                 200                 205

<210> SEQ ID NO 28
<211> LENGTH: 401
<212> TYPE: PRT
<213> ORGANISM: Salmonella typhimurium

<400> SEQUENCE: 28

Met Asn Ser Ser Thr Lys Ile Ala Leu Val Ile Thr Leu Leu Asp Ala
1               5                   10                  15

Met Gly Ile Gly Leu Ile Met Pro Val Leu Pro Thr Leu Leu Arg Glu
            20                  25                  30

Phe Ile Ala Ser Glu Asp Ile Ala Asn His Phe Gly Val Leu Leu Ala
        35                  40                  45

Leu Tyr Ala Leu Met Gln Val Ile Phe Ala Pro Trp Leu Gly Lys Met
    50                  55                  60
```

| | | | | | | | | | | | | | | | |
|---|---|---|---|---|---|---|---|---|---|---|---|---|---|---|---|
|Ser|Asp|Arg|Phe|Gly|Arg|Pro|Val|Leu|Leu|Ser|Leu|Ile|Gly|
|65| | | | |70| | | |75| | | |80|

Ala Ser Leu Asp Tyr Leu Leu Leu Ala Phe Ser Ser Ala Leu Trp Met
                    85                            90                            95

Leu Tyr Leu Gly Arg Leu Leu Ser Gly Ile Thr Gly Ala Thr Gly Ala
                100                          105                        110

Val Ala Ala Ser Val Ile Ala Asp Thr Thr Ser Ala Ser Gln Arg Val
                115                          120                        125

Lys Trp Phe Gly Trp Leu Gly Ala Ser Phe Gly Leu Gly Leu Ile Ala
            130                          135                        140

Gly Pro Ile Ile Gly Gly Phe Ala Gly Glu Ile Ser Pro His Ser Pro
145                      150                          155                        160

Phe Phe Ile Ala Ala Leu Leu Asn Ile Val Thr Phe Leu Val Val Met
                165                          170                        175

Phe Trp Phe Arg Glu Thr Lys Asn Thr Arg Asp Asn Thr Asp Thr Glu
            180                          185                        190

Val Gly Val Glu Thr Gln Ser Asn Ser Val Tyr Ile Thr Leu Phe Lys
                195                          200                        205

Thr Met Pro Ile Leu Leu Ile Ile Tyr Phe Ser Ala Gln Leu Ile Gly
210                      215                          220

Gln Ile Pro Ala Thr Val Trp Val Leu Phe Thr Glu Asn Arg Phe Gly
225                      230                          235                        240

Trp Asn Ser Met Met Val Gly Phe Ser Leu Ala Gly Leu Gly Leu Leu
                245                          250                        255

His Ser Val Phe Gln Ala Phe Val Ala Gly Arg Ile Ala Thr Lys Trp
            260                          265                        270

Gly Glu Lys Thr Ala Val Leu Leu Gly Phe Ile Ala Asp Ser Ser Ala
            275                          280                        285

Phe Ala Phe Leu Ala Phe Ile Ser Glu Gly Trp Leu Val Phe Pro Val
            290                          295                        300

Leu Ile Leu Leu Ala Gly Gly Ile Ala Leu Pro Ala Leu Gln Gly
305                      310                          315                        320

Val Met Ser Ile Gln Thr Lys Ser His Gln Gln Gly Ala Leu Gln Gly
                325                          330                        335

Leu Leu Val Ser Leu Thr Asn Ala Thr Gly Val Ile Gly Pro Leu Leu
            340                          345                        350

Phe Ala Val Ile Tyr Asn His Ser Leu Pro Ile Trp Asp Gly Trp Ile
            355                          360                        365

Trp Ile Ile Gly Leu Ala Phe Tyr Cys Ile Ile Leu Leu Ser Met
            370                          375                        380

Thr Phe Met Leu Thr Pro Gln Ala Gln Gly Ser Lys Gln Glu Thr Ser
385                      390                          395                        400

Ala

<210> SEQ ID NO 29
<211> LENGTH: 2189
<212> TYPE: DNA
<213> ORGANISM: Salmonella typhimurium

<400> SEQUENCE: 29

```
tcatatgatc tcgggaaaag cgttggtgac caaaggtgcc ttttatcatc actttaaaaa    60
taaaaaacaa ttactcagtg cctgttataa gcagcaatta attatgattg atgcctacat   120
aaatcttctt tatcgtaaaa aatgccctct tgggttatca agagggtcat tatatttcgc   180
```

```
ggaataacat catttggtga cgaaataact aagcacttgt ctcctgttta ctcccctgag    240
cttgaggggt taacatgaag gtcatcgata gcaggataat aatacagtaa aacgctaaac    300
caataatcca aatccagcca tcccaaattg gtagtgaatg attataaata acagcaaaca    360
gtaatgggcc aataacaccg gttgcattgg taaggctcac caataatccc tgtaaagcac    420
cttgctgatg actctttgtt tggatagaca tcactccctg taatgcaggt aaagcgatcc    480
caccaccagc caataaaatt aaaacaggga aaactaacca accttcagat ataaacgcta    540
aaaaggcaaa tgcactacta tctgcaataa atccgagcag tactgccgtt ttttcgcccc    600
atttagtggc tattcttcct gccacaaagg cttggaatac tgagtgtaaa agaccaagac    660
ccgctaatga aaagccaacc atcatgctat tccatccaaa acgattttcg gtaaatagca    720
cccacaccgt tgcgggaatt tggcctatca attgcgctga aaaataaata atcaacaaaa    780
tgggcatcgt tttaaataaa gtgatgtata ccgaattcga ttgcgtctca accccctactt    840 cggtatctgt attatcacgt gtattttttgg tttcacggaa ccaaaacata accacaagga    900
aagtgacaat atttagcaac gcagcgataa aaaagggact atgcggtgaa atctctcctg    960 caaaccacc aataataggc cccgctatta aaccaagccc aaaacttgcc cctaaccaac    1020
cgaaccactt cacgcgttga gaagctgagg tggtatcggc aatgaccgat gccgcgacag    1080
ccccagtagc tcctgtgatc cctgaaagca aacggcctaa atacagcatc caaagcgcac    1140
ttgaaaaagc cagcaataag taatccagcg atgcgcctat taatgacaac aacagcactg    1200
ggcgccgacc aaatcggtca gacattttc caagccaagg agcaaagata acctgcatta    1260
acgcataaag tgcaagcaat acgccaaagt ggttagcgat atcttccgaa gcaataaatt    1320
cacgtaataa cgttggcaag actggcatga taaggccaat ccccatggca tcgagtaacg    1380
taattaccaa tgcgatcttt gtcgaactat tcatttcact tttctctatc actgataggg    1440
agtggtaaaa taactctatc aatgatagag tgtcaacaaa aattaggaat taatgatgtc    1500
tagattagat aaaagtaaag tgattaacag cgcattagag ctgcttaatg aggtcggaat    1560
cgaaggttta acaacccgta aactcgccca gaagctaggt gtagagcagc ctacattgta    1620
ttggcatgta aaaaataagc gggctttgct cgacgcctta gccattgaga tgttagatag    1680
gcaccatact cacttttgcc ctttagaagg ggaaagctgg caagattttt tacgtaataa    1740
cgctaaaagt tttagatgtg ctttactaag tcatcgcgat ggagcaaaag tacatttagg    1800
tacacggcct acagaaaaac agtatgaaac tctcgaaaat caattagcct ttttatgcca    1860
acaaggtttt tcactagaga atgcattata tgcactcagc gctgtggggc attttactttt   1920 aggttgcgta ttggaagatc aagagcatca agtcgctaaa aagaaaggg aaacacctac    1980 tactgatagt atgccgccat tattacgaca agctatcgaa ttatttgatc accaaggtgc    2040
agagccagcc ttcttattcg gccttgaatt gatcatatgc ggattagaaa aacaacttaa    2100
atgtgaaagt gggtcttaaa agcagcataa ccttttttccg tgatggtaac cttaatgatt    2160
ttgataaaaa tcattagggg attcatcag                                       2189
```

<210> SEQ ID NO 30
<211> LENGTH: 248
<212> TYPE: DNA
<213> ORGANISM: Bacteriophage lambda

<400> SEQUENCE: 30

```
taatcgacct tattcctaat taaatagagc aaatcccctt attgggggta agacatgaag    60
```

```
atgccagaaa acatgacct gttggccgcc attctcgcgg caaaggaaca aggcatcggg    120
gcaatccttg cgtttgcaat ggcgtacctt cgcggcagat ataatggcgg tgcgtttaca    180
aaaacagtaa tcgacgcaac gatgtcgcca ataatcgcct agttcattcg tgaccttctg    240
cacttcgc                                                             248
```

<210> SEQ ID NO 31
<211> LENGTH: 107
<212> TYPE: PRT
<213> ORGANISM: Bacteriophage lambda

<400> SEQUENCE: 31

```
Met Lys Met Pro Glu Lys His Asp Leu Leu Ala Ile Leu Ala Ala
1               5                   10                  15

Lys Glu Gln Gly Ile Gly Ala Ile Leu Ala Phe Ala Met Ala Tyr Leu
            20                  25                  30

Arg Gly Arg Tyr Asn Gly Gly Ala Phe Thr Lys Thr Val Ile Asp Ala
        35                  40                  45

Thr Met Cys Ala Ile Ile Ala Trp Phe Ile Arg Asp Leu Leu Asp Phe
    50                  55                  60

Ala Gly Leu Ser Ser Asn Leu Ala Tyr Ile Thr Ser Val Phe Ile Gly
65                  70                  75                  80

Tyr Ile Gly Thr Asp Ser Ile Gly Ser Leu Ile Lys Arg Phe Ala Ala
                85                  90                  95

Lys Lys Ala Gly Val Glu Asp Gly Arg Asn Gln
            100                 105
```

<210> SEQ ID NO 32
<211> LENGTH: 77
<212> TYPE: DNA
<213> ORGANISM: artificial sequence
<220> FEATURE:
<223> OTHER INFORMATION: oligonucleotide

<400> SEQUENCE: 32

```
acgaaacgaa gcattggccg taagtgcgat tccggattac taatcgcccg gcatttcgcg    60
ggcgatattt tcacagc                                                   77
```

<210> SEQ ID NO 33
<211> LENGTH: 70
<212> TYPE: DNA
<213> ORGANISM: artificial sequence
<220> FEATURE:
<223> OTHER INFORMATION: oligonucleotide

<400> SEQUENCE: 33

```
aagtcgcggt cggaaccgta ttgcagcagc tttaccatct gccgctggac ggcgcacaaa    60
tcgcgcttaa                                                           70
```

<210> SEQ ID NO 34
<211> LENGTH: 70
<212> TYPE: DNA
<213> ORGANISM: artificial sequence
<220> FEATURE:
<223> OTHER INFORMATION: oligonucleotide

<400> SEQUENCE: 34

```
aagtggcggt gggcaccgtc ttccagcagc tttagtgttc accgctggac ggcgcgcaaa    60
ttgcgctcaa                                                           70
```

```
<210> SEQ ID NO 35
<211> LENGTH: 70
<212> TYPE: DNA
<213> ORGANISM: artificial sequence
<220> FEATURE:
<223> OTHER INFORMATION: oligonucleotide

<400> SEQUENCE: 35
aagtggcggt gggcaccgtc ttccagcagc tttaccacct gccgctggac ggcgcgcaaa    60
ttgcgctcaa                                                          70
```

The invention claimed is:

1. A method for producing a plasmid, comprising:
transfecting a bacterial cell comprising a lysogenic lambda prophage with a linear nucleic acid molecule, wherein the linear nucleic acid molecule comprises two homology arms that flank a plasmid origin of replication, wherein one of the homology arms is a homology arm of 30 to 1000 nucleotides in length that is homologous to a lambda nucleic acid sequence between a nucleic acid sequence encoding excisionase (xis) and a nucleic acid sequence encoding $P_L$ and another of the homology arms is a homology arm of 30 to 1000 nucleotides in length that is homologous to a lambda nucleic acid sequence encoding a c1857 repressor, $P_R$ and/or Cro; and
inducing expression of Beta from the lysogenic lambda prophage;
thereby inducing recombination of the linear nucleic acid molecule with the lambda prophage and producing a plasmid comprising the plasmid origin of replication and a lambda prophage nucleic acid sequence,
wherein the lysogenic lambda prophage comprises $P_L$; the nucleic acid sequence encoding Beta operably linked to $P_L$; a nucleic acid sequence encoding P; a nucleic acid sequence encoding O; a nucleic acid sequence encoding Cro; a nucleic acid sequence encoding integrase (int), a nucleic acid encoding xis, and att;
a phage origin of replication, and
a nucleic acid sequence encoding c1857 repressor;
and the lambda nucleic acid sequence located between the nucleic acid sequence encoding xis and the nucleic acid sequence encoding Beta and the lambda nucleic acid sequence encoding the c1857 repressor, $P_R$ and Cro;
wherein the nucleic acid sequence encoding Cro comprises an amber codon, the nucleic acid sequence encoding P, the nucleic acid sequence encoding O, or both the nucleic acid sequence encoding P and the nucleic acid sequence encoding O comprise an amber codon, such that Cro and P, Cro and O, or Cro, P and O are not produced when the lambda phage is introduced into a suppressor minus host cell;
wherein the lambda prophage does not comprise an active bacterial origin of replication; and wherein the lambda prophage is lysogenic in a suppressor minus host cell and is lytic and produces phage at 42° C. in a host cell that produces an amber suppressive tRNA.

2. The method of claim 1, wherein the plasmid origin of replication is a conditional origin of replication.

3. The method of claim 1, wherein the resultant plasmid can replicate at 32° C. but not at 37° C.

4. The method of claim 1, wherein the bacterial cell is a gram negative bacterial cell.

5. The method of claim 1, wherein the prophage comprises an amber mutation in P.

6. The method of claim 1, wherein the prophage comprises an amber mutation in O.

7. The method of claim 1, wherein the prophage further comprises a promoter operably linked to a nucleic acid sequence encoding a heterologous nucleic acid sequence.

8. The method of claim 7, wherein the promoter operably linked to the heterologous nucleic acid is inserted into a nucleic acid encoding rexAB of the phage.

9. The method of claim 8, wherein the heterologous nucleic acid confers drug resistance to a host cell.

10. The method of claim 9, wherein the heterologous nucleic acid confers resistance of the host cell to kanamycin, ampicillin, tetracycline, chloramphenicol, neomycin, hygromycin or zeocin.

11. The method of claim 1, wherein the prophage comprises an amber mutation in P and an amber mutation in O.

12. The method of claim 1, wherein the prophage comprises a nucleic acid sequence encoding Exo operably linked to the $P_L$, promoter.

13. The method of claim 1, wherein the prophage comprises a nucleic acid sequence encoding Gam operably linked to the $P_L$, promoter.

14. The method of claim 1, wherein the prophage nucleic acid sequence does not encode Gam or Exo.

15. The method of claim 1, wherein the plasmid origin of replication is a pBR322, pBBR1, IncQ, pSC101, pUC5, pUC8, RK2, or P1 origin of replication.

16. The method of claim 1, wherein the lambda nucleic acid sequence between the nucleic acid encoding xis and the nucleic acid sequence encoding $P_L$, comprises a nucleic acid sequence encoding tL3, and wherein one of the homologoy arms comprises a nucleic acid sequence homologous to tL3.

17. The method of claim 1, wherein the one of the two homology arms is homologous to pR.

18. The method of claim 1, further comprising
replacing the plasmid origin of replication with a different origin of replication.

19. The method of claim 1, wherein the lysogenic lambda prophage comprises a nucleic acid encoding Exo.

20. The method of claim 19, wherein the lysogenic lambda prophage comprises a nucleic acid sequence encoding Gam.

21. A method for producing a plasmid, comprising:
transfecting a bacterial cell comprising a lysogenic lambda prophage with a linear nucleic acid molecule,
wherein the lysogenic lambda prophage comprises a nucleic acid sequence encoding Beta operably linked to $P_L$; a nucleic acid sequence encoding c1857; a nucleic acid sequence encoding P; a nucleic acid sequence encoding O; and a nucleic acid sequence encoding Cro;

wherein the linear nucleic acid molecule comprises first and second homology arms that flank a plasmid origin of replication, wherein each of the first and second homology arms is a homology arm of 30 to 1000 nucleotides in length that is homologous to the lysongenic prophage;

wherein the lambda prophage does not comprise an active bacterial origin of replication; and wherein the lambda prophage is lysogenic in a suppressor minus host cell and is lytic and produces phage at 42° C. in a host cell that produces an amber suppressive tRNA; and inducing expression of Beta from the lysogenic lambda prophage in the bacterial cell, thereby inducing recombination of the linear nucleic acid molecule with the lambda prophage and producing a plasmid comprising the plasmid origin of replication and a lambda prophage nucleic acid sequence, wherein the lambda prophage nucleic acid sequence comprises the nucleic acid sequence encoding Beta.

22. The method of claim 21, wherein the plasmid origin of replication is a conditional origin of replication.

23. The method of claim 21, wherein the resultant plasmid can replicate at 32° C. but not at 37° C.

24. The method of claim 21, wherein the bacterial cell is a gram negative bacterial cell.

25. The method of claim 21, wherein the prophage comprises an amber mutation in P.

26. The method of claim 25, wherein the prophage comprises an amber mutation in O.

27. The method of claim 21, wherein the prophage further comprises a promoter operably linked to a nucleic acid sequence encoding a heterologous nucleic acid sequence.

28. The method of claim 27, wherein the promoter operably linked to the heterologous nucleic acid is inserted into a nucleic acid encoding rexAB of the phage.

29. The method of claim 28, wherein the heterologous nucleic acid confers drug resistance to a host cell.

30. The method of claim 29, wherein the heterologous nucleic acid confers resistance of the host cell to kanamycin, ampicillin, tetracycline, chloramphenicol, neomycin, hygromycin or zeocin.

31. The method of claim 21, wherein the prophage comprises an amber mutation in P and an amber mutation in O.

32. The method of claim 21, wherein the prophage comprises a nucleic acid sequence encoding Exo operably linked to the $P_L$ promoter.

33. The method of claim 21, wherein the prophage comprises a nucleic acid sequence encoding Gam operably linked to the $P_L$ promoter.

34. The method of claim 21, wherein the prophage nucleic acid sequence does not encode Gam or Exo.

35. The method of claim 21, wherein the plasmid origin of replication is a pBR322, pBBR1, IncQ, pSC101, pUC5, pUC8, RK2, or P1 origin of replication.

36. The method of claim 21, wherein the lambda prophage comprises a nucleic acid sequence encoding tL3, and the first homology arm comprises sequence homologous to tL3.

37. The method of claim 21, wherein the lambda prophage comprises a nucleic acid sequence encoding pR, and the second homology arm comprises sequence homologous to pR.

38. The method of claim 21, further comprising replacing the plasmid origin of replication with a different origin of replication.

39. The method of claim 21, wherein the lysogenic lambda prophage comprises a nucleic acid encoding Exo.

40. The method of claim 39, wherein the lysogenic lambda prophage comprises a nucleic acid sequence encoding Gam.

* * * * *